United States Patent
Lori et al.

(10) Patent No.: US 10,294,218 B2
(45) Date of Patent: *May 21, 2019

(54) 4,6-DISUBSTITUTED AMINOPYRIMIDINE DERIVATIVES HAVE ANTI-HIV ACTIVITY

(71) Applicant: VIROSTATICS SRL, Alghero (SS) OT (IT)

(72) Inventors: Franco Lori, Bethesda, MD (US); James Chafouleas, Ste-Threse (CA); Davide De Forni, Alghero (IT); Antonio Solinas, Sassari (IT); Zoltán Varga, Budapest (HU); Zoltán Greff, Budapest (HU); László Õrfi, Budapest (HU); György Kéri, Budapest (HU)

(73) Assignee: VIROSTATICS SRL, Alghero (SS) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/442,651

(22) Filed: Feb. 25, 2017

(65) Prior Publication Data

US 2017/0204084 A1    Jul. 20, 2017

Related U.S. Application Data

(62) Division of application No. 13/974,228, filed on Aug. 23, 2013, now Pat. No. 9,617,225.

(60) Provisional application No. 61/692,641, filed on Aug. 23, 2012.

(51) Int. Cl.
| C07D 403/12 | (2006.01) |
| C07D 401/12 | (2006.01) |
| C07D 239/42 | (2006.01) |

(52) U.S. Cl.
CPC ......... *C07D 403/12* (2013.01); *C07D 239/42* (2013.01); *C07D 401/12* (2013.01)

(58) Field of Classification Search
CPC ... C07D 403/12; C07D 401/12; C07D 239/42
See application file for complete search history.

(56) References Cited

U.S. PATENT DOCUMENTS 9,617,225 B2 *  4/2017  Lori ................. C07D 239/42
2002/0012198 A1  2/2002  Grant et al.

FOREIGN PATENT DOCUMENTS

WO    2005/012262 A1 *  2/2005

OTHER PUBLICATIONS

Office Action in Eurasia, App No. 201590417/28, PCT, translation dated Jul. 18, 2016.
EP Extended Search Report, App. No. 13831626.0-1452/2887943 PCT/US2013056347.
EP Annex to Communication dated Nov. 30, 2016, App No. 13 831 626.
Japanese Office Action dated May 16, 2017 Appln No. 2015-528679.

* cited by examiner

*Primary Examiner* — Alexander R Pagano
*Assistant Examiner* — Ebenezer O Sackey
(74) *Attorney, Agent, or Firm* — Valerie E. Looper; The Law Offices of Valerie E. Looper

(57) ABSTRACT

Novel 4,6-disubstituted aminopyrimidine derivatives with the following structure (I)

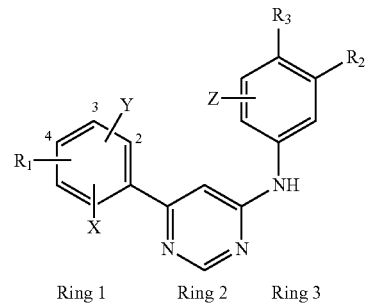

have anti-HIV activity.

20 Claims, No Drawings

4,6-DISUBSTITUTED AMINOPYRIMIDINE DERIVATIVES HAVE ANTI-HIV ACTIVITY

RELATED APPLICATION

This application is a Division of U.S. Ser. No. 13/974,228, filed Aug. 23, 2013, which is a continuation-in-part of U.S. provisional application 61/692,641, re "AV-HALT Compounds for treatment of Viral Infections," filed 23 Aug. 2012.

BACKGROUND OF INVENTION

Human immunodeficiency virus (HIV) infection (which results in Acquired Immune Deficiency Syndrome, AIDS) is a relatively new infection in the human population, but it has quickly risen to one of the foremost health problems in the world. HIV/AIDS has now become the leading cause of death in sub-Saharan Africa, as well as the fourth biggest killer worldwide (BMJ 2001; 323(7324):1271). At the end of 2010, it was estimated that more than 34 million people were living with HIV infection worldwide, including around 16.8 million women and 3.4 million children (World Health Organisation data). In 2010, there were 2.7 million people newly infected with HIV, and the death toll due to AIDS reached 1.5 million people.

Low- and middle-income countries are the most plagued by HIV (about 97% of new infections are registered there), but adult and child deaths due to AIDS in 2010 were 30,000 in western industrialised countries.

Better treatment methods are now known to prolong the life of patients with HIV infection, but no cure has been found yet for this disease.

Current anti-HIV drugs target several different stages of the HIV life cycle, and several of the enzymes that HIV requires to replicate and survive (Arts et al. Cold Spring harb Perspect Med 2012:2(4):a007161). Some of the commonly used anti-HIV drugs include nucleoside/nucleotide reverse transcriptase inhibitors, NRTIs (such as emtricitabine, stavudine, ddI, ddC, d4T, 3TC, zidovudine, abacavir, tenofovir etc); non-nucleoside reverse transcriptase inhibitors, NNRTIs (such as rilpivirine, etravirine, nevirapine, efavirenz and delavirdine); protease inhibitors, PIs (such as saquinavir, ritonavir, indinavir, nelfinavir, amprenavir, lopinavir and atazanavir); entry inhibitors, including fusion inhibitors (such as enfuvirtide, maraviroc, ibalizumab etc) and others, such as the integrase inhibitor isentress (raltegravir) (http://www.fda.gov/ForConsumers/byAudience/ForPatientAdvocates/HIVandAIDSActivities/ucm118915.htm).

The condition where T cells engage in uncontrolled cell division is called T cell hyperproliferation, leading to immune hyperactivation. T cells are immune system cells that can develop the capacity to kill infected or neoplastic cells. When T cells are contacted by antigens they become activated, or sensitised, and proliferate, that is, appear in greater numbers (Grossman et al. Nat Med 2006; 12; 289-295, Brenchley et al. Nat Med 2006; 12:1365-1371). This is a normal physiological process, which is useful to protect the host from "sick cells" (tumor cells and infected cells).

However, excessive T cell activation, and particularly prolonged, excessive activation can contribute to disease progression and is considered a key pathogenetic factor in several chronic diseases such as cancer and chronic infectious diseases including HIV/AIDS (Sodora et al. AIDS 2008 22:439-446, Hellerstein et al. J Clin Invest 2003; 112:956-966, Liovat et al. PLOS ONE 2012; 7(10):e46143, Cossarizza et al. PLOS ONE 2012:7(12):e50728, Hunt et al. AIDS 2011; 25(17):2123-2131).

In addition, HIV infection of T cells depends on active division and proliferation of such cells. Firstly, infected dividing T cells produce a large amount of HIV particles (approximately 8-10 fold more than in quiescent T cells). Secondly, antigenic stimulation by such HIV particles sustains further T cell activation or proliferation, as mentioned before. This results in a dangerous "vicious cycle". In addition to direct antigenic stimulation by HIV, microbial translocation across impaired gut-associated lymphoid tissues (GALT) throughout the course of HIV disease also sustains elevated T cell activation/proliferation (Brenchley et al. Nat Med, 2006. 12(12): p. 1365-71). This chronic cycle of events, over time, exhausts the immune system. Therefore, limiting T cell hyperactivation and hyperproliferation will have a dual effect: it will not only suppress HIV replication, but it will also prevent the loss of functional CD4 T helper cells and slow down disease progression.

In order to try to address this unmet medical need we have tried to develop compounds designed to provide both an antiviral and an antiproliferative component. In order to establish the proof of concept for this approach in humans, we combined into a single capsule, two readily available generic drugs, hydroxyurea (HU) and didanosine (ddI), which we called VS411. In VS411, ddI is the antiviral component and HU is the antiproliferative component. The NRTI, ddI has been used extensively in the treatment of HIV in combination cocktails as a direct acting antiretroviral agent targeting the HIV encoded reverse transcriptase enzyme activity. HU is an antiproliferative agent indicated for the treatment of different neoplastic as well as non-neoplastic diseases such as sickle cell anemia and psoriasis. HU has been used for the treatment of HIV-infected individuals, especially in combination with antiretroviral drugs, such as ddI. HU inhibits the cellular enzyme ribonucleotide reductase, blocking the transformation of ribonucleotides into deoxyribonucleotides, thus depleting the intracellular deoxynucleotide triphosphate (dNTP) pool, and arresting the cell cycle in the G1/S phase (Lori AIDS, 1999; 13(12):1433-42). By depleting the dNTP pool, HU also strongly inhibits viral deoxyribonucleic acid (DNA) synthesis through the virally encoded reverse transcriptase. Moreover, HU can also suppress virus replication by slowing down the rate of T-cell proliferation (as stated above, HIV-1 needs actively dividing cells to optimally replicate).

VS411, was first studied in a Phase I clinical trial in which it exhibited a favourable safety profile and the best formulation was identified (De Forni et al. Br J Pharmacol 2010; 161(4):830-843). VS411 was then investigated in a Proof-of-Concept multinational Phase II trial. In the course of this Phase II study, VS411 exhibited excellent safety and tolerability profiles and reduction in viral load and immune activation after just 28 days of therapy. These results provided solid Proof-of-Concept evidence that therapeutics with antiviral and antiproliferative activities can provide a clinically significant benefit in the treatment of HIV/AIDS (Lori et al. PloS ONE 2012; 7(10): e47485. doi:10.1371/journal.pone.0047485).

Recently, attention has also been turned to cyclin-dependent kinases (CDKs), key regulators of the cell cycle and RNA polymerase II transcription. Cyclin-dependent kinases (CDKs) are non-receptor serine-threonine protein kinases that require cyclin for their activity and play a fundamental role in controlling cell cycle progression. Cell division is a highly regulated process responding to cellular signals both within the cell and from external sources (Gerard et al. Front Physiol 2012; 3:413).

To date, thirteen CDKs have been identified in humans (Chen et al. Biochem Biophys Res Commun. 2007, 354, 735-40; Mani et al. Exp. Opin. Invest. Drugs 2000; 9(8): 1849-1870, Sergere et al. Biochem. Biophys. Res. Commun. 2000, 276, 271-277, Hu et al. J. Biochem. Chem. 2003; 278(1 0):8623-8629).

Because CDKs play an important role in the regulation of cellular proliferation, CDK inhibitors could be useful in the treatment of cell proliferative disorders such as cancer, neuro-fibromatosis, psoriasis, fungal infections, endotoxic shock, transplantation rejection, vascular smooth cell proliferation associated with artheroscelerosis, pulmonary fibrosis, arthritis, glomerulonephritis and post-surgical stenosis and restenosis (U.S. Pat. No. 6,114,365).

CDKs are also known to play a role in apoptosis. Therefore CDK inhibitors could be useful in the treatment of cancer; autoimmune diseases, for example systemic lupus, erythematosus, autoimmune mediated glomerulonephritis, rheumatoid arthritis, psoriasis, inflammatory bowel disease, and autoimmune diabetes (Roberts et al. J Natl Cancer 2012; 104(6):476-487, Zoja Arthritis Rheum 2007; 56:1629-1637). Indeed several pharmacological CDK inhibitors (PCIs) are currently in clinical trials as potential cancer therapeutics (Benson et al. Br J Cancer 2007; 96(1):29-37, Luke et al. Clin Cancer 2012; 18(9):2638-2647).

During the last few years, the antiviral effect of PCIs has also been observed against a number of viruses, including HIV. It has been described that HIV-1 replication could be affected by inhibiting CDKs (de la Fuente, et al. Current HIV Research, 2003, 1(2), 131-152; Y. K. Kim et al. Molecular and Cellular Biology, 2002; 22(13):4622-4637). In particular, CDK9 has been reported as being essential for HIV-1 replication. CDK9 forms together with cyclin T1 the human positive transcription elongation factor (PTEFb) regulating elongation phase of RNA polymerase II (RNA Pol II) dependent transcription (Price et al. Mol Cell Biol 2000, 20:2629-2634; Peterlin et al. Mol Cell 2006; 23:297-305). P-TEFb specifically activates transcription from the HIV-1 long-terminal repeat (LTR) promoter (Bieniasz et al. PNAS 1999; 96:7791-7796). After transcription initiation at the LTR, the newly transcribed transactivation responsive (TAR) RNA hairpin recruits the HIV-1 Tat protein, which binds to the cyclin T1 subunit of P-TEFb and recruits the kinase complex to phosphorylate Pol II (Bieniasz et al. PNAS 1999; 96:7791-7796, Zhang et al. J Biol Chem 2000; 275:34314-34319). HIV-1 Tat has recently been suggested to manipulate P-TEFb functional equilibrium by recruiting it from the large inactive complex thus increasing the active pool for efficient HIV-1 transcription (Barboric et al. Nucl Acids Res 2007; 35:2003-2012, Sedore Nucl Acids Res 2007; 35:4347-4358). The P-TEFb kinase activity is both essential and limiting for viral replication, and inhibition of P-TEFb by small molecules such as DRB 1 abrogates both viral transcription and replication (Flores et al. Proc. Natl. Acad. Sci. USA. 1999, 96(13):7208-13). The most potent P-TEFb inhibitor flavopiridol 2 effectively blocks HIV-1 Tat-transactivation and viral replication by inhibiting P-TEFb kinase activity at non-cytotoxic concentrations without affecting cellular transcription (Chao J Biol Chem 2000; 275:28345-28348, Chao J Biol Chem 2001; 276: 31793-31799). RNAi-mediated gene silencing of PTEFb inhibits Tat-transactivation and HIV-1 replication in host cells with no effects on cell viability (Chiu J Virol 2004; 78:2517-2529). Furthermore, direct inhibition of CDK9 using a dominant negative form has been shown to potently inhibit HIV-1 replication without affecting RNA Pol II transcription and cell viability (Flores et al. Proc. Natl. Acad. Sci. USA. 1999, 96(13):7208-13, Salerno et al. Gene 2007; 405:65-78).

When pathogens infect a host, they must manipulate its signal-transduction pathways (the intracellular circuits that transmit extracellular signals from the cell surface to the nucleus and back) required for cellular function and survival (Coley et al. Exp Opin Biol Ther 2009). Preventing pathogens from hijacking such pathways via compounds exerting their action against certain cellular kinases that play key roles in cell signaling, generates a firewall against infection. The benefit of such an approach is that the target for the therapeutic intervention is directed primarily on the host-cell kinases, rather than on pathogen encoded targets. An important consequence of such an approach is that it minimizes the problem of drug resistance. Treatment with typical anti-infective drugs, which act directly on a pathogen encoded target, can be rendered ineffective due to generation of drug resistant variants (Thompson et al. JAMA 2012; 304(3):321-333, UK Coll Group J Inf Dis 2005). These drug resistant variants can occur rapidly, due to spontaneous mutations to the pathogen encoded target and poor proofreading mechanisms during the very short replication cycle of the pathogen. Mammalian host cellular enzymes are much less prone to mutations than microbial ones due to the fact that the mammalian host cell has a much more efficient proofreading mechanism and substantially longer replication cycle. Moreover, since targeting a host-cell kinase would be distal to a pathogen-encoded target this approach should therefore diminish the chances for developing pathogen resistance to such a drug.

Based on this rationale, we embarked on an initial screen for anti-HIV compounds chosen among a library of CDK9 inhibitors, PCT international application (published 30 Jun. 2011 as WO2011077171) "4-Phenylamino-Pyrimidine Derivatives having Protein Kinase Inhibitor Activity" ("PKI") by Greff et al.

Unexpectedly, the results of the activity tests on such a library (which produced a number of initial hits) highlighted the lack of a direct correlation between CDK9 activity and the anticipated anti-HIV activity. In most cases there was no correlation whatsoever between CDK9 inhibition and anti-HIV activity, as compounds with potent CDK9-related $IC_{50}$ exhibited poor anti-HIV profiles and vice versa.

This prompted us to explore a new approach: modifications on the original library compounds were proposed, synthetic routes were designed and reduced to practice by synthesizing the novel compounds, the compounds were then tested one by one, resulting in a novel class of molecules with the required properties, that are the subject of the present invention. As the CDK9 inhibitory activity and selectivity of these molecules is not predictive of the antiviral and/or antiproliferative activity they act by an as yet unknown mechanism.

FIELD OF THE INVENTION

The invention therefore encompasses the discovery of novel drugs whose discovery required the experimental testing for their antiviral activity, as their anti-HIV properties could not be deduced a priori just by examination of their CDK9 activity. In addition, to their stand-alone antiviral activity, these novel compounds preferably exhibit the additional attractive antiproliferative activity, thus providing a means for anti-HIV and antiproliferative activity with a single molecule.

Based on their properties, the compounds described in this current invention have the potential to be applied to a variety of additional antiviral indications and chronic conditions. Inflammation, immune hyperactivation and immune cell hyperproliferation are, in fact, hallmarks of many chronic infections, as well as the cardiovascular, inflammatory and metabolic disorders, tumors, and aging that result from chronic, uncontrolled inflammation.

DESCRIPTION OF RELATED ART

In the context of the current invention, the following references present the general state of the art:

Most of the known CDK inhibitors, such as Roscovitine, Olomoucine, purvalanols, paullones, indolinones and 7-hydroxy-staurosporine, rely on the inhibition of CDK1 and CDK2 for antitumor activity (Current Opinion in Pharmacology, 2003, 3, 1-9). A summary of known CDK inhibitors is given by M. Huwe et al. (A. Huwe et al. Angew. Chem. Int. Ed. Engl. 2003; 42(19):2122-38).

WO2011077171 A1 discloses certain 4-phenylamino-pyrimidine derivatives having protein kinase inhibitor activity. In particular, the invention described in WO2011077171 A1 relating to novel 4,6-disubstituted aminopyrimidine compounds, has a main element of novelty based on arylaminopyrimidines that have a substituted aryl part containing —(CH$_2$)$_n$—W substituents (with n being preferably 1 to 3). Preferred meanings for W include methanesulfonamide, thiophene, indolyl or isoindolyl, phthalimido or benzoimidazo-1-yl groups.

The compounds in the patent represent a library of compounds linking their CDK9-inhibition activity with protein kinase-related diseases such as infectious diseases and cell proliferative diseases. Their structure is different from the compounds we claim in this patent, because the compounds in patent WO2011077171 A1 are only mono substituted pyrimidin-4-ylaminophenyl derivatives.

Bioorganic & Medicinal Chemistry Letters 19 (2009) 17-20 (Steele et al.) reports small molecule β-secretase inhibitors with structural analogies to the compounds herein described. Despite the degree of structural analogy to compounds herein claimed, it is worth noting that the compounds presented in the Steele paper show two main differences:
1) they are presented as Alzheimer's disease (AD) inhibitors acting on β-secretase BACE1 (belonging to the aspartyl protease class of catabolic enzymes);
2) des-dimethylamine compounds described have structure

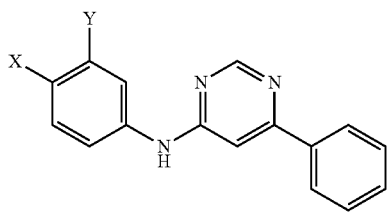

and specifically lack any substituent on the aryl ring positioned in the 6-position of the pyrimidine ring. Moreover, substituents X have been chosen among Me, H, Cl, Br, F, OMe, Ph and allyl, while Y substituents listed are HO$_2$, NH$_2$, NHAc and N-Methyl mesilamide.

In a further refinement of the SAR for the 6-position of the pyrimidine, the authors study Z substituents where Z is Ph, 2' (N,N dimethyl)benzene, 4' (N,N dimethyl)benzene, 2'-methylbenzene, 4'-biphenyl,

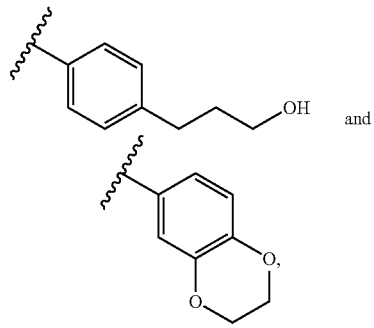

but no Z substituents with —OR have been reported in the paper.

US 2009/0099183 A1 discloses lysophosphatidic acid acyltransferase inhibitors based on pyrimidines with structural analogies to the compounds herein described. The structures originally covered in the initial application were generally of the formula:

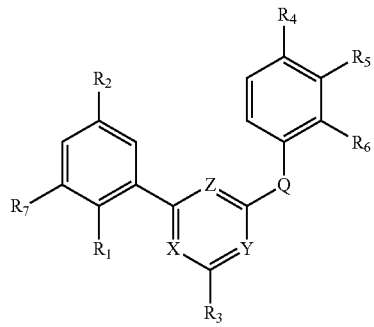

where $R^1$-$R^7$ are hydrogen or non-hydrogen substituents, Q is a heteroatom or heteroatom attached to one or more methylene groups, and two of X, Y and Z are N with the third being CH or a substituted C. The requirement that two of X, Y and Z are N is consistent with the compounds including a pyrimidine ring.

Preferred embodiments include the following selections for the general formula above. Such preferred embodiments include where X, Y and Z are N, CH or CR. R of CR is alkyl, alkoxy, halo (preferably Cl or Br), NH$_2$, NHR' or NR'R" where R' and R" independently are alkyl. Particularly preferred is where X and Y are N.

Preferred embodiments include where Q is a heteroatom (preferably N, O or S) and may be attached to one or more methylene groups to provide additional spacing between the pyrimidine ring and the phenyl ring possessing $R^4$, $R^5$ and/or $R^6$. Q may be NR where R is H or alkyl. Where there are one or more methylene groups, the heteroatom may be oriented such that it is attached directly to the pyrimidine ring or attached directly to the phenyl ring possessing $R^4$, $R^5$ and/or $R^6$. For example, Q may be RN—(CH$_2$)$_n$, (CH$_2$)$_n$NR, O—(CH$_2$)$_n$, (CH$_2$)$_n$—O, S—(CH$_2$)$_n$ or (CH$_2$)$_n$—S, where n is typically 1-10 and R is H or alkyl. Particularly preferred is where Q is NH.

The inventors had to elect one species as the lead, which is quite different from the compounds claimed in the present patent. The elected species represents the same formula described above wherein: X and Y are N, Z is CH; Q is NH; $R^1$ is Phenyl-$CH_2$—O—; $R^2$ is Br; $R^3$ is $NH_2$; $R^4$ is $N^+$(=O)$O^-$; and $R^5$, $R^6$ and $R^7$ are H.

Current Medicinal Chemistry 2011; 18(3): 342-358 (Németh et al.) reports a selective family of CDK9 inhibitors based on the 4-phenylamino-6-phenylpyrimidine nucleus that could have potential as anti-HIV compounds. The starting point for the synthesis of these selective CDK9 inhibitors and their evaluation in the treatment of HIV infection was derived from two other publications:

a) Choidas, A.; Backes, A.; Cotten, M.; Engkvist, O.; Felber, B.; Freisleben, A.; Gold, K.; Greff, Z.; Habenberger, P.; Hafenbradl, D.; Hartung, C.; Herget, T.; Hoppe, E.; Klebl, B.; Missio, A.; Willer, G.; Schwab, W.; Zech, B.; Bravo, J.; Harris, J.; Le, J.; Macritchie, J. Pharmaceutically active 4,6-disubstituted aminopyrimidine derivatives as modulators of protein kinases. PCT Int. Appl. WO 2005026129, 2005; Chem. Abstr., 2005, 142, 336376;

b) Wabnitz, P.; Schanerte, H.; Stumm, G.; Freitag, J. Pyrimidine-based CDK inhibitors for treating pain. PCT Int. Appl. WO 2006/125616, 2006; Chem. Abstr. 2007, 146, 781.

The described compounds are synthesised starting from 4-chloro-6-(substituted-phenyl)-pyrimidines and fall into different categories, described by the general structure:

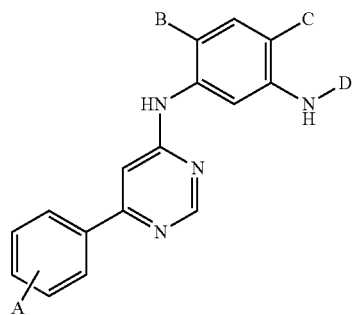

B is described as H or Me. In the cases of B=H, depending on C (H, Me, Cl, F, $NO_2$, $NH_2$), the compounds reported in the paper can be either monosubstituted or disubstituted. The key aspect of the paper is that the compounds described are derived making modifications on the (6-phenyl-pyrimidin-4-yl)-phenylamine core structure in order to yield selective CDK9/CycT1 kinase inhibitors, with the assumption that selectivity in CDK9 inhibition is a major aspect for the potential to inhibit HIV-1 propagation. However, the experimental data set that is presented in this paper is certainly not conclusive for the activity of the compounds in HIV. As a matter fact when the present inventors tested the activity of the most promising CDK9 inhibitors it became clear that there is no direct correlation between CDK9 activity and viral inhibition.

BRIEF SUMMARY OF THE INVENTION

As discussed before, several aminopyrimidine derivatives have been disclosed in the literature, and some of them have been described as potential compounds with applications in the HIV field. However, none of the compounds exemplified therein has been encompassed in the general formula (I) of the present application, nor is the evidence of anti-HIV activity very convincing.

In fact during their research the present inventors surprisingly found that only few compounds with good CDK9 activity exhibited potent anti-HIV activity. This inconsistency suggests that these compounds target a cellular mechanism that is as yet not identified.

The present inventors have now discovered that compounds of formula (I), described below, exert a potent stand alone anti-HIV activity which in the preferred cases is also combined with a potentially attractive antiproliferative activity in the same molecule, irrespective of whether they exhibit a good or bad CDK9 inhibitor activity. Thus, these compounds provide for a potentially new method to treat HIV disease.

Compounds claimed in paper Current Medicinal Chemistry 2011; 18(3):342-358 (Németh et al.), which would fall in the claims of the present application, are excluded from the present general formula.

Accordingly, a first object of the present invention is to provide novel 4,6-disubstituted aminopyrimidine compounds represented by formula (I), which possess aromatic substituents, which are directly or indirectly attached to two non-adjacent carbons of the pyrimidine ring. The general formula of the compounds is the following:

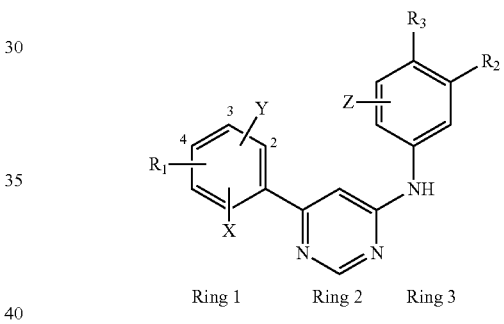

where X, Y and Z are hydrogen or halogen substituents, $R_1$ is an alkoxy, benzyloxy or aryloxy group, $R_2$ is a group attached to heteroatom and $R_3$ is a group attached to a carbon or heteroatom or heteroatom. In preferred embodiments:

X, Y and Z are H, F, Cl;

$R_1$ is OR, where R is hydrogen or an optionally substituted group selected from straight or branched $C_1$-$C_6$ alkyl, $C_2$-$C_6$ alkenyl, $C_2$-$C_6$ alkynyl, $C_3$-$C_6$ cycloalkyl and heterocyclyl, $CF_3$, $CCl_3$, aryl or substituted aryl in positions 2, 3 and/or 4, benzyl or substituted benzyl in positions 2, 3 and/or 4;

$R_2$ is H, OH, alkoxy, aryloxy, benzyloxy, $CH_2OR$ (where R is H, linear or branched aryl, cycloalkyl or alkyl), $CH_2NR'R''$ (where R' and R'' are independently H, linear or branched aryl, cycloalkyl or alkyl), CHO, OCOW (where W is linear or branched aryl or alkyl or C-halogen$_3$), CONR'R'' (where R' and R'' independently are H, alkyl, $C_{2-6}$ ring closed alkyl, $(CH_2)_{2-6}$-heterocycle, $(CH_2)_{2-6}$—OH, cycloalkyl and aryl), COOR (where R is H, alkyl, cycloalkyl and aryl), $CH_2NHSO_2R$ (where R is H, alkyl, cycloalkyl and aryl), Cl, Br, F, saturated or unsaturated 4-piperidine, substituted and unsubstituted $CH_2$—N-benzymidazole, substituted and unsubstituted NH-2-benzymidazole, CONRNR'R'' (where R, R' and R'' independently are H, alkyl, cycloalkyl and aryl), NRCOOR' (where R and R' are independently H, alkyl, cycloalkyl and aryl), NR'R'' (where R' and R'' independently are H, alkyl, cycloalkyl and aryl), NHCOR (where R is H, alkyl, cycloalkyl and aryl), nitro, OCH$_2$CH$_2$-heterocycle, OCOR (where R is H, alkyl, cycloalkyl and aryl), OCONR'R" (where R' and R" are independently H, alkyl, cycloalkyl and aryl), OCOOR (where R is H, alkyl, cycloalkyl and aryl), NHCOOR (where R is H, alkyl, CH$_2$C-halo$_3$, cycloalkyl and aryl), NRCONR'R" (where R, R' and R" independently are H, alkyl, cycloalkyl and aryl), NRCOOR' (where R and R' independently are H, alkyl, cycloalkyl and aryl), NHSO$_2$R (where R is H, alkyl, cycloalkyl and aryl), NHSO$_2$NR'R" (where R' and R" independently are H, alkyl, cycloalkyl and aryl),

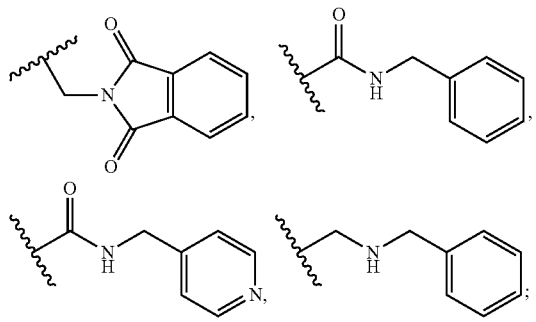

R$_3$ is OH, alkoxy, aryloxy, benzyloxy, Cl, F, morpholino, N-methylpiperazino, nitro, NR'R" (where R' and R" independently are H, alkyl), NHCOR (where R is H, alkyl, cycloalkyl and aryl), NHSO$_2$R (where R is H, alkyl, cycloalkyl and aryl), COOR (where R is H, alkyl, cycloalkyl and aryl), CONR'R" (where R' and R" independently are H, alkyl, (CH$_2$)$_{2-6}$-OH, cycloalkyl and aryl).

In particular embodiments of the invention, the compound of general formula (I) is selected from the following group:

Example 1

N-(3-((benzylamino)methyl)-4-methoxyphenyl)-6-(2-methoxyphenyl)pyrimidin-4-amine;

Example 2

N-(3-((1H-benzo[d]imidazol-1-yl)methyl)-4-(4-methylpiperazin-1-yl)phenyl)-6-(2-methoxyphenyl)pyrimidin-4-amine;

Example 3

2-(2-methoxy-5-(6-(2-methoxyphenyl)pyrimidin-4-ylamino)benzyl)isoindoline-1,3-dione;

Example 4

N-(2-methoxy-5-(6-(2-methoxyphenyl)pyrimidin-4-ylamino)benzyl)methanesulfonamide;

Example 5

N$^1$-(6-(2-methoxyphenyl)pyrimidin-4-yl)-N$^4$,N$^4$-dimethylbenzene-1,4-diamine;

Example 6

(2-chloro-5-(6-(2-methoxyphenyl)pyrimidin-4-ylamino)phenyl)methanol;

Example 7

2-chloro-5-(6-(2-methoxyphenyl)pyrimidin-4-ylamino)benzohydrazide;

Example 8

N-(4-methoxy-3-(2-morpholinoethoxy)phenyl)-6-(2-methoxyphenyl)pyrimidin-4-amine;

Example 9

N-(2-methoxy-5-(6-(2-methoxyphenyl)pyrimidin-4-ylamino)phenyl)methanesulfonamide;

Example 10

(2-methoxy-5-(6-(2-methoxyphenyl)pyrimidin-4-ylamino)phenyl)(methylsulfamoyl)amine;

Example 11

N-(4-methoxy-3-nitrophenyl)-6-(2-methoxyphenyl)pyrimidin-4-amine;

Example 12

4-(6-(2-methoxyphenyl)pyrimidin-4-ylamino)-2-nitrophenol;

Example 13

(2-methoxy-5-(6-(2-methoxyphenyl)pyrimidin-4-ylamino)phenyl) (cyclohexylsulfamoyl)amine;

Example 14 ethyl 2-chloro-5-(6-(2-methoxyphenyl)pyrimidin-4-ylamino)benzoate;

Example 15

(2-chloro-5-(6-(2-methoxyphenyl)pyrimidin-4-ylamino)phenyl)(pyrrolidin-1-yl)methanone;

Example 16

N-(3-((1H-benzo[d]imidazol-1-yl)methyl)-4-chlorophenyl)-6-(2-methoxyphenyl)pyrimidin-4-amine;

Example 17

(5-(6-(2-methoxyphenyl)pyrimidin-4-ylamino)-2-(4-methylpiperazin-1-yl)phenyl)methanol;

Example 18 ethyl 5-(6-(2-methoxyphenyl)pyrimidin-4-ylamino)-2-morpholinobenzoate;

Example 19

(5-(6-(2-methoxyphenyl)pyrimidin-4-ylamino)-2-morpholinophenyl)methanol;

Example 20

2-(2-chloro-5-(6-(2-methoxyphenyl)pyrimidin-4-ylamino)benzyl)isoindoline-1,3-dione;

Example 21 methyl 2-hydroxy-5-(6-(2-methoxyphenyl)pyrimidin-4-ylamino)benzoate;

Example 22

N-(3-fluoro-4-methoxyphenyl)-6-(2-methoxyphenyl)pyrimidin-4-amine;

Example 23

N-benzyl-2-methoxy-5-(6-(2-methoxyphenyl)pyrimidin-4-ylamino)benzamide;

Example 24

(2-methoxy-5-(6-(2-methoxyphenyl)pyrimidin-4-ylamino)phenyl)methanol;

Example 25

2-methoxy-5-(6-(2-methoxyphenyl)pyrimidin-4-ylamino)-N-methylbenzamide;

Example 26

2-methoxy-5-(6-(2-methoxyphenyl)pyrimidin-4-ylamino)phenyl pivalate;

Example 27

2,2,2-trichloroethyl 2-methoxy-5-(6-(2-methoxyphenyl)pyrimidin-4-ylamino)phenylcarbamate;

Example 28

2-methoxy-5-(6-(2-methoxyphenyl)pyrimidin-4-ylamino)-N-(pyridin-4-ylmethyl)benzamide;

Example 29

2-methoxy-5-(6-(2-methoxyphenyl)pyrimidin-4-ylamino)benzaldehyde;

Example 30 methyl 2-methoxy-5-(6-(2-methoxyphenyl)pyrimidin-4-ylamino)benzoate

Example 31

N-(3-((1H-benzo[d]imidazol-1-yl)methyl)-4-methoxyphenyl)-6-(2-methoxyphenyl)pyrimidin-4-amine;

Example 32

2-methoxy-5-(6-(2-methoxyphenyl)pyrimidin-4-ylamino)phenol;

Example 33

2-methoxy-5-(6-(2-methoxyphenyl)pyrimidin-4-ylamino)benzohydrazide;

Example 34

N-(4-methoxy-3-((phenylamino)methyl)phenyl)-6-(2-methoxyphenyl)pyrimidin-4-amine;

Example 35

N-(3-((dimethylamino)methyl)-4-methoxyphenyl)-6-(2-methoxyphenyl)pyrimidin-4-amine;

Example 36

N-(3-(benzyloxy)-4-methoxyphenyl)-6-(2-methoxyphenyl)pyrimidin-4-amine

Example 37

N-(4-methoxy-3-((methylamino)methyl)phenyl)-6-(2-methoxyphenyl)pyrimidin-4-amine;

Example 38

5-(6-(2-methoxyphenyl)pyrimidin-4-ylamino)-2-(4-methylpiperazin-1-yl)benzenesulfonamide

Example 39

N-(3-((1H-benzo[d]imidazol-1-yl)methyl)-4-ethoxyphenyl)-6-(2-methoxyphenyl)pyrimidin-4-amine;

Example 40

N-(3-((1H-benzo[d]imidazol-1-yl)methyl)-4-fluorophenyl)-6-(2-methoxyphenyl)pyrimidin-4-amine;

Example 41

4-methoxy-$N^1$-(6-(2-methoxyphenyl)pyrimidin-4-yl)benzene-1,3-diamine;

Example 42

2-((1H-benzo[d]imidazol-1-yl)methyl)-$N^4$-(6-(2-methoxyphenyl)pyrimidin-4-yl)-$N^1$,$N^1$-dimethylbenzene-1,4-diamine;

Example 43

N-(3-(aminomethyl)-4-methoxyphenyl)-6-(2-methoxyphenyl)pyrimidin-4-amine;

Example 44

2-chloro-5-(6-(2-methoxyphenyl)pyrimidin-4-ylamino)benzamide;

Example 45

2-methoxy-5-(6-(2-methoxyphenyl)pyrimidin-4-ylamino)benzamide;

Example 46

2-Methoxy-5-[6-(2-methoxy-phenyl)-pyrimidin-4-ylamino]-benzoic acid N-methyl-hydrazide;

Example 47

2-Methoxy-5-[6-(2-methoxy-phenyl)-pyrimidin-4-ylamino]-N-[3-(4-methyl-piperazin-1-yl)-propyl]-benzamide;

Example 48

N-(2-Hydroxy-ethyl)-2-methoxy-5-[6-(2-methoxy-phenyl)-pyrimidin-4-ylamino]-benzamide;

Example 49

2-Methoxy-5-[6-(2-methoxy-phenyl)-pyrimidin-4-ylamino]-benzoic acid;

Example 50

N-{2-Methoxy-5-[6-(2-methoxy-phenyl)-pyrimidin-4-ylamino]-phenyl}-acetamide;

Example 51

{2-Methoxy-5-[6-(2-methoxy-phenyl)-pyrimidin-4-ylamino]-phenyl}-carbamic acid methyl ester;

Example 52

1-{2-Methoxy-5-[6-(2-methoxy-phenyl)-pyrimidin-4-ylamino]-phenyl}-3-methyl-urea;

Example 53

N-{2-Methoxy-5-[6-(2-methoxy-phenyl)-pyrimidin-4-ylamino]-phenyl}-2,2-dimethyl-propionamide;

Example 54

$N^3$-(1H-Benzoimidazol-2-yl)-4-methoxy-$N^1$-[6-(2-methoxy-phenyl)-pyrimidin-4-yl]benzene-1,3-diamine;

Example 55

N-{2-Methoxy-5-[6-(2-methoxy-phenyl)-pyrimidin-4-ylamino]-phenyl}-formamide;

Example 56

{2-Methoxy-5-[6-(2-methoxy-phenyl)-pyrimidin-4-ylamino]-phenyl}-urea;

Example 57

(3-Fluoro-4-nitro-phenyl)-[6-(2-methoxy-phenyl)-pyrimidin-4-yl]-amine;

Example 58

(3-Methoxy-4-nitro-phenyl)-[6-(2-methoxy-phenyl)-pyrimidin-4-yl]-amine;

Example 59

2-Methoxy-$N^4$-[6-(2-methoxy-phenyl)-pyrimidin-4-yl]-benzene-1,4-diamine;

Example 60

N-{2-Methoxy-4-[6-(2-methoxy-phenyl)-pyrimidin-4-ylamino]-phenyl}-methanesulfonamide;

Example 61

[6-(2-Ethoxy-phenyl)-pyrimidin-4-yl]-(4-methoxy-3-nitro-phenyl)-amine;

Example 62

$N^1$-[6-(2-Ethoxy-phenyl)-pyrimidin-4-yl]-4-methoxy-benzene-1,3-diamine;

Example 63

[6-(4-Fluoro-2-methoxy-phenyl)-pyrimidin-4-yl]-(4-methoxy-3-nitro-phenyl)-amine;

Example 64

$N^1$-[6-(4-Fluoro-2-methoxy-phenyl)-pyrimidin-4-yl]-4-methoxy-benzene-1,3-diamine;

Example 65

(4-Methoxy-3-nitro-phenyl)-[6-(4-methoxy-phenyl)-pyrimidin-4-yl]-amine;

Example 66

4-Methoxy-$N^1$-[6-(4-methoxy-phenyl)-pyrimidin-4-yl]-benzene-1,3-diamine;

Example 67

(4-Methoxy-3-nitro-phenyl)-[6-(3-methoxy-phenyl)-pyrimidin-4-yl]-amine;

Example 68

4-Methoxy-$N^1$-[6-(3-methoxy-phenyl)-pyrimidin-4-yl]-benzene-1,3-diamine;

Example 69

[6-(2-Benzyloxy-phenyl)-pyrimidin-4-yl]-(4-methoxy-3-nitro-phenyl)-amine;

Example 70

2-[6-(3-Amino-4-methoxy-phenylamino)-pyrimidin-4-yl]-phenol;

Example 71

$N^1$-[6-(2-Benzyloxy-phenyl)-pyrimidin-4-yl]-4-methoxy-benzene-1,3-diamine;

Example 72

[6-(2-Ethoxy-4-fluoro-phenyl)-pyrimidin-4-yl]-(4-methoxy-3-nitro-phenyl)-amine;

Example 73

$N^1$-[6-(2-Ethoxy-4-fluoro-phenyl)-pyrimidin-4-yl]-4-methoxy-benzene-1,3-diamine;

Example 74

[6-(5-Fluoro-2-methoxy-phenyl)-pyrimidin-4-yl]-(4-methoxy-3-nitro-phenyl)-amine;

Example 75

$N^1$-[6-(5-Fluoro-2-methoxy-phenyl)-pyrimidin-4-yl]-4-methoxy-benzene-1,3-diamine;

Example 76

(4-Methoxy-3-nitro-phenyl)-[6-(2-phenoxy-phenyl)-pyrimidin-4-yl]-amine;

Example 77

4-Methoxy-$N^1$-[6-(2-phenoxy-phenyl)-pyrimidin-4-yl]-benzene-1,3-diamine;

Example 78

[6-(2-Isopropoxy-phenyl)-pyrimidin-4-yl]-(4-methoxy-3-nitro-phenyl)-amine;

Example 79

$N^1$-[6-(2-Isopropoxy-phenyl)-pyrimidin-4-yl]-4-methoxy-benzene-1,3-diamine;

Example 80

[6-(3-Fluoro-2-methoxy-phenyl)-pyrimidin-4-yl]-(4-methoxy-3-nitro-phenyl)-amine;

Example 81

$N^1$-[6-(3-Fluoro-2-methoxy-phenyl)-pyrimidin-4-yl]-4-methoxy-benzene-1,3-diamine;

Example 82

[6-(4,5-Difluoro-2-methoxy-phenyl)-pyrimidin-4-yl]-(4-methoxy-3-nitro-phenyl)-amine;

Example 83

$N^1$-[6-(4,5-Difluoro-2-methoxy-phenyl)-pyrimidin-4-yl]-4-methoxy-benzene-1,3-diamine;

Example 84

N-{5-[6-(4,5-Difluoro-2-methoxy-phenyl)-pyrimidin-4-ylamino]-2-methoxy-phenyl}-formamide;

Example 85

[6-(4-Fluoro-2-isopropoxy-phenyl)-pyrimidin-4-yl]-(4-methoxy-3-nitro-phenyl)-amine;

Example 86

$N^1$-[6-(4-Fluoro-2-isopropoxy-phenyl)-pyrimidin-4-yl]-4-methoxy-benzene-1,3-diamine;

Example 87

(3-Fluoro-4-methoxy-5-nitro-phenyl)-[6-(2-methoxy-phenyl)-pyrimidin-4-yl]-amine;

Example 88

5-Fluoro-4-methoxy-$N^1$-[6-(2-methoxy-phenyl)-pyrimidin-4-yl]-benzene-1,3-diamine;

Example 89

$N^1$-[6-(2-Ethoxy-4-fluoro-phenyl)-pyrimidin-4-yl]-5-fluoro-4-methoxy-benzene-1,3-diamine;

Example 90

5-Fluoro-$N^1$-[6-(4-fluoro-2-methoxy-phenyl)-pyrimidin-4-yl]-4-methoxy-benzene-1,3-diamine;

Example 91

5-Fluoro-$N^1$-[6-(5-fluoro-2-methoxy-phenyl)-pyrimidin-4-yl]-4-methoxy-benzene-1,3-diamine;

Example 92

4-Fluoro-6-methoxy-$N^3$-[6-(2-methoxy-phenyl)-pyrimidin-4-yl]-benzene-1,3-diamine;

Example 93

Acetic acid 2-methoxy-5-[6-(2-methoxy-phenyl)-pyrimidin-4-ylamino]-phenyl ester;

Example 94

Dimethyl-carbamic acid 2-methoxy-5-[6-(2-methoxy-phenyl)-pyrimidin-4-ylamino]-phenyl ester;

Example 95

Carbonic acid 2-methoxy-5-[6-(2-methoxy-phenyl)-pyrimidin-4-ylamino]-phenyl ester methyl ester;

Example 96

[6-(2-Methoxy-phenyl)-pyrimidin-4-yl]-(3-nitro-4-phenoxy-phenyl)-amine;

Example 97

$N^1$-[6-(2-Methoxy-phenyl)-pyrimidin-4-yl]-4-phenoxy-benzene-1,3-diamine;

Example 98

{2-Methoxy-5-[6-(2-methoxy-phenyl)-pyrimidin-4-ylamino]-phenyl}-methyl-carbamic acid methyl ester;

Example 99

4-Methoxy-$N^1$-[6-(2-methoxy-phenyl)-pyrimidin-4-yl]-$N^3$-methyl-benzene-1,3-diamine;

Example 100

(4-Ethoxy-3-nitro-phenyl)-[6-(2-methoxy-phenyl)-pyrimidin-4-yl]-amine;

Example 101

4-Ethoxy-$N^1$-[6-(2-methoxy-phenyl)-pyrimidin-4-yl]-benzene-1,3-diamine;

Example 102

[6-(4-Fluoro-2-methoxy-phenyl)-pyrimidin-4-yl]-(4-fluoro-3-nitro-phenyl)-amine;

Example 103

(4-Ethoxy-3-nitro-phenyl)-[6-(4-fluoro-2-methoxy-phenyl)-pyrimidin-4-yl]-amine;

Example 104

4-Fluoro-$N^1$-[6-(4-fluoro-2-methoxy-phenyl)-pyrimidin-4-yl]-benzene-1,3-diamine;

Example 105

4-Ethoxy-$N^1$-[6-(4-fluoro-2-methoxy-phenyl)-pyrimidin-4-yl]-benzene-1,3-diamine;

Example 106

2-Fluoro-$N^4$-[6-(2-methoxy-phenyl)-pyrimidin-4-yl]-$N^1$,$N^1$-dimethyl-benzene-1,4-diamine;

Example 107

2-Chloro-5-[6-(2-methoxy-phenyl)-pyrimidin-4-ylamino]-phenol;

Example 108

2-Dimethylamino-5-[6-(2-methoxy-phenyl)-pyrimidin-4-ylamino]-phenol;

Example 109

2-Dimethylamino-5-[6-(2-methoxy-phenyl)-pyrimidin-4-ylamino]-benzamide;

Example 110

2-Ethoxy-5-[6-(2-methoxy-phenyl)-pyrimidin-4-ylamino]-phenol;

Example 111

2-Ethoxy-5-[6-(2-methoxy-phenyl)-pyrimidin-4-ylamino]-benzamide;

Example 112

2-Ethoxy-5-[6-(4-fluoro-2-methoxy-phenyl)-pyrimidin-4-ylamino]-benzamide;

Example 113

2-Dimethylamino-5-[6-(4-fluoro-2-methoxy-phenyl)-pyrimidin-4-ylamino]-benzamide;

Example 114

2-Ethoxy-5-[6-(4-fluoro-2-methoxy-phenyl)-pyrimidin-4-ylamino]-phenol;

Example 115

(3-Bromo-4-methoxy-phenyl)-[6-(2-methoxy-phenyl)-pyrimidin-4-yl]-amine;

Example 116

[6-(2-Methoxy-phenyl)-pyrimidin-4-yl]-[4-methoxy-3-(1,2,3,6-tetrahydro-pyridin-4-yl)-phenyl]-amine;

Example 117

N-{5-[6-(4-Fluoro-2-methoxy-phenyl)-pyrimidin-4-ylamino]-2-methoxy-phenyl}-acetamide;

Example 118

{5-[6-(4-Fluoro-2-methoxy-phenyl)-pyrimidin-4-ylamino]-2-methoxy-phenyl}-carbamic acid methyl ester;

Example 119

{5-[6-(4-Fluoro-2-methoxy-phenyl)-pyrimidin-4-ylamino]-2-methoxy-phenyl}-urea;

Example 120

(4-Benzyloxy-3-methoxy-phenyl)-[6-(2-methoxy-phenyl)-pyrimidin-4-yl]-amine;

Example 121

2-Methoxy-4-[6-(2-methoxy-phenyl)-pyrimidin-4-ylamino]-phenol;

Example 122

5-[6-(5-Fluoro-2-methoxy-phenyl)-pyrimidin-4-ylamino]-2-methoxy-phenol;

Example 123

5-[6-(4-Fluoro-2-methoxy-phenyl)-pyrimidin-4-ylamino]-2-methoxy-phenol;

Example 124

5-[6-(2-Ethoxy-phenyl)-pyrimidin-4-ylamino]-2-methoxy-phenol;

Example 125

Carbonic acid 5-[6-(4-fluoro-2-methoxy-phenyl)-pyrimidin-4-ylamino]-2-methoxy-phenyl ester methyl ester;

Example 126

Acetic acid 5-[6-(4-fluoro-2-methoxy-phenyl)-pyrimidin-4-ylamino]-2-methoxy-phenyl ester;

Example 127

5-[6-(5-Fluoro-2-methoxy-phenyl)-pyrimidin-4-ylamino]-2-methoxy-benzamide;

Example 128

5-[6-(4-Fluoro-2-methoxy-phenyl)-pyrimidin-4-ylamino]-2-methoxy-benzamide;

Example 129

5-[6-(2-Ethoxy-phenyl)-pyrimidin-4-ylamino]-2-methoxy-benzamide;

Example 130

5-[6-(2-Ethoxy-4-fluoro-phenyl)-pyrimidin-4-ylamino]-2-methoxy-benzamide;

Example 131

5-[6-(2-Ethoxy-5-fluoro-phenyl)-pyrimidin-4-ylamino]-2-methoxy-benzamide;

Example 132

2-Chloro-4-[6-(2-methoxy-phenyl)-pyrimidin-4-ylamino]-benzamide;

Example 133

2-Methoxy-4-[6-(2-methoxy-phenyl)-pyrimidin-4-ylamino]-benzoic acid methyl ester;

Example 134

2-Methoxy-4-[6-(2-methoxy-phenyl)-pyrimidin-4-ylamino]-N-methylbenzamide;

Example 135

N-(2-Hydroxy-ethyl)-2-methoxy-4-[6-(2-methoxy-phenyl)-pyrimidin-4-ylamino]-benzamide;

Example 136

2-Methoxy-4-[6-(2-methoxy-phenyl)-pyrimidin-4-ylamino]-benzamide;

Example 137

3-Fluoro-2-methoxy-5-[6-(2-methoxy-phenyl)-pyrimidin-4-ylamino]-benzamide;

Example 138

3-Fluoro-5-[6-(4-fluoro-2-methoxy-phenyl)-pyrimidin-4-ylamino]-2-methoxy-benzamide;

Example 139

5-[6-(2-Ethoxy-4-fluoro-phenyl)-pyrimidin-4-ylamino]-3-fluoro-2-methoxy-benzamide;

Example 140

3-Fluoro-5-[6-(5-fluoro-2-methoxy-phenyl)-pyrimidin-4-ylamino]-2-methoxy-benzamide;

Example 141

5-[6-(2-Ethoxy-phenyl)-pyrimidin-4-ylamino]-3-fluoro-2-methoxy-benzamide;

Example 142

5-[6-(2-Ethoxy-5-fluoro-phenyl)-pyrimidin-4-ylamino]-3-fluoro-2-methoxy-benzamide;

Example 143

4-Fluoro-2-methoxy-5-[6-(2-methoxy-phenyl)-pyrimidin-4-ylamino]-benzamide;

Example 144

4-Fluoro-5-[6-(5-fluoro-2-methoxy-phenyl)-pyrimidin-4-ylamino]-2-methoxy-benzamide;

Example 145

5-[6-(2-Ethoxy-phenyl)-pyrimidin-4-ylamino]-4-fluoro-2-methoxy-benzamide;

Example 146

4-Fluoro-5-[6-(4-fluoro-2-methoxy-phenyl)-pyrimidin-4-ylamino]-2-methoxy-benzamide;

Example 147

5-[6-(2-Ethoxy-4-fluoro-phenyl)-pyrimidin-4-ylamino]-4-fluoro-2-methoxy-benzamide;

Example 148

5-[6-(2-Ethoxy-5-fluoro-phenyl)-pyrimidin-4-ylamino]-4-fluoro-2-methoxy-benzamide;

A compound or salt thereof as described above may be combined with at least a pharmaceutical carrier or diluent to form a pharmaceutical composition of the present invention.

A compound, salt thereof or pharmaceutical composition of the present invention may be used in one or more methods. In one method, viral infection may be reduced by the step comprising administration of a compound, salt thereof or pharmaceutical composition of the present invention in an amount effective to reduce viral load.

In another method, inflammation and/or immune hyperactivation related to viral infection can be treated administering to a patient in need a compound, salt thereof or pharmaceutical composition of the present invention in an amount effective to reduce inflammation and/or hyperactivation of the immune system.

In a further method, inflammation and/or immune hyperactivation related to viral infection can be treated administering to a patient in need a compound, salt thereof or pharmaceutical composition of the present invention in an amount effective to reduce both viral load and inflammation and/or hyperactivation of the immune system.

These and other aspects of the present invention will become evident upon reference to the following detailed description.

DETAILED DESCRIPTION OF THE INVENTION

Prior to setting forth the invention, it may be helpful to an understanding thereof to set forth definitions of certain terms to be used hereinafter.

In the present description, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The alkyl group may be substituted or unsubstituted. When substituted, the substituted group(s) is preferably one or more independently selected from alkyl, cycloalkyl, heteroalicyclic, aryl, heteroaryl, haloalkyl, halo, hydroxy, alkoxy, mercapto, cyano, sulfonamidyl, aminosulfonyl, acyl, acyloxy, substituted imino and substituted amino.

The term "cycloalkyl" refers to any monocyclic or bicyclic ring of an alkane with a number of carbon atoms in the specified range. For example, "$C_{3-8}$ cycloalkyl" (or "$C_3$-$C_8$ cycloalkyl") is therefore referred to cyclopropyl, cyclobutyl, cyclopentyl, cyclohexyl, cycloheptyl, and cyclooctyl.

"Azacycloalkyl" is referred to a cycloalkyl group as defined above, in which one replacement of the ring carbons with a nitrogen occurs.

The term "heterocycloalkyl" refers to a cycloalkyl group as defined above in which one of the ring carbons has been replaced with a heteroatom chosen among N, O, S.

"Alkenyl" includes monovalent hydrocarbon radicals having straight, cyclic, or branched moieties, and combinations thereof, which comprise at least one carbon-carbon double bond. The alkenyl group may be substituted or unsubstituted.

When substituted, the substituted group(s) is preferably one or more independently selected from alkyl, acyl, cycloalkyl, heteroalicyclic, aryl, haloalkyl, alkoxy and substituted amino.

"Alkoxy" refers to the group "—O-alkyl" which includes, by way of example, methoxy, ethoxy, n-propoxy, i-propoxy, n-butoxy, t-butoxy and the like. It further refers to the group "—O-alkyl-W-alkyl" where W is O or N; for example, —O—$(CH_2)_n$—W—$(CH_2)_m$ where n and m are independently 1-10. The alkoxy group may be unsubstituted or substituted, for example with an alkyl, cycloalkyl, alkenyl, acyl, aryl or heterocycle group(s).

"Substituted amino" denotes the group —NRR, wherein each R group is independently selected from hydrogen, hydroxy, acyl, alkyl, cycloalkyl, aryl, or the R groups can be joined together with the nitrogen to form a heterocyclic ring (e.g., piperidine, piperazine, or a morpholine ring).

"Substituted imino" denotes the group =NR, wherein R is preferably selected from hydrogen, hydroxy, alkyl and acyl.

"Aryl" refers to an unsaturated aromatic carbocyclic group of 6 to 14 carbon atoms having a single ring (e.g., phenyl) or multiple condensed rings (e.g., naphthyl or anthryl). The aryl group may be unsubstituted or substituted; in the latter case, the substituent or substituents preferably are selected independently from alkyl, aryl, haloalkyl, halo, hydroxy, alkoxy, mercapto, cyano, sulfonamidyl, aminosulfonyl, acyl, acyloxy, nitro, and substituted amino.

"Heterocycle" includes "heteroaryl" and "heteroalicyclic".

Examples of heterocycles include oxazole, piperidine, piperazine and morpholine.

The term "heteroaryl" is referred to (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system which contains from 1 to 4 heteroatoms independently selected from N, O and S, and wherein in the fused ring system any one or more of the rings contain one or more of the heteroatoms, at least one ring is aromatic, each N in a ring is optionally in the form of an oxide, and each S is optionally S(O) or S(O)$_2$. Suitable heteroaryls include, for example, pyridinyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, quinolinyl, tetrahydroquinolinyl, isoquinolinyl, tetrahydroisoquinolinyl, indolyl, isoindolyl, benzodioxolyl, benzopiperidinyl, benzisoxazolyl, benzoxazolyl, chromenyl, chromanyl, isochromanyl, cinnolinyl, quinazolinyl, benzothienyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, 2,3-dihydrobenzo-1,4-dioxinyl (i.e. 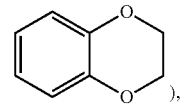 ), benzo-1,3-dioxolyl (i.e. 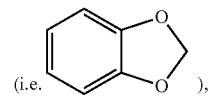 ), thiazolyl, and isothiazolyl.

"Cycloalkyl" encompasses cyclic alkyl groups that contain between 3 and 8 carbon atoms and have a single cyclic ring, illustrated by cyclopropyl, cyclobutyl, cyclopentyl, and cyclooctyl. The cycloalkyl ring may be substituted or unsubstituted.

Again, a substituted cycloalkyl ring carries one or more substituent groups, independently selected preferably from alkyl, aryl, haloalkyl, halo, hydroxy, alkoxy, mercapto, cyano, sulfonamidyl, aminosulfonyl, acyl, acyloxy, vitro, and substituted amino.

"Heteroalicyclic" refers to monocyclic or fused ring groups having in the ring(s) one or more atoms, preferably selected from nitrogen, oxygen and sulfur. The rings may also have one or more double bonds. However, the rings do not possess a completely conjugated π-electron system. The heteroalicyclic ring may be either substituted or unsubstituted.

When substituted, the substituted group(s) preferably are selected independently from alkyl, aryl, haloalkyl, halo, hydroxy, alkoxy, mercapto, cyano, sulfonamidyl, aminosulfonyl, acyl, acyloxy, nitro, and substituted or unsubstituted amino.

The term "saturated or mono-unsaturated heterocyclic ring" refers to (i) a 4- to 7-membered, saturated or mono-unsaturated heterocyclic ring containing at least one carbon atom and from 1 to 4 heteroatoms independently selected from N, O and S, where each S is optionally oxidized to S(O) or S(O)$_2$ or (ii) a 6- to 10-membered saturated or mono-unsaturated, bridged or fused heterobicyclic ring containing from 1 to 4 heteroatoms independently selected from N, O and S, where each S is optionally oxidized to S(O) or S(O)$_2$. Suitable saturated heterocycles include, for example, azetidinyl, pyrrolidinyl, imidazolinyl, tetrahydrofuranyl, pyrazolidinyl, piperidinyl, piperazinyl, hexahydropyrimidinyl, morpholinyl, thiomorpholinyl, thiazolidinyl, isothiazolidinyl, oxazolidinyl, isoxazolidinyl, thiazinanyl azepanyl and diazepanyl. A class of suitable saturated or mono-unsaturated heterocyclic rings is represented by 4- to 7-membered rings containing at least one carbon atom and from 1 to 4 heteroatoms independently selected from N, O and S, where each S is optionally oxidized to S(O) or S(O)$_2$. Another suitable class consists of 5- or 6-membered saturated heterocyclic rings containing a total of from 1 to 2 heteroatoms selected from 1 to 2 N atoms, zero to 1 O atom, and zero to 1 S atom, wherein the S atom is optionally S(O) or SO$_2$. Suitable mono-unsaturated heterocyclic rings include those corresponding to the saturated heterocyclic rings listed in the preceding sentence in which replacement of a single bond with a double bond occurs (e.g., a carbon-carbon single bond is replaced with a carbon-carbon double bond). It is understood that the specific rings and ring systems suitable for use in the present invention are not limited to those listed in the preceding paragraphs. These rings and ring systems are merely representative.

Unless it is expressly stated to the contrary or is otherwise clear from the context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive.

For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, a phenyl or naphthyl described as optionally substituted with "from 1 to 5 substituents" is intended to include as aspects thereof, a phenyl or naphthyl substituted with 1 to 5 substituents, 2 to 5 substituents, 3 to 5 substituents, 4 to 5 substituents, 5 substituents, 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

When any variable occurs more than one time in any constituent or in any formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring provided such ring substitution is chemically allowed and the result is a stable compound.

As would be recognized by one of ordinary skill in the art, certain of the compounds of the present invention can exist as tautomers. All tautomeric forms of these compounds, whether isolated individually or in mixtures, are within the scope of the present invention. For example, in instances where a hydroxy (—OH) substituent is permitted on a heteroaromatic ring and keto-enol tautomerism is possible, it is understood that the substituent might in fact be present, in whole or in part, in the keto form, as exemplified here for a hydroxypyridinyl substituent:

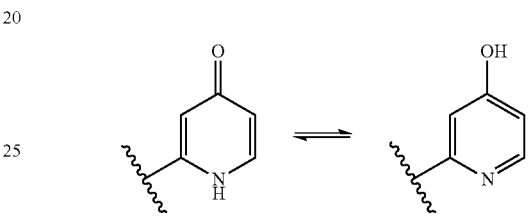

Compounds of the present invention having a hydroxy substituent on a carbon atom of a heteroaromatic ring are understood to include compounds in which only the hydroxy is present, compounds in which only the tautomeric keto form (i.e., an oxo substituent) is present, and compounds in which the keto and enol forms are both present.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "C$_{1-6}$ haloalkyl" (or "C$_1$-C$_6$ haloalkyl") refers to a C$_1$ to C$_6$ linear or branched alkyl group as defined above with one or more halogen substituents. The term "fluoroalkyl" has an analogous meaning except that the halogen substituents are restricted to fluoro. Suitable fluoroalkyl groups include the series (CH$_2$)$_{0-4}$CF$_3$ (i.e., trifluoromethyl, 2,2,2-trifluoroethyl, 3,3,3-trifluoro-n-propyl, etc.). A fluoroalkyl of particular interest is CF$_3$.

The term "C(O)" refers to carbonyl. The terms "S(O)$_2$" and "SO$_2$" each refer to sulfonyl. The term "S(O)" refers to sulfinyl.

"Acyl" group refers to the C(O)—R" group, where R" is selected preferably from hydrogen, hydroxy, alkyl, haloalkyl, cycloalkyl, substituted amino, aryl optionally substituted with one or more alkyl, haloalkyl, alkoxy, halo and substituted amino groups, heteroaryl (bonded through a ring carbon) optionally substituted with one or more alkyl, haloalkyl, alkoxy, halo and substituted amino groups and heteroalicyclic (bonded through a ring carbon) optionally substituted with one or more alkyl, haloalkyl, alkoxy, halo and substituted amino groups. Acyl groups include aldehydes, ketones, acids, acid halides, esters and amides. Preferred acyl groups are carboxy groups, e.g., acids and esters.

Esters include amino acid ester derivatives. The acyl group may be attached to a compound's backbone at either end of the acyl group, i.e., via the C or the R". Where the acyl group is attached via the R", then C will bear another substituent, such as hydrogen or alkyl.

The term "sulfonyl" means a —SO$_2$—R group in which R is hydrogen, alkyl, a carbocycle, a heterocycle, carbocycle-substituted alkyl or heterocycle-substituted alkyl wherein the alkyl, alkoxy, carbocycle and heterocycle are as defined herein. Particular sulfonyl groups are alkylsulfonyl (i.e., —SO$_2$-alkyl), for example methylsulfonyl; arylsulfonyl, for example phenylsulfonyl; aralkylsulfonyl, for example benzylsulfonyl.

The term "sulfamoyl" means a —SO$_2$—NRR' group in which R and R' are independently hydrogen, alkyl, a carbocycle, a heterocycle, carbocycle-substituted alkyl or heterocycle-substituted alkyl wherein the alkyl, alkoxy, carbocycle and heterocycle are as defined herein. Particular sulfamoyl groups are alkylsulfamoyl (i.e., —SO$_2$—NH-alkyl and —SO$_2$—N— alkyl$_2$), for example methylsulfamoyl; arylsulfamoyl, for example phenylsulfamoyl; aralkylsulfamoyl, for example benzylsulfamoyl.

From all of the above, it is clear to the skilled person that any group whose name is a composite name such as, for instance, cycloalkylalkyl, arylalkyl, heterocyclylalkyl, alkoxy, alkylthio, aryloxy, arylalkyloxy, alkylcarbonyloxy, arylalkyl, heterocyclylalkyl and the like, have to be intended as conventionally construed by the parts from which they derive. As an example, a group such as heterocyclylalkyloxy is an alkoxy group, e.g. alkyloxy, wherein the alkyl moiety is further substituted by a heterocyclyl group, and wherein alkyl and heterocyclyl are as above defined.

The term "salt" means any ionic compound formed between one of the embodiments of the present invention and an acidic or basic molecule that can donate or accept ionic particle to/from its partner. Quaternary amine salts are also included.

Pharmaceutically acceptable (i.e., non-toxic, physiologically acceptable) salts are preferred, although other salts are also useful. Salts of the compounds of the formula (I) may be formed, for example, by reacting a compound of formula (I) with an amount of acid or base, such as an equivalent amount, in a medium such as one in which the salt precipitates or in an aqueous medium followed by lyophilisation.

The term "physiologically acceptable salt" refers to those salts that retain the biological effectiveness and properties of the particular compound. Physiologically acceptable salts are often useful because they may have improved stability and/or solubility in pharmaceutical compositions over the free base form or free acid form of the compound. A physiologically acceptable salt may be obtained by reaction of a free base with an inorganic acid such as hydrochloric acid, hydrobromic acid, nitric acid, phosphoric acid, sulfuric acid, and perchloric acid and the like, or with an organic acid such as acetic acid, oxalic acid, malic acid, maleic acid, methanesulfonic acid, ethanesulfonic acid, p-toluenesulfonic acid, salicylic acid, tartaric acid, citric acid, succinic acid or malonic acid, and the like. A physiologically acceptable salt may also be obtained by reaction of a free acid with a base such as sodium, potassium or lithium hydroxide, bicarbonate or carbonate, and the like.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates, tartarates, thiocyanates, toluenesulfonates (or tosylates) undecanoates, and the like. Additionally, acids which are generally considered suitable for the formation of pharmaceutically useful salts from basic pharmaceutical compounds are known.

Physiologically acceptable salts of the compounds of formula (I) also include the salts with inorganic or organic bases, e.g., alkali or alkaline-earth metals, in particular sodium, potassium, lithium, calcium, magnesium, ammonium, iron, copper, zinc, manganese, aluminum salts and the like. Particularly base addition salts are the ammonium, potassium, sodium, calcium and magnesium salts. Salts derived from pharmaceutically acceptable organic non-toxic bases includes salts of primary, secondary, and tertiary amines, substituted amines (including naturally occurring substituted amines), cyclic amines and basic ion exchange resins, such as isopropylamine, diethylamine, trimethylamine, tripropylamine, triethylamine, ethanolamine, 2-diethylaminoethanol, trimethamine, dicyclohexylamine, lysine, arginine, histidine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, trimethamine, dicyclohexylamine, choline, and caffeine.

The term "solvate" means a compound formed by the combination of solvent molecules with molecules or ions of the solute (solvation). Solute can be any of the embodiments of the present invention and the solvent can be water or any organic solvent.

As noted above, the present invention provides 4,6 disubstituted aminopyrimidines, physiologically acceptable salts thereof and uses thereof. The compounds are generally of the formula:

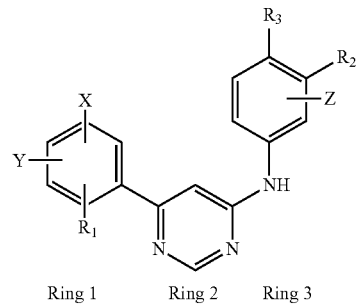

where X, Y and Z are hydrogen or halogen substituents in different positions on Ring 1 and Ring 3 of the compounds and R$_2$ is hydrogen, halogen, substituted or unsubstituted amino, hydroxyl, OR, where R is alkyl, aryl, C$_{3-8}$ cycloalkyl, azacycloalkyl, heterocycloalkyl, OCOR' (R' is alkyl or aryl) sulfonylamino, N-sulfonylamino, N-sulfamoylamino, sulfamoylamino, alkyl or aryl sulfonylamino, N-alkyl or N-arylsulfonylamino, CH$_2$R, where R is OH, OR' (R' is alkyl or aryl), substituted or unsubstituted amino, heteroaryl, CHO, COOR" (where R' is alkyl or aryl), CONR$^a$R$^b$, where R$^a$ and R$^b$ are independently alkyl or aryl, NHC(O)NR$^c$R$^d$, where R$^c$ and R$^d$ are independently hydrogen, alkyl or aryl, and R$_3$ is halogen, substituted or unsubstituted amino, N-morpholino, N—(N'-methyl)piperazine, hydroxyl, OR, where R is alkyl or aryl, OCOR' (R' is alkyl or aryl) sulfonylamino, N-sulfonylamino, N-sulfamoylamino, sulfamoylamino, alkyl or aryl sulfonylamino, N-alkyl or N-arylsulfonylamino.

Preferred embodiments include the following selections for the general formula above.
Preferred embodiments include the following structure:

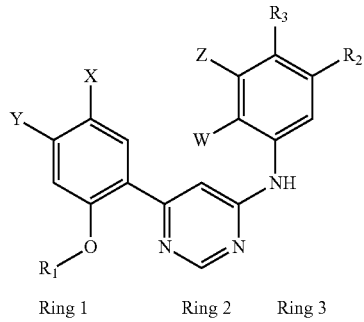

Ring 1    Ring 2    Ring 3 where W, X, Y and Z are independently H or F; $R_1$ is $CH_3$ or $CH_2CH_3$, i-Pr, n-Bu, i-Bu and t-Bu, $CH_2$-Ph; $R_2$ is NH2, NHCH3, NHCOCH2-piperidine, NHCOOCH$_2$CCl$_3$, NHSO$_2$CH$_3$, NH(SO$_2$)NHCH$_3$, NH(SO$_2$)N(CH$_3$)$_2$, NSO$_2$NHCH$_2$CH$_2$CH$_3$, NSO$_2$NH-cyclohexyl, NO$_2$, OH, O-benzyl, OCH$_2$CH$_2$-morpholino, CONH$_2$; $R_3$ is Cl, F, OH, OCH$_3$, OCH$_2$CH$_3$, NHCH$_3$, NHCH$_2$CH$_3$, CH$_3$, CH$_2$CH$_3$, morpholino and N-methylpiperazino, OCOC(CH$_3$)$_3$, CH$_2$OH, CH$_2$NH$_2$, CH$_2$NHCH$_3$, CH$_2$N(CH$_3$)$_2$, CH$_2$NH-phenyl, CH$_2$NH-benzyl, CH$_2$-benzimidazole, CH$_2$-phthalimide, CHO, COOCH$_3$, COOCH$_2$CH$_3$, CON-cyclopentyl, CONHCH$_2$-pyrimidine, CONHNH$_2$, SO$_2$NH$_2$, SO$_2$NHCH$_3$.

Particularly preferred compounds of the present invention are shown in the following list, and physiologically acceptable salts thereof.

Example 5

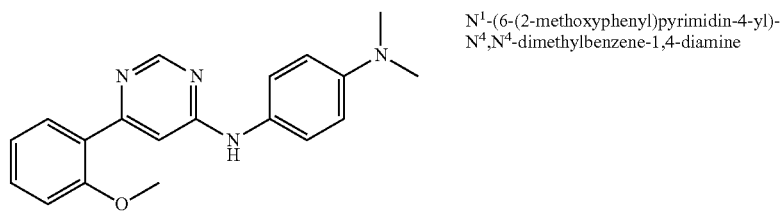

$N^1$-(6-(2-methoxyphenyl)pyrimidin-4-yl)-$N^4,N^4$-dimethylbenzene-1,4-diamine

Example 10

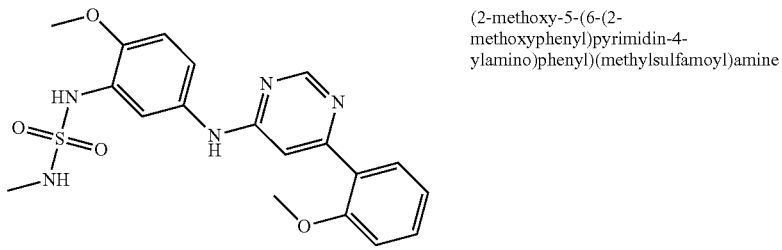

(2-methoxy-5-(6-(2-methoxyphenyl)pyrimidin-4-ylamino)phenyl)(methylsulfamoyl)amine Example 13

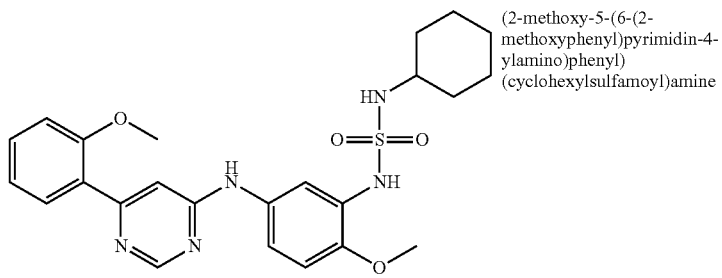

(2-methoxy-5-(6-(2-methoxyphenyl)pyrimidin-4-ylamino)phenyl)(cyclohexylsulfamoyl)amine Example 16

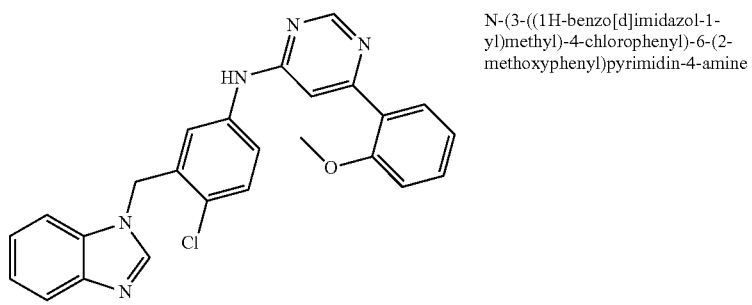

N-(3-((1H-benzo[d]imidazol-1-yl)methyl)-4-chlorophenyl)-6-(2-methoxyphenyl)pyrimidin-4-amine -continued

| | | |
|---|---|---|
| Example 26 | 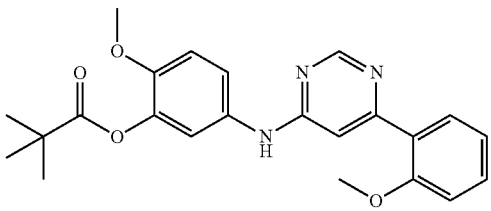 [SMILES: COc1ccc(Nc2cc(-c3ccccc3OC)ncn2)cc1OC(=O)C(C)(C)C] | 2-methoxy-5-(6-(2-methoxyphenyl)pyrimidin-4-ylamino)phenyl pivalate |
| Example 31 | 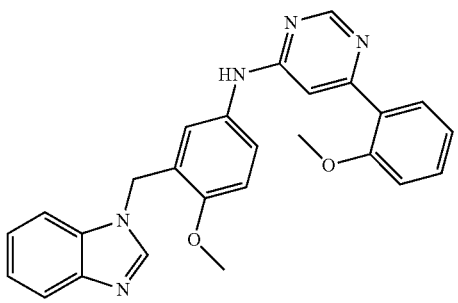 [SMILES: COc1ccc(Nc2cc(-c3ccccc3OC)ncn2)cc1Cn1cnc2ccccc21] | N-(3-((1H-benzo[d]imidazol-1-yl)methyl)-4-methoxyphenyl)-6-(2-methoxyphenyl)pyrimidin-4-amine |
| Example 32 | 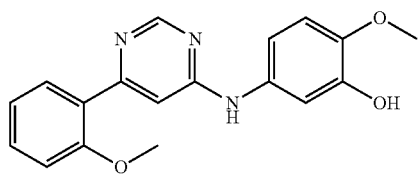 [SMILES: COc1ccc(Nc2cc(-c3ccccc3OC)ncn2)cc1O] | 2-methoxy-5-(6-(2-methoxyphenyl)pyrimidin-4-ylamino)phenol |
| Example 41 | 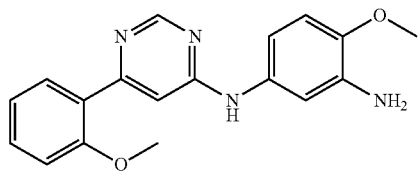 [SMILES: COc1ccc(Nc2cc(-c3ccccc3OC)ncn2)cc1N] | 4-methoxy-$N^1$-(6-(2-methoxyphenyl)pyrimidin-4-yl)benzene-1,3-diamine |
| Example 43 | 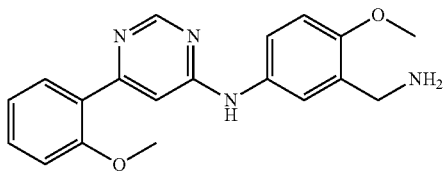 [SMILES: COc1ccc(Nc2cc(-c3ccccc3OC)ncn2)cc1CN] | N-(3-(aminomethyl)-4-methoxyphenyl)-6-(2-methoxyphenyl)pyrimidin-4-amine |
| Example 45 | 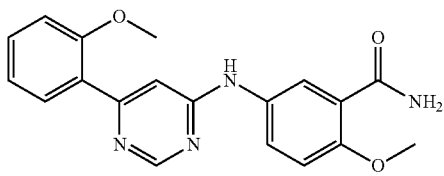 [SMILES: COc1ccc(Nc2cc(-c3ccccc3OC)ncn2)cc1C(N)=O] | 2-methoxy-5-(6-(2-methoxyphenyl)pyrimidin-4-ylamino)benzamide |
| Example 62 | 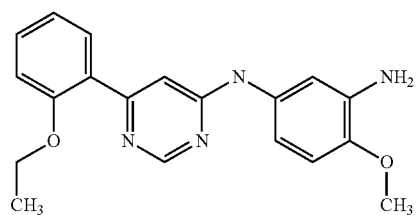 [SMILES: CCOc1ccccc1-c1cc(Nc2ccc(OC)c(N)c2)ncn1] | $N^1$-[6-(2-Ethoxy-phenyl)-pyrimidin-4-yl]-4-methoxy-benzene-1,3-diamine |

-continued

| Example 64 | 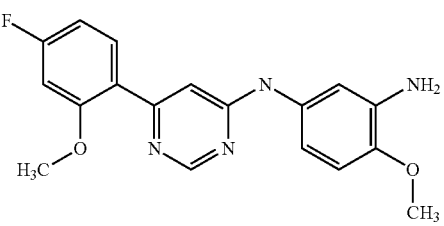 [SMILES: COc1ccc(Nc2cc(-c3ccc(F)cc3OC)ncn2)cc1N] | N¹-[6-(4-Fluoro-2-methoxy-phenyl)-pyrimidin-4-yl]-4-methoxy-benzene-1,3-diamine |
| Example 73 | 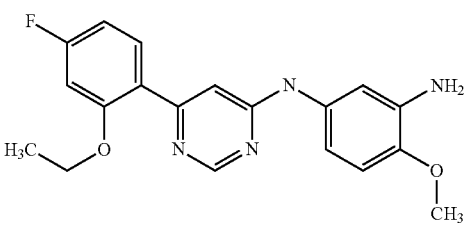 [SMILES: CCOc1cc(F)ccc1-c1cc(Nc2ccc(OC)c(N)c2)ncn1] | N¹-[6-(2-Ethoxy-4-fluoro-phenyl)-pyrimidin-4-yl]-4-methoxy-benzene-1,3-diamine |
| Example 75 | 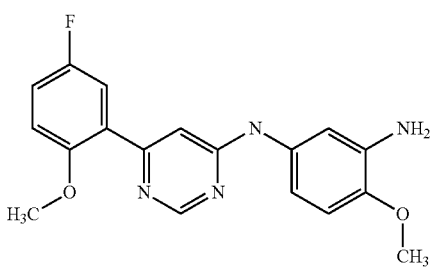 [SMILES: COc1ccc(Nc2cc(-c3cc(F)ccc3OC)ncn2)cc1N] | N¹-[6-(5-Fluoro-2-methoxy-phenyl)-pyrimidin-4-yl]-4-methoxy-benzene-1,3-diamine |
| Example 79 | 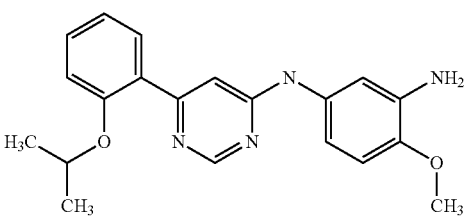 [SMILES: COc1ccc(Nc2cc(-c3ccccc3OC(C)C)ncn2)cc1N] | N¹-[6-(2-Isopropoxy-phenyl)-pyrimidin-4-yl]-4-methoxy-benzene-1,3-diamine |
| Example 83 | 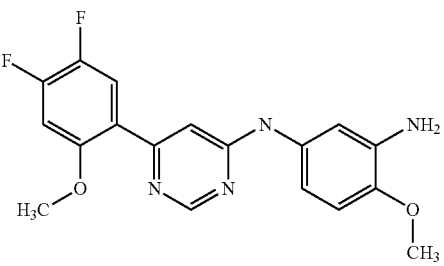 [SMILES: COc1ccc(Nc2cc(-c3cc(F)c(F)cc3OC)ncn2)cc1N] | N¹-[6-(4,5-Difluoro-2-methoxy-phenyl)-pyrimidin-4-yl]-4-methoxy-benzene-1,3-diamine |
| Example 111 | 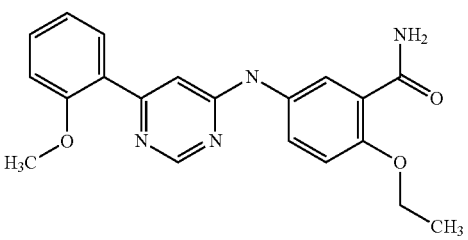 [SMILES: CCOc1ccc(Nc2cc(-c3ccccc3OC)ncn2)cc1C(N)=O] | 2-Ethoxy-5-[6-(2-methoxy-phenyl)-pyrimidin-4-ylamino]-benzamide |

-continued

Example 112 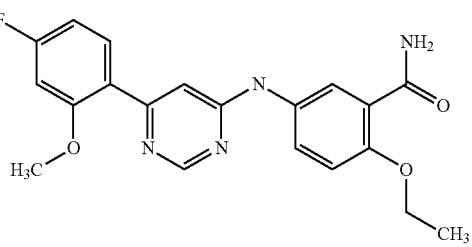 2-Ethoxy-5-[6-(4-fluoro-2-methoxy-phenyl)-pyrimidin-4-ylamino]-benzamide Example 123 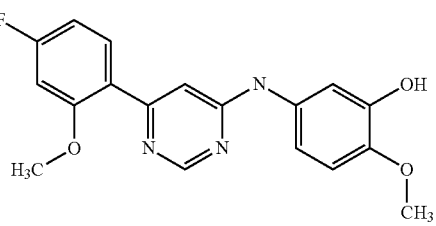 5-[6-(4-Fluoro-2-methoxy-phenyl)-pyrimidin-4-ylamino]-2-methoxy-phenol Example 127 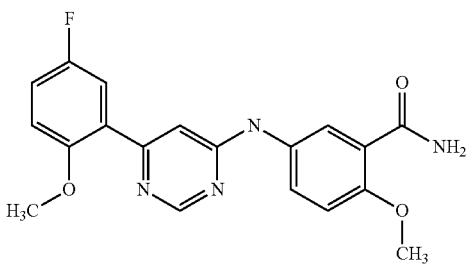 [SMILES: COc1ccc(Nc2cc(-c3cc(F)ccc3OC)ncn2)cc1C(N)=O] 5-[6-(5-Fluoro-2-methoxy-phenyl)-pyrimidin-4-ylamino]-2-methoxy-benzamide Example 128 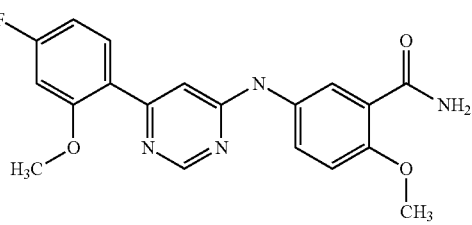 5-[6-(4-Fluoro-2-methoxy-phenyl)-pyrimidin-4-ylamino]-2-methoxy-benzamide Example 129 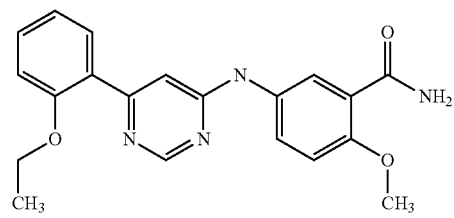 [SMILES: CCOc1ccccc1-c1cc(Nc2ccc(OC)c(C(N)=O)c2)ncn1] 5-[6-(2-Ethoxy-phenyl)-pyrimidin-4-ylamino]-2-methoxy-benzamide Example 130 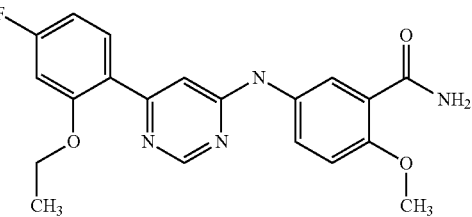 5-[6-(2-Ethoxy-4-fluoro-phenyl)-pyrimidin-4-ylamino]-2-methoxy-benzamide -continued

| Example 131 | 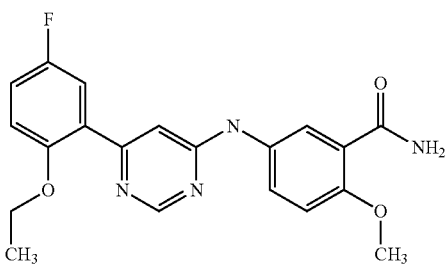 [SMILES: CCOc1ccc(F)cc1-c1cc(Nc2ccc(OC)c(C(N)=O)c2)ncn1] | 5-[6-(2-Ethoxy-5-fluoro-phenyl)-pyrimidin-4-ylamino]-2-methoxy-benzamide |
| Example 141 | 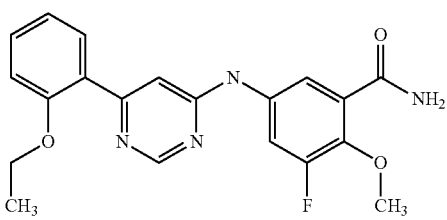 [SMILES: CCOc1ccccc1-c1cc(Nc2cc(F)c(OC)c(C(N)=O)c2)ncn1] | 5-[6-(2-Ethoxy-phenyl)-pyrimidin-4-ylamino]-3-fluoro-2-methoxy-benzamide |
| Example 142 | 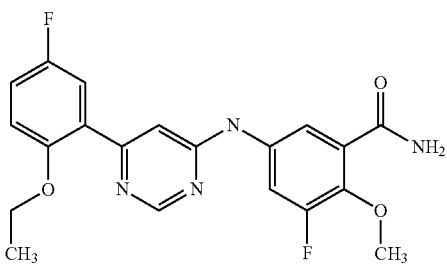 [SMILES: CCOc1ccc(F)cc1-c1cc(Nc2cc(F)c(OC)c(C(N)=O)c2)ncn1] | 5-[6-(2-Ethoxy-5-fluoro-phenyl)-pyrimidin-4-ylamino]-3-fluoro-2-methoxy-benzamide |
| Example 143 | 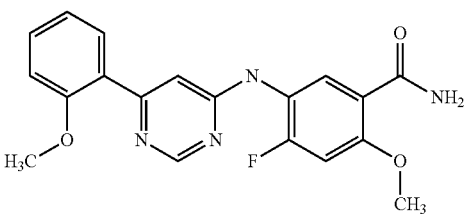 [SMILES: COc1cc(F)c(Nc2cc(-c3ccccc3OC)ncn2)cc1C(N)=O] | 4-Fluoro-2-methoxy-5-[6-(2-methoxy-phenyl)-pyrimidin-4-ylamino]-benzamide |
| Example 144 | 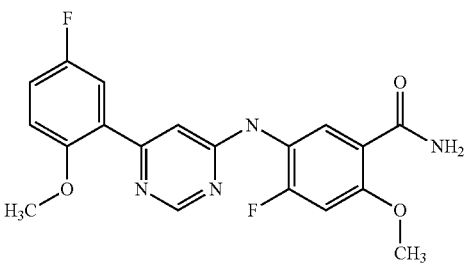 [SMILES: COc1cc(F)c(Nc2cc(-c3cc(F)ccc3OC)ncn2)cc1C(N)=O] | 4-Fluoro-5-[6-(5-fluoro-2-methoxy-phenyl)-pyrimidin-4-ylamino]-2-methoxy-benzamide |
| Example 145 | 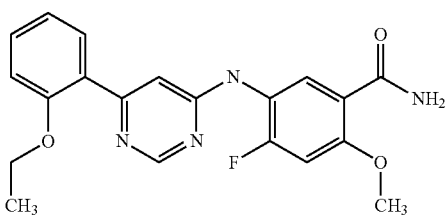 [SMILES: CCOc1ccccc1-c1cc(Nc2cc(C(N)=O)c(OC)cc2F)ncn1] | 5-[6-(2-Ethoxy-phenyl)-pyrimidin-4-ylamino]-4-fluoro-2-methoxy-benzamide |

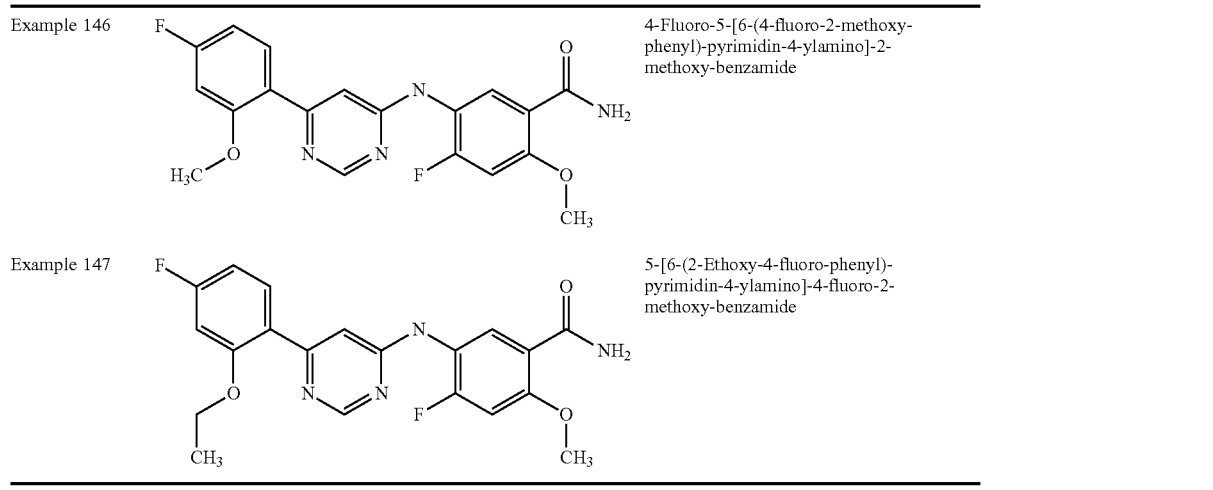

| Example 146 | | 4-Fluoro-5-[6-(4-fluoro-2-methoxy-phenyl)-pyrimidin-4-ylamino]-2-methoxy-benzamide |
| Example 147 | | 5-[6-(2-Ethoxy-4-fluoro-phenyl)-pyrimidin-4-ylamino]-4-fluoro-2-methoxy-benzamide |

It may be advantageous for certain uses to enhance the solubility and/or bioavailability of one or more of the compounds of the present invention.

Unless otherwise specified, when referring to the compounds of formula (I) per se as well as to any pharmaceutical composition thereof or to any therapeutic treatment comprising them, the present invention includes all of the isomers, tautomers, hydrates, solvates, complexes, metabolites, pro-drugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compounds of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

It may be advantageous for certain uses to prepare a compound (or physiologically acceptable salt thereof) as a "prodrug." As used herein, the term "compound" encompasses a prodrug form of the parent compound. "Prodrug" herein refers to a chemical substance, preferably but not only covalently bonded, that is converted into the parent compound (I) in vivo. Prodrugs often are useful because, in some situations, they may be easier to administer than the parent compound. They may, for instance, be bioavailable by oral administration whereas the parent compound is not. The prodrug may also have improved solubility in pharmaceutical compositions over the parent compound. An example of a prodrug would be a parent compound of the present invention which is administered as an ester (the "prodrug") to facilitate transmittal across a cell membrane where water solubility is detrimental to mobility. The ester is then metabolically hydrolyzed to the carboxylic acid, the active entity, once inside the cell where water solubility is beneficial. Such a prodrug is generally inactive (or less active) until converted to the active form.

N-oxides are compounds of formula (I) wherein nitrogen and oxygen are tethered through a dative bond.

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

Pharmaceutical compositions of the compounds and the physiologically acceptable salts thereof are preferred embodiments of this invention. Pharmaceutical compositions of the compounds of the present invention (i.e., compounds and salts thereof as described above) may be manufactured by processes well known in the art; e.g., by means of conventional mixing, dissolving, granulating, dragee-making, levigating, emulsifying, encapsulating, entrapping or lyophilizing processes.

Pharmaceutical compositions may be formulated in a conventional manner using one or more physiologically acceptable carriers or diluents. Proper formulation is generally dependent upon the route of administration chosen.

Methods and Results

In Vitro CDK9/CyclinT Assay

The activity of the compounds described in the present invention can be determined by measuring the phosphorylation of a fluorescently-labeled peptide by human CDK9/CyclinT kinase complex by fluorescent polarization using a commercially available IMAP Screening Express Assay Kit (Molecular devices).

Test compounds were diluted in 100% DMSO to 5 mM stock concentration, then further dilutions were made in $H_2O$ or 100% DMSO to desirable concentrations.

Each reaction consisted of 5 nM enzyme: CDK9/CyclinT (Proqinase cat#0371-0345-1), 400 nM TAMRA-Rbtide (synthetic 15-mer peptide derived from human retinoblastoma tumor suppressor protein labeled with TAMRA dye, Genecust Europe), 12 μM ATP (=$Km_{app}$, Sigma-Aldrich)

and kinase buffer: 20 mM MOPS pH 7 (Sigma-Aldrich), 1 mM DTT (Sigma-Aldrich), 10 mM $MgCl_2$ (Sigma-Aldrich), 0.01% Tween 20 (Sigma-Aldrich).

For each reaction, 4 or 6 μl containing TAMRA-Rbtide, ATP and kinase buffer were combined with 2 μl diluted compound in $H_2O$ or 0.028 μl compound in 100% DMSO. The kinase reaction was started by the addition of 2 μl diluted enzyme. The reaction was allowed to run for 1 hour at room temperature. The reaction was stopped by adding 15 μl IMAP beads (1:400 beads in progressive (100% buffer A) 1× buffer). After an additional 1 hour, fluorescence polarization (Ex: 550-10 nm, Em: 590-10 nm, Dich: 561 nm) was measured using an Analyst GT (Molecular devices).

Biological Assays

The biological activity of the compounds described in the present invention was evaluated in the following assays:

Antiviral Activity Against HIV (AV)

Activated primary T cells are infected with a laboratory strain of HIV-1, then cultured and exposed to different concentrations of the test compounds. HIV replication is analysed by measuring the viral protein p24 and expressed as percentage of untreated control. Inhibition of viral replication (AV) is then calculated (AV=100 minus the % p24 compared to control, AV of control=0%). Inhibitory concentration 50% for antiviral activity ($AV_{50}$) is calculated.

Antiproliferative Activity (AP)

Primary T cells are cultured and exposed to different concentrations of the test compounds. Cell proliferation is analysed by measuring mitotic index (ie the number of cell divisions a population of cells undergoes) through flow cytometry based techniques. Mitotic index is expressed as percentage of untreated control. Inhibition of cell proliferation (AP) is then calculated (AP=100 minus % mitotic index compared to control, AP of control=0%). Inhibitory concentration 50% for antiproliferative capacity ($AP_{50}$) is calculated.

Cytotoxicity

Primary T cells are cultured and treated with different concentrations of the test compound. Viability is analysed by measuring through flow cytometry based techniques the percentage of viable cells, compared to untreated control=100%). Toxic dose 50% ($TD_{50}$) is calculated.

In all the biological assays, commercially available CDK9 inhibitors were also included in the analysis: Flavopiridol (Alvocidib, Sanofi-Aventis) and Roscovitine (Seliciclib, Cyclacel). In Tables 2, 3 and 4, ND means Not Determined.

TABLE 1

CDK9 $IC_{50}$ values of the compounds.

| Example number | CDK9 $IC_{50}$ |
|---|---|
| 1 | B |
| 2 | A |
| 3 | B |
| 4 | A |
| 5 | B |
| 6 | B |
| 7 | A |
| 8 | B |
| 9 | A |
| 10 | A |
| 11 | B |
| 12 | B |
| 13 | B |
| 14 | B |
| 15 | B |
| 16 | A |

TABLE 1-continued

CDK9 $IC_{50}$ values of the compounds.

| Example number | CDK9 $IC_{50}$ |
|---|---|
| 17 | A |
| 18 | B |
| 19 | B |
| 20 | C |
| 21 | B |
| 22 | B |
| 23 | B |
| 24 | B |
| 25 | B |
| 26 | C |
| 27 | C |
| 28 | B |
| 29 | B |
| 30 | A |
| 31 | A |
| 32 | A |
| 33 | A |
| 34 | C |
| 35 | A |
| 36 | C |
| 37 | A |
| 38 | A |
| 39 | A |
| 40 | A |
| 41 | B |
| 42 | B |
| 43 | B |
| 44 | B |
| 45 | A |
| 46 | B |
| 47 | B |
| 48 | B |
| 49 | B |
| 50 | B |
| 51 | B |
| 52 | B |
| 53 | B |
| 54 | C |
| 55 | A |
| 56 | B |
| 57 | C |
| 58 | C |
| 59 | B |
| 60 | B |
| 61 | B |
| 62 | B |
| 63 | B |
| 64 | B |
| 65 | D |
| 66 | D |
| 67 | D |
| 68 | D |
| 69 | C |
| 70 | D |
| 71 | B |
| 72 | B |
| 73 | B |
| 74 | C |
| 75 | B |
| 76 | D |
| 77 | C |
| 78 | C |
| 79 | B |
| 80 | D |
| 81 | C |
| 82 | D |
| 83 | B |
| 84 | B |
| 85 | B |
| 86 | B |
| 87 | C |
| 88 | B |
| 89 | B |
| 90 | B |
| 91 | B |

TABLE 1-continued

CDK9 IC$_{50}$ values of the compounds.

| Example number | CDK9 IC$_{50}$ |
|---|---|
| 92 | C |
| 93 | B |
| 94 | B |
| 95 | B |
| 96 | D |
| 97 | C |
| 98 | B |
| 99 | B |
| 100 | C |
| 101 | B |
| 102 | C |
| 103 | B |
| 104 | B |
| 105 | B |
| 106 | B |
| 107 | B |
| 108 | B |
| 109 | B |
| 110 | B |
| 111 | B |
| 112 | B |
| 113 | A |
| 114 | B |
| 115 | C |
| 116 | A |
| 117 | B |
| 118 | B |
| 119 | B |
| 120 | C |
| 121 | A |
| 122 | B |
| 123 | B |
| 124 | B |
| 125 | B |
| 126 | B |
| 127 | B |
| 128 | B |
| 129 | A |
| 130 | A |
| 131 | B |
| 132 | B |
| 133 | B |
| 134 | B |
| 135 | B |
| 136 | B |
| 137 | C |
| 138 | C |
| 139 | C |
| 140 | C |
| 141 | B |
| 142 | B |
| 143 | B |
| 144 | B |
| 145 | B |
| 146 | B |
| 147 | B |
| 148 | C |
| Roscovitine | A |
| Flavopiridol | A |

The IC$_{50}$ values are expressed using the code A, B, C, and D as described below:
A <0.1 μM
B <1.0 μM
C <10 μM
D >10 μM Tested compounds showed a wide range of CDK9 IC$_{50}$ values, from low nanomolar to the micromolar range

TABLE 2

Antiviral Activity (AV$_{50}$) values of the compounds.

| Example number | AV$_{50}$ (μM) |
|---|---|
| 1 | ND |
| 2 | ND |
| 3 | >1 |
| 4 | ND |
| 5 | 0.3 |
| 6 | >1.5 |
| 7 | ND |
| 8 | 0.4 |
| 9 | <1.5 |
| 10 | 0.8 |
| 11 | >1.5 |
| 12 | >1.5 |
| 13 | 0.3 |
| 14 | ND |
| 15 | ND |
| 16 | 0.11 |
| 17 | >1.5 |
| 18 | >1.5 |
| 19 | 1 |
| 20 | >1.5 |
| 21 | <1.5 |
| 22 | <1.5 |
| 23 | >0.5 |
| 24 | >0.5 |
| 25 | >0.5 |
| 26 | 0.1 |
| 27 | >0.5 |
| 28 | >0.5 |
| 29 | >0.5 |
| 30 | >1.5 |
| 31 | 0.2 |
| 32 | 0.15 |
| 33 | ND |
| 34 | ND |
| 35 | ND |
| 36 | ND |
| 37 | >1.5 |
| 38 | <1.5 |
| 39 | >1 |
| 40 | 0.5 |
| 41 | 0.06 |
| 42 | >5 |
| 43 | >1 |
| 44 | ND |
| 45 | 0.05 |
| 46 | 5 |
| 47 | ND |
| 48 | ND |
| 49 | >10 |
| 50 | ND |
| 51 | ND |
| 52 | ND |
| 53 | ND |
| 54 | ND |
| 55 | ND |
| 56 | ND |
| 57 | ND |
| 58 | ND |
| 59 | >2 |
| 60 | ND |
| 61 | ND |
| 62 | <0.08 |
| 63 | ND |
| 64 | 5 |
| 65 | ND |
| 66 | >10 |
| 67 | ND |
| 68 | 1 |
| 69 | ND |
| 70 | >10 |
| 71 | 2 |
| 72 | ND |
| 73 | 0.0002 |
| 74 | ND |
| 75 | 0.01 |

TABLE 2-continued

Antiviral Activity ($AV_{50}$) values of the compounds.

| Example number | $AV_{50}$ (μM) |
|---|---|
| 76 | ND |
| 77 | 10 |
| 78 | ND |
| 79 | 0.008 |
| 80 | ND |
| 81 | 0.06 |
| 82 | ND |
| 83 | 0.007 |
| 84 | ND |
| 85 | ND |
| 86 | 0.1 |
| 87 | ND |
| 88 | >0.4 |
| 89 | >0.4 |
| 90 | >0.4 |
| 91 | ND |
| 92 | 0.25 |
| 93 | ND |
| 94 | ND |
| 95 | ND |
| 96 | ND |
| 97 | ND |
| 98 | ND |
| 99 | ND |
| 100 | ND |
| 101 | 0.06 |
| 102 | ND |
| 103 | ND |
| 104 | ND |
| 105 | 0.016 |
| 106 | ND |
| 107 | ND |
| 108 | ND |
| 109 | ND |
| 110 | ND |
| 111 | 0.007 |
| 112 | 0.006 |
| 113 | ND |
| 114 | ND |
| 115 | ND |
| 116 | ND |
| 117 | 0.2 |
| 118 | 1.5 |
| 119 | ND |
| 120 | ND |
| 121 | ND |
| 122 | 0.08 |
| 123 | 0.05 |
| 124 | ND |
| 125 | ND |
| 126 | 0.1 |
| 127 | 0.003 |
| 128 | <0.003 |
| 129 | 0.01 |
| 130 | 0.016 |
| 131 | <0.08 |
| 132 | 5 |
| 133 | 7 |
| 134 | >10 |
| 135 | ND |
| 136 | >2 |
| 137 | >2 |
| 138 | >0.4 |
| 139 | 0.4 |
| 140 | >0.4 |
| 141 | 0.08 |
| 142 | 0.04 |
| 143 | 0.016 |
| 144 | <0.003 |
| 145 | 0.03 |
| 146 | <0.003 |
| 147 | 0.005 |
| 148 | <0.08 |

TABLE 2-continued

Antiviral Activity ($AV_{50}$) values of the compounds.

| Example number | $AV_{50}$ (μM) |
|---|---|
| Roscovitine | 9 |
| Flavopiridol | 0.1 |

TABLE 3

Antiproliferative capacity ($AP_{50}$) values of the compounds.

| Example number | $AP_{50}$ (μM) |
|---|---|
| 1 | 2.5 |
| 2 | 0.4 |
| 3 | >1 |
| 4 | 1.5 |
| 5 | 0.15 |
| 6 | >0.5 |
| 7 | 4 |
| 8 | >1.5 |
| 9 | >1.5 |
| 10 | 0.5 |
| 11 | >1.5 |
| 12 | >1.5 |
| 13 | 0.6 |
| 14 | >0.5 |
| 15 | >0.5 |
| 16 | 0.1 |
| 17 | 0.35 |
| 18 | >0.5 |
| 19 | >0.5 |
| 20 | >0.5 |
| 21 | >0.5 |
| 22 | >0.5 |
| 23 | >0.5 |
| 24 | >0.5 |
| 25 | >0.5 |
| 26 | 0.1 |
| 27 | >0.5 |
| 28 | >0.5 |
| 29 | >0.5 |
| 30 | >0.5 |
| 31 | 0.35 |
| 32 | 0.07 |
| 33 | 2 |
| 34 | >5 |
| 35 | 2.2 |
| 36 | >5 |
| 37 | 2 |
| 38 | >0.5 |
| 39 | 0.3 |
| 40 | >0.2 |
| 41 | 0.08 |
| 42 | 1.8 |
| 43 | 0.5 |
| 44 | 5 |
| 45 | 0.08 |
| 46 | ND |
| 47 | ND |
| 48 | ND |
| 49 | ND |
| 50 | ND |
| 51 | ND |
| 52 | ND |
| 53 | ND |
| 54 | ND |
| 55 | ND |
| 56 | ND |
| 57 | ND |
| 58 | ND |
| 59 | ND |
| 60 | ND |
| 61 | ND |
| 62 | ND |

TABLE 3-continued

Antiproliferative capacity (AP$_{50}$) values of the compounds.

| Example number | AP$_{50}$ (μM) |
|---|---|
| 63 | ND |
| 64 | <0.08 |
| 65 | ND |
| 66 | ND |
| 67 | ND |
| 68 | ND |
| 69 | ND |
| 70 | ND |
| 71 | ND |
| 72 | ND |
| 73 | ND |
| 74 | ND |
| 75 | <0.08 |
| 76 | ND |
| 77 | ND |
| 78 | ND |
| 79 | <0.08 |
| 80 | ND |
| 81 | ND |
| 82 | ND |
| 83 | ND |
| 84 | ND |
| 85 | ND |
| 86 | ND |
| 87 | ND |
| 88 | ND |
| 89 | ND |
| 90 | ND |
| 91 | ND |
| 92 | ND |
| 93 | ND |
| 94 | ND |
| 95 | ND |
| 96 | ND |
| 97 | ND |
| 98 | ND |
| 99 | ND |
| 100 | ND |
| 101 | ND |
| 102 | ND |
| 103 | ND |
| 104 | ND |
| 105 | ND |
| 106 | ND |
| 107 | ND |
| 108 | ND |
| 109 | ND |
| 110 | ND |
| 111 | 0.016 |
| 112 | <0.003 |
| 113 | ND |
| 114 | ND |
| 115 | ND |
| 116 | ND |
| 117 | ND |
| 118 | ND |
| 119 | ND |
| 120 | ND |
| 121 | ND |
| 122 | ND |
| 123 | ND |
| 124 | ND |
| 125 | ND |
| 126 | ND |
| 127 | <0.08 |
| 128 | 0.03 |
| 129 | <0.08 |
| 130 | ND |
| 131 | ND |
| 132 | ND |
| 133 | ND |
| 134 | ND |
| 135 | ND |
| 136 | ND |
| 137 | ND |
| 138 | ND |
| 139 | ND |
| 140 | ND |
| 141 | ND |
| 142 | 0.04 |
| 143 | >0.08 |
| 144 | 0.09 |
| 145 | 0.05 |
| 146 | 0.04 |
| 147 | 0.04 |
| 148 | ND |
| Roscovitine | 3 |
| Flavopiridol | 0.03 |

TABLE 4

TD$_{50}$ values of the compounds.

| Example number | TD$_{50}$ (μM) |
|---|---|
| 1 | 3.5 |
| 2 | 0.4 |
| 3 | >5 |
| 4 | 2.1 |
| 5 | >10 |
| 6 | >0.5 |
| 7 | >5 |
| 8 | >1.5 |
| 9 | >1.5 |
| 10 | 3 |
| 11 | >1.5 |
| 12 | >1.5 |
| 13 | 5 |
| 14 | >0.5 |
| 15 | >0.5 |
| 16 | 1.5 |
| 17 | >0.5 |
| 18 | >0.5 |
| 19 | >0.5 |
| 20 | >0.5 |
| 21 | >0.5 |
| 22 | >0.5 |
| 23 | >0.5 |
| 24 | >0.5 |
| 25 | >0.5 |
| 26 | 6 |
| 27 | >0.5 |
| 28 | >0.5 |
| 29 | >0.5 |
| 30 | >0.5 |
| 31 | 1.8 |
| 32 | 20 |
| 33 | >5 |
| 34 | >5 |
| 35 | 3 |
| 36 | >5 |
| 37 | 2 |
| 38 | <1.5 |
| 39 | 0.6 |
| 40 | 0.4 |
| 41 | 8.5 |
| 42 | 4 |
| 43 | 2 |
| 44 | >5 |
| 45 | 15 |
| 46 | >10 |
| 47 | ND |
| 48 | ND |
| 49 | >10 |
| 50 | ND |
| 51 | ND |

TABLE 4-continued

TD$_{50}$ values of the compounds.

| Example number | TD$_{50}$ (μM) |
|---|---|
| 52 | ND |
| 53 | ND |
| 54 | ND |
| 55 | ND |
| 56 | ND |
| 57 | ND |
| 58 | ND |
| 59 | >2 |
| 60 | ND |
| 61 | ND |
| 62 | 4 |
| 63 | ND |
| 64 | 5 |
| 65 | ND |
| 66 | >10 |
| 67 | ND |
| 68 | >10 |
| 69 | ND |
| 70 | >10 |
| 71 | >10 |
| 72 | ND |
| 73 | 6 |
| 74 | ND |
| 75 | 10 |
| 76 | ND |
| 77 | 10 |
| 78 | ND |
| 79 | 15 |
| 80 | ND |
| 81 | 3 |
| 82 | ND |
| 83 | 12 |
| 84 | ND |
| 85 | ND |
| 86 | 4 |
| 87 | ND |
| 88 | >20 |
| 89 | >20 |
| 90 | >20 |
| 91 | ND |
| 92 | >20 |
| 93 | ND |
| 94 | ND |
| 95 | ND |
| 96 | ND |
| 97 | ND |
| 98 | ND |
| 99 | ND |
| 100 | ND |
| 101 | 12 |
| 102 | ND |
| 103 | ND |
| 104 | ND |
| 105 | 7 |
| 106 | ND |
| 107 | ND |
| 108 | ND |
| 109 | ND |
| 110 | ND |
| 111 | 12 |
| 112 | 10 |
| 113 | ND |
| 114 | 10 |
| 115 | ND |
| 116 | ND |
| 117 | >2 |
| 118 | >2 |
| 119 | ND |
| 120 | ND |
| 121 | ND |
| 122 | >2 |
| 123 | 7 |
| 124 | ND |
| 125 | ND |
| 126 | >2 |
| 127 | 7 |
| 128 | 5 |
| 129 | 5 |
| 130 | 15 |
| 131 | 2 |
| 132 | >10 |
| 133 | >10 |
| 134 | >10 |
| 135 | ND |
| 136 | >2 |
| 137 | >2 |
| 138 | >20 |
| 139 | >20 |
| 140 | >20 |
| 141 | >20 |
| 142 | >20 |
| 143 | 15 |
| 144 | 12 |
| 145 | 15 |
| 146 | 10 |
| 147 | 15 |
| 148 | 1 |
| Roscovitine | 8 |
| Flavopiridol | 0.1 |

We identified several compounds with good antiviral and antiproliferative activity and a good cytotoxicity profile: examples 5, 10, 13, 16, 26, 31, 32, 41, 43, 45, 62, 64, 73, 75, 79, 83, 111, 112, 123, 127, 128, 129, 130, 131, 141, 142, 143, 144, 145, 146, 147. The analysis of the commercially available compounds showed that there is no correlation between CDK9 inhibition and anti-HIV activity. In fact despite having a potent CDK9 IC$_{50}$ value Roscovitine and Flavopiridol demonstrated a poor anti-HIV and cytotoxicity profile in our assay.

When we tested compounds with potent anti-CDK9 activity (already published in the patent application WO2011077171 A1) we compared these test results to those of the commercially available compounds Roscovitine and Flavopiridol. Unexpectedly we didn't find a direct correlation between CDK9 inhibition and good antiviral activity. The following table shows some examples of compounds with potent CDK9 IC$_{50}$ values though not having a good antiviral activity profile.

TABLE 5

Examples of compounds with potent anti-CDK9 activity and poor anti-HIV activity. The CDK9 IC$_{50}$ is represented by the code described in Table 1.

| Example number | CDK9 IC$_{50}$ | TD$_{50}$ (μM) | AV$_{50}$ (μM) |
|---|---|---|---|
| 3 | B | >5 | >1 |
| 11 | B | >1.5 | >1.5 |
| 12 | B | >1.5 | >1.5 |
| 42 | B | 4 | >5 |
| 43 | B | 2 | >1 |
| 46 | B | >10 | 5 |
| 49 | B | >10 | >10 |
| 59 | B | >2 | >2 |
| 64 | B | 5 | 5 |
| 71 | B | >10 | 2 |
| 118 | B | >2 | 1.5 |
| 132 | B | >10 | 5 |
| 133 | B | >10 | 7 |

TABLE 5-continued

Examples of compounds with potent anti-CDK9 activity and poor anti-HIV activity. The CDK9 IC$_{50}$ is represented by the code described in Table 1.

| Example number | CDK9 IC$_{50}$ | TD$_{50}$ (μM) | AV$_{50}$ (μM) |
|---|---|---|---|
| 134 | B | >10 | >10 |
| 136 | B | >2 | >2 |

Analytical Methods (HPLC-MS, NMR)
Waters HPLC/MS:
MS detector: Waters SQD
UV detector: Waters 996 DAD
Separation module: Waters Alliance 2795
HPLC:
Column: Waters XBridge C18, 5 cm×4.6 mm, 3.5 μm.
Solvent A: Water/0.1% HCOOH
Solvent B: AcCN
Acetonitrile: Riedel-deHaën; G Chromasolv (34998)
Water: Mili-Q Academic
Formic Acid: Riedel-deHaën; extra pure (27001)
Flow Rate: 2 ml/min Gradient:

| min | B % |
|---|---|
| 0.00 | 5 |
| 0.50 | 5 |
| 5.50 | 95 |
| 6.00 | 95 |
| 6.50 | 5 |
| 7.00 | 5 |

Injection: 5 μg
MS:
Ionization: ES+/ES−
Source block temp: 110° C.
Desolvation temp: 250° C.
Desolvation Gas: 500 L/h
Cone Gas: 80 L/h
Capillary: 3000 V
Cone: 30 V
Extractor: 6 V
Rf Lens: 0.1 V
Scan: 80 to 1000 m/z in 1 sec.
Inter-scan delay: 0.1 s
$^1$H NMR spectra were recorded on a Brucker Avanve 300 MHz AV spectrometer in deuterated solvents (DMSO-d$_6$). Chemical shifts δ are in parts per million (ppm).

Syntheses of Examples

2-Methoxy-5-(6-(2-methoxyphenyl)pyrimidin-4-ylamino)phenol (Example 32)

Step 1:

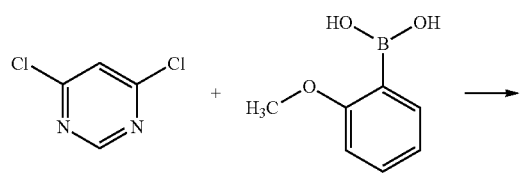

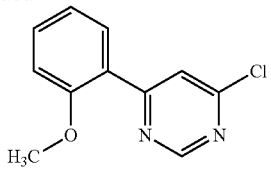

14.898 g 4,6-Dichloropyrimidine (100 mmol) was dissolved in 600 ml 1,2-dimethoxyethane and the flask was filled with argon properly. 2.311 g Tetrakis(thriphenylphosphine) palladium[0] (2 mmol) was added and the mixture was stirred at room temperature for 30 minutes. Then 15.196 g 2-methoxyphenyl-boronic acid (100 mmol), 31.80 g anhydrous Na$_2$CO$_3$ (300 mmol) and 150 ml water was added under argon atmosphere. The mixture was heated to reflux temperature during 2 hours and was refluxed for additional 2 hours. The reaction mixture was poured to 1000 ml cold water and it was extracted three times with 200-200 ml of ethyl acetate. The combined organic layer was washed with brine, dried over MgSO$_4$, decolorized with activated carbon and evaporated under reduced pressure. The residue was purified by column chromatography eluting with 25% ethyl acetate in hexanes. Fractions were evaporated to dryness and the residue was filtered from hexanes to get the pure product as a white solid. Yield: 18.76 g (85%). Ret. time: 3.88 min., (M+H)$^+$=221; $^1$HNMR (DMSO-d$_6$, 300 MHz), δ (ppm): 9.10 (s, 1H), 8.12 (s, 1H), 7.98 (d, J=7.77 Hz, 1H), 7.55 (t, 1H), 7.23 (d, J=8.34 Hz, 1H), 7.13 (t, 1H), 3.91 (s, 3H).

Step 2:

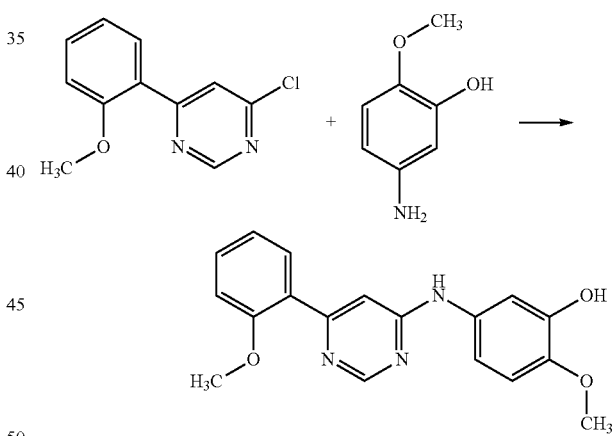

1.088 g 3-Hydroxy-4-methoxyaniline (5 mmol) was added to a solution of 1.214 g 4-chloro-6-(2-methoxyphenyl)-pyrimidine (obtained in Step 1) (5.5 mmol) in 50 ml of tert-butanol. 4 ml dry ethyl acetate saturated with HCl gas was added and the mixture was refluxed for 3 hours. Then it was cooled to 30° C., the precipitated solid was filtered off and washed well with tert-butanol and diethyl ether. The solid was suspended in 250 ml 5% NaHCO$_3$ solution and extracted four times with 100-100 ml ethyl acetate-tertahydrofurane=5:1 mixture. The combined organic layer was washed with brine, dried over MgSO$_4$ and evaporated to dryness. The residue was refluxed in 50 ml of acetonitrile and cooled to 0° C. The pure product was filtered off after an hour as an off white solid. Yield: 1.43 g (88%). Ret. time: 2.08-2.36 min., (M+H)$^+$=324, (M+H)$^−$=322; $^1$HNMR (DMSO-d$_6$, 300 MHz), δ (ppm): 9.31 (s, 1H), 9.02 (bs, 1H), 8.61 (s, 1H), 7.92 (d, J=7.11 Hz, 1H), 7.42 (m, 1H), 7.35 (s, 1H), 7.16 (m, 2H), 7.06 (m, 1H), 6.92 (m, 1H), 6.88 (m, 1H), 3.88 (s, 3H), 3.74 (s, 3H).

2-Methoxy-5-(6-(2-methoxyphenyl)pyrimidin-4-ylamino)phenyl Pivalate (Example 26)

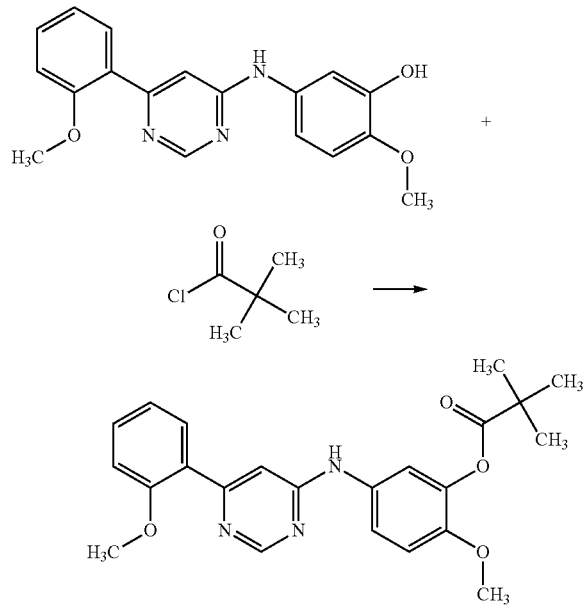

226 mg 2-Methoxy-5-(6-(2-methoxyphenyl)pyrimidin-4-ylamino)phenol (obtained in Example 32, Step 2) (0.7 mmol) was dissolved in 10 ml N,N-dimethylformamide and cooled to 0° C. 79 mg KOtBu (0.7 mmol) was added and stirred for half an hour. 95 µl Pivaloyl chloride was added and it was stirred at room temperature overnight. Reaction mixture was poured onto 50 g ice and 1 ml saturated Na$_2$CO$_3$ solution was added. It was stirred until ice melts and then the precipitated solid was filtered off, washed well with water. Crude product was recrystallized from a minimal amount of acetonitrile, washed with diethyl ether and air-dried. Yield: 156 mg (55%). Ret. time: 3.01 min., (M+H)$^+$= 408, (M+H)$^-$=406; $^1$HNMR (DMSO-d$_6$, 300 MHz), δ (ppm): 9.52 (s, 1H), 8.65 (s, 1H), 7.95 (d, J=6.15 Hz, 1H), 7.50 (s, 1H), 7.43 (d, J=8.01 Hz, 1H), 7.38 (m, 2H), 7.17 (d, J=8.01 Hz, 1H), 7.09 (m, 2H), 3.89 (s, 3H), 3.74 (s, 3H), 1.31 (s, 9H).

4-Methoxy-N1-(6-(2-methoxyphenyl)pyrimidin-4-yl)benzene-1,3-diamine (Example 41)

Step 1

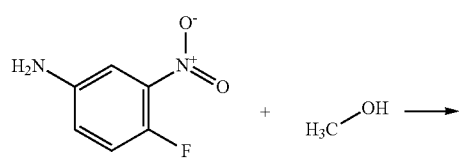

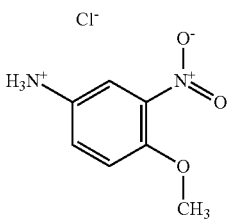

3.45 g Sodium (150 mmol) was dissolved in 250 ml methanol and 15.612 g 4-fluoro-3-nitroaniline (100 mmol) was added in one portion. The mixture was refluxed for 3 days. It was evaporated under reduced pressure and 400 ml water was added. Mixture was extracted three times with 150-150 ml ethyl acetate. The combined organic layer was washed with brine, dried over MgSO$_4$ and evaporated to 100 ml. After cooling it to 0° C. 40 ml ethyl acetate saturated with HCl gas was added and it was stirred at this temperature for 30 minutes. The precipitated solid was filtered off, washed well with ethyl acetate, diethyl ether and dried in vacuum desiccator over P$_2$O$_5$. Product was used directly in the subsequent step without any further purification. Yield: 19.51 g (95%). Ret. time: 1.43 min., (M+H)$^+$=169, (M+H)$^-$= 167.

Step 2

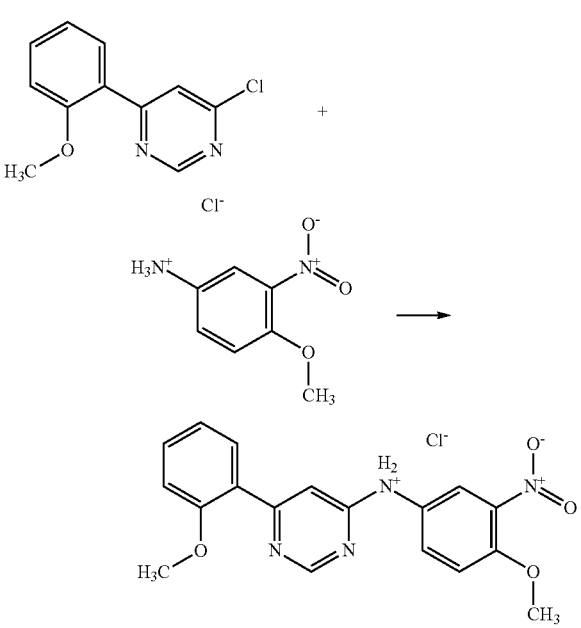

5.115 g 4-Methoxy-3-nitro-phenyl-ammonium chloride (obtained in Step 1) (25 mmol) was added to a solution of 5.517 g 4-chloro-6-(2-methoxy-phenyl)-pyrimidine (obtained in Example 32, Step 1) (25 mmol) in 80 ml of tert-butanol and the mixture was refluxed for 6 hours. Then it was cooled to 30° C., the precipitated yellow solid was filtered off and washed well with tert-butanol, diethyl ether and dried in vacuum desiccator over P$_2$O$_5$. Product was used directly in the subsequent step without any further purification. Yield: 9.08 g (93%). Ret. time: 2.82 min., (M+H)$^+$= 353, (M+H)$^-$=351.

Step 3

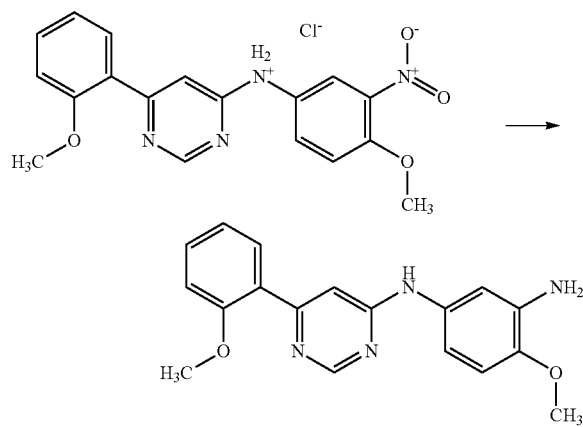

9.00 g (4-Methoxy-3-nitro-phenyl)-[6-(2-methoxy-phenyl)-pyrimidin-4-yl]-ammonium chloride (obtained in Step 2) (23.14 mmol) was suspended in 200 ml methanol-dichloromethane=3-1 and 3.23 ml triethylamine (2.34 g, 23.14 mmol) was added to get a clear solution. 1.50 g Pd catalyst (10% Pd on activated carbon) was added carefully and it was stirred vigorously in $H_2$ atmosphere under standard pressure at room temperature until TLC indicates the end of the reaction. Catalyst was filtered off and the filtrate was evaporated under reduced pressure. Crude product was purified by column chromatography on silica gel eluting with 0%→1% methanol in chloroform. Finally it was recrystallized from a minimal amount of acetonitrile to get a light orange solid. Yield: 4.71 g (63%). Ret. time: 0.50-1.93-2.28 min., $(M+H)^+= 323$, $(M+H)^-=321$; $^1$HNMR (DMSO-$d_6$, 300 MHz), δ (ppm): 9.18 (s, 1H), 8.58 (s, 1H), 7.91 (d, J=6.69 Hz, 1H), 7.41 (m, 1H), 7.33 (s, 1H), 7.15 (d, J=8.01 Hz, 1H), 7.06 (t, J=7.17 Hz, 1H), 6.92 (s, 1H), 6.75 (s, 2H), 4.78 (s, 2H), 3.87 (s, 3H), 3.74 (s, 3H).

2-methoxy-5-(6-(2-methoxyphenyl)pyrimidin-4-ylamino)benzamide (Example 45)

Step 1

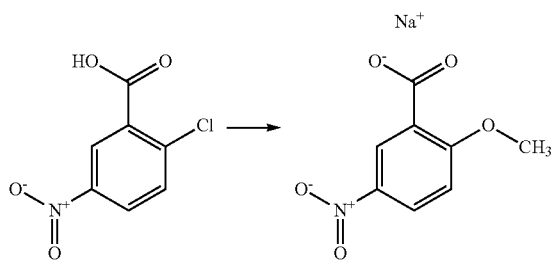

11.50 g Sodium (500 mmol) was dissolved in 250 ml methanol and 20.157 g 2-chloro-5-nitrobenzoic acid (100 mmol) was added in one portion. The mixture was refluxed for 3 days. It was then cooled to 0° C., the precipitated solid was filtered off and washed well with diethyl ether and dried in vacuum desiccator over $P_2O_5$. Product was used directly in the subsequent step without any further purification. Yield: 21.26 g (97%). Ret. time: 2.46 min., $(M+H)^-=196$; $^1$HNMR (DMSO-$d_6$, 300 MHz), δ (ppm): 8.07 (s, 2H), 7.10 (d, J=9.30 Hz, 1H), 3.85 (s, 3H).

Step 2

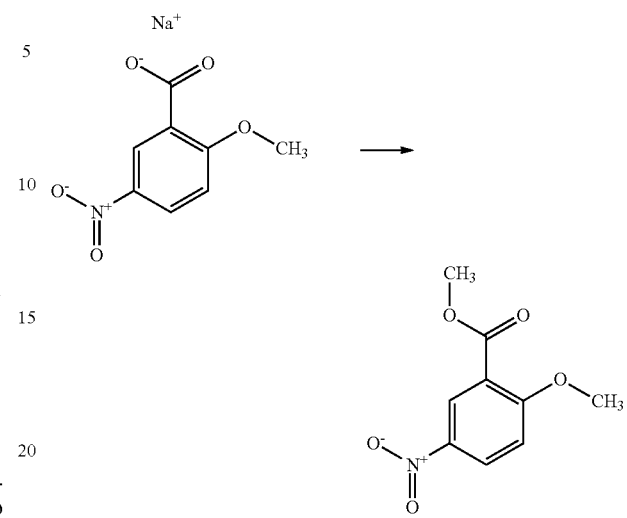

300 ml Methanol was cooled to 0° C. and 100 ml thionyl chloride was added dropwise. Then 21.91 g 2-Methoxy-5-nitro-benzoic acid sodium salt (obtained in Step 1) (100 mmol) was added in one portion. The mixture was stirred at room temperature for an hour and refluxed overnight. Then it was evaporated under reduced pressure, 300 ml saturated $NaHCO_3$ solution was added and stirred for and hour. The precipitated solid was filtered off, washed well with water and dried in vacuum desiccator over $P_2O_5$. Product was used directly in the subsequent step without any further purification. Yield: 16.04 g (76%). Ret. time: 3.19 min., $(M+H)^+= 212$, $(M+H)^-=210$ (low intensity); $^1$HNMR (DMSO-$d_6$, 300 MHz), δ (ppm): 8.48 (s, 1H), 8.43 (d, J=9.24 Hz, 1H), 7.40 (d, J=9.09 Hz, 1H), 3.98 (s, 3H), 3.84 (s, 3H).

Step 3

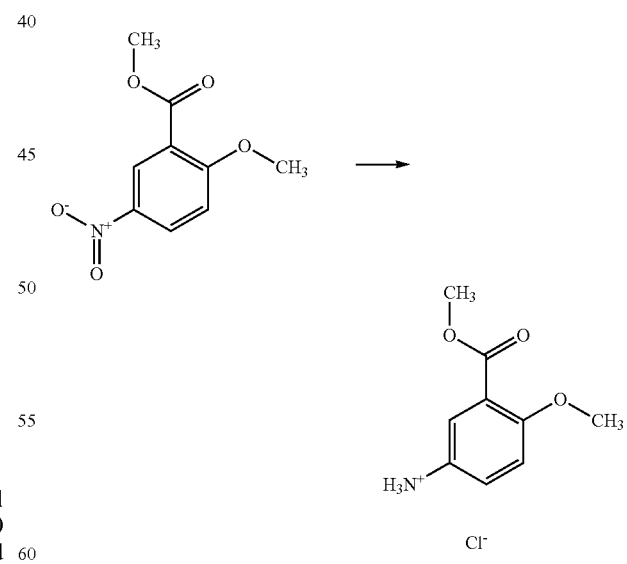

16.00 g 2-Methoxy-5-nitro-benzoic acid methyl ester (obtained in Step 2) (75.76 mmol) was dissolved in 400 ml methanol and 68.82 g $SnCl_2 \times 2H_2O$ (305 mmol) was added. The mixture was refluxed for one day. Then it was evaporated under reduced pressure, cooled in an ice bath and 300 ml saturated $Na_2CO_3$ solution was added. Mixture was extracted four times with 150-150 ml ethyl acetate. The combined organic layer was washed with brine, dried over MgSO₄ and evaporated to 100 ml. After cooling it to 0° C. 40 ml ethyl acetate saturated with HCl gas was added and it was stirred at this temperature for 30 minutes. The precipitated light brown solid was filtered off, washed well with ethyl acetate, diethyl ether and dried in vacuum desiccator over P₂O₅. Product was used directly in the subsequent step without any further purification. Yield: 9.81 g (59%). Ret. time: 0.43-0.96 min., (M+H)⁺=182 (low intensity).

Step 4

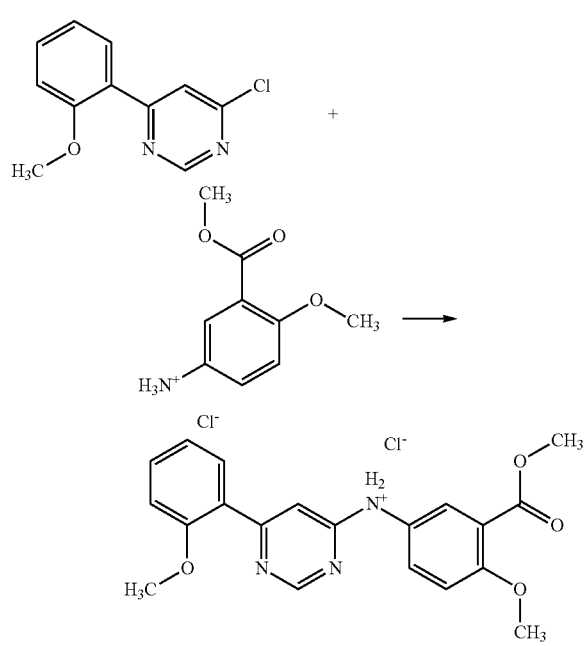

4.135 g 4-Methoxy-3-methoxycarbonyl-phenyl-ammonium chloride (obtained in Step 3) (19 mmol) was added to a solution of 4.413 g 4-chloro-6-(2-methoxy-phenyl)-pyrimidine (obtained in Example 32, Step 1) (20 mmol) in 80 ml of tert-butanol and the mixture was refluxed for 6 hours. Then it was cooled to 30° C., the precipitated solid was filtered off and washed well with tert-butanol and diethyl ether. Yield: 7.04 g, yellow solid (92%).

A portion of the above prepared hydrochloric acid salt was converted to basic form and purified as follows: 300 mg (4-Methoxy-3-methoxycarbonyl-phenyl)-[6-(2-methoxy-phenyl)-pyrimidin-4-yl]-ammonium chloride was suspended in 100 ml saturated NaHCO₃ solution and it was extracted three times with 40-40 ml ethyl acetate. The combined organic layer was washed with brine, dried over MgSO₄ and evaporated under reduced pressure. Crude product was purified by column chromatography on silica gel eluting with chloroform. Finally it was recrystallized from a minimal amount of acetonitrile to get a yellow solid. Yield: 172 mg (63%). Ret. time: 2.57 min., (M+H)⁺=366, (M+H)⁻= 364; ¹HNMR (DMSO-d₆, 300 MHz), δ (ppm): 11.55 (bs, 1H), 8.90 (s, 1H), 7.99 (s, 1H), 7.85 (d, J=6.27 Hz, 1H), 7.63 (m, 2H), 7.34 (s, 1H), 7.27 (m, 2H), 7.17 (t, J=7.41 Hz, 1H), 3.90 (s, 3H), 3.85 (s, 3H), 3.81 (s, 3H).

Step 5

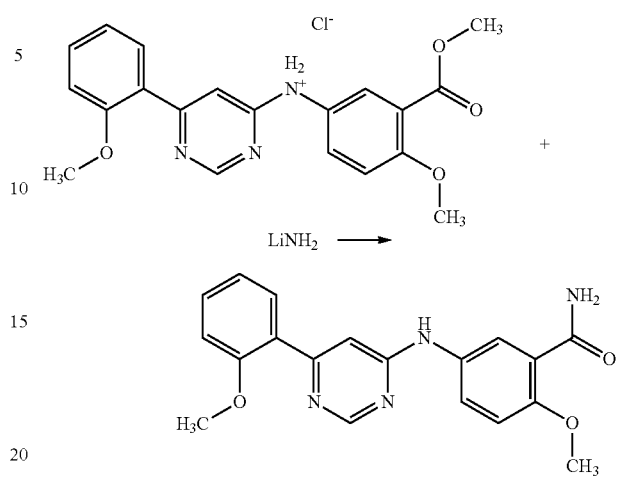

201 mg (4-Methoxy-3-methoxycarbonyl-phenyl)-[6-(2-methoxy-phenyl)-pyrimidin-4-yl]-ammonium chloride (obtained in Step 4) (0.5 mmol) was suspended in 15 ml tetrahyrdofurane, 115 mg lithium amide (4 mmol) was added and it was stirred in a sealed tube for four days. It was poured onto ice and was extracted three times with 40-40 ml ethyl acetate. The combined organic layer was washed with brine, dried over MgSO₄ and evaporated under reduced pressure. Residue was recrystallized from a minimal amount of acetonitrile to get the pure product as a white solid. Yield: 104 mg (59%). Ret. time: 0.46-1.90-2.25 min., (M+H)⁺= 351, (M+H)⁻=349; ¹HNMR (DMSO-d₆, 300 MHz), δ (ppm): 9.57 (s, 1H), 8.65 (s, 1H), 8.05 (s, 1H), 7.95 (d, J=6.48 Hz, 1H), 7.86 (d, J=7.20 Hz, 1H), 7.68 (bs, 1H), 7.55 (bs, 1H), 7.45 (m, 1H), 7.09 (s, 1H), 7.10 (m, 3H), 3.89 (s, 6H).

N¹-(6-(2-Methoxyphenyl)pyrimidin-4-yl)-N⁴,N⁴-dimethylbenzene-1,4-diamine (Example 5)

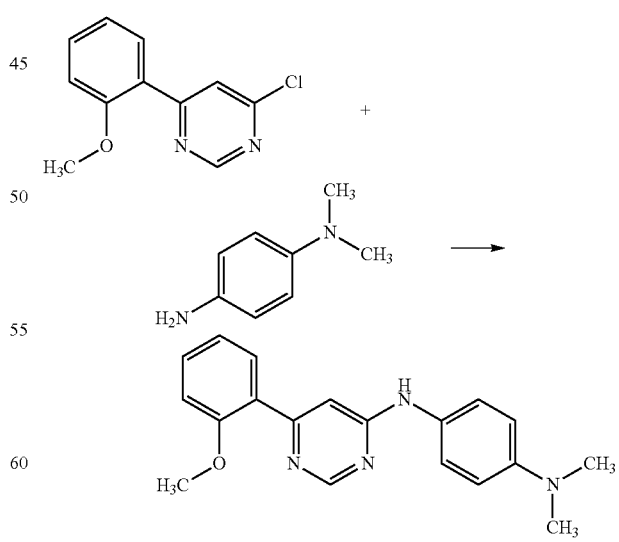

123 mg N,N-Dimethyl-benzene-1,4-diamine (0.9 mmol) was added to a solution of 220 mg 4-chloro-6-(2-methoxy-phenyl)-pyrimidine (obtained in Example 32, Step 1) (1 mmol) in 25 ml of tert-butanol and 2 ml dry ethyl acetate saturated with HCl gas was added and the mixture was refluxed for 5 hours. Then it was cooled to 30° C., the precipitated solid was filtered off and washed well with tert-butanol and diethyl ether. The solid was suspended in 50 ml 5% NaHCO$_3$ solution and extracted four times with 30-30 ml ethyl acetate. The combined organic layer was washed with brine, dried over MgSO$_4$ and evaporated to dryness. The residue was recrystallized from a minimal amount of acetonitrile to get pure product as an off white solid. Yield: 112 mg (38%). Ret. time: 0.49-2.29-2.47 min., (M+H)$^+$=321, (M+H)$^-$=319; $^1$HNMR (DMSO-d$_6$, 300 MHz), δ (ppm): 9.23 (s, 1H), 9.56 (s, 1H), 7.91 (dd, J$^3$=7.68 Hz, J$^4$=1.71 Hz, 1H), 7.43 (m, 3H), 7.28 (s, 1H), 7.15 (d, J=8.22 Hz, 1H), 7.05 (t, 1H), 6.75 (d, J=9.00 Hz, 2H), 3.86 (s, 3H), 2.67 (s, 6H).

N-(3-((1H-Benzo[d]imidazol-1-yl)methyl)-4-chlorophenyl)-6-(2-methoxyphenyl)pyrimidin-4-amine (Example 16)

Step 1

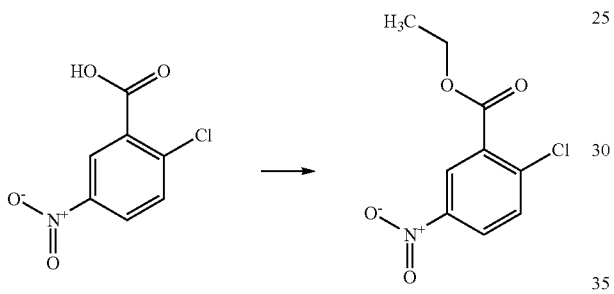

60 ml Ethanol was cooled to 0° C. and 20 ml thionyl chloride was added dropwise. Then 20.16 g 2-Chloro-5-nitrobenzoic acid (100 mmol) was added in one portion. The mixture was stirred at room temperature for an hour and refluxed overnight. Then it was evaporated under reduced pressure, 200 ml saturated NaHCO$_3$ solution was added and extracted three times with 100-100 ml ethyl acetate. The combined organic layer was washed with brine, dried over MgSO$_4$ and evaporated under reduced pressure to get product as a yellow oil. Product was used directly in the subsequent step without any further purification or analytical investigation. Yield: 22.3 g (97%).

Step 2

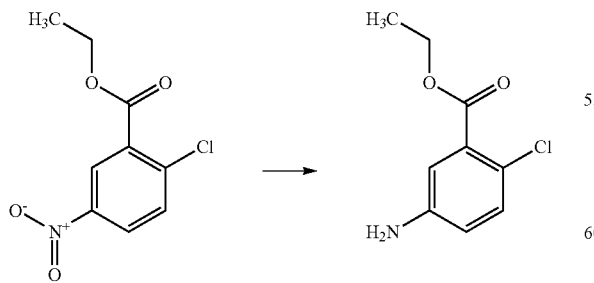

9.185 g 2-Chloro-5-nitro-benzoic acid ethyl ester (obtained in Step 1) (40 mmol) was dissolved in the mixture of 225 ml ethanol and 150 ml 3M hydrochloric acid and 36.10 g SnCl$_2$×2H$_2$O (160 mmol) was added. The mixture was stirred at room temperature for one day. Then it was poured onto 300 g ice and the pH was adjusted to 7-8 by addition of 53 g solid Na$_2$CO$_3$ carefully. Mixture was extracted four times with 150-150 ml ethyl acetate. The combined organic layer was washed with brine, dried over MgSO$_4$ and evaporated to a brown oil. The product was used up directly in the next step without any further purification or analytical investigation. Yield was considered as it had been 100%.

Step 3

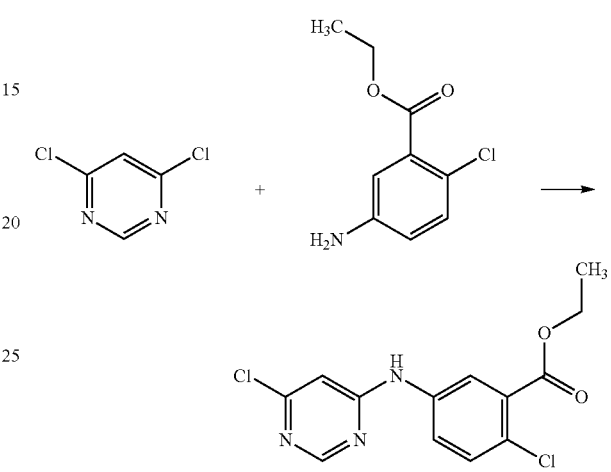

7.99 g 5-Amino-2-chloro-benzoic acid ethyl ester (obtained in Step 2) (40 mmol) was dissolved in 150 ml 2-propanol, 6.257 g 4,6-Dichloropyrimidine (42 mmol) and 6.97 ml triethylamine (5.06 g, 50 mmol) was added. The mixture was refluxed for 5 days. Then it was evaporated under reduced pressure, 150 ml water was added and it was extracted four times with 50-50 ml ethyl acetate. The combined organic layer was washed with brine, dried over MgSO$_4$ and evaporated to dryness. Crude product was purified by column chromatography on silica gel eluting with chloroform. Finally it was recrystallized from a minimal amount of acetonitrile to get a white solid. Yield (for two steps): 4.74 g (38%). Ret. time: 3.99 min., (M+H)$^+$=312, (M+H)$^-$=310; $^1$HNMR (DMSO-d$_6$, 300 MHz), δ (ppm): 10.15 (bs, 1H), 8.55 (s, 1H), 8.07 (s, 1H), 7.91 (d, J=8.70 Hz, 1H), 7.54 (d, J=7.41 Hz, 1H), 6.63 (s, 1H), 4.34 (q, 2H), 1.32 (t, 3H).

Step 4:

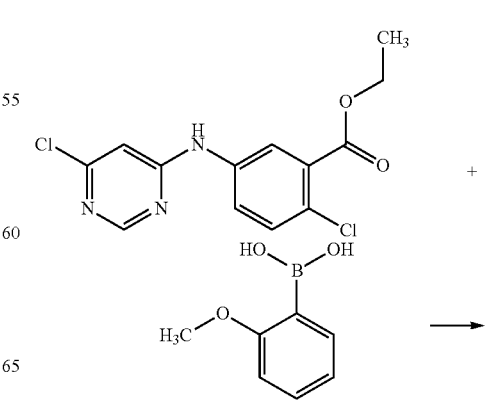

-continued

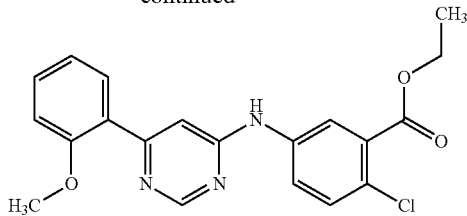

5.00 g 2-Chloro-5-(6-chloro-pyrimidin-4-ylamino)-benzoic acid ethyl ester (obtained in Step 3) (16 mmol) was dissolved in 200 ml ethanol and the flask was filled with argon properly. 1.322 g Tetrakis(thriphenylphosphine) palladium[0] (1.15 mmol) was added and the mixture was stirred at 50° C. for 30 minutes. Then 3.477 g 2-methoxyphenyl-boronic acid (23 mmol) and 12.76 ml triethylamine (9.26 g, 92 mmol) was added under argon atmosphere. The mixture was refluxed for 7 days. Then it was evaporated under reduced pressure, 150 ml water was added and it was extracted three times with 40-40 ml ethyl acetate. The combined organic layer was washed with brine, decolorized with activated carbon, dried over MgSO$_4$ and evaporated under reduced pressure. Crude product was purified by column chromatography on silica gel eluting with chloroform. After the evaporation of selected fractions product was filtered from diisopropyl ether as a white solid. Yield: 2.68 g (44%). Ret. time: 3.37 min., (M+H)$^+$=384, (M+H)$^-$=382; $^1$HNMR (DMSO-d$_6$, 300 MHz), δ (ppm): 9.95 (s, 1H), 8.75 (s, 1H), 8.18 (s, 1H), 8.00 (m, 2H), 7.52 (m, 3H), 7.19 (d, J=7.50 Hz, 1H), 7.05 (m, 1H), 4.35 (m, 2H), 3.91 (s, 3H), 1.34 (m, 3H).

Step 5:

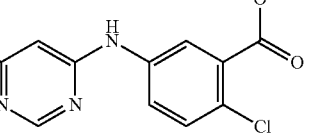

1.00 g 2-Chloro-5-[6-(2-methoxy-phenyl)-pyrimidin-4-ylamino]-benzoic acid ethyl ester (obtained in Step 4) (2.6 mmol) was dissolved in 50 ml dry tetrahydrofurane and cooled to 0° C. 396 mg LiAlH$_4$ (10.42 mmol) was added portionwise and it was stirred at room temperature for an additional hour. 2-propanol was added in order to decompose the excess of LiAlH$_4$ and it was poured onto 80 g ice. The solution was extracted four times with 40-40 ml ethyl acetate-tertahydrofurane=5:1 mixture. The combined organic layer was washed with brine, dried over MgSO$_4$ and evaporated to dryness. The residue was refluxed in 10 ml of acetonitrile and cooled to 0° C. The pure product was filtered off after an hour as a light yellow solid. Yield: 550 mg (62%). Ret. time: 2.63 min., (M+H)$^+$=342, (M+H)$^-$=340; $^1$HNMR (DMSO-d$_6$, 300 MHz), δ (ppm): 9.76 (s, 1H), 8.71 (s, 1H), 7.96 (d, J=5.97 Hz, 1H), 7.81 (m, 2H), 7.48 (m, 2H), 7.34 (d, J=6.00 Hz, 1H), 7.18 (d, J=6.18 Hz, 1H), 7.08 (m, 1H), 5.42 (m, 1H), 4.57 (s, 2H), 3.90 (s, 3H).

Step 6:

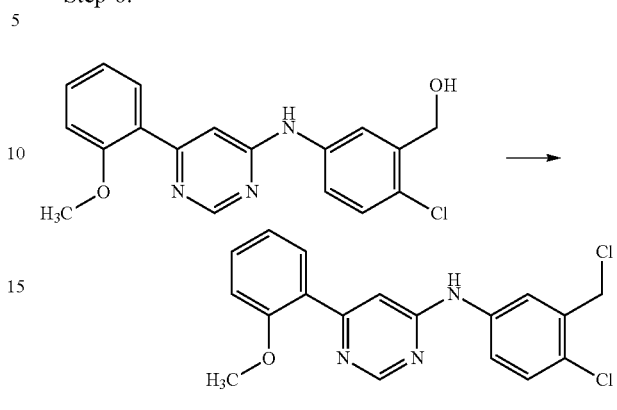

500 mg {2-Chloro-5-[6-(2-methoxy-phenyl)-pyrimidin-4-ylamino]-phenyl}-methanol (obtained in Step 5) (1.46 mmol) was dissolved in the mixture of 50 ml dry dichloromethane and 5 ml dry N,N-dimethylformamide. 256 µl Phosphorus trichloride (402 mg, 2.93 mmol) was added in one portion and it was stirred overnight at room temperature. Then the mixture was poured onto 60 ml 5% NaHCO$_3$ solution and extracted four times with 30-30 ml dichloromethane. The combined organic layer was washed twice with brine, dried over MgSO$_4$ and evaporated under reduced pressure. The product was used up directly in the next step without any further purification or analytical investigation. Yield was considered as it had been 100%.

Step 7:

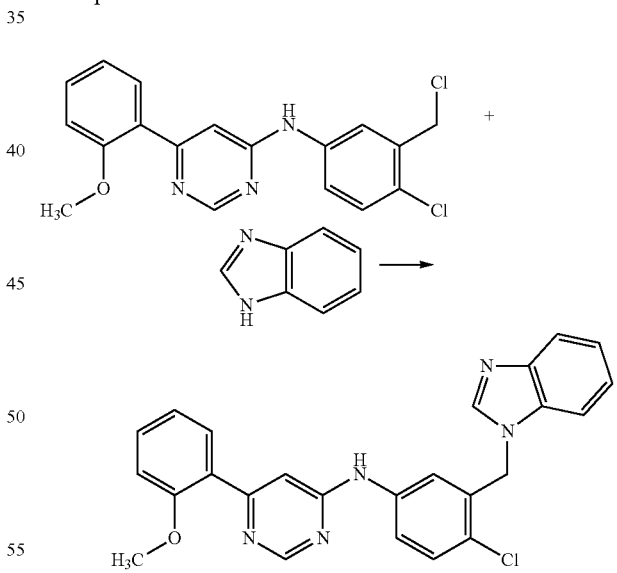

71 mg Benzimidazole (0.6 mmol) was dissolved in 8 ml N,N-dimethylformamide and cooled to 0° C. 28 mg Sodium hydride (60% in mineral oil, 0.7 mmol) was added and the mixture was stirred at this temperature for 30 minutes. A solution of 180 mg (4-Chloro-3-chloromethyl-phenyl)-[6-(2-methoxy-phenyl)-pyrimidin-4-yl]-amine (obtained in Step 6) (0.5 mmol) in 2 ml N,N-dimethylformamide and it was stirred at room temperature for an additional hour. Then the mixture was poured onto 60 ml 5% NaHCO$_3$ solution and extracted four times with 30-30 ml ethyl acetate. The combined organic layer was washed twice with brine, dried over MgSO₄ and evaporated under reduced pressure. The residue was refluxed in 10 ml of acetonitrile and cooled to 0° C. The pure product was filtered off after an hour as a light yellow solid. Yield: 43 mg (19%). Ret. time: 2.62 min., (M+H)⁺=442, (M+H)⁻=440; ¹HNMR (DMSO-d₆, 300 MHz), δ (ppm): 9.69 (s, 1H), 8.54 (s, 1H), 8.37 (s, 1H), 7.90 (m, 2H), 7.71 (s, 1H), 7.48 (m, 3H), 7.34 (s, 1H), 7.20 (m, 4H), 7.06 (s, 1H), 5.60 (s, 2H), 3.85 (s, 3H).

2-Chloro-5-(6-(2-methoxyphenyl)pyrimidin-4-ylamino)benzohydrazide (Example 7)

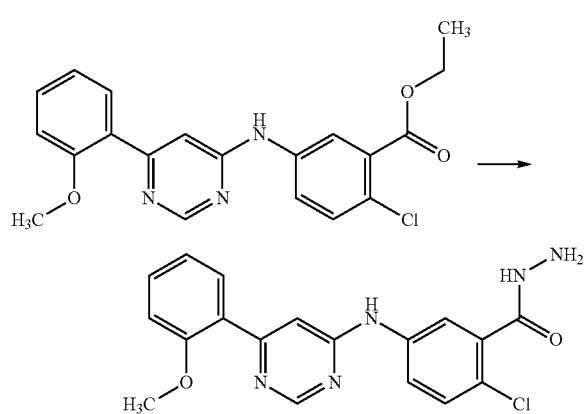

40 mg 2-Chloro-5-[6-(2-methoxy-phenyl)-pyrimidin-4-ylamino]-benzoic acid ethyl ester (obtained in Example 16, Step 4) (0.1 mmol) was dissolved in 250 μl hydrazine hydrate and was heated in a sealed tube at 150° C. for half an hour. Then 20 g of ice was added and the precipitated solid was collected by filtration, washed well with water and dried in vacuum desiccator over P₂O₅. Off white solid. Yield: 32 mg (91%). Ret. time: 0.46-2.12 min., (M+H)⁺= 370, (M+H)⁻=368; ¹HNMR (DMSO-d₆, 300 MHz), δ (ppm): 9.85 (s, 1H), 9.56 (s, 1H), 8.73 (m, 1H), 7.96 (m, 1H), 7.88 (m, 1H), 7.75 (m, 1H), 7.47 (m, 3H), 7.18 (m, 1H), 7.08 (m, 1H), 4.51 (s, 2H), 3.90 (s, 3H).

N-(4-Methoxy-3-(2-morpholinoethoxy)phenyl)-6-(2-methoxyphenyl)pyrimidin-4-amine (Example 8)

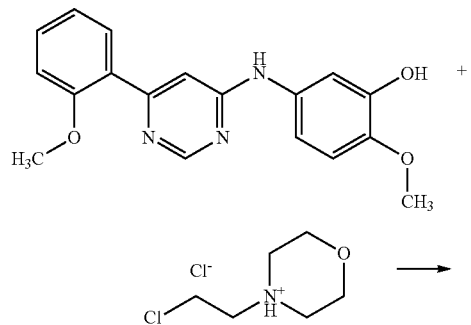

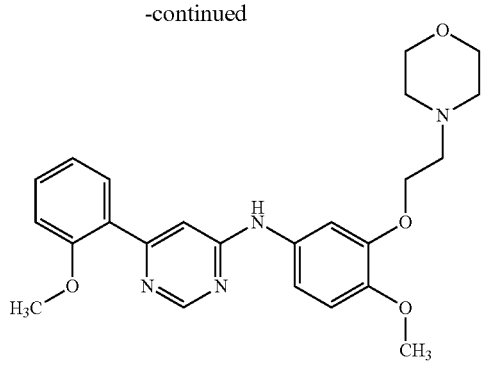

200 mg 2-Methoxy-5-(6-(2-methoxyphenyl)pyrimidin-4-ylamino)phenol (obtained in Example 32, Step 2) (0.62 mmol) was dissolved in 50 ml dry acetonitrile, 173 mg 4-(2-Chloro-ethyl)-morpholin-4-ium chloride (0.93 mmol) and 257 mg K₂CO₃ (1.86 mmol) was added. The mixture was refluxed for 3 days. Then it was evaporated under reduced pressure, 70 ml water and 1 ml saturated Na₂CO₃ solution was added and it was extracted four times with 30-30 ml ethyl acetate. The combined organic layer was washed with brine, dried over MgSO₄ and evaporated under reduced pressure. Crude product was recrystallized from a minimal amount of acetonitrile, washed with diethyl ether and air-dried to get off white solid. Yield: 176 mg (66%). Ret. time: 0.50-2.02 min., (M+H)⁺=437, (M+H)⁻=435; ¹HNMR (DMSO-d₆, 300 MHz), δ (ppm): 9.39 (s, 1H), 8.62 (s, 1H), 7.94 (dd, J³=8.49 Hz, J⁴=1.59 Hz, 1H), 7.44 (t, 1H), 7.35 (s, 1H), 7.33 (d, J=2.04 Hz, 1H), 7.18 (m, 2H), 7.07 (t, 1H), 6.94 (d, J=8.70 Hz, 1H) 4.07 (t, 2H), 3.88 (s, 3H), 3.74 (s, 3H), 3.58 (t, 4H), 2.71 (t, 2H), 2.48 (t, 4H).

N-(2-Methoxy-5-(6-(2-methoxyphenyl)pyrimidin-4-ylamino)phenyl)methanesulfonamide (Example 9)

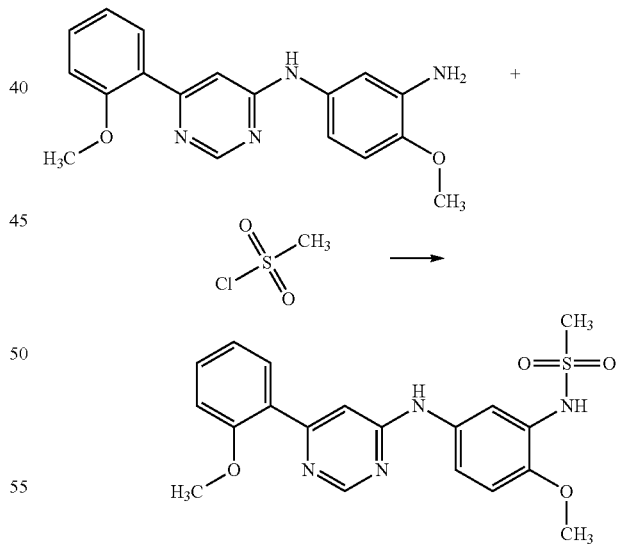

97 mg 4-Methoxy-N1-(6-(2-methoxyphenyl)pyrimidin-4-yl)benzene-1,3-diamine (obtained in Example 41, Step 3) (0.30 mmol) was dissolved in 10 ml dry pyridine and cooled to 0° C. 31 μl Methanesulfonyl chloride (46 mg, 0.4 mmol) was added in one portion and the mixture was stirred at room temperature overnight. Then it was evaporated under reduced pressure, 50 ml water was added and was extracted three times with 30-30 ml ethyl acetate. The combined organic layer was washed with brine, dried over MgSO₄ and evaporated off. Crude product was recrystallized from a minimal amount of acetonitrile to get an off white solid. Yield: 46 mg (38%). Ret. time: 0.51-2.14-2.39 min., (M+H)⁺= 441, (M+H)⁻=439; ¹HNMR (DMSO-d₆, 300 MHz), δ (ppm): 9.84 (bs, 1H), 8.94 (s, 1H), 8.68 (s, 1H), 7.87 (d, J=7.41 Hz, 1H), 7.57 (m, 2H), 7.48 (t, J=7.50 Hz, 1H), 7.37 (s, 1H), 7.19 (d, J=8.27 Hz, 1H), 7.09 (m, 2H), 3.89 (s, 3H), 3.82 (s, 3H), 2.98 (s, 3H).

(2-Methoxy-5-(6-(2-methoxyphenyl)pyrimidin-4-ylamino)phenyl)(methylsulfamoyl)amine (Example 10)

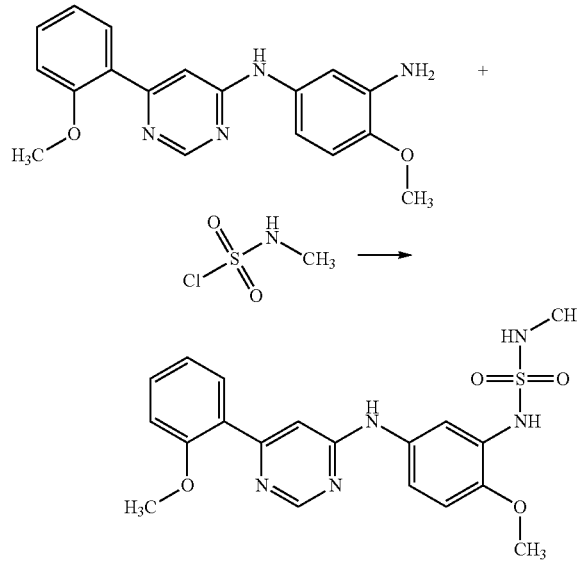

97 mg 4-Methoxy-N1-(6-(2-methoxyphenyl)pyrimidin-4-yl)benzene-1,3-diamine (obtained in Example 41, Step 3) (0.3 mmol) was dissolved in 15 ml dry acetonitrile, 55 mg potassium carbonate (0.4 mmol) and 52 mg methylsulfamoyl chloride (0.4 mmol) was added in one portion and the mixture was refluxed overnight. Then it was evaporated under reduced pressure, 50 ml water was added and was extracted three times with 30-30 ml ethyl acetate. The combined organic layer was washed with brine, dried over MgSO₄ and evaporated off. Crude product was recrystallized from a minimal amount of acetonitrile to get an off white solid. Yield: 51 mg (41%). Ret. time: 0.50-2.26-2.44 min., (M+H)⁺=416, (M+H)⁻=414; ¹HNMR (DMSO-d₆, 300 MHz), δ (ppm): 11.21 (bs, 1H), 8.85 (s, 1H), 8.57 (s, 1H), 7.84 (d, J=6.69 Hz, 1H), 7.60 (m, 2H), 7.43 (m, 1H), 7.27 (d, J=8.37 Hz, 1H), 7.24 (m, 1H), 7.17 (t, J=7.44 Hz, 1H), 7.09 (d, J=8.82 Hz, 1H), 7.06 (m, 1H), 3.90 (s, 3H), 3.87 (s, 3H), 2.50 (s, 3H).

N-(4-Methoxy-3-nitrophenyl)-6-(2-methoxyphenyl)pyrimidin-4-amine (Example 11) and 4-(6-(2-methoxyphenyl)pyrimidin-4-ylamino)-2-nitrophenol (Example 12)

Step 1:

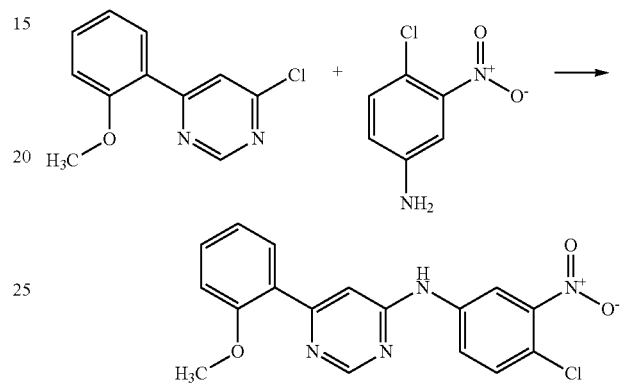

4.692 g 4-Chloro-3-nitroaniline (27.19 mmol) was added to a solution of 6.00 g 4-chloro-6-(2-methoxy-phenyl)-pyrimidine (obtained in Example 32, Step 1) (27.19 mmol) in 100 ml of tert-butanol. 5 ml dry ethyl acetate saturated with HCl gas was added and the mixture was refluxed overnight. Then it was cooled to 30° C., the precipitated solid was filtered off and washed well with tert-butanol and diethyl ether. The solid was suspended in 250 ml 5% NaHCO₃ solution and extracted four times with 80-80 ml ethyl acetate-tertahydrofurane=5:1 mixture. The combined organic layer was washed with brine, dried over MgSO₄ and evaporated to dryness. The residue was refluxed in 30 ml of acetonitrile and cooled to 0° C. The pure product was filtered off after an hour as a yellow solid. Yield: 8.16 g (84%). Ret. time: 3.65 min., (M+H)⁺=357, (M+H)⁻=355; ¹HNMR (DMSO-d₆, 300 MHz), δ (ppm): 10.31 (s, 1H) 9.81 (s, 1H), 8.68 (s, 1H), 7.97 (t, 2H), 7.71 (d, J=8.88 Hz, 1H), 7.56 (s, 1H), 7.48 (t, 1H), 7.20 (d, J=8.31 Hz, 1H), 7.09 (t, 1H), 3.92 (s, 3H).

Step 2:

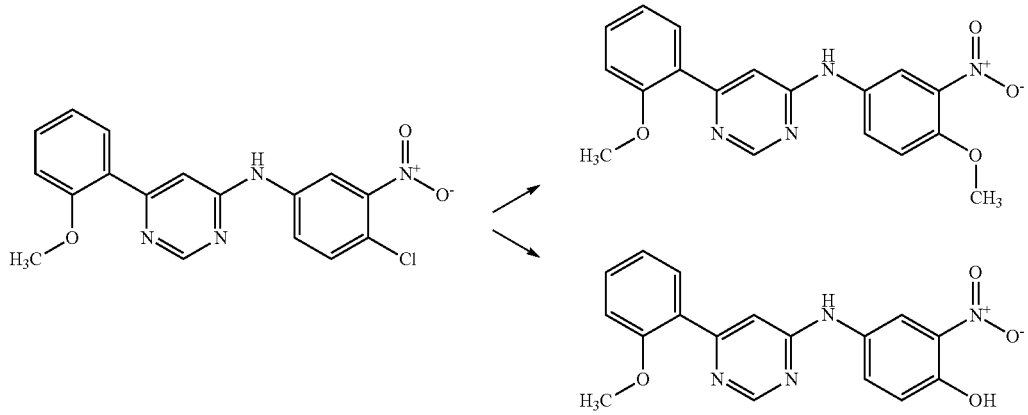 [SMILES: COc1ccccc1-c1cc(Nc2ccc(Cl)c([N+](=O)[O-])c2)ncn1 ; COc1ccccc1-c1cc(Nc2ccc(O)c([N+](=O)[O-])c2)ncn1 ; COc1ccccc1-c1cc(Nc2ccc(OC)c([N+](=O)[O-])c2)ncn1]

2.25 g (4-Chloro-3-nitro-phenyl)-[6-(2-methoxy-phenyl)-pyrimidin-4-yl]-amine (obtained in Step 1) (6.3 mmol) in 30 ml of methanol, 1.70 g sodium methoxyde (31.45 mmol) was added and it was heated in a sealed tube at 140° C. for 2 hours applying microwave irradiation. Then it was evaporated off, 100 g ice was added and the pH was adjusted to 6-8 with 1M hydrochloric acid. The solution was extracted four times with 80-80 ml ethyl acetate. The combined organic layer was washed with brine, dried over MgSO$_4$ and evaporated to dryness. The residue was purified by column chromatography on silica gel eluting with 20%→80% ethyl acetate in hexanes. After evaporation of the selected fractions products were filtered off from diethyl ether and air-dried. Two main products were isolated:

N-(4-Methoxy-3-nitrophenyl)-6-(2-methoxyphenyl)pyrimidin-4-amine was obtained as a yellow solid (higher Rf). Yield: 932 mg (42%). Ret. time: 2.57-2.79 min., (M+H)$^+$=353, (M+H)$^-$=351; $^1$HNMR (DMSO-d$_6$, 300 MHz), δ (ppm): 9.82 (bs, 1H), 8.72 (s, 1H), 8.43 (d, J=2.67 Hz, 1H), 7.97 (dd, J$^4$=7.71 Hz, J$^5$=1.74 Hz, 1H), 7.86 (dd, J$^4$=9.09 Hz, J$^5$=2.70 Hz, 1H), 7.46 (m, 2H), 7.38 (d, J=9.18 Hz, 1H), 7.19 (d, J=8.13 Hz, 1H), 7.09 (t, J=7.14 Hz, 1H), 3.91 (s, 3H), 3.90 (s, 3H).

4-(6-(2-Methoxyphenyl)pyrimidin-4-ylamino)-2-nitrophenol was obtained as an orange solid (lower Rf). Yield: 121 mg (6%). Ret. time: 2.42-2.69 min., (M+H)$^+$=339, (M+H)$^-$=337; $^1$HNMR (DMSO-d$_6$, 300 MHz), δ (ppm): 10.60 (bs, 1H), 9.73 (s, 1H), 8.70 (s, 1H), 8.46 (d, J=2.61 Hz, 1H), 7.96 (dd, J$^4$=7.67 Hz, J$^5$=1.62 Hz, 1H), 7.76 (dd, J$^4$=9.00 Hz, J$^5$=2.67 Hz, 1H), 7.48 (dt, J$^4$=8.85 Hz, J$^5$=1.71 Hz, 1H), 7.41 (d, J=0.72 Hz, 1H), 7.19 (d, J=8.46 Hz, 1H), 7.14 (d, J=9.00 Hz, 1H), 7.08 (t, J=7.32 Hz, 1H), 3.90 (s, 3H).

(2-Methoxy-5-(6-(2-methoxyphenyl)pyrimidin-4-ylamino)phenyl) (cyclohexylsulfamoyl)amine (Example 13)

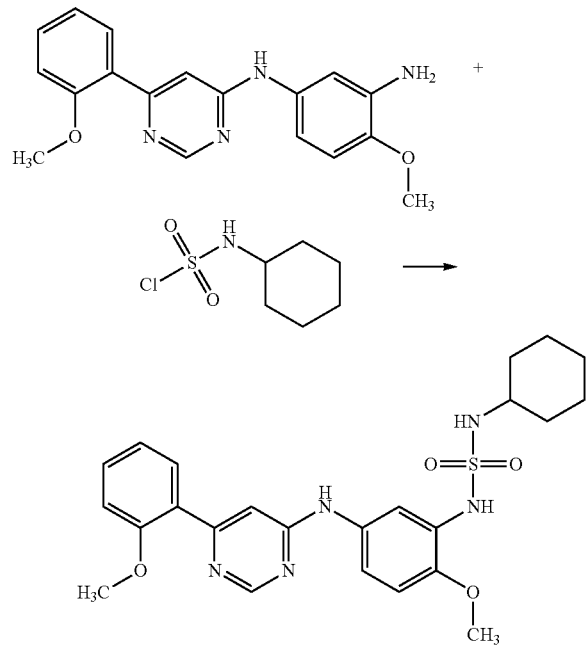

97 mg 4-Methoxy-N1-(6-(2-methoxyphenyl)pyrimidin-4-yl)benzene-1,3-diamine (obtained in Example 41, Step 3) (0.3 mmol) was dissolved in 15 ml dry acetonitrile, 55 mg potassium carbonate (0.4 mmol) and 79 mg Cyclohexylsulfamoyl chloride (0.4 mmol) was added in one portion and the mixture was refluxed overnight. Then it was evaporated under reduced pressure, 50 ml water was added and was extracted three times with 30-30 ml ethyl acetate. The combined organic layer was washed with brine, dried over MgSO$_4$ and evaporated off. Crude product was recrystallized from a minimal amount of acetonitrile to get an off white solid. Yield: 55 mg (38%). Ret. time: 3.12 min., (M+H)$^+$=484, (M+H)$^-$=482; $^1$HNMR (DMSO-d$_6$, 300 MHz), δ (ppm): 9.41 (s, 1H), 8.60 (s, 1H), 8.24 (bs, 1H), 7.92 (d, J=7.50 Hz, 1H), 7.62 (d, J=2.01 Hz, 1H), 7.44 (m, 2H), 7.35 (s, 1H), 7.15 (m, 2H), 7.06 (t, J=7.59 Hz, 1H), 6.99 (d, J=8.85 Hz, 1H), 3.87 (s, 3H), 3.80 (s, 3H), 3.10 (m, 1H), 1.70 (m, 2H), 1.61 (m, 2H), 1.48 (m, 1H), 1.10 (m, 5H).

Ethyl 2-chloro-5-(6-(2-methoxyphenyl)pyrimidin-4-ylamino)benzoate (Example 14)

Synthesis is described before as Step 4 of Example 16.

(2-Chloro-5-(6-(2-methoxyphenyl)pyrimidin-4-ylamino)phenyl)(pyrrolidin-1-yl)methanone (Example 15)

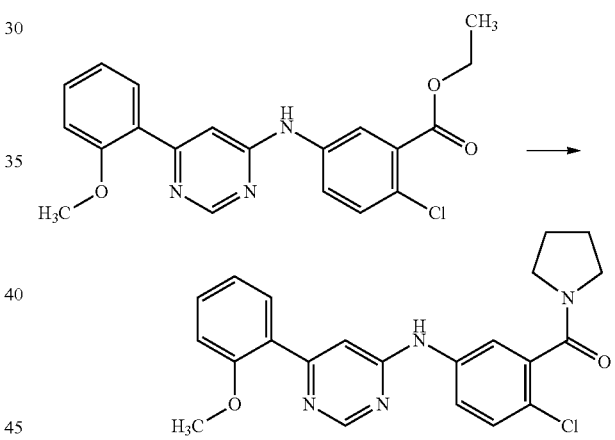

77 mg 2-Chloro-5-[6-(2-methoxy-phenyl)-pyrimidin-4-ylamino]-benzoic acid ethyl ester (obtained in Example 16, Step 4) (0.2 mmol) was dissolved in 1.74 ml pyrrolidine and was heated 50° C. for five days. Then 80 ml water was added and it was extracted four times with 30-30 ml ethyl acetate. The combined organic layer was washed twice with brine, dried over MgSO$_4$ and evaporated under reduced pressure. Residue was crystallized from 2 ml acetonitrile at 0° C. White solid was collected by filtration, washed with diethyl ether and air-dried. Yield: 65 mg (79%). Ret. time: 2.79 min., (M+H)$^+$=409, (M+H)$^-$=407; $^1$HNMR (DMSO-d$_6$, 300 MHz), δ (ppm): 9.84 (s, 1H), 8.74 (s, 1H), 7.96 (d, J=6.48 Hz, 1H), 7.86 (s, 1H), 7.68 (d, J=8.25 Hz, 1H), 7.47 (m, 3H), 7.19 (d, J=7.17 Hz, 1H), 7.08 (m, 1H), 3.90 (s, 3H), 3.49 (m, 2H), 3.15 (m, 2H), 1.86 (m, 4H).

(2-Chloro-5-(6-(2-methoxyphenyl)pyrimidin-4-ylamino)phenyl)methanol (Example 6)

Synthesis is described before as Step 5 of Example 16.

5-(6-(2-Methoxyphenyl)pyrimidin-4-ylamino)-2-(4-methylpiperazin-1-yl)phenyl)methanol (Example 17)

Step 1

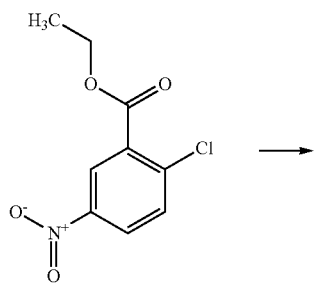

22.963 g 2-Chloro-5-nitro-benzoic acid ethyl ester (obtained in Example 16, Step 1) (100 mmol) was dissolved in 300 ml dry acetonitrile and 33.28 ml 1-methylpiperazine (30.05 g, 300 mmol) was added. The mixture was stirred at room temperature for one day. Then it was poured onto 800 g ice and it was extracted four times with 120-120 ml ethyl acetate. The combined organic layer was washed with brine, dried over MgSO$_4$ and evaporated under reduced pressure. Residue was crystallized by addition of diethyl ether and the yellow solid was collected by filtration after stirring for 30 minutes at 0° C. Yield: 22.57 g (77%). Ret. time: 0.45-1.98-2.37 min., (M+H)$^+$=294; $^1$HNMR (DMSO-d$_6$, 300 MHz), δ (ppm): 8.33 (s, 1H), 8.18 (d, J=9.06 Hz, 1H), 7.18 (d, J=9.06 Hz, 1H), 4.33 (m, 2H), 3.25 (bs, 4H), 2.42 (bs, 4H), 2.22 (s, 3H), 1.33 (t, 3H).

Step 2

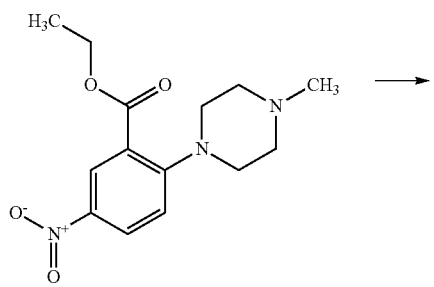

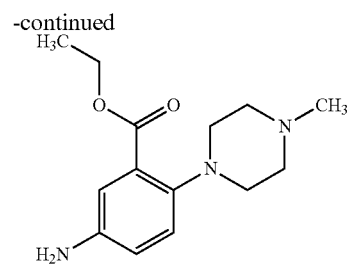

14.67 g 2-(4-Methyl-piperazin-1-yl)-5-nitro-benzoic acid ethyl ester (obtained in Step 1) (50 mmol) was dissolved in the mixture of 250 ml ethanol and 185 ml 3M hydrochloric acid and 45.13 g SnCl$_2$×2H$_2$O (200 mmol) was added. The mixture was stirred at room temperature for 3 days. Then it was poured onto 800 g ice and the pH was basified by addition of 70 g solid Na$_2$CO$_3$ carefully. Mixture was extracted four times with 150-150 ml ethyl acetate. The combined organic layer was washed with brine, dried over MgSO$_4$ and evaporated to a yellow oil. Residue was crystallized from 40 ml acetonitrile to get pure product as a yellow solid. Yield: 4.87 g (39%). Ret. time: 0.44 min., (M+H)$^+$=264; $^1$HNMR (DMSO-d$_6$, 300 MHz), δ (ppm): 6.91 (d, J=8.13 Hz, 1H), 6.70 (s, 1H), 6.64 (d, J=7.80 Hz, 1H), 4.97 (s, 2H), 4.21 (q, 2H), 2.78 (bs, 4H), 2.37 (bs, 4H), 2.18 (s, 3H), 1.30 (t, 3H).

Step 3

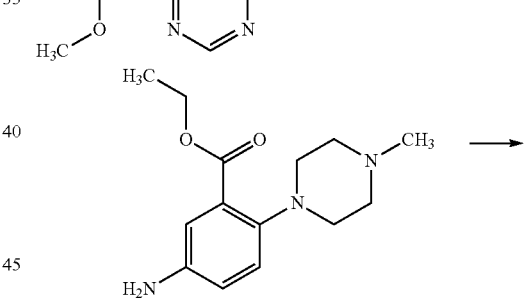

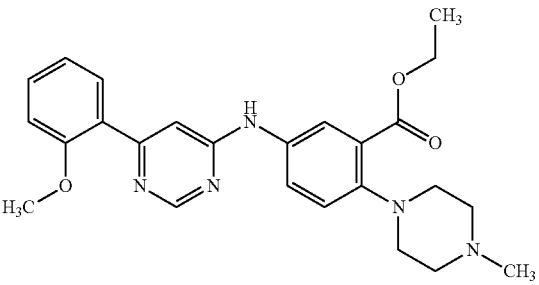

2.107 g 5-Amino-2-(4-methyl-piperazin-1-yl)-benzoic acid ethyl ester (obtained in Step 2) (8 mmol) was added to a solution of 2.206 g 4-chloro-6-(2-methoxy-phenyl)-pyrimidine (obtained in Example 32, Step 1) (10 mmol) in 80 ml of 2-propanol and 4 ml dry ethyl acetate saturated with HCl gas was added and the mixture was refluxed for 5 hours. Then it was poured onto 150 ml water, 50 ml of saturated Na$_2$CO$_3$ solution was added and extracted four times with 50-50 ml ethyl acetate. The combined organic layer was washed with brine, dried over MgSO₄ and evaporated to a brown oil. Crude product was purified by column chromatography on silica gel eluting with 2%→10% methanol in chloroform. Finally it was recrystallized from a minimal amount of acetonitrile to get a light yellow solid. Yield: 1.88 g (53%). Ret. time: 2.15 min., (M+H)⁺=448, (M+H)⁻=446. According to HPLC analysis the product contains about 30% of isopropyl ester as a side product. It was used in the next step without any further purification and NMR characterization.

Step 4:

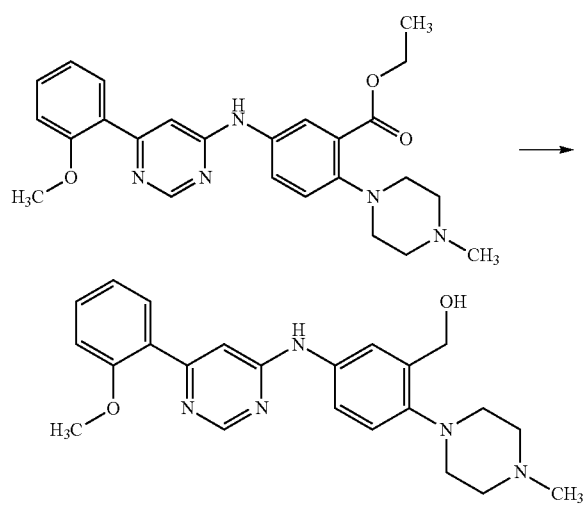

1.88 g 5-[6-(2-Methoxy-phenyl)-pyrimidin-4-ylamino]-2-(4-methyl-piperazin-1-yl)-benzoic acid ethyl ester (obtained in Step 3) (4.2 mmol) was dissolved in 100 ml dry tetrahydrofurane and cooled to 0° C. 639 mg LiAlH₄ (16.80 mmol) was added portionwise and it was stirred at room temperature for additional two hours. 2-propanol was added in order to decompose the excess of LiAlH₄ and it was poured onto the mixture of 150 g ice and 30 ml of saturated Na₂CO₃ solution. The solution was extracted four times with 50-50 ml ethyl acetate-tertahydrofurane=5:1 mixture. The combined organic layer was washed with brine, dried over MgSO₄ and evaporated to dryness. The residue was refluxed in 20 ml of acetonitrile and cooled to 0° C. The pure product was filtered off after an hour as a light yellow solid. Yield: 1.64 g (96%). Ret. time: 0.47-1.80 min., (M+H)⁺=406, (M+H)⁻=404; ¹HNMR (DMSO-d₆, 300 MHz), δ (ppm): 9.50 (s, 1H), 8.62 (s, 1H), 7.93 (d, J=6.72 Hz, 1H), 7.60 (m, 2H), 7.42 (m, 2H), 7.16 (d, J=7.23 Hz, 1H), 7.05 (m, 2H), 5.11 (bs, 1H), 4.55 (s, 2H), 3.89 (s, 3H), 2.81 (m, 4H), 2.46 (m, 4H), 2.23 (s, 3H).

Ethyl 5-(6-(2-methoxyphenyl)pyrimidin-4-ylamino)-2-morpholinobenzoate (Example 18)

Step 1

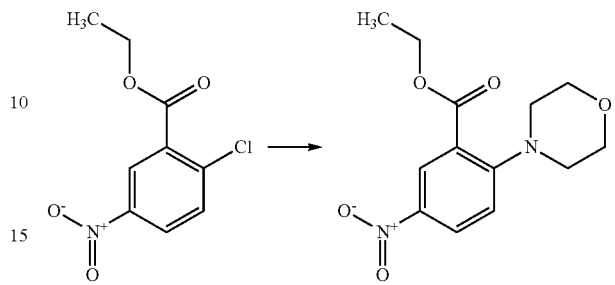

22.963 g 2-Chloro-5-nitro-benzoic acid ethyl ester (obtained in Example 16, Step 1) (100 mmol) was dissolved in 300 ml dry acetonitrile and 26.16 ml morpholine (26.14 g, 300 mmol) was added. The mixture was stirred at room temperature for one day. Then it was poured onto 800 g ice and it was extracted four times with 120-120 ml ethyl acetate. The combined organic layer was washed with brine, dried over MgSO₄ and evaporated under reduced pressure. Residue was crystallized by addition of diethyl ether and the yellow solid was collected by filtration after stirring for 30 minutes at 0° C. Yield: 24.6 g (88%). Ret. time: 3.61 min., (M+H)⁺=281; ¹HNMR (DMSO-d₆, 300 MHz), δ (ppm): 9.37 (s, 1H), 8.22 (d, J=9.09 Hz, 1H), 7.20 (d, J=9.24 Hz, 1H), 4.32 (q, 2H), 3.71 (bs, 4H), 3.25 (bs, 4H), 1.32 (t, 3H).

Step 2

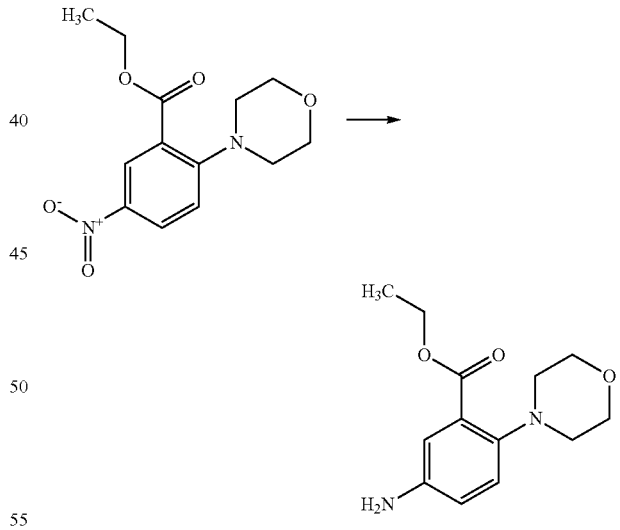

14.01 g 2-Morpholin-4-yl-5-nitro-benzoic acid ethyl ester (obtained in Step 1) (50 mmol) was dissolved in the mixture of 250 ml ethanol and 185 ml 3M hydrochloric acid and 45.13 g SnCl₂×2H₂O (200 mmol) was added. The mixture was stirred at room temperature for 3 days. Then it was poured onto 800 g ice and the pH was basified by addition of 70 g solid Na₂CO₃ carefully. Mixture was extracted four times with 150-150 ml ethyl acetate. The combined organic layer was washed with brine, dried over MgSO₄ and evaporated to a dark yellow oil. Crude product was purified by column chromatography on silica gel eluting with 1%→5% methanol in chloroform. Finally it was crystallized from a minimal amount of acetonitrile to get a brown solid. Yield: 5.60 g (45%). Ret. time: 0.45-1.66 min., (M+H)$^+$=251; $^1$HNMR (DMSO-d$_6$, 300 MHz), δ (ppm): 6.93 (d, J=8.34 Hz, 1H), 6.74 (s, 1H), 6.66 (d, J=7.71 Hz, 1H), 5.01 (s, 2H), 4.22 (q, 2H), 3.63 (bs, 4H), 2.77 (bs, 4H), 1.26 (t, 3H).

Step 3

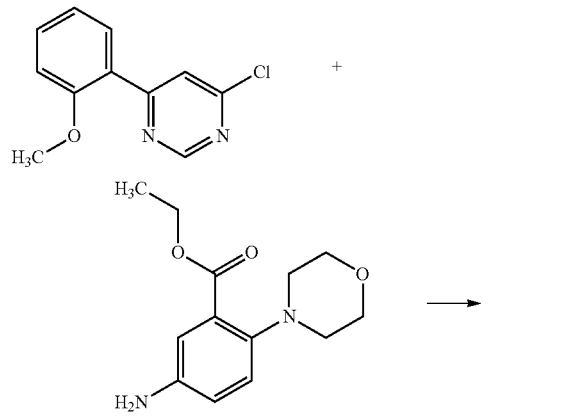

2.64 g 5-Amino-2-morpholin-4-yl-benzoic acid ethyl ester (obtained in Step 2) (10.55 mmol) was added to a solution of 2.91 g 4-chloro-6-(2-methoxy-phenyl)-pyrimidine (obtained in Example 32, Step 1) (13.2 mmol) in 100 ml of 2-propanol and 4 ml dry ethyl acetate saturated with HCl gas was added and the mixture was refluxed for 2 hours. Then it was poured onto 150 ml water, 50 ml of saturated Na$_2$CO$_3$ solution was added and extracted four times with 50-50 ml ethyl acetate. The combined organic layer was washed with brine, dried over MgSO$_4$ and evaporated under reduced pressure. Residue was recrystallized from a minimal amount of acetonitrile to get a light brown solid. Yield: 3.20 g (70%). Ret. time: 2.81 min., (M+H)$^+$=435, (M+H)$^-$=433; $^1$HNMR (DMSO-d$_6$, 300 MHz), δ (ppm): 9.63 (s, 1H), 8.66 (s, 1H), 7.95 (d, J=6.78 Hz, 1H), 7.91 (s, 1H), 7.82 (d, J=8.04 Hz, 1H), 7.43 (m, 2H) 7.15 (m, 2H), 7.08 (t, J=7.26 Hz, 1H), 4.29 (m, 2H), 3.90 (s, 3H), 3.70 (m, 4H), 2.91 (m, 4H), 1.31 (m, 3H).

(5-(6-(2-Methoxyphenyl)pyrimidin-4-ylamino)-2-morpholinophenyl)methanol (Example 19)

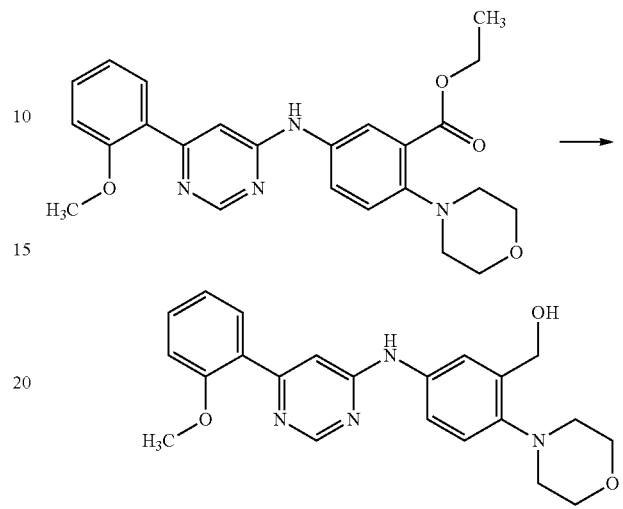

1.83 g Ethyl 5-(6-(2-methoxyphenyl)pyrimidin-4-ylamino)-2-morpholinobenzoate (obtained in Example 18, Step 3) (4.2 mmol) was dissolved in 100 ml dry tetrahydrofurane and cooled to 0° C. 639 mg LiAlH$_4$ (16.80 mmol) was added portionwise and it was stirred at room temperature for an additional hour. 2-propanol was added in order to decompose the excess of LiAlH$_4$ and it was poured onto the mixture of 150 g ice and 30 ml of saturated Na$_2$CO$_3$ solution. The solution was extracted four times with 50-50 ml ethyl acetate-tertahydrofurane=5:1 mixture. The combined organic layer was washed with brine, dried over MgSO$_4$ and evaporated to dryness. The residue was recrystallized from a minimal amount of acetonitrile to get pure product as a yellow solid. Yield: 1.37 g (83%). Ret. time: 2.27-2.42 min., (M+H)$^+$=393, (M+H)$^-$=391; $^1$HNMR (DMSO-d$_6$, 300 MHz), δ (ppm): 9.52 (s, 1H), 8.63 (s, 1H), 7.94 (d, J=6.87 Hz, 1H), 7.65 (m, 2H), 7.40 (m, 2H), 7.17 (d, J=7.47 Hz, 1H), 7.06 (m, 2H), 5.12 (s, 1H), 4.58 (s, 2H), 3.89 (s, 3H), 3.72 (m, 4H), 2.81 (m, 4H).

2-(2-Chloro-5-(6-(2-methoxyphenyl)pyrimidin-4-ylamino)benzyl)isoindoline-1,3-dione (Example 20)

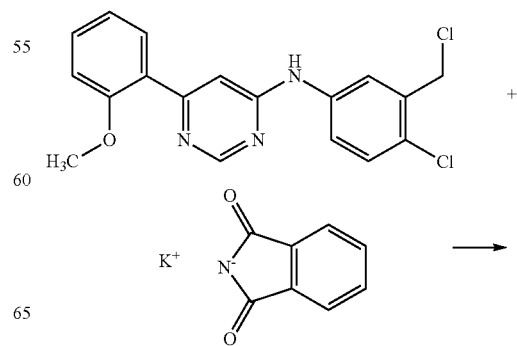

-continued

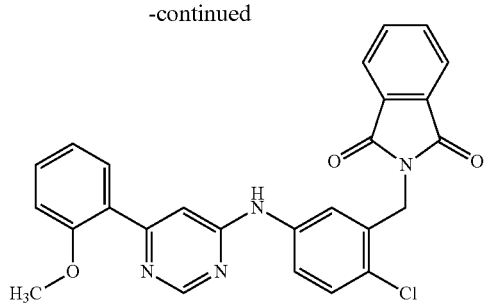

293 mg Phthalimide potassium derivative (1.58 mmol) was added to the solution of 475 mg (4-Chloro-3-chloromethyl-phenyl)-[6-(2-methoxy-phenyl)-pyrimidin-4-yl]-amine (obtained in Example 16, Step 6) (1.32 mmol) in 10 ml dry N,N-dimethylformamide and it was stirred 50° C. for five hours. Then the mixture was poured onto the mixture of 100 g ice and 10 ml of saturated $Na_2CO_3$ solution. The solution was extracted four times with 50-50 ml ethyl acetate-tertahydrofurane=5:1 mixture. The combined organic layer was washed with brine, dried over $MgSO_4$ and evaporated to dryness. The residue was refluxed in 20 ml of acetonitrile and cooled to 0° C. The pure product was filtered off after an hour as a light yellow solid. Yield: 178 mg (29%). Ret. time: 3.48 min., $(M+H)^+=471$, $(M+H)^-=469$; $^1$HNMR (DMSO-$d_6$, 300 MHz), δ (ppm): 9.68 (s, 1H), 8.37 (s, 1H), 7.90 (m, 6H), 7.52 (s, 1H), 7.45 (d, J=8.04 Hz, 2H), 7.35 (s, 1H), 7.15 (d, J=7.80 Hz, 1H), 7.05 (t, J=6.42 Hz, 1H), 4.83 (s, 2H), 3.85 (s, 3H).

Methyl 2-hydroxy-5-(6-(2-methoxyphenyl)pyrimidin-4-ylamino)benzoate (Example 21)

Step 1

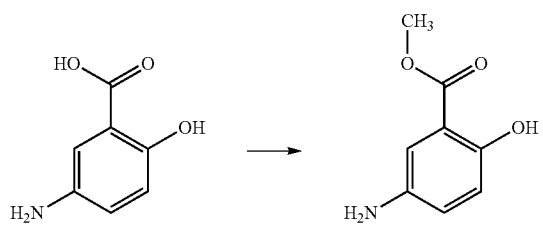

15.31 g 5-Aminosalycilic acid (100 mmol) was dissolved in 120 ml methanol and 15 ml concentrated sulfuric acid was added. The mixture was refluxed for one day. 600 g Ice was added to the solution and it was extracted with 100 ml dichloromethane once. Organic layer was discarded, pH of the inorganic layer was set to neutral by the addition of 5M NaOH solution and it was extracted further four times with 100-100 ml dichloromethane. The combined organic layer was washed with brine, dried over $MgSO_4$ and evaporated under reduced pressure. Residual brown solid was used directly in the subsequent step without further purification. Yield: 10.79 g (65%). Ret. time: 0.45-1.12 min., $(M+H)^+=168$, $(M+H)^-=166$.

Step 2

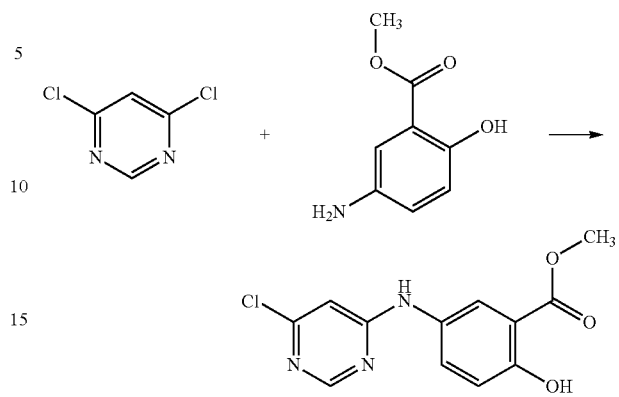

2.32 g 5-Amino-2-hydroxy-benzoic acid methyl ester (obtained in Step 1) (13.87 mmol) was dissolved in 100 ml 2-propanol, 2.250 g 4,6-Dichloropyrimidine (15.26 mmol) and 3.48 ml N-ethyl-diisopropylamine (6.46 g, 20 mmol) was added. The mixture was refluxed overnight. Then it was evaporated under reduced pressure, 150 ml water was added and it was extracted four times with 50-50 ml ethyl acetate. The combined organic layer was washed with brine, dried over $MgSO_4$ and evaporated to dryness. The residue was refluxed in 20 ml of acetonitrile and cooled to 0° C. The pure product was filtered off after an hour as a light brown solid. Yield: 2.40 g (62%). Ret. time: 3.41 min., $(M+H)^+=280$, $(M+H)^-=278$; $^1$HNMR (DMSO-$d_6$, 300 MHz), δ (ppm): 10.31 (s, 1H), 9.80 (s, 1H), 8.43 (s, 1H), 8.00 (s, 1H), 7.72 (d, J=7.95 Hz, 1H), 7.00 (d, J=8.58 Hz, 1H), 6.69 (s, 1H), 3.90 (s, 3H).

Step 3:

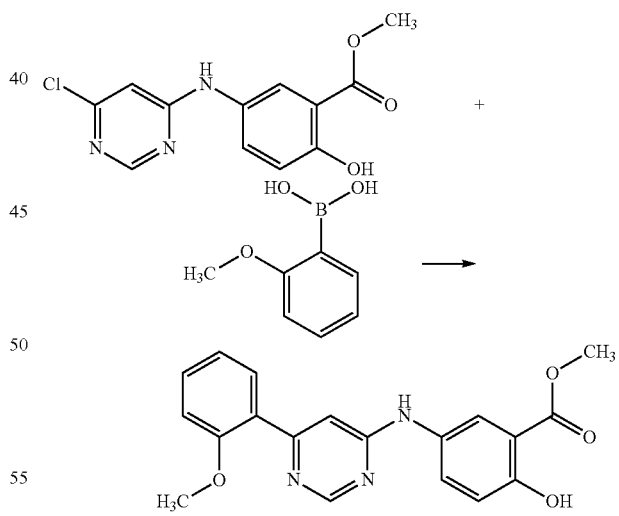

582 mg 5-(6-Chloro-pyrimidin-4-ylamino)-2-hydroxy-benzoic acid methyl ester (obtained in Step 2) (2.08 mmol) was dissolved in 50 ml 1,2-dimethoxyethane and the flask was filled with argon properly. 116 mg Tetrakis(thriphenylphosphine) palladium[0] (0.10 mmol) was added and the mixture was stirred at room temperature for 30 minutes. Then 380 mg 2-methoxyphenyl-boronic acid (2.5 mmol), 1.06 g $Na_2CO_3$ (10 mmol) and 5 ml water were added under argon atmosphere. The mixture was refluxed for 5 hours. Then it was evaporated under reduced pressure, 150 ml water was added and it was extracted three times with 40-40 ml ethyl acetate. The combined organic layer was washed with brine, decolorized with activated carbon, dried over MgSO₄ and evaporated under reduced pressure. Residue was recrystallized from a minimal amount of acetonitrile to get pure product as a yellow solid. Yield: 165 mg (23%). Ret. time: 2.79 min., (M+H)⁺=352, (M+H)⁻=350; ¹HNMR (DMSO-d₆, 300 MHz), δ (ppm): 10.26 (s, 1H), 9.57 (s, 1H), 8.65 (s, 1H), 8.14 (s, 1H), 7.95 (d, J=5.79 Hz, 1H), 7.82 (d, J=7.44 Hz, 1H), 7.45 (m, 1H), 7.37 (s, 1H), 7.17 (d, J=7.14 Hz, 1H), 7.07 (m, 1H), 7.00 (d, J=8.52 Hz, 1H), 3.91 (s, 3H), 3.89 (s, 3H).

N-(3-Fluoro-4-methoxyphenyl)-6-(2-methoxyphenyl)pyrimidin-4-amine (Example 22)

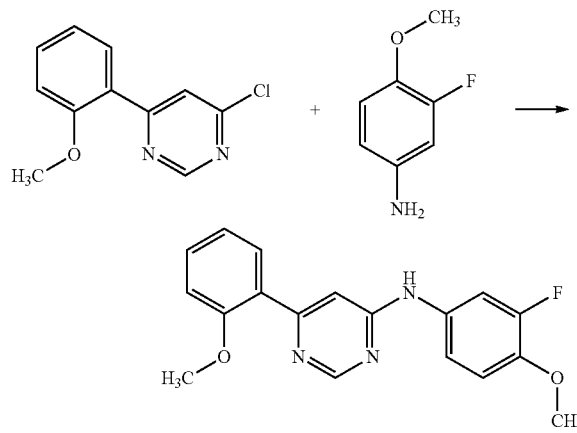

113 mg 3-Fluoro-4-methoxyaniline (0.8 mmol) was added to a solution of 221 g 4-chloro-6-(2-methoxy-phenyl)-pyrimidine (obtained in Example 32, Step 1) (1 mmol) in 40 ml of tert-butanol. 1 ml dry ethyl acetate saturated with HCl gas was added and the mixture was refluxed for 3 hours. Then it was evaporated off, 50 ml 5% NaHCO₃ solution was added and extracted three times with 40-40 ml ethyl acetate. The combined organic layer was washed with brine, dried over MgSO₄ and evaporated to dryness. The residue was crystallized from a minimal amount of acetonitrile. Yield: 53 mg (15%). Ret. time: 2.78 min., (M+H)⁺=326, (M+H)⁻=324; ¹HNMR (DMSO-d₆, 300 MHz), δ (ppm): 9.61 (s, 1H), 8.68 (s, 1H), 7.95 (d, J=6.24 Hz, 1H), 7.77 (d, J=13.20 Hz, 1H), 7.45 (m, 1H), 7.39 (s, 1H), 7.32 (d, J=7.98 Hz, 1H), 7.12 (m, 3H), 3.90 (s, 3H), 3.82 (s, 3H).

N-Benzyl-2-methoxy-5-(6-(2-methoxyphenyl)pyrimidin-4-ylamino)benzamide (Example 23)

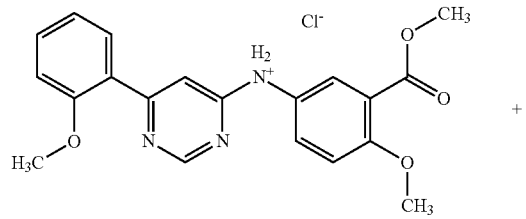

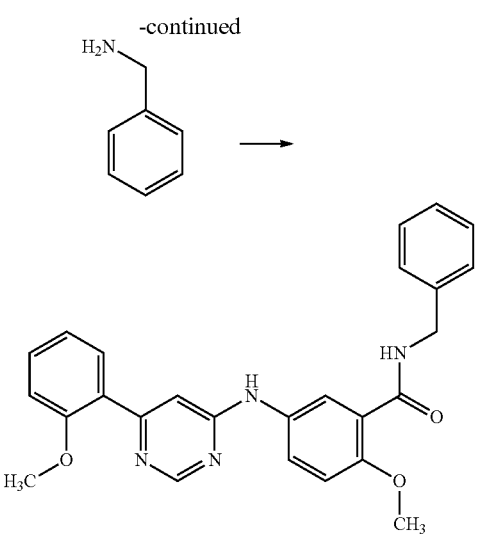

402 mg (4-Methoxy-3-methoxycarbonyl-phenyl)-[6-(2-methoxy-phenyl)-pyrimidin-4-yl]-ammonium chloride (obtained in Example 45, Step 4) (1 mmol) was heated in 2.2 ml benzylamine at 100° C. for 4 hours. 50 g Of ice was added and it was extracted four times with 30-30 ml ethyl acetate. The combined organic layer was washed twice with brine, dried over MgSO₄ and evaporated under reduced pressure. Crude product was purified by column chromatography on silica gel eluting with chloroform. After the evaporation of selected fractions product was crystallized from diisopropyl ether as an off white solid. Yield: 293 g (66%). Ret. time: 3.06 min., (M+H)⁺=441, (M+H)⁻=439; ¹HNMR (DMSO-d₆, 300 MHz), δ (ppm): 9.58 (s, 1H), 8.73 (bs, 1H), 8.64 (s, 1H), 8.01 (s, 1H), 7.95 (d, J=6.36 Hz, 1H), 7.85 (m, 1H), 7.39 (m, 6H), 7.25 (bs, 1H), 7.16 (d, J=7.56 Hz, 2H), 7.07 (m, 1H), 4.52 (s, 2H), 3.88 (s, 6H).

(2-Methoxy-5-(6-(2-methoxyphenyl)pyrimidin-4-ylamino)phenyl)methanol (Example 24)

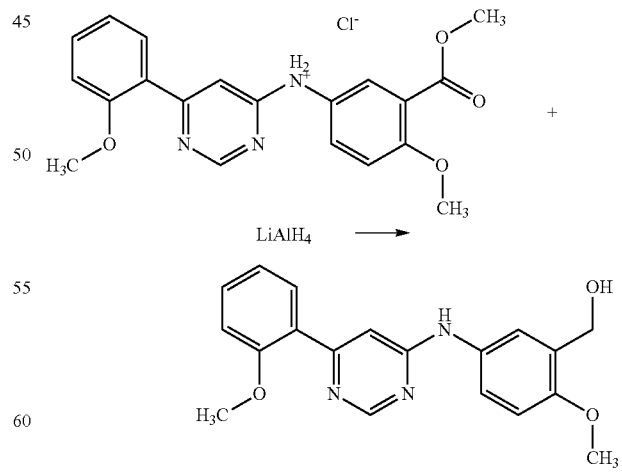

2.01 g (4-Methoxy-3-methoxycarbonyl-phenyl)-[6-(2-methoxy-phenyl)-pyrimidin-4-yl]-ammonium chloride (obtained in Example 45, Step 4) (5 mmol) was suspended in 60 ml dry tetrahydrofurane and cooled to 0° C. 760 mg LiAlH₄

(20 mmol) was added portionwise and it was stirred at room temperature for additional two hours. 2-propanol was added in order to decompose the excess of LiAlH$_4$ and it was poured onto the mixture of 150 g ice and 20 ml of saturated Na$_2$CO$_3$ solution. The solution was extracted four times with 50-50 ml ethyl acetate-tertahydrofurane=5:1 mixture. The combined organic layer was washed with brine, dried over MgSO$_4$ and evaporated to dryness. The residue was refluxed in 30 ml of acetonitrile and cooled to 0° C. The pure product was filtered off after an hour as a light yellow solid. Yield: 1.28 g (76%). Ret. time: 2.35 min., (M+H)$^+$=338, (M+H)$^-$=336; $^1$HNMR (DMSO-d$_6$, 300 MHz), δ (ppm): 9.45 (s, 1H), 8.61 (s, 1H), 7.92 (d, J=6.45 Hz, 1H), 7.56 (s, 2H), 7.44 (m, 1H), 7.36 (s, 1H), 7.16 (d, J=7.95 Hz, 1H), 7.07 (m, 1H), 6.93 (d, J=8.64 Hz, 1H), 5.07 (bs, 1H), 4.50 (s, 2H), 3.88 (s, 3H), 3.77 (s, 3H).

2-Methoxy-5-(6-(2-methoxyphenyl)pyrimidin-4-ylamino)-N-methylbenzamide (Example 25)

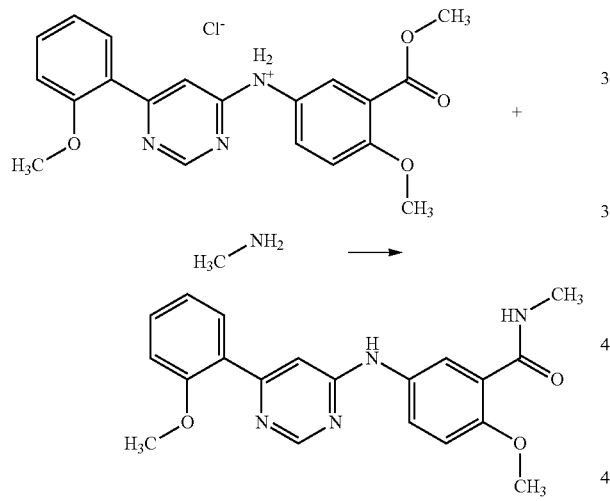

603 mg (4-Methoxy-3-methoxycarbonyl-phenyl)-[6-(2-methoxy-phenyl)-pyrimidin-4-yl]-ammonium chloride (obtained in Example 45, Step 4) (1.5 mmol) was dissolved in 4 ml of methylamine (8M solution in ethanol) and was heated in a sealed tube at 150° C. for half an hour applying microwave irradiation. Then it was evaporated under reduced pressure, 20 g of ice was added and the precipitated solid was collected by filtration, washed well with water and dried in vacuum desiccator over P$_2$O$_5$. Finally it was recrystallized from a minimal amount of acetonitrile to get the pure product as an off white solid. Yield: 417 mg (76%). Ret. time: 0.46-2.15-2.35 min., (M+H)$^+$=365, (M+H)$^-$=363; $^1$HNMR (DMSO-d$_6$, 300 MHz), δ (ppm): 9.58 (s, 1H), 8.64 (s, 1H), 8.18 (bs, 1H), 8.00 (s, 1H), 7.95 (d, J=6.48 Hz, 1H), 7.86 (d, J=7.02 Hz, 1H), 7.45 (m, 1H), 7.39 (s, 1H), 7.12 (m, 3H), 3.88 (s, 6H), 2.81 (s, 3H).

N-(3-((1H-Benzo[d]imidazol-1-yl)methyl)-4-(4-methylpiperazin-1-yl)phenyl)-6-(2-methoxyphenyl)pyrimidin-4-amine (Example 2)

Step 1

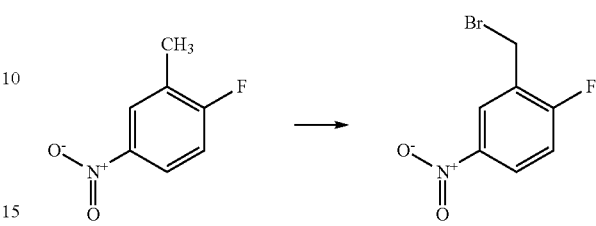

9.31 g 2-Fluoro-5-nitrotoluene (60 mmol) was dissolved in 100 ml carbon tetrachloride, 10.68 g N-bromosuccinimide (60 mmol) and 1.97 g 2,2'-Azobis(2-methyl)propionitrile (12 mmol) were added. Mixture was refluxed for two days. Then it was cooled to room temperature and the precipitated solid was filtered off. The filtrate was evaporated under reduced pressure and used up directly in the next step without any further purification or analytical investigation. Yield was considered as it had been 100%.

Step 2

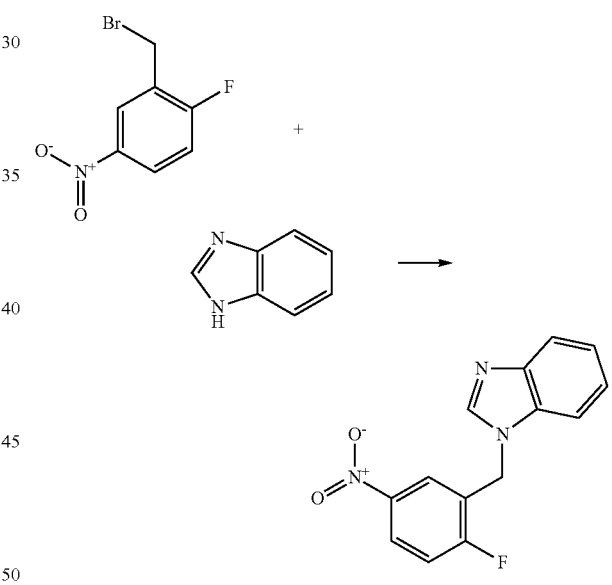

14.04 g 2-Bromomethyl-1-fluoro-4-nitro-benzene (obtained in Step 1) (60 mmol) was dissolved in 60 ml dry dichloromethane, 7.09 g benzimidazole (60 mmol) and 16.59 g K$_2$CO$_3$ were added. The mixture was heated to reflux temperature during 1 hour and refluxed overnight. Then 200 ml water was added and it was extracted three times with 150-150 ml ethyl acetate. The combined organic layer was washed with brine, dried over MgSO$_4$ and evaporated to a dark oil. Crude product was purified by column chromatography on silica gel eluting with 0%→1% methanol in chloroform. Finally it was crystallized from a minimal amount of acetonitrile to get a light yellow solid. Yield: 5.70 g (35% for two steps). Ret. time: 2.47 min., (M+H)$^+$=272, (M+H)$^-$=270; $^1$HNMR (DMSO-d$_6$, 300 MHz), δ (ppm): 8.29 (s, 1H), 8.25 (m, 2H), 7.68 (m, 1H), 7.57 (m, 2H), 7.23 (m, 2H), 6.70 (s, 2H).

Step 3

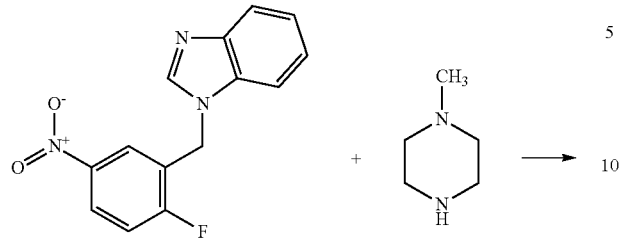

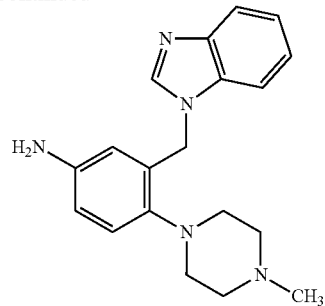

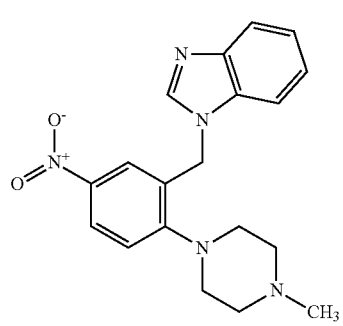

814 mg 1-(2-Fluoro-5-nitro-benzyl)-1H-benzoimidazole (obtained in Step 2) (3 mmol) was dissolved in 20 ml ethanol and 1.11 ml 1-methylpiperazine was added. Mixture was refluxed for two days. Reaction mixture was poured onto 60 g ice and 5 ml saturated $Na_2CO_3$ solution was added. The solution was extracted four times with 30-30 ml ethyl acetate. The combined organic layer was washed with brine, dried over $MgSO_4$ and evaporated under reduced pressure. Finally it was crystallized from a minimal amount of acetonitrile to get a yellow solid. Yield: 430 mg (40%). Ret. time: 0.46-1.82 min., $(M+H)^+=352$; $^1$HNMR (DMSO-$d_6$, 300 MHz), δ (ppm): 8.41 (s, 1H), 8.11 (dd, $J^4=8.82$, $J^5=2.25$, 1H), 7.69 (m, 1H), 7.57 (d, J=1.92 Hz, 1H), 7.35 (d, J=8.94 Hz, 1H), 7.31 (m, 1H), 7.21 (m, 2H), 5.57 (s, 2H), 3.10 (bs, 4H), 2.57 (bs, 4H), 2.27 (s, 3H).

Step 4

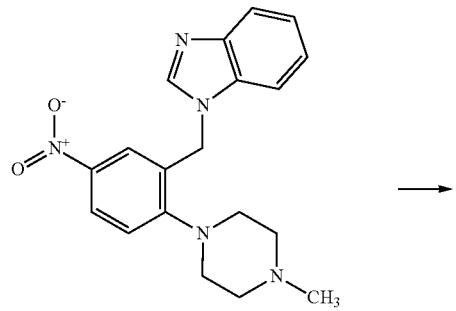

600 mg 1-[2-(4-Methyl-piperazin-1-yl)-5-nitro-benzyl]-1H-benzoimidazole (obtained in Step 3) (1.71 mmol) was dissolved in the mixture of 50 ml and 2.31 g $SnCl_2\times2H_2O$ (10.24 mmol) was added. The mixture was refluxed for 4 hours. Then it was poured onto 100 g ice and the pH was basified by addition of 5M NaOH solution. Mixture was extracted four times with 50-50 ml ethyl acetate. The combined organic layer was washed with brine, dried over $MgSO_4$ and evaporated to a dark oil. Residue was used in the subsequent step without any further purification or analytical investigation. Yield was considered as it had been 100%.

Step 5:

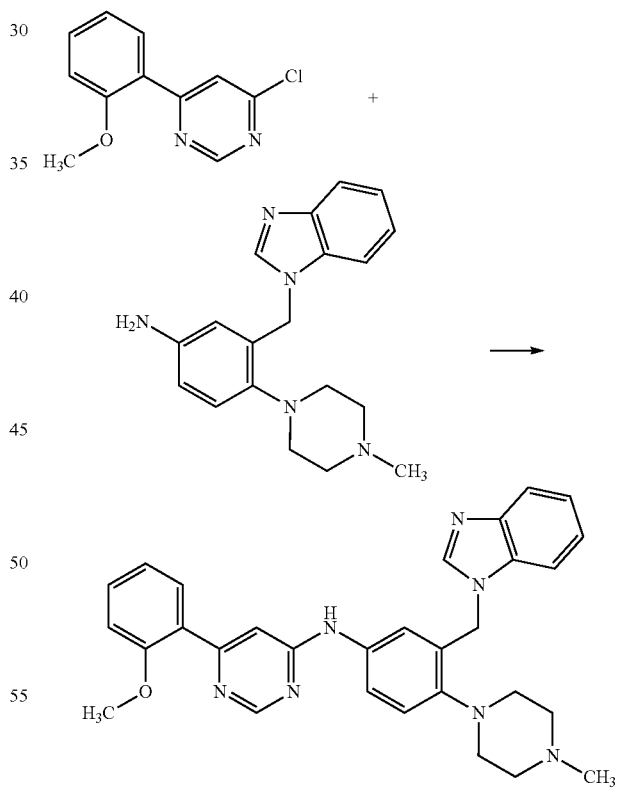

225 mg 3-Benzoimidazol-1-ylmethyl-4-(4-methyl-piperazin-1-yl)-phenylamine (obtained in Step 4) (0.7 mmol) was added to a solution of 176 mg 4-chloro-6-(2-methoxy-phenyl)-pyrimidine (obtained in Example 32, Step 1) (0.8 mmol) in 40 ml tert-butanol. 3 ml Dry ethyl acetate saturated with HCl gas was added and the mixture was refluxed for 3 hours. Reaction mixture was poured onto 100 g ice and 20 ml 2M NaOH solution was added. The solution was extracted four times with 50-50 ml ethyl acetate. The combined organic layer was washed with brine, dried over MgSO$_4$ and evaporated under reduced pressure. Finally it was crystallized from a minimal amount of acetonitrile to get a light brown solid. Yield: 50 mg (14% for two steps). Ret. time: 0.45-1.90 min., (M+H)$^+$=506, (M+H)$^-$=504; $^1$HNMR (DMSO-d$_6$, 300 MHz), δ (ppm): 8.57 (s, 1H), 8.38 (s, 1H), 7.98 (d, J=7.38 Hz, 1H), 7.43 (d, J=8.55 Hz, 1H), 7.65 (m, 1H), 7.42 (m, 2H), 7.20 (m, 6H), 7.13 (s, 1H), 7.05 (t, J=7.35 Hz, 1H), 5.52 (s, 2H), 3.84 (s, 3H), 2.89 (m, 4H), 2.55 (m, 4H), 2.26 (s, 3H).

2,2,2-Trichloroethyl 2-methoxy-5-(6-(2-methoxyphenyl)pyrimidin-4-ylamino)phenylcarbamate (Example 27)

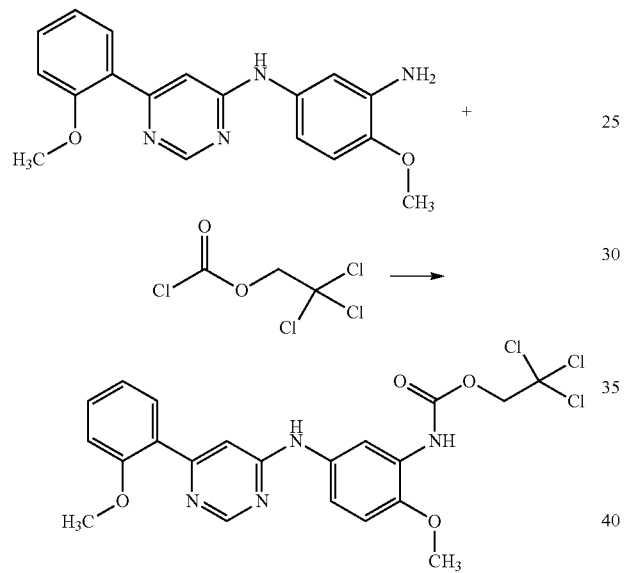

322 mg 4-Methoxy-N1-(6-(2-methoxyphenyl)pyrimidin-4-yl)benzene-1,3-diamine (obtained in Example 41, Step 3) (1 mmol) was dissolved in 15 ml dry pyridine and cooled to 0° C. 151 µl 2,2,2-Trichloroethyl chloroformate (233 mg, 1.1 mmol) was added in one portion and the mixture was stirred at room temperature for additional 3 hours. Then it was evaporated under reduced pressure, 80 ml water was added and was extracted three times with 30-30 ml ethyl acetate. The combined organic layer was washed with brine, dried over MgSO$_4$ and evaporated off. Crude product was purified by column chromatography on silica gel eluting with chloroform. Finally it was recrystallized from a minimal amount of acetonitrile to get an off white solid. Yield: 264 mg (53%). Ret. time: 3.42 min., (M+H)$^+$=497, (M+H)$^-$=495; $^1$HNMR (DMSO-d$_6$, 300 MHz), δ (ppm): 9.48 (s, 1H), 9.02 (s, 1H), 8.62 (s, 1H), 7.93 (d, J=7.05 Hz, 1H), 7.85 (s, 1H), 7.53 (d, J=7.89 Hz, 1H), 7.44 (m, 1H), 7.37 (s, 1H), 7.16 (d, J=7.86 Hz, 1H), 7.03 (m, 2H), 4.92 (s, 2H), 3.88 (s, 3H), 3.80 (s, 3H).

2-Methoxy-5-(6-(2-methoxyphenyl)pyrimidin-4-ylamino)-N-(pyridin-4-ylmethyl)benzamide (Example 28)

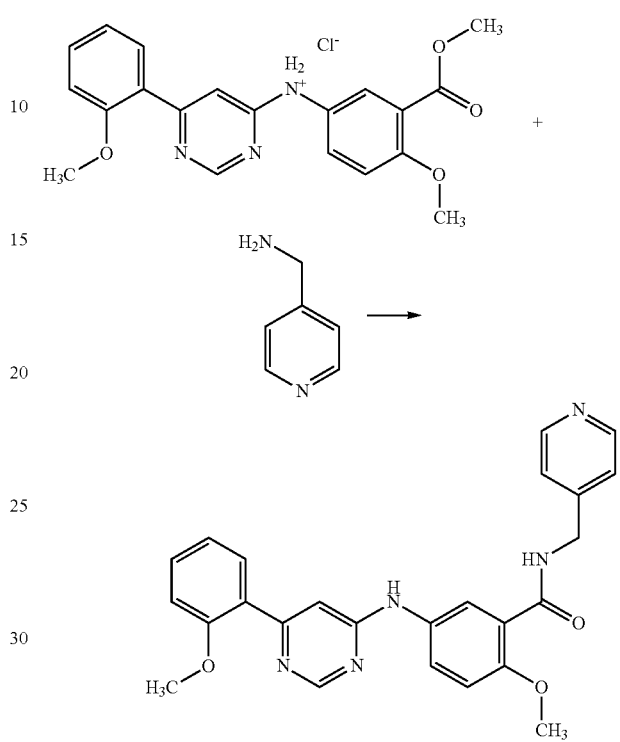

402 mg (4-Methoxy-3-methoxycarbonyl-phenyl)-[6-(2-methoxy-phenyl)-pyrimidin-4-yl]-ammonium chloride (obtained in Example 45, Step 4) (1 mmol) was heated in 710 µl 4-(aminomethyl)pyridine at 100° C. for 36 hours. 50 g Of ice was added and it was extracted four times with 30-30 ml ethyl acetate. The combined organic layer was washed twice with brine, dried over MgSO$_4$ and evaporated under reduced pressure. Crude product was purified by column chromatography on silica gel eluting with chloroform. After the evaporation of selected fractions product was crystallized from acetonitrile as a light yellow solid. Yield: 225 mg (51%). Ret. time: 0.44-2.00 min., (M+H)$^+$=442, (M+H)$^-$=440; $^1$HNMR (DMSO-d$_6$, 300 MHz), δ (ppm): 9.58 (s, 1H), 8.85 (bs, 1H), 8.65 (s, 1H), 8.51 (bs, 2H), 8.01 (s, 1H), 7.95 (d, J=6.51 Hz, 1H), 7.87 (d, J=8.52 Hz, 1H), 7.45 (m, 1H), 7.39 (s, 1H), 7.33 bs, 2H), 7.17 (d, J=4.62 Hz, 2H), 7.07 (t, J=7.56 Hz, 1H), 4.53 (s, 2H), 3.92 (s, 3H), 3.88 (s, 3H).

2-Methoxy-5-(6-(2-methoxyphenyl)pyrimidin-4-ylamino)benzaldehyde (Example 29)

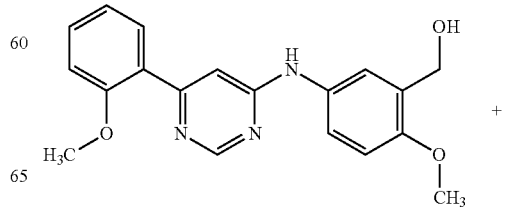

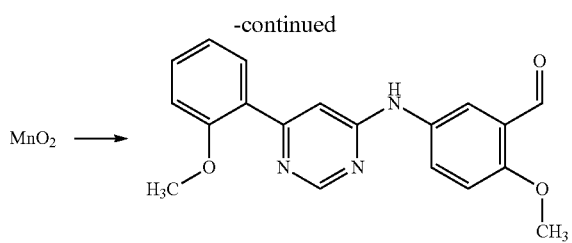

1.27 g (2-Methoxy-5-(6-(2-methoxyphenyl)pyrimidin-4-ylamino)phenyl) methanol (obtained in Example 24) (3.76 mmol) was dissolved in 100 ml toluene and 1.64 g MnO$_2$ (18.82 mmol) was added. The mixture was refluxed until TLC indicates the presence of the starting material. It took about two days and further addition of MnO$_2$ was necessary once. It was filtered through celit pad and the filtrate was evaporated to dryness. The residue was recrystallized from a minimal amount of acetonitrile to get the pure product as a white solid. Yield: 683 mg (54%). Ret. time: 2.36-2.60 min., (M+H)$^+$=336, (M+H)$^-$=334; $^1$HNMR (DMSO-d$_6$, 300 MHz), δ (ppm): 10.38 (s, 1H), 9.64 (s, 1H), 8.67 (s, 1H), 8.05 (s, 1H), 7.95 (d, J=6.90 Hz, 2H), 7.45 (m, 1H), 7.40 (s, 1H), 7.26 (d, J=8.88 Hz, 1H), 7.18 (d, J=7.95 Hz, 1H), 7.08 (m, 1H), 3.91 (s, 3H), 3.89 (s, 3H).

Methyl 2-methoxy-5-(6-(2-methoxyphenyl)pyrimidin-4-ylamino)benzoate (Example 30)

Synthesis is described before as Step 4 of Example 45.

N-(3-((1H-Benzo[d]imidazol-1-yl)methyl)-4-methoxyphenyl)-6-(2-methoxyphenyl)pyrimidin-4-amine (Example 31)

Step 1:

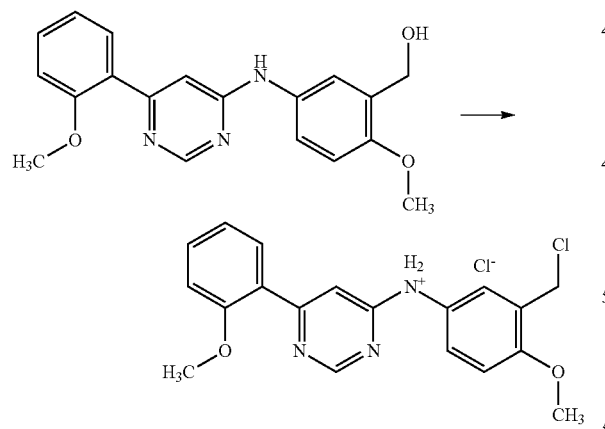

4.77 g (2-Methoxy-5-(6-(2-methoxyphenyl)pyrimidin-4-ylamino)phenyl) methanol (obtained in Example 24) (14.14 mmol) was dissolved in the mixture of 100 ml dry dichloromethane and 10 ml dry N,N-dimethylformamide. 2.50 ml Phosphorus trichloride (3.89 g, 28.29 mmol) was added in one portion at 0° C. and it was stirred overnight at room temperature. The reaction mixture was cooled in an ice bath and the precipitated yellow solid was filtered off and washed with dichloromethane. The combined organic layer was washed twice with brine, dried over MgSO$_4$ and evaporated under reduced pressure. The product was used up directly in the next step without any further purification. Yield: 3.77 g (68%). Ret. time: 2.97 min., (M+H)$^+$=356, (M+H)$^-$=354.

Step 2:

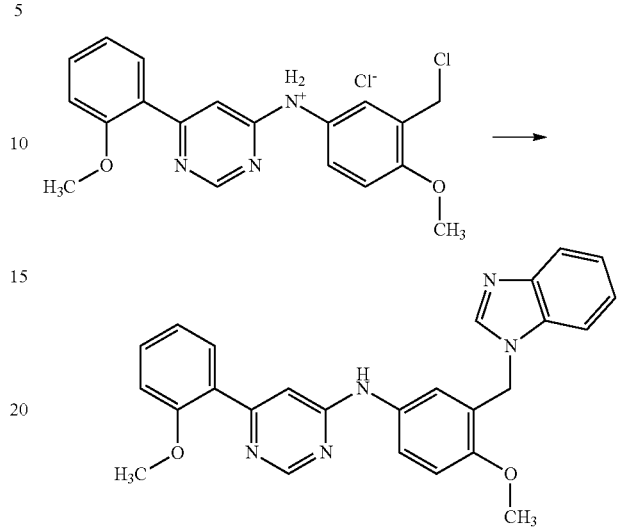

392 mg (3-Chloromethyl-4-methoxy-phenyl)-[6-(2-methoxy-phenyl)-pyrimidin-4-yl]-ammonium chloride (obtained in Step 1) (1 mmol) was dissolved in 20 ml dry N,N-dimethylformamide, 414 mg potassium carbonate (3 mmol) and 142 mg benzimidazole (1.2 mmol) were added and the mixture was heated at 75° C. overnight. Then it was evaporated under reduced pressure, 80 ml water was added and was extracted three times with 40-40 ml ethyl acetate. The combined organic layer was washed twice with brine, dried over MgSO$_4$ and evaporated off. Crude product was purified by column chromatography on silica gel eluting with 1%→5% methanol in chloroform. It was then recrystallized from a minimal amount of acetonitrile to get a yellow solid. Yield: 137 mg (31%). Ret. time: 0.48-2.00-2.23 min., (M+H)$^+$=438, (M+H)$^-$=436; $^1$HNMR (DMSO-d$_6$, 300 MHz), δ (ppm): 9.33 (bs, 1H), 8.59 (s, 1H), 8.28 (s, 1H), 7.90 (d, J=7.32 Hz, 1H), 7.65 (m, 2H), 7.53 (m, 1H), 7.42 (m, 1H), 7.26 (m, 2H), 7.18 (m, 3H), 7.05 (d, J=8.37 Hz, 2H), 5.44 (s, 2H), 3.86 (s, 3H), 8.84 (s, 3H).

N-(3-((Benzylamino)methyl)-4-methoxyphenyl)-6-(2-methoxyphenyl)pyrimidin-4-amine (Example 1)

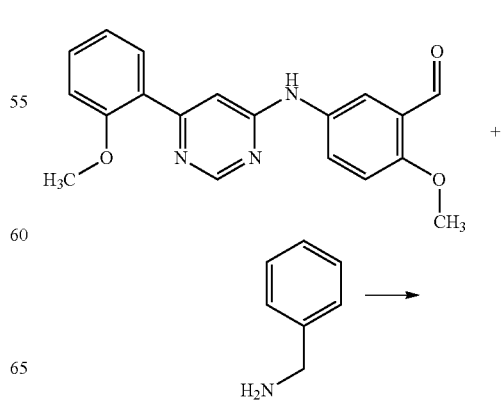

-continued

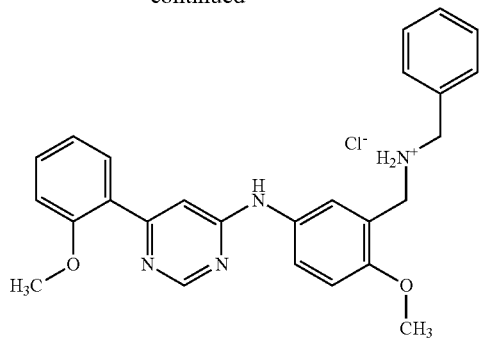

186 mg 2-Methoxy-5-(6-(2-methoxyphenyl)pyrimidin-4-ylamino) benzaldehyde (obtained in Example 29) (0.5 mmol) was dissolved in 20 ml ethanol, 5 mg p-toluenesulfonic acid and 66 μl benzylamine (64 mg, 0.6 mmol) were added. The mixture was refluxed overnight. It was cooled to room temperature and 38 mg sodium borohydride (1 mmol) was added. The mixture was stirred for further 3 hours at room temperature. Then it was evaporated under reduced pressure, 80 ml water, 10 ml saturated $Na_2CO_3$ solution were added and was extracted three times with 40-40 ml ethyl acetate. The combined organic layer was washed twice with brine, dried over $MgSO_4$ and evaporated off. Crude product was purified by column chromatography on silica gel eluting with 5%→10% methanol in chloroform. Selected fractions were evaporated under reduced pressure and then it was taken up in 20 ml ethyl acetate. 1 ml dry ethyl acetate saturated with HCl gas was added at 0° C. The precipitated yellow hydrochloride salt was collected by filtration and was washed well with ethyl acetate, diethyl ether and dried in vacuum desiccator over $P_2O_5$. Yield: 155 mg (67%). Ret. time: 0.46-2.01-2.23 min., $(M+H)^+=427$, $(M+H)^-=425$; $^1HNMR$ (DMSO-$d_6$, 300 MHz), δ (ppm): 11.50 (bs, 1H), 9.61 (bs, 2H), 8.82 (s, 1H), 7.74 (s, 1H), 7.68 (d, J=6.63 Hz, 2H), 7.59 (m, 3H), 7.43 (m, 4H), 7.27 (d, J=8.34 Hz, 1H), 7.15 (d, J=7.98 Hz, 2H), 4.17 (s, 2H), 4.06 (s, 2H), 3.90 (s, 3H), 3.83 (s, 3H).

2-Methoxy-5-(6-(2-methoxyphenyl)pyrimidin-4-ylamino)benzohydrazide (Example 33)

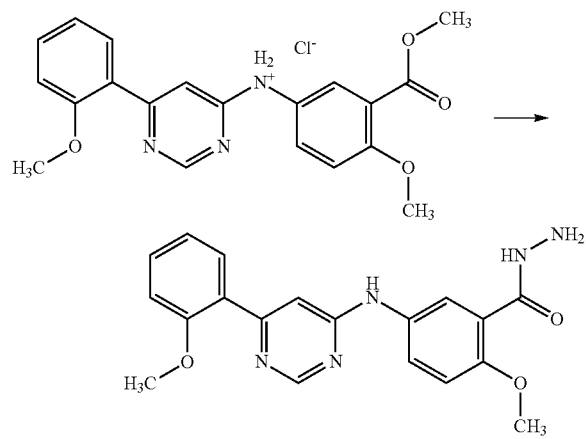

321 mg (4-Methoxy-3-methoxycarbonyl-phenyl)-[6-(2-methoxy-phenyl)-pyrimidin-4-yl]-ammonium chloride (obtained in Example 45, Step 4) (0.8 mmol) was dissolved in 3 ml hydrazine hydrate and was heated in a sealed tube at 150° C. for an hour. Then 50 g of ice was added and the precipitated solid was collected by filtration, washed well with water and dried in vacuum desiccator over $P_2O_5$. Off white solid. Yield: 252 mg (86%). Ret. time: 0.45-2.07 min., $(M+H)^+=366$, $(M+H)^-=364$; $^1HNMR$ (DMSO-$d_6$, 300 MHz), δ (ppm): 9.57 (s, 1H), 9.23 (s, 1H), 8.64 (s, 1H), 7.96 (m, 2H), 7.83 (d, J=9.21 Hz, 1H), 7.44 (t, J=8.16 Hz, 1H), 7.39 (s, 1H), 7.17 (d, J=8.55 Hz, 1H), 7.12 (d, J=9.00 Hz, 1H), 7.07 (t, J=7.47 Hz, 1H), 4.55 (s, 2H), 3.89 (s, 3H), 3.86 (s, 3H).

N-(4-Methoxy-3-((phenylamino)methyl)phenyl)-6-(2-methoxyphenyl)pyrimidin-4-amine (Example 34)

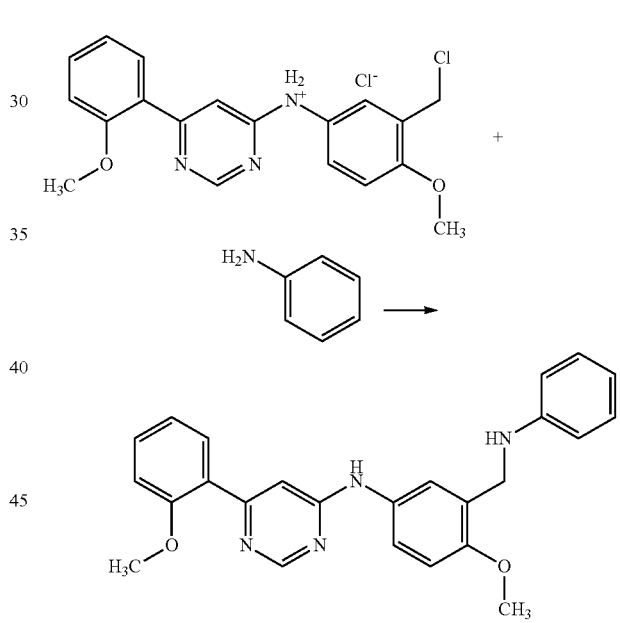

392 mg (3-Chloromethyl-4-methoxy-phenyl)-[6-(2-methoxy-phenyl)-pyrimidin-4-yl]-ammonium chloride (obtained in Example 31, Step 1) (1 mmol) was dissolved in 1 ml aniline and it was heated at 50° C. for 4 hours. Then 50 ml water, 10 ml diethyl ether were added and the mixture was put into ultrasonic cleaner for 10 minutes. Pure product was filtered off as a yellow solid. It was washed with diethyl ether and dried in vacuum desiccator over $P_2O_5$. Yield: 150 mg (36%). Ret. time: 3.02 min., $(M+H)^+=413$, $(M+H)^-=411$; $^1HNMR$ (DMSO-$d_6$, 300 MHz), δ (ppm): 11.12 (bs, 1H), 8.77 (s, 1H), 7.60 (m, 3H), 7.40 (s, 1H), 7.26 (d, J=7.50 Hz, 1H), 7.01 (m, 5H), 6.56 (m, 3H), 4.24 (s, 2H), 3.87 (s, 6H).

N-(3-((Dimethylamino)methyl)-4-methoxyphenyl)-6-(2-methoxyphenyl)pyrimidin-4-amine (Example 35)

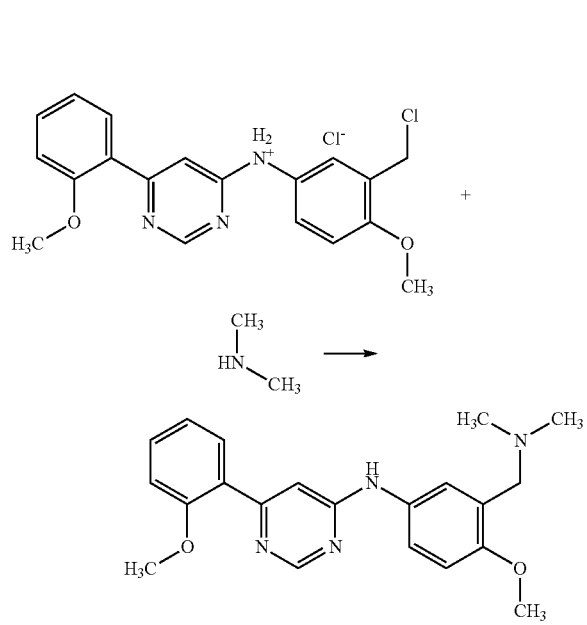

392 mg (3-Chloromethyl-4-methoxy-phenyl)-[6-(2-methoxy-phenyl)-pyrimidin-4-yl]-ammonium chloride (obtained in Example 31, Step 1) (1 mmol) was dissolved in 2 ml ethanol containing 5.6M dimethylamine and it was heated at 50° C. for 3 hours in a sealed tube. Then 70 ml water was added and it was extracted three times with 30-30 ml ethyl acetate. The combined organic layer was washed with brine, dried over MgSO$_4$ and evaporated off. Crude product was recrystallized from a minimal amount of acetonitrile to get a yellow solid. Yield: 85 mg (25%). Ret. time: 0.45-1.82 min., (M+H)$^+$=365, (M+H)$^-$=363; $^1$HNMR (DMSO-d$_6$, 300 MHz), δ (ppm): 9.41 (s, 1H), 8.61 (s, 1H), 7.92 (d, J=5.91 Hz, 1H), 7.61 (s, 1H), 7.46 (m, 2H), 7.35 (s, 1H), 7.15 (d, J=6.60 Hz, 1H), 7.06 (m, 1H), 6.96 (d, J=7.68 Hz, 1H), 3.87 (s, 3H), 3.76 (s, 3H), 3.39 (s, 2H), 2.18 (s, 6H).

N-(3-(Benzyloxy)-4-methoxyphenyl)-6-(2-methoxyphenyl)pyrimidin-4-amine (Example 36)

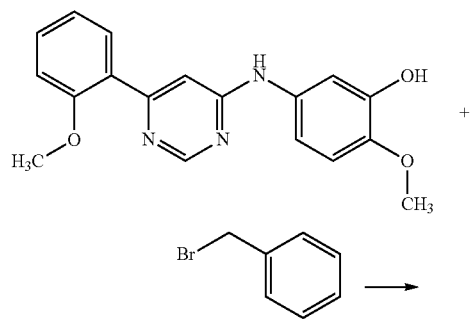

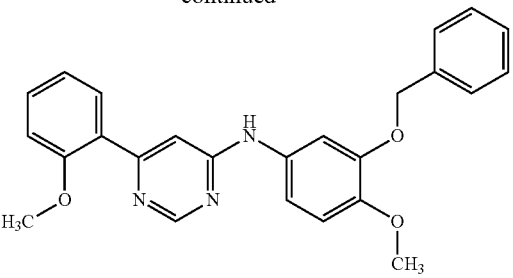

323 mg 2-Methoxy-5-(6-(2-methoxyphenyl)pyrimidin-4-ylamino)phenol (obtained in Example 32, Step 2) (1 mmol) was dissolved in 15 ml N,N-dimethylformamide and cooled to 0° C. 124 mg KOtBu (1.1 mmol) was added and stirred for half an hour at this temperature. 131 μl Benzyl bromide was added and it was stirred at room temperature overnight. Reaction mixture was poured onto 70 g ice, 2 ml 5M NaOH solution were added and it was extracted three times with 30-30 ml ethyl acetate. The combined organic layer was washed with brine, dried over MgSO$_4$ and evaporated under reduced pressure. Crude product was recrystallized from a minimal amount of acetonitrile to get a light brown solid. Yield: 260 mg (63%). Ret. time: 3.12 min., (M+H)$^+$=414, (M+H)$^-$=412; $^1$HNMR (DMSO-d$_6$, 300 MHz), δ (ppm): 9.39 (s, 1H), 8.62 (s, 1H), 7.93 (s, 1H), 7.43 (m, 8H), 7.18 (m, 2H), 7.07 (m, 1H), 6.96 (m, 1H), 5.09 (s, 2H), 3.88 (s, 3H), 3.77 (s, 3H).

N-(4-Methoxy-3-((methylamino)methyl)phenyl)-6-(2-methoxyphenyl)pyrimidin-4-amine (Example 37)

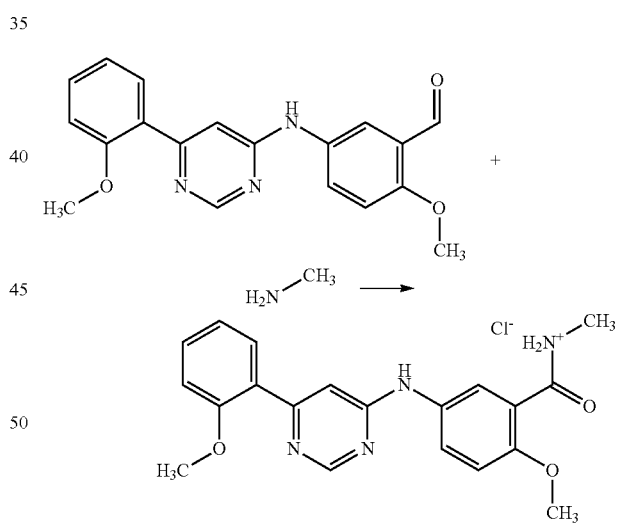

335 mg 2-Methoxy-5-(6-(2-methoxyphenyl)pyrimidin-4-ylamino) benzaldehyde (obtained in Example 29) (1 mmol) was dissolved in 20 ml ethanol, 5 mg p-toluenesulfonic acid and 500 μl methylamine 8M solution in ethanol (4 mmol) were added. The mixture was stirred at room temperature for 3 hours. It was cooled to room temperature and 76 mg sodium borohydride (2 mmol) was added. The mixture was stirred for further 2 hours at room temperature. Then it was evaporated under reduced pressure, 80 ml water, 10 ml saturated Na$_2$CO$_3$ solution were added and was extracted three times with 40-40 ml ethyl acetate. The combined organic layer was washed twice with brine, dried over MgSO$_4$ and evaporated to a yellow oil. Crude product was purified by column chromatography on silica gel eluting with 5%→10% methanol in chloroform. Selected fractions were evaporated under reduced pressure and then it was taken up in 30 ml ethyl acetate. 1 ml dry ethyl acetate saturated with HCl gas was added at 0° C. The precipitated yellow hydrochloride salt was collected by filtration and was washed well with ethyl acetate, diethyl ether and dried in vacuum desiccator over P$_2$O$_5$. Yield: 108 mg (28%). Ret. time: 0.44-1.81 min., (M+H)$^+$=351, (M+H)$^-$=349; $^1$HNMR (DMSO-d$_6$, 300 MHz), δ (ppm): 11.59 (bs, 1H), 9.16 (bs, 2H), 8.83 (s, 1H), 7.73 (m, 3H), 7.62 (m, 1H), 7.40 (s, 1H), 7.27 (m, 1H), 7.17 (m, 2H), 4.09 (s, 2H), 3.89 (s, 6H), 3.45 (bs, 3H).

5-(6-(2-Methoxyphenyl)pyrimidin-4-ylamino)-2-(4-methylpiperazin-1-yl)benzenesulfonamide (Example 38)

Step 1

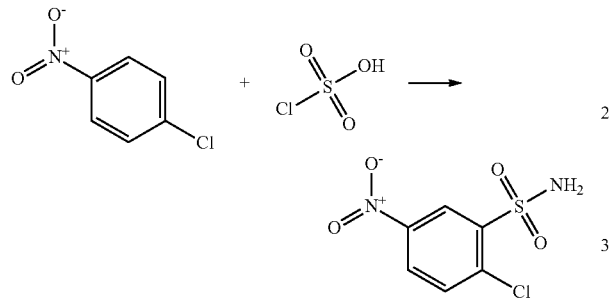

9.45 g 1-Chloro-4-nitrobenzene (60 mmol) was heated in 20 ml chlorosulfonic acid at 120° C. overnight. The mixture was then poured onto 400 g ice and it was extracted four times with 50-50 ml dichloromethane. The combined organic layer was washed twice with brine, dried over MgSO$_4$. Then it was added dropwise to an ice cold solution of 50 ml tetrahydrofurane and 40 ml of 25% NH$_4$OH solution. After the addition it was stirred for an additional hour at room temperature. Then it was evaporated under reduced pressure, 200 ml water, 10 ml concentrated hydrochloric acid solution were added carefully and was extracted three times with 100-100 ml ethyl acetate. The combined organic layer was washed with brine, dried over MgSO$_4$ and evaporated off again. Product was filtered from diethyl ether as a brown solid. Yield: 6.53 g (46%). Ret. time: 2.55 min., (M+H)$^-$=235.

Step 2

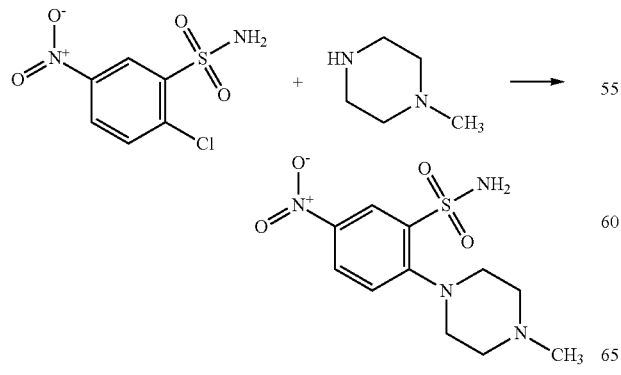

4.50 g 2-Chloro-5-nitro-benzenesulfonamide (obtained in Step 1) (19 mmol) was heated in 15 ml 1-methylpiperazine at 100° C. for 4 hours. The mixture was then poured onto 200 g ice and it was extracted four times with 50-50 ml ethyl acetate. The combined organic layer was washed twice with brine, dried over MgSO$_4$ and evaporated under reduced pressure. Crude product was recrystallized from a minimal amount of acetonitrile to get a yellow solid. Yield: 3.28 g (57%). Ret. time: 0.48-1.62 min., (M+H)$^+$=301, (M+H)$^-$=299; $^1$HNMR (DMSO-d$_6$, 300 MHz), δ (ppm): 8.68 (d, J=2.76 Hz, 1H), 8.31 (dd, J$^4$=9.00 Hz, J$^5$=2.79 Hz, 1H), 7.49 (d, J=9.03 Hz, 1H), 7.42 (s, 2H), 2.20 (m, 4H), 2.48 (m, 4H), 2.21 (s, 3H).

Step 3

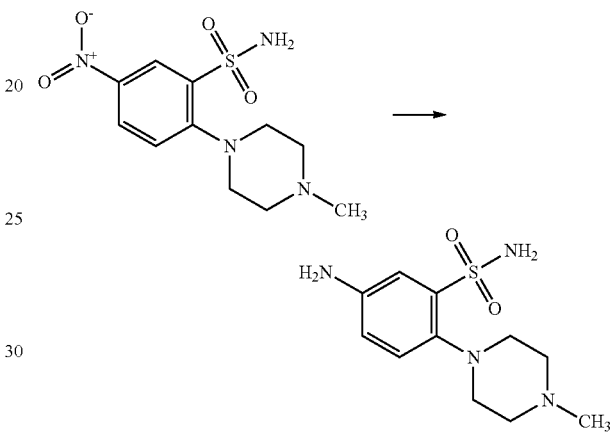

2.36 g 2-(4-Methyl-piperazin-1-yl)-5-nitro-benzenesulfonamide (obtained in Step 2) (0.7 mmol) was dissolved in 200 ml methanol-dichloromethane=3-1, 150 mg Pd catalyst (10% Pd on activated carbon) was added carefully and it was stirred vigorously in H$_2$ atmosphere under standard pressure at room temperature until TLC indicates the end of the reaction. Catalyst was filtered off and the filtrate was evaporated under reduced pressure. Finally it was crystallized from acetonitrile to get a brown solid. Yield: 860 mg (40%). Ret. time: 0.46 min., (M+H)$^+$=271, (M+H)$^-$=269; $^1$HNMR (DMSO-d$_6$, 300 MHz), δ (ppm): 7.23 (d, J=8.46 Hz, 1H), 7.05 (d, J=2.28 Hz, 1H), 6.78 (s, 2H), 6.73 (dd, J$^4$=8.37 Hz, J$^5$=2.16 Hz, 1H), 5.41 (s, 2H), 3.31 (s, 4H), 2.82 (s, 4H), 2.21 (s, 3H).

Step 4

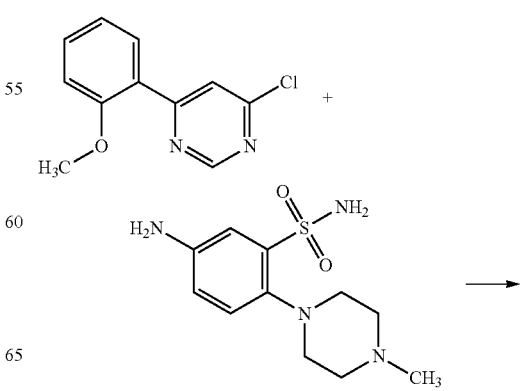

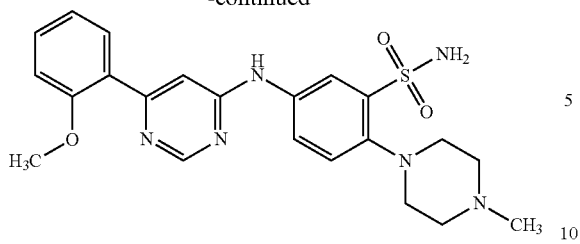

270 mg 5-Amino-2-(4-methyl-piperazin-1-yl)-benzenesulfonamide (obtained in Step 3) (1 mmol) was added to a solution of 176 mg 4-chloro-6-(2-methoxy-phenyl)-pyrimidine (obtained in Example 32, Step 1) (1.1 mmol) in 40 ml 2-propanol. 3 ml Dry ethyl acetate saturated with HCl gas was added and the mixture was refluxed for 3 hours. Reaction mixture was poured onto 150 ml NaH$_2$PO$_4$ solution was added. The solution was extracted four times with 50-50 ml ethyl acetate. The combined organic layer was washed with brine, dried over MgSO$_4$ and evaporated under reduced pressure. Finally it was crystallized from a minimal amount of acetonitrile to get a light brown solid. Yield: 97 mg (21%). Ret. time: 0.46-1.96 min., (M+H)$^+$=455, (M+H)$^-$= 453; $^1$HNMR (DMSO-d$_6$, 300 MHz), δ (ppm): 9.87 (s, 1H), 8.71 (s, 1H), 8.22 (s, 1H), 8.02 (d, J=9.39 Hz, 1H), 7.98 (d, J=7.77 Hz, 1H), 7.57 (d, J=8.64 Hz, 1H), 7.45 (m, 2H), 7.19 (d, J=8.28 Hz, 1H), 7.08 (t, J=7.23 Hz, 1H), 6.90 (s, 2H), 3.91 (s, 3H), 2.93 (m, 4H), 2.48 (m, 4H), 2.24 (s, 3H).

N-(3-((1H-Benzo[d]imidazol-1-yl)methyl)-4-ethoxyphenyl)-6-(2-methoxyphenyl)pyrimidin-4-amine
(Example 39)

Step 1

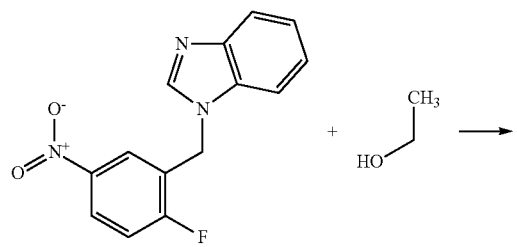

615 mg Sodium (26.73 mmol) was dissolved in 20 ml ethanol and 2.90 g 1-(2-fluoro-5-nitro-benzyl)-1H-benzoimidazole (obtained in Example 2, Step 2) (10.69 mmol) was added. Mixture was refluxed for 3 hours. Reaction mixture was poured onto 200 g ice and it was stirred until the ice melted. Precipitated solid was collected by filtration and washed well with water. Finally it was recrystallized from a minimal amount of acetonitrile to get a light brown solid. Yield: 880 mg (28%). Ret. time: 2.11 min., (M+H)$^+$=298, (M+H)$^-$=296 (low intensity); $^1$HNMR (DMSO-d$_6$, 300 MHz), δ (ppm): 8.31 (s, 1H), 8.22 (s, 1H), 8.18 (s, 1H), 7.65 (d, J=6.12 Hz, 1H), 7.57 (d, J=6.30 Hz, 1H), 7.21 (m, 3H), 5.54 (s, 2H), 4.21 (q, 2H), 1.36 (t, 3H).

Step 2

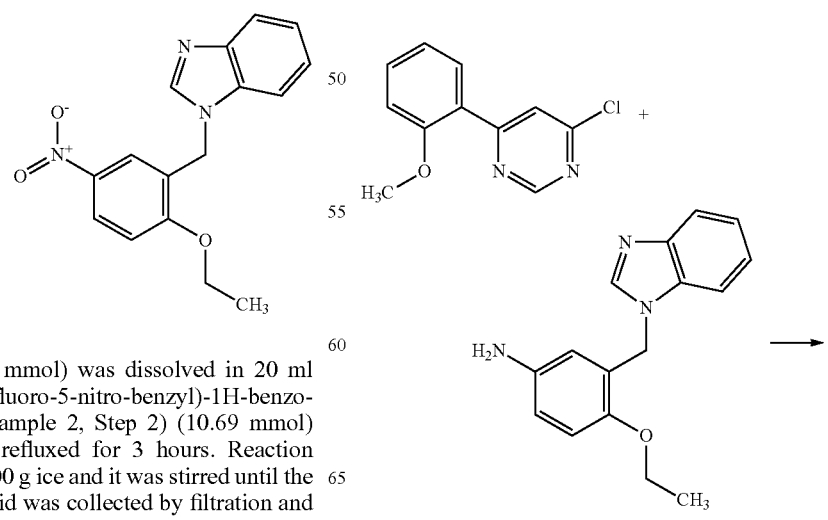

830 mg 1-(2-Ethoxy-5-nitro-benzyl)-1H-benzoimidazole (obtained in Step 1) (2.79 mmol) was dissolved in 50 ml ethanol and 2.52 g SnCl$_2$×2H$_2$O (11.17 mmol) was added. The mixture was refluxed for 3 hours. Then it was poured onto 100 g ice and the pH was basified by addition of 5M NaOH solution. Mixture was extracted four times with 50-50 ml ethyl acetate. The combined organic layer was washed with brine, dried over MgSO$_4$ and evaporated to a dark oil. Residue was used in the subsequent step without any further purification or analytical investigation. Yield: 690 mg (93%).

Step 3:

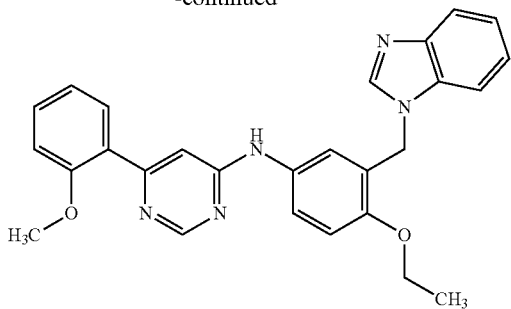

167 mg 3-Benzoimidazol-1-ylmethyl-4-ethoxy-phenylamine (obtained in Step 2) (0.63 mmol) was added to a solution of 138 mg 4-chloro-6-(2-methoxy-phenyl)-pyrimidine (obtained in Example 32, Step 1) (0.63 mmol) in 30 ml tert-butanol. 2 ml Dry ethyl acetate saturated with HCl gas was added and the mixture was refluxed for 5 hours. Reaction mixture was poured onto 70 g ice and 10 ml saturated $Na_2CO_3$ solution was added. The solution was extracted three times with 40-40 ml ethyl acetate. The combined organic layer was washed with brine, dried over $MgSO_4$ and evaporated under reduced pressure. Finally it was crystallized from a minimal amount of acetonitrile to get a light yellow solid. Yield: 48 mg (17%). Ret. time: 0.45-2.27-2.45 min., $(M+H)^+=452$, $(M+H)^-=450$; $^1$HNMR (DMSO-$d_6$, 300 MHz), δ (ppm): 9.38 (s, 1H), 8.55 (s, 1H), 8.28 (s, 1H), 7.90 (d, J=6.09 Hz, 1H), 7.64 (m, 2H), 7.55 (m, 1H), 7.43 (m, 1H), 7.36 (s, 1H), 7.28 (s, 1H), 7.17 (m, 3H), 7.03 (m, 2H), 5.44 (s, 2H), 4.06 (m, 2H), 3.84 (s, 3H), 1.36 (m, 3H).

N-(3-((1H-Benzo[d]imidazol-1-yl)methyl)-4-fluorophenyl)-6-(2-methoxyphenyl)pyrimidin-4-amine (Example 40)

Step 1

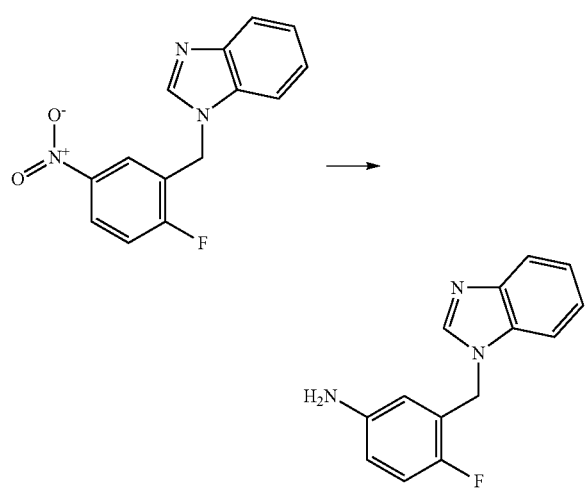

814 mg 1-(2-fluoro-5-nitro-benzyl)-1H-benzoimidazole (obtained in Example 2, Step 2) (3 mmol) was dissolved in 50 ml methanol-dichloromethane=3-1 and 1.50 g Pd catalyst (10% Pd on activated carbon) was added carefully and it was stirred vigorously in $H_2$ atmosphere under standard pressure at room temperature until TLC indicates the end of the reaction. Catalyst was filtered off and the filtrate was evaporated under reduced pressure to a brown oil. The product was used up directly in the next step without any further purification. Yield was considered as it had been 100%. Ret. time: 0.45-1.70 min., $(M+H)^+=242$, $(M+H)^-=240$.

Step 2:

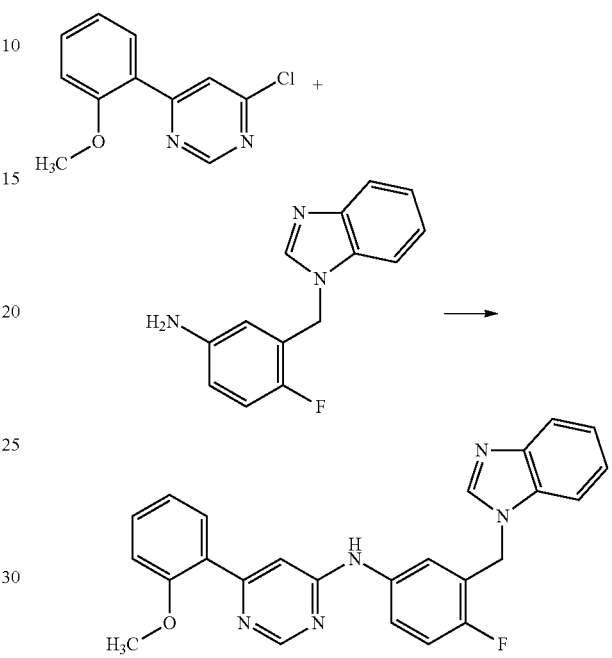

661 mg 3-Benzoimidazol-1-ylmethyl-4-fluoro-phenylamine (obtained in Step 1) (3 mmol) was added to a solution of 724 mg 4-chloro-6-(2-methoxy-phenyl)-pyrimidine (obtained in Example 32, Step 1) (3 mmol) in 50 ml tert-butanol. 3 ml Dry ethyl acetate saturated with HCl gas was added and the mixture was refluxed for 2 days. Reaction mixture was poured onto 200 ml 5% $NaHCO_3$ solution was added. The solution was extracted four times with 40-40 ml ethyl acetate. The combined organic layer was washed with brine, dried over $MgSO_4$ and evaporated under reduced pressure. Finally it was crystallized from a minimal amount of acetonitrile to get an off white solid. Yield: 470 mg (37%). Ret. time: 0.45-2.39 min., $(M+H)^+=426$, $(M+H)^-=424$; $^1$HNMR (DMSO-$d_6$, 300 MHz), δ (ppm): 9.58 (s, 1H), 8.57 (s, 1H), 8.36 (s, 1H), 7.91 (d, J=5.82 Hz, 1H), 7.77 (s, 1H), 7.68 (m, 1H), 7.53 (m, 1H), 7.42 (m, 2H), 7.33 (s, 1H), 7.17 (m, 4H), 7.06 (m, 1H), 5.58 (s, 2H), 3.85 (s, 3H).

2-(2-Methoxy-5-(6-(2-methoxyphenyl)pyrimidin-4-ylamino)benzyl)isoindoline-1,3-dione (Example 3)

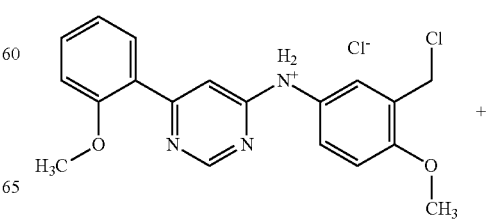

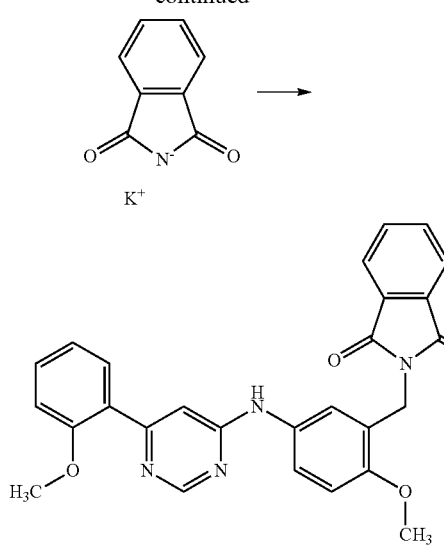

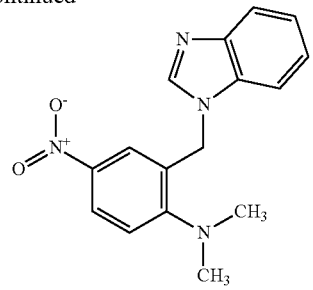

814 mg 1-(2-fluoro-5-nitro-benzyl)-1H-benzoimidazole (obtained in Example 2, Step 2) (3 mmol) was dissolved in 10 ml ethanol containing 5.6M dimethylamine and it was heated at 50° C. for 3 hours in a sealed tube. Reaction mixture was poured onto 100 g ice and it was stirred until the ice melted. Precipitated yellow solid was collected by filtration, washed well with water and dried in vacuum desiccator over $P_2O_5$. Yield: 866 mg (97%). Ret. time: 2.73 min., (M+H)$^+$=297; $^1$HNMR (DMSO-d$_6$, 300 MHz), δ (ppm): 8.38 (s, 1H), 8.06 (d, J=6.42 Hz, 1H), 7.69 (m, 1H), 7.47 (s, 1H), 7.24 (m, 4H), 5.60 (s, 2H), 2.96 (s, 6H).

Step 2

1.852 mg Phthalimide potassium derivative (10 mmol) was added to the solution of 785 mg (3-Chloromethyl-4-methoxy-phenyl)-[6-(2-methoxy-phenyl)-pyrimidin-4-yl]-ammonium chloride (obtained in Example 31, Step 1) (2 mmol) in 20 ml dry N,N-dimethylformamide and it was stirred 50° C. for 4 days. Then the mixture was poured onto the mixture of 200 g ice and 10 ml of saturated $Na_2CO_3$ solution. The solution was extracted four times with 70-70 ml ethyl acetate-tertahydrofurane=5:1 mixture. The combined organic layer was washed twice with brine, dried over $MgSO_4$ and evaporated to dryness. Crude product was purified by column chromatography on silica gel eluting with 0%→2% methanol in chloroform. The residue was crystallized from acetonitrile to get pure product as a yellow solid. Yield: 458 mg (49%). Ret. time: 3.15 min., (M+H)$^+$=467, (M+H)$^-$=465; $^1$HNMR (DMSO-d$_6$, 300 MHz), δ (ppm): 9.36 (s, 1H), 8.36 (s, 1H), 7.91 (m, 5H), 7.71 (s, 1H), 7.42 (s, 1H), 7.24 (m, 2H), 7.15 (m, 1H), 7.04 (m, 2H), 4.75 (s, 2H), 3.83 (s, 6H).

2-((1H-Benzo[d]imidazol-1-yl)methyl)-N4-(6-(2-methoxyphenyl)pyrimidin-4-yl)-N1,N1-dimethyl-benzene-1,4-diamine (Example 42)

Step 1

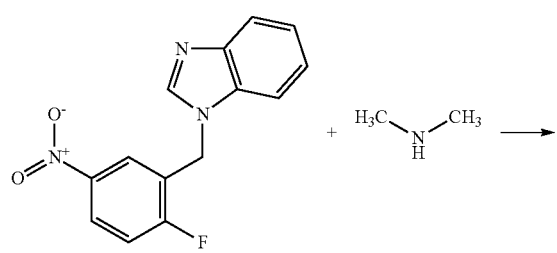

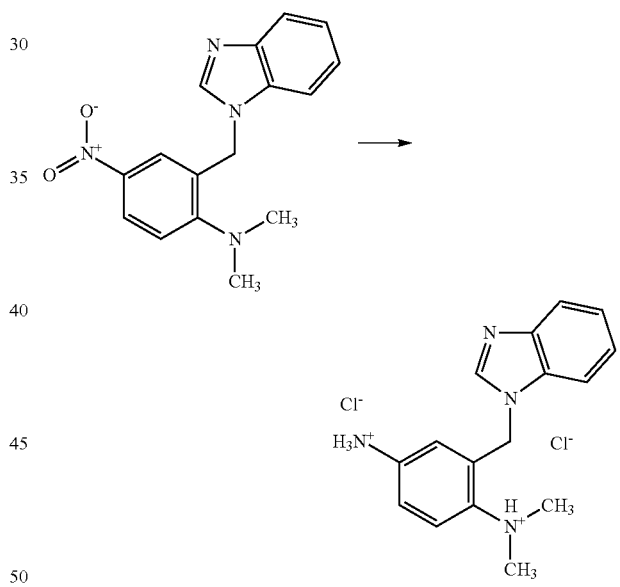

593 mg (2-Benzoimidazol-1-ylmethyl-4-nitro-phenyl)-dimethyl-amine (obtained in Step 1) (2 mmol) was dissolved in 50 ml ethanol and 1.805 g $SnCl_2 \times 2H_2O$ (8 mmol) was added. The mixture was refluxed for 4 hours. Then it was poured onto 150 g ice and the pH was basified by addition of 5M NaOH solution. Mixture was extracted four times with 50-50 ml ethyl acetate. The combined organic layer was washed with brine, dried over $MgSO_4$ and evaporated to 50 ml. 2 ml Dry ethyl acetate saturated with HCl gas was added to the residue and it was evaporated off to get a pink oil which was crystallized by next day. It was used in the subsequent step without any further purification or analytical investigation. Yield: 590 mg (87%).

Step 3:

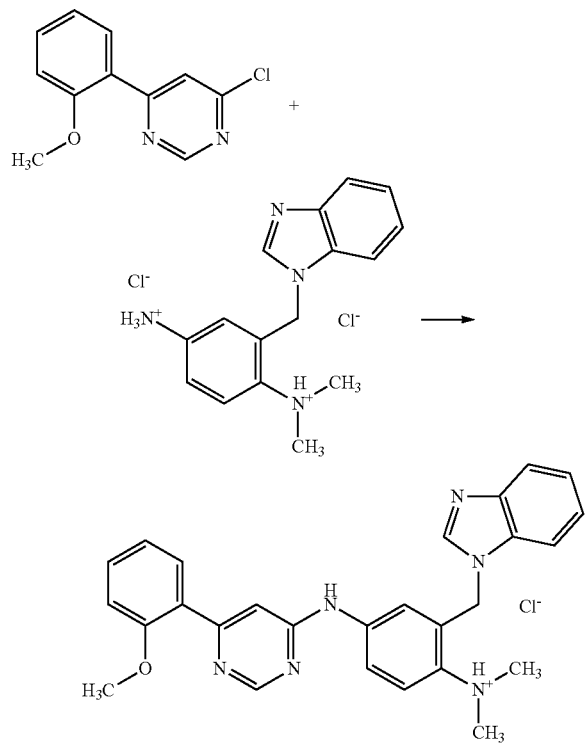

238 mg 2-Benzoimidazol-1-ylmethyl-N',N'-dimethyl-benzene-1,4-diamine dihydrochloride (obtained in Step 2) (0.7 mmol) was added to a solution of 177 mg 4-chloro-6-(2-methoxy-phenyl)-pyrimidine (obtained in Example 32, Step 1) (0.8 mmol) in 50 ml tert-butanol and it was refluxed for 3 hours. The mixture was cooled to room temperature and the precipitated white solid was collected by filtration. It was washed with small amount of 2-propanol and well with diethyl ether. Yield: 286 mg (84%). Ret. time: 0.45-2.32-2.53 min., (M+H)$^+$=451, (M+H)$^-$=449; $^1$HNMR (DMSO-d$_6$, 300 MHz), δ (ppm): 11.81 (s, 1H), 9.86 (s, 1H), 8.75 (s, 1H), 7.90 (m, 1H), 7.76 (m, 2H), 7.59 (m, 5H), 7.45 (m, 2H), 7.33 (m, 1H), 7.27 (d, J=7.44 Hz, 1H), 7.16 (m, 1H), 5.94 (s, 2H), 3.87 (s, 3H), 2.81 (s, 6H).

N-(3-(Aminomethyl)-4-methoxyphenyl)-6-(2-methoxyphenyl)pyrimidin-4-amine (Example 43)

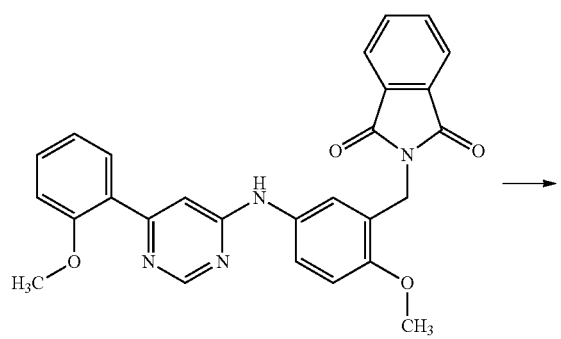

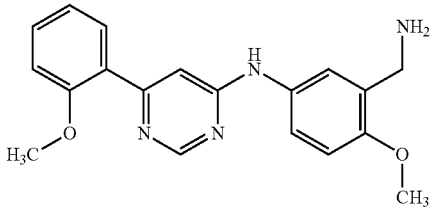

390 mg 2-(2-Methoxy-5-(6-(2-methoxyphenyl)pyrimidin-4-ylamino)benzyl) isoindoline-1,3-dione (obtained in Example 3) (0.84 mmol) was dissolved in 50 ml ethyl-alcohol, 0.41 ml hydrazine hydrate (418 mg 8.36 mmol) and refluxed for an hour. The reaction mixture was evaporated to dryness and 70 ml 0.5 N HCl was added to the residue. The mixture was extracted well three times with 30-30 ml ethyl-acetate. If insoluble material appears it have to be filtered off before separation of layers. The pH of the inorganic layer was then set to basic by addition of 5N NaOH ad then extracted well four times with 50-50 ml ethyl-acetate. The combined organic layer was washed with brine, dried over MgSO$_4$ and evaporated under reduced pressure. The residue was refluxed in 30 ml diisopropyl ether for 15 minutes. The product was filtered off as a yellow solid after cooling the mixture for an hour in ice bath. Yield: 153 mg (54%). Ret. time: 0.44-1.84 min., (M+H)$^+$=337, (M+H)$^-$=335; $^1$HNMR (CDCl$_3$, 300 MHz), δ (ppm): 8.73 (s, 1H), 7.90 (d, J=7.50 Hz, 1H), 7.39 (t, J=6.96 Hz, 1H), 7.25 (m, 3H), 7.07 (t, J=7.44 Hz, 1H), 6.93 (m, 2H), 3.88 (s, 3H), 3.85 (s, 5H).

2-Chloro-5-(6-(2-methoxyphenyl)pyrimidin-4-ylamino)benzamide (Example 44)

Step 1

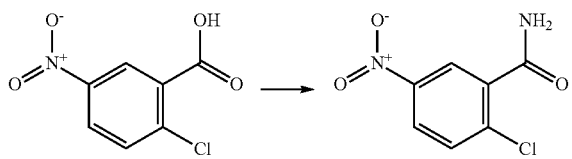 [SMILES: O=C(O)c1cc([N+](=O)[O-])ccc1Cl ; NC(=O)c1cc([N+](=O)[O-])ccc1Cl]

20.157 g 2-Chloro-5-nitrobenzoic acid (100 mmol) was heated at reflux temperature in 100 ml thionyl chloride for 3 hours in the presence of 3 drops of dry N,N-dimethylformamide as catalyst. Reaction mixture was evaporated under reduced pressure and 100 ml dry dichloromethane was added. 100 ml Of 12% NH$_4$OH solution was added dropwise to the ice cold solution and it was stirred for further 2 hours. 400 g ice was then added and it was stirred until the ice melted. Precipitated solid was collected by filtration and washed well with water. The white solid was dried in vacuum desiccator over P$_2$O$_5$. Yield: 17.07 g (85%). Ret. time: 1.93 min., (M+H)$^+$=201, (M+H)$^-$=199; $^1$HNMR (DMSO-d$_6$, 300 MHz), δ (ppm): 8.24 (bs, 2H), 8.13 (s, 1H), 7.87 (s, 1H), 7.81 (d, J=8.04 Hz, 1H).

Step 2

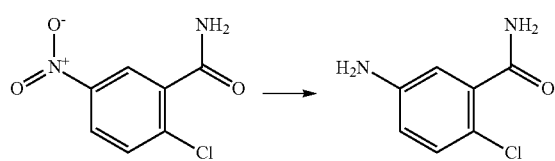 [SMILES: NC(=O)c1cc([N+](=O)[O-])ccc1Cl ; NC(=O)c1cc(N)ccc1Cl]

3.29 mg 2-Chloro-5-nitro-benzamide (obtained in Step 1) (16.4 mmol) was dissolved in 100 ml ethanol and 14.80 g SnCl$_2$×2H$_2$O (65.6 mmol) was added. The mixture was refluxed for 3 hours. Then it was poured onto 400 g ice and the pH was basified by addition of 5M NaOH solution. Mixture was extracted four times with 150-150 ml ethyl acetate. The combined organic layer was washed with brine, dried over MgSO$_4$ and evaporated to dryness. Residue was refluxed in 50 ml acetonitril. Yellow solid was filtered off after cooling the suspension back to room temperature. Filtrate was evaporated under reduced pressure and used up in the next step without any further purification or analytical investigation. Yield: 2.6 g (93%).

Step 3:

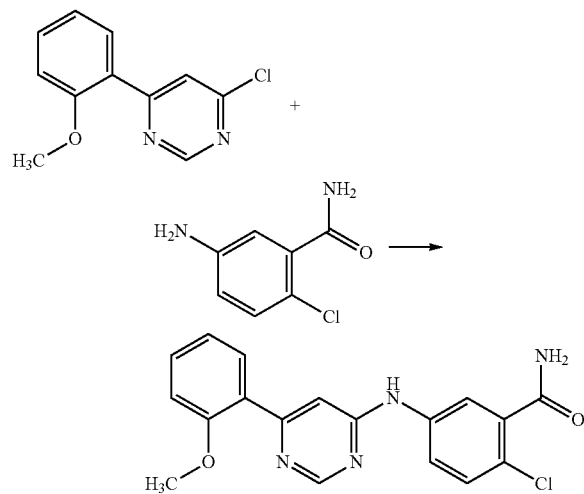

2.60 g 5-Amino-2-chloro-benzamide (obtained in Step 2) (15.24 mmol) was added to a solution of 3.36 g 4-chloro-6-(2-methoxy-phenyl)-pyrimidine (obtained in Example 32, Step 1) (15.24 mmol) in 80 ml tert-butanol. 3 ml Dry ethyl acetate saturated with HCl gas was added and the mixture was refluxed for 5 hours. Reaction mixture was poured onto 200 g ice and 10 ml saturated Na$_2$CO$_3$ solution was added. The solution was extracted three times with 100-100 ml ethyl acetate. The combined organic layer was washed with brine, dried over MgSO$_4$ and evaporated under reduced pressure. Finally it was crystallized from a minimal amount of acetonitrile to get an off white solid. Yield: 4.18 g (77%). Ret. time: 0.46-1.96-2.24 min., (M+H)$^+$=355, (M+H)$^-$=353; $^1$HNMR (DMSO-d$_6$, 300 MHz), δ (ppm): 9.84 (s, 1H), 8.75 (s, 1H), 7.97 (d, J=7.71 Hz, 1H), 7.87 (s, 2H), 7.79 (d, J=8.52 Hz, 1H), 7.57 (s, 1H), 7.48 (s, 2H), 7.43 (d, J=8.61 Hz, 1H), 7.19 (d, J=8.37 Hz, 1H), 7.09 (t, J=7.11 Hz, 1H), 3.91 (s, 3H).

N-(2-Methoxy-5-(6-(2-methoxyphenyl)pyrimidin-4-ylamino)benzyl)methanesulfonamide (Example 4)

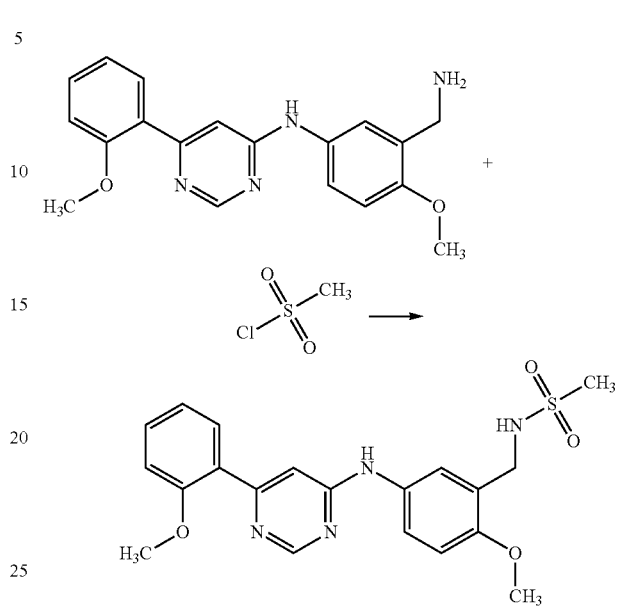

160 mg N-(3-(Aminomethyl)-4-methoxyphenyl)-6-(2-methoxyphenyl) pyrimidin-4-amine (obtained in Example 43) (0.48 mmol) was dissolved in 15 ml dry pyridine and cooled to 0° C. 41 μl Methanesulfonyl chloride (60 mg, 0.52 mmol) was added in one portion and the mixture was stirred at room temperature for additional 3 hours. Then it was evaporated under reduced pressure, 80 ml water was added and was extracted three times with 30-30 ml ethyl acetate. The combined organic layer was washed with brine, dried over MgSO$_4$ and evaporated off. Crude product was purified by column chromatography on silica gel eluting with 0%→3% methanol in chloroform. Finally it was recrystallized from a minimal amount of acetonitrile to get a light yellow solid. Yield: 37 mg (19%). Ret. time: 0.44-2.29-2.54 min., (M+H)$^+$=415, (M+H)$^-$=413; $^1$HNMR (DMSO-d$_6$, 300 MHz), δ (ppm): 9.46 (s, 1H), 8.61 (s, 1H), 7.92 (d, J=7.53 Hz, 1H), 7.67 (d, J=7.68 Hz, 1H), 7.50 (s, 1H), 7.44 (t, J=7.41 Hz, 1H), 7.36 (s, 2H), 7.16 (d, J=8.16 Hz, 1H), 7.06 (t, J=7.23 Hz, 1H), 7.00 (d, J=8.61 Hz, 1H), 4.14 (d, J=5.97 Hz, 2H), 3.88 (s, 3H), 3.80 (s, 3H), 2.90 (s, 3H).

2-Methoxy-5-[6-(2-methoxy-phenyl)-pyrimidin-4-ylamino]-benzoic acid N-methyl-hydrazide (Example 46)

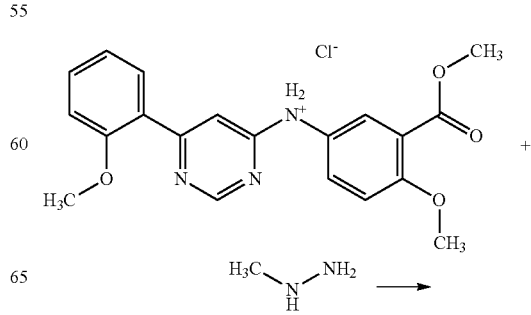

-continued

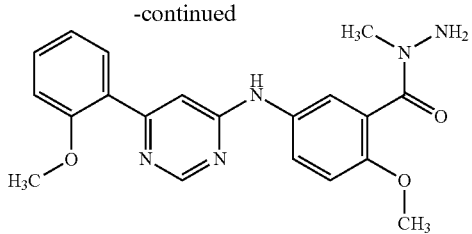

300 mg (4-Methoxy-3-methoxycarbonyl-phenyl)-[6-(2-methoxy-phenyl)-pyrimidin-4-yl]-ammonium chloride (obtained in Example 45, Step 4) (0.8 mmol) was suspended in 4 ml methylhydrazine and refluxed for four hours. It was poured onto ice and the crude product was filtered off and washed well with water. Filtrate was purified by column chromatography on silica gel eluting with chloroform containing 5% methanol. Finally it was recrystallized from a minimal amount of acetonitrile to get the pure product as a white solid. Yield: 80 mg (26%). Ret. time: 0.46-2.11 min., $(M+H)^+=380$, $(M+H)^-=378$; $^1$HNMR (DMSO-d$_6$, 300 MHz), δ (ppm): 9.57 (s, 1H), 9.48 (s, 1H), 8.65 (bs, 1H), 7.95 (m, 2H), 7.84 (bs, 1H), 7.42 (m, 2H), 7.13 (m, 3H), 5.14 (bs, 2H), 3.88 (s, 6H), 3.28 (s, 3H).

2-Methoxy-5-[6-(2-methoxy-phenyl)-pyrimidin-4-ylamino]-N-[3-(4-methyl-piperazin-1-yl)-propyl]-benzamide (Example 47)

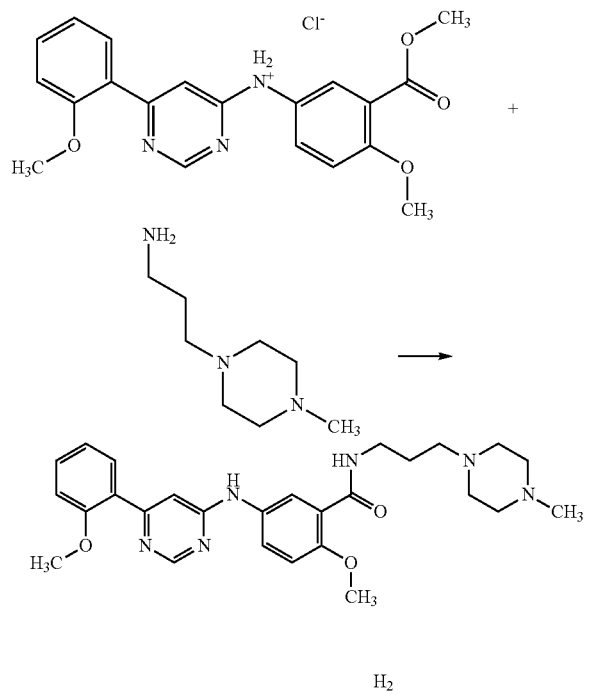

Title compound was prepared according to the method described in case of Example 46 using 1-(3-aminopropyl)-4-methylpiperazine as reactant Yield: 220 mg (56%). Ret. time: 0.45-1.87 min., $(M+H)^+=491$, $(M+H)^-=489$; $^1$HNMR (DMSO-d$_6$, 300 MHz), δ (ppm): 9.55 (s, 1H), 8.64 (s, 1H), 8.20 (t, 1H), 7.97 (s, 1H), 7.95 (d, 1H), 7.84 (d, 1H), 7.45 (t, 1H), 7.34 (s, 1H), 7.11 (m, 3H), 3.89 (s, 6H), 2.33 (m, 12H), 2.13 (s, 3H), 1.67 (m, 2H).

N-(2-Hydroxy-ethyl)-2-methoxy-5-[6-(2-methoxy-phenyl)-pyrimidin-4-ylamino]-benzamide (Example 48)

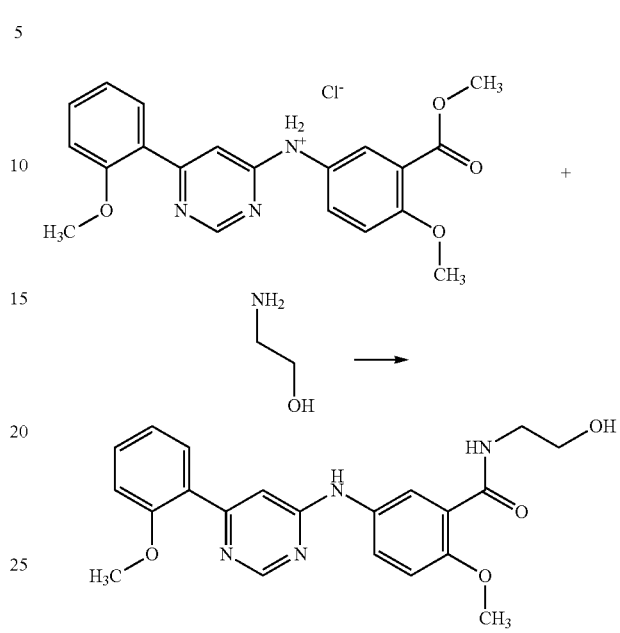

Title compound was prepared according to the method described in case of Example 46 using 2-aminoethanol as reactant Yield: 160 mg (54%). Ret. time: 0.45-1.87-2.22 min., $(M+H)^+=395$, $(M+H)^-=393$; $^1$HNMR (DMSO-d$_6$, 300 MHz), δ (ppm): 9.57 (s, 1H), 8.64 (s, 1H), 8.29 (t, 1H), 8.05 (s, 1H), 7.95 (d, 1H), 7.90 (d, 1H), 7.44 (t, 1H), 7.39 (s, 1H), 7.17 (m, 2H), 7.07 (t, 1H), 4.77 (t, 1H), 3.89 (s, 3H), 3.53 (m, 2H), 3.38 (m, 2H).

2-Methoxy-5-[6-(2-methoxy-phenyl)-pyrimidin-4-ylamino]-benzoic acid (Example 49)

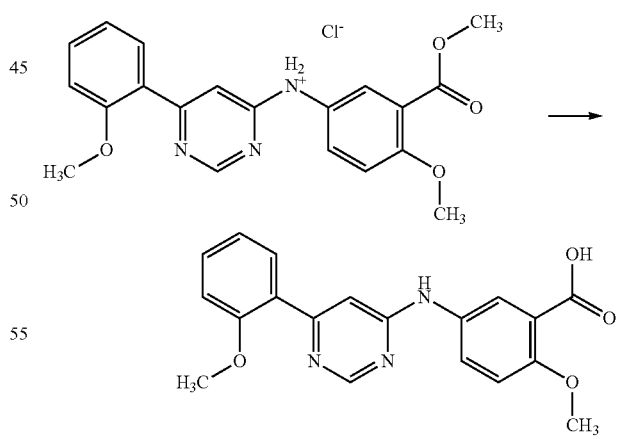

201 mg (4-Methoxy-3-methoxycarbonyl-phenyl)-[6-(2-methoxy-phenyl)-pyrimidin-4-yl]-ammonium chloride (obtained in Example 45, Step 4) (0.5 mmol) was dissolved in 20 ml methanol and 20 ml of water was added. 80 mg NaOH was added and the mixture was stirred at room temperature overnight. It was poured onto ice and pH was adjusted to 5-6 by addition of 1M HCl solution. It was extracted four times with 40-40 ml ethyl acetate. The combined organic layer was washed with brine, dried over MgSO$_4$ and evaporated under reduced pressure. Residue was recrystallized from a minimal amount of acetonitrile to get the pure product as a white solid. Yield: 42 mg (23%). Ret. time: 0.45-1.90-2.27 min., (M+H)$^+$=352, (M+H)$^-$=350; $^1$HNMR (DMSO-d$_6$, 300 MHz), δ (ppm): 2.61 (bs, 1H), 9.55 (s, 1H), 8.65 (s, 1H), 7.96 (bs, 2H), 7.79 (s, 1H), 7.40 (m, 2H), 7.11 (m, 3H), 3.89 (s, 3H), 3.81 (s, 3H).

N-{2-Methoxy-5-[6-(2-methoxy-phenyl)-pyrimidin-4-ylamino]-phenyl}-acetamide (Example 50)

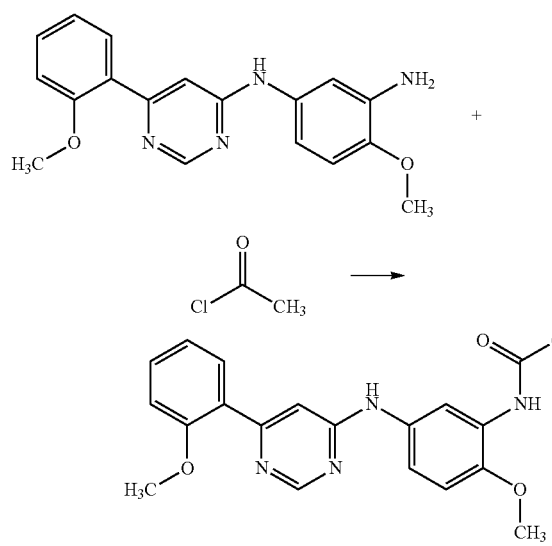

Title compound was prepared according to the method described in case of Example 27 using acetyl chloride as reactant Yield: 126 mg (35%). Ret. time: 0.45-2.20-2.42 min., (M+H)$^+$=365, (M+H)$^-$=363; $^1$HNMR (DMSO-d$_6$, 300 MHz), δ (ppm): 9.46 (s, 1H), 8.13 (bs, 1H), 8.60 (s, 1H), 8.15 (bs, 1H), 7.93 (d, 1H), 7.54 (d, 1H), 7.44 (t, 1H), 7.38 (s, 1H), 7.16 (d, 1H), 7.08 (d, 1H), 7.05 (d, 1H), 3.87 (s, 3H), 3.82 (s, 3H), 2.99 (s, 3H).

{2-Methoxy-5-[6-(2-methoxy-phenyl)-pyrimidin-4-ylamino]-phenyl}-carbamic Acid Methyl Ester (Example 51)

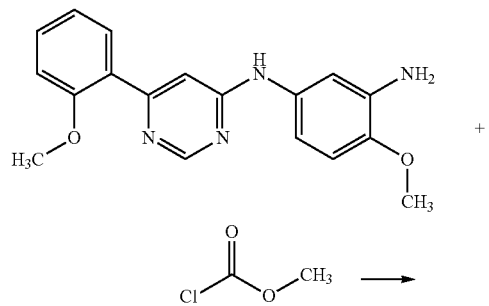

-continued

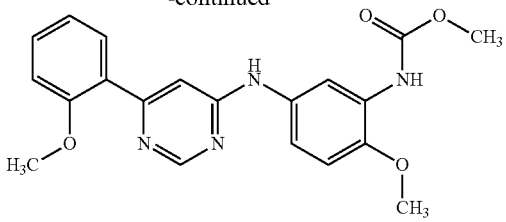

Title compound was prepared according to the method described in case of Example 27 using methyl chloroformate as reactant Yield: 158 mg (42%). Ret. time: 0.45-2.49-2.69 min., (M+H)$^+$=381, (M+H)$^-$=379; $^1$HNMR (DMSO-d$_6$, 300 MHz), δ (ppm): 9.45 (s, 1H), 8.62 (s, 1H), 8.43 (bs, 1H), 7.94 (d, 1H), 7.92 (s, 1H), 7.44 (m, 2H), 7.37 (s, 1H), 7.17 (d, 1H), 7.04 (m, 2H), 3.88 (s, 3H), 3.79 (s, 3H), 3.66 (s, 3H).

1-{2-Methoxy-5-[6-(2-methoxy-phenyl)-pyrimidin-4-ylamino]-phenyl}-3-methyl-urea (Example 52)

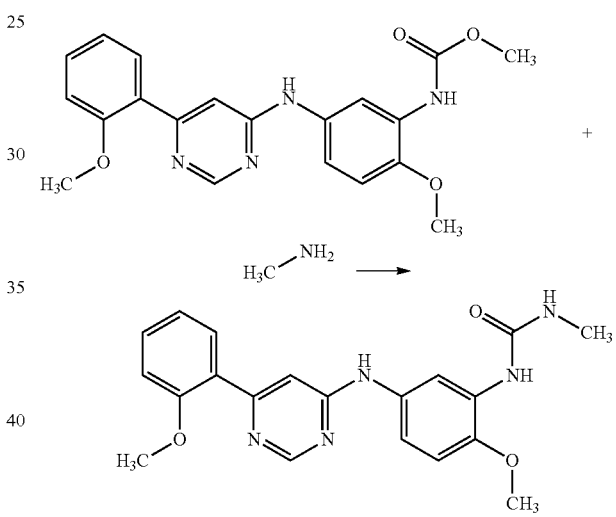

228 mg {2-Methoxy-5-[6-(2-methoxy-phenyl)-pyrimidin-4-ylamino]-phenyl}-carbamic acid methyl ester (obtained in Example 51) (0.6 mmol) was dissolved in 4 ml of methylamine (8M solution in ethanol) and was heated in a sealed tube at 120° C. for 5 hours applying microwave irradiation. Then it was evaporated under reduced pressure and purified by column chromatography on silica gel eluting with chloroform applying 0%-2% methanol gradient. Finally it was recrystallized from a minimal amount of acetonitrile to get the pure product as a white solid. Yield: 56 mg (25%). Ret. time: 0.46-2.14-2.43 min., (M+H)$^+$=380, (M+H)$^-$=378; $^1$HNMR (DMSO-d$_6$, 300 MHz), δ (ppm): 9.32 (s, 1H), 8.60 (s, 1H), 8.22 (s, 1H), 7.92 (d, 1H), 7.89 (s, 1H), 7.43 (t, 1H), 7.35 (m, 2H), 7.15 (d, 1H), 7.06 (t, 1H), 6.94 (d, 1H), 6.75 (m, 1H), 3.87 (s, 3H), 3.82 (s, 3H), 2.64 (d, 3H).

N-{2-Methoxy-5-[6-(2-methoxy-phenyl)-pyrimidin-4-ylamino]-phenyl}-2,2-dimethyl-propionamide (Example 53)

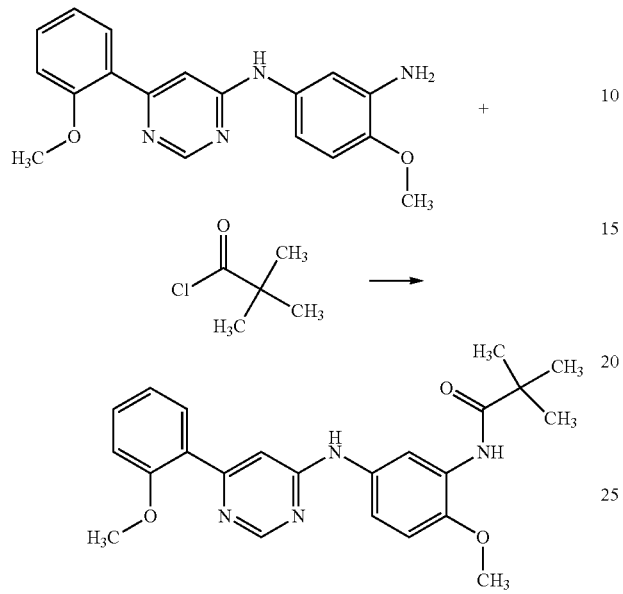

Title compound was prepared according to the method described in case of Example 27 using pivaloyl chloride as reactant Yield: 92 mg (23%). Ret. time: 3.10 min., (M+H)⁺= 407, (M+H)⁻=405; ¹HNMR (DMSO-d₆, 300 MHz), δ (ppm): 9.43 (s, 1H), 8.61 (s, 1H), 8.40 (s, 1H), 8.13 (s, 1H), 7.95 (t, 1H), 7.53 (d, 1H), 7.43 (t, 1H), 7.37 (s, 1H), 7.17 (d, 1H), 7.06 (bs, 2H), 3.87 (s, 3H), 3.84 (s, 3H), 1.24 (s, 9H).

N³-(1H-Benzoimidazol-2-yl)-4-methoxy-N¹-[6-(2-methoxy-phenyl)-pyrimidin-4-yl]-benzene-1,3-diamine (Example 54)

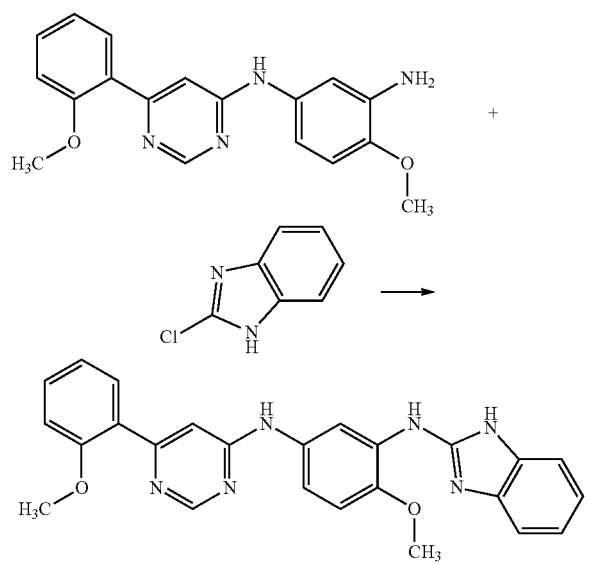

258 mg 4-Methoxy-N1-(6-(2-methoxyphenyl)pyrimidin-4-yl)benzene-1,3-diamine (obtained in Example 41) (0.8 mmol) was suspended in 10 ml dry n-BuOH 137 mg 2-chlorobenzimidazole (0.9 mmol) and 143 mg potassium dihydrogenphosphate (1.05 mmol) was added. The mixture was refluxed for 2 days. Then it was evaporated under reduced pressure, 80 ml water was added and was extracted three times with 30-30 ml ethyl acetate. The combined organic layer was washed with brine, dried over MgSO₄ and evaporated off. Crude product was purified by column chromatography on silica gel eluting with chloroform applying 0%-4% methanol gradient. Finally it was recrystallized from a minimal amount of acetonitrile to get an off white solid. Yield: 52 mg (15%). Ret. time: 0.45-2.22 min., (M+H)⁺=439, (M+H)⁻=437; ¹HNMR (DMSO-d₆, 300 MHz), δ (ppm): 10.89 (s, 1H), 9.52 (s, 1H), 8.61 (t, 2H), 7.93 (d, 1H), 7.44 (bs, 3H), 7.31 (m, 2H), 7.15 (d, 1H), 7.05 (m, 4H), 3.92 (s, 3H), 3.84 (s, 3H).

N-{2-Methoxy-5-[6-(2-methoxy-phenyl)-pyrimidin-4-ylamino]-phenyl}-formamide (Example 55)

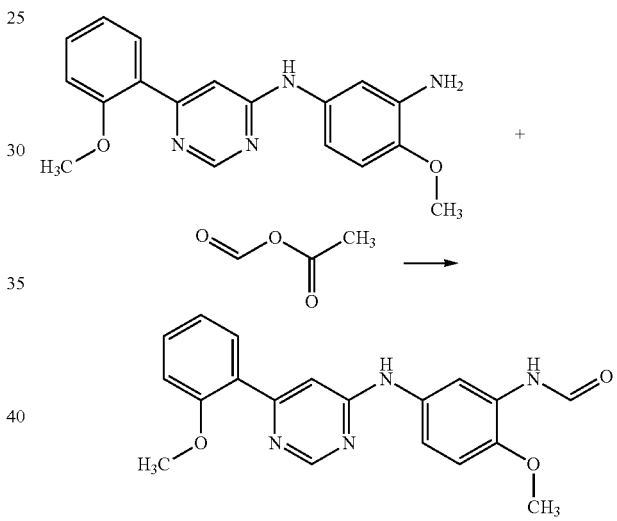

0.075 ml Formic acid was dissolved in 10 ml dry dichloromethane and 0.190 ml acetic anhydride was added. Mixture was stirred at room temperature for an hour. 226 mg 4-Methoxy-N1-(6-(2-methoxyphenyl)pyrimidin-4-yl)benzene-1,3-diamine (obtained in Example 41) (0.7 mmol) was dissolved in 50 ml dry dichloromethane, 0.325 ml of dry pyridine was added and it was cooled to 0° C. The previously prepared solution was then added dropwise and the mixture was stirred at room temperature overnight. Then it was evaporated under reduced pressure, water was added and it was extracted three times with 30-30 ml ethyl acetate. The combined organic layer was washed with brine, dried over MgSO₄ and evaporated off. Crude product was purified by column chromatography on silica gel eluting with chloroform applying 0%-4% methanol gradient. Finally it was recrystallized from a minimal amount of acetonitrile to get an off white solid. Yield: 80 mg (33%). Ret. time: 0.46-2.05-2.38 min., (M+H)⁺=351, (M+H)⁻=349; ¹HNMR (DMSO-d₆, 300 MHz), δ (ppm): 9.67 (bs, 1H), 9.47 (s, 1H), 8.61 (s, 1H), 8.34 (d, 1H), 8.32 (s, 1H), 7.94 (dd, 1H), 7.60 (bd, 1H), 7.43 (t, 1H), 7.38 (s, 1H), 7.16 (d, 1H), 7.05 (m, 2H), 3.88 (s, 3H), 3.84 (s, 3H).

{2-Methoxy-5-[6-(2-methoxy-phenyl)-pyrimidin-4-ylamino]-phenyl}-urea (Example 56)

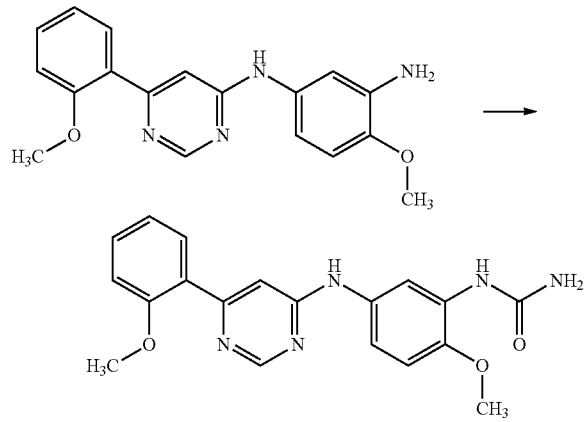

322 mg 4-Methoxy-N1-(6-(2-methoxyphenyl)pyrimidin-4-yl)benzene-1,3-diamine (obtained in Example 41) (1 mmol) was dissolved in 25 ml dry THF, 0.122 ml dry pyridine was added and cooled to 0° C. 198 mg Trichloromethyl chloroformate (1 mmol) was dissolved in 25 ml dry THF and was added dropwise to the previously prepared solution. The mixture was stirred at room temperature for additional 2 hours before 2 ml of 25% NH$_4$OH solution was added in one portion. After stirring it for an additional hour the mixture was poured onto ice and it was extracted three times with 30-30 ml ethyl acetate. The combined organic layer was washed with brine, dried over MgSO$_4$ and evaporated off. Crude product was recrystallized from a minimal amount of acetonitrile to get an off white solid. Yield: 98 mg (27%). Ret. time: 2.28 min., (M+H)$^+$=366, (M+H)$^-$=364; $^1$HNMR (DMSO-d$_6$, 300 MHz), δ (ppm): 9.37 (s, 1H), 8.59 (s, 1H), 8.20 (d, 1H), 7.96 (s, 1H), 7.92 (dd, 1H), 7.42 (m, 3H), 7.15 (d, 1H), 7.06 (t, 1H), 6.94 (d, 1H), 6.22 (bs, 2H), 3.87 (s, 3H), 3.83 (s, 3H).

(3-Fluoro-4-nitro-phenyl)-[6-(2-methoxy-phenyl)-pyrimidin-4-yl]-amine (Example 57)

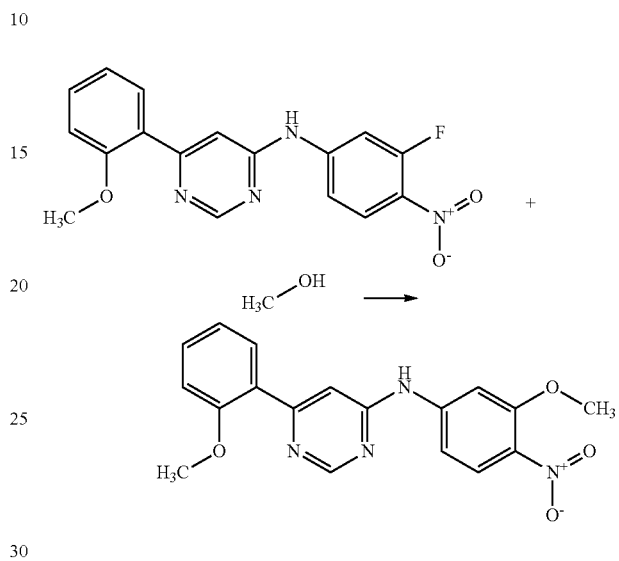

Title compound was prepared according to the method described in case of Example 32 using 3-fluoro-4-nitroaniline as reactant. Yield: 1.57 g (92%). Ret. time: 3.87 min., (M+H)$^+$=341, (M+H)$^-$=339; $^1$HNMR (DMSO-d$_6$, 300 MHz), δ (ppm): 10.53 (s, 1H), 8.90 (s, 1H), 8.19 (m, 2H), 8.00 (d, 1H), 7.63 (s, 1H), 7.57 (d, 1H), 7.49 (t, 1H), 7.21 (d, 1H), 7.10 (t, 1H), 3.92 (s, 3H).

(3-Methoxy-4-nitro-phenyl)-[6-(2-methoxy-phenyl)-pyrimidin-4-yl]-amine (Example 58)

138 mg Sodium (6 mmol) was dissolved in 40 ml methanol and 681 mg (3-fluoro-4-nitro-phenyl)-[6-(2-methoxyphenyl)-pyrimidin-4-yl]-amine (obtained in Example 57) (2 mmol) was added in one portion. The mixture was refluxed for 2 hours. It was evaporated under reduced pressure and ice was added. The mixture was extracted three times with 30-30 ml ethyl acetate. The combined organic layer was washed with brine, dried over MgSO$_4$ and evaporated to dryness. Crude product was recrystallized from a minimal amount of acetonitrile to get an off yellow solid. Yield: 573 mg (81%). Ret. time: 3.32 min., (M+H)$^+$=353, (M+H)$^-$= 351; $^1$HNMR (DMSO-d$_6$, 300 MHz), δ (ppm): 10.27 (bs, 1H), 8.85 (s, 1H), 8.00 (m, 2H), 7.85 (s. 1H), 7.60 (s, 1H), 7.49 (m, 2H), 7.21 (d, 1H), 7.10 (t, 1H), 3.95 (s, 3H), 3.93 (s, 3H).

2-Methoxy-N$^4$-[6-(2-methoxy-phenyl)-pyrimidin-4-yl]-benzene-1,4-diamine (Example 59)

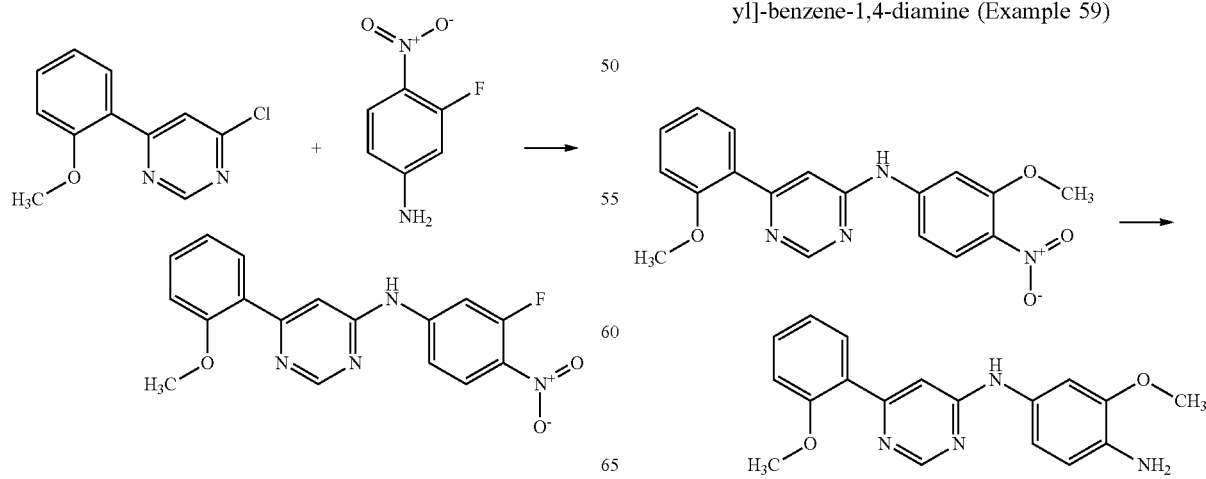

352 mg (3-Methoxy-4-nitro-phenyl)-[6-(2-methoxy-phenyl)-pyrimidin-4-yl]-amine (obtained in Example 58) (1 mmol) was dissolved in 50 ml methanol-dichloromethane=3-1 and 505 mg ammonium formate (8 mmol) was added. 50 mg Pd catalyst (10% Pd on activated carbon) was added carefully and it was stirred vigorously while the mixture was gently warmed to reflux temperature. As soon as TLC indicates the end of the reaction (0.5-2 hours), catalyst was filtered off and the filtrate was evaporated under reduced pressure. Crude product was purified by column chromatography on silica gel eluting with chloroform applying 0%-3% methanol gradient. Finally it was recrystallized from a minimal amount of acetonitrile to get an off white solid. Yield: 233 mg (50%). Ret. time: 0.46-1.98 min., (M+H)$^+$=323, (M+H)$^-$=321; $^1$HNMR (DMSO-d$_6$, 300 MHz), δ (ppm): 9.16 (bs, 1H), 8.56 (s, 1H), 7.91 (d, 1H), 7.42 (t, 1H), 7.26 (s, 1H), 7.15 (d, 1H), 7.04 (m, 2H), 6.94 (d, 1H), 6.62 (d, 1H), 4.53 (bs, 2H), 3.85 (s, 3H), 3.77 (s, 3H).

N-{2-Methoxy-4-[6-(2-methoxy-phenyl)-pyrimidin-4-ylamino]-phenyl}-methanesulfonamide (Example 60)

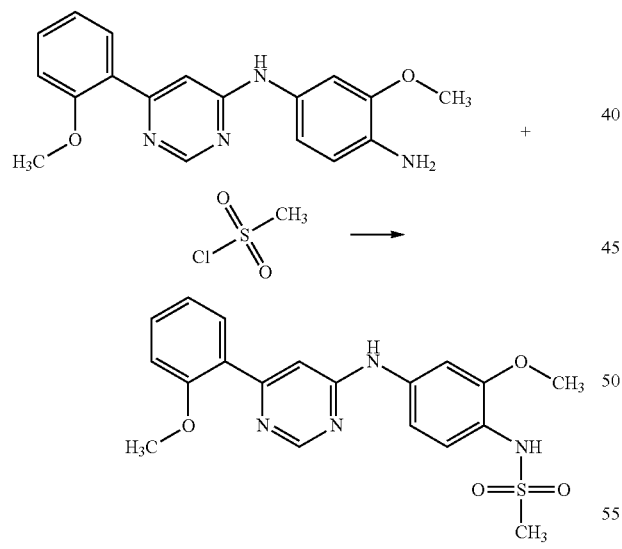

Title compound was prepared according to the method described in case of Example 9 using 2-Methoxy-N$^4$-[6-(2-methoxy-phenyl)-pyrimidin-4-yl]-benzene-1,4-diamine (obtained in Example 59) as starting material. Yield: 90 mg (75%). Ret. time: 0.46-2.19-2 46 min., (M+H)$^+$=401, (M+H)$^-$=399; $^1$HNMR (DMSO-d$_6$, 300 MHz), δ (ppm): 9.68 (s, 1H), 8.78 (bs, 1H), 8.71 (s, 1H), 7.97 (d, 1H), 7.53 (s, 1H), 7.46 (bs, 2H), 7.29 (d, 1H), 7.19 (m, 2H), 7.08 (t, 1H), 3.90 (s, 3H), 3.84 (s, 3H), 2.91 (s, 3H).

[6-(2-Ethoxy-phenyl)-pyrimidin-4-yl]-(4-methoxy-3-nitro-phenyl)-amine (Example 61)

Step 1

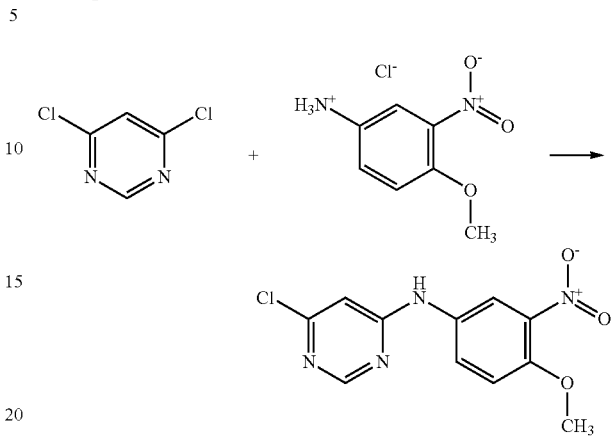

3.070 g 4-Methoxy-3-nitro-phenyl-ammonium chloride (obtained in Example 41, Step 1) (15 mmol) was dissolved in 100 ml 2-propanol, 2.235 g 4,6-dichloropyrimidine (15 mmol) and 5.58 ml triethylamine (4.05 g, 40 mmol) was added. The mixture was refluxed overnight. Then it was evaporated under reduced pressure, 150 ml water was added and it was extracted three times with 50-50 ml ethyl acetate. The combined organic layer was washed with brine, dried over MgSO$_4$ and evaporated to dryness. Crude product was recrystallized from a minimal amount of acetonitrile to get a yellow solid. Yield: 2.29 g (54%). Ret. time: 3.36 min., (M+H)$^+$=281, (M+H)$^-$=279.

Step 2

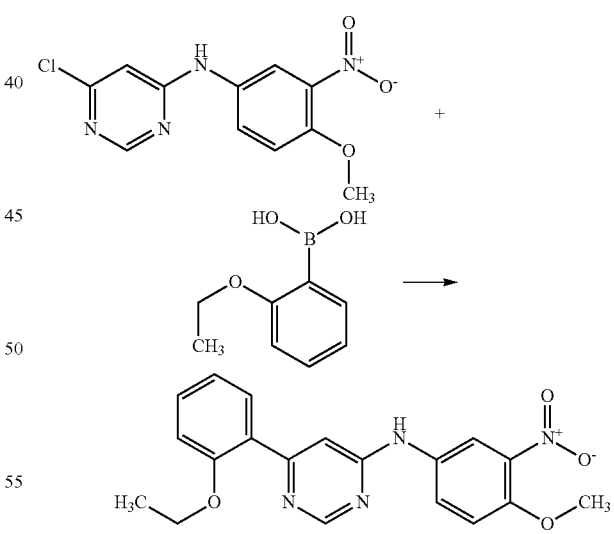

281 mg (6-Chloro-pyrimidin-4-yl)-(4-methoxy-3-nitro-phenyl)-amine (obtained in Step 1) (1 mmol) was dissolved in 50 ml 1,2-dimethoxyethane and the flask was filled with argon properly. 58 mg Tetrakis(thriphenylphosphine) palladium[0] (0.05 mmol) was added and the mixture was stirred at room temperature for 30 minutes. Then 199 mg 2-ethoxy-phenylboronic acid (1.2 mmol), 318 mg Na$_2$CO$_3$ (3 mmol) and 10 ml water were added under argon atmosphere. The mixture was refluxed for 3 hours. Then it was evaporated under reduced pressure, 150 ml water was added and it was extracted three times with 40-40 ml ethyl acetate. The combined organic layer was washed with brine, decolorized with activated carbon, dried over MgSO$_4$ and evaporated under reduced pressure. Residue was recrystallized from a minimal amount of acetonitrile to get pure product as a yellow solid. Yield: 270 mg (74%). Ret. time: 3 03 min., (M+H)$^+$=367, (M+H)$^-$=365; $^1$HNMR (DMSO-d$_6$, 300 MHz), δ (ppm): 9.75 (s, 1H), 8.71 (s, 1H), 8.38 (s, 1H), 7.97 (d, 1H), 7.88 (d, 1H), 7.42 (m, 3H), 7.16 (d, 1H), 7.06 (t, 1H), 4.17 (q, 2H), 3.92 (s, 3H), 1.40 (t, 3H).

N$^1$-[6-(2-Ethoxy-phenyl)-pyrimidin-4-yl]-4-methoxy-benzene-1,3-diamine (Example 62)

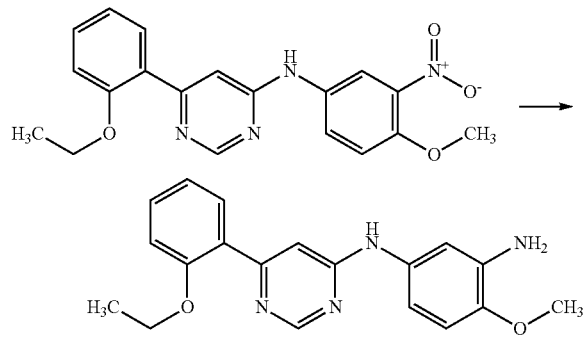

Title compound was prepared according to the method described in case of Example 59 using [6-(2-Ethoxy-phenyl)-pyrimidin-4-yl]-(4-methoxy-3-nitro-phenyl)-amine (obtained in Example 61) as starting material. Yield: 74 mg (22%). Ret. time: 0.45-2.25-248 min., (M+H)$^+$=337, (M+H)$^-$=335; $^1$HNMR (DMSO-d$_6$, 300 MHz), δ (ppm): 9.10 (s, 1H), 8.57 (s, 1H), 7.95 (d, 1H), 7.40 (d, 1H), 7.36 (s, 1H), 7.11 (d, 1H), 7.04 (t, 1H), 6.83 (s, 1H), 6.77 (d, 1H), 6.69 (d, 1H), 4.77 (s, 2H), 4.10 (q, 2H), 3.75 (s, 3H), 1.31 (t, 3H).

[6-(4-Fluoro-2-methoxy-phenyl)-pyrimidin-4-yl]-(4-methoxy-3-nitro-phenyl)-amine (Example 63)

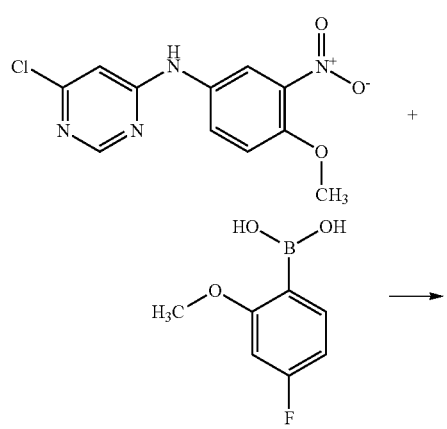

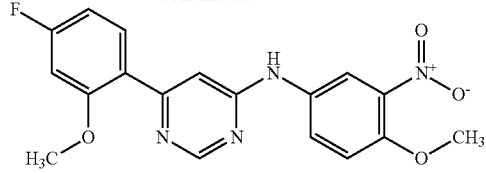

Title compound was prepared according to the method described in case of Example 61 using 4-fluoro-2-methoxy-phenylboronic acid as reactant. Yield: 152 mg (41%). Ret. time: 3 03 min., (M+H)$^+$=371, (M+H)$^-$=369; $^1$HNMR (DMSO-d$_6$, 300 MHz), δ (ppm): 9.82 (bs, 1H), 8.70 (s, 1H), 8.42 (s, 1H), 8.05 (t, 1H), 7.86 (d, 1H), 7.42 (s, 1H), 7.38 (d, 1H), 7.10 (d, 1H), 6.92 (t, 1H), 3.92 (s, 6H).

[6-(4-Fluoro-2-methoxy-phenyl)-pyrimidin-4-yl]-(4-methoxy-3-nitro-phenyl)-amine (Example 64)

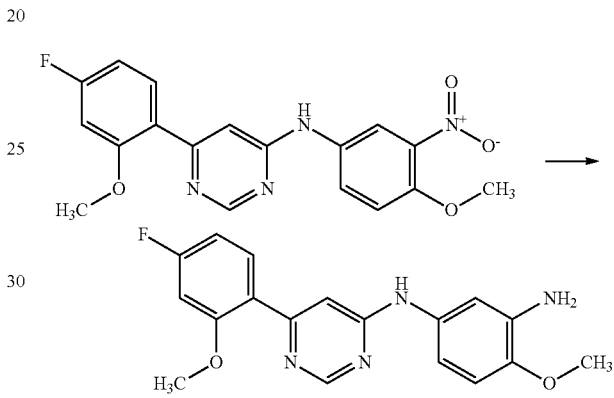

Title compound was prepared according to the method described in case of Example 59 using [6-(2-Ethoxy-phenyl)-pyrimidin-4-yl]-(4-methoxy-3-nitro-phenyl)-amine (obtained in Example 63) as starting material. Yield: 162 mg (48%). Ret. time: 0.46-2.06-2.36 min., (M+H)$^+$=341, (M+H)$^-$=339; $^1$HNMR (DMSO-d$_6$, 300 MHz), δ (ppm): 9.18 (s, 1H), 8.56 (s, 1H), 7.80 (t, 1H), 7.32 (s, 1H), 7.06 (d, 1H), 6.89 (m, 2H), 6.75 (bs, 2H), 4.77 (bs, 2H), 3.90 (s, 3H), 3.75 (s, 3H).

(4-Methoxy-3-nitro-phenyl)-[6-(4-methoxy-phenyl)-pyrimidin-4-yl]-amine (Example 65)

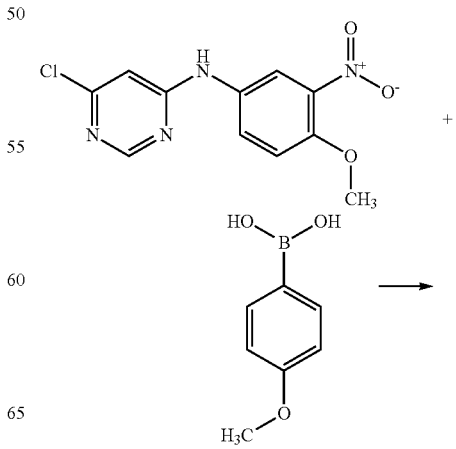

113
-continued

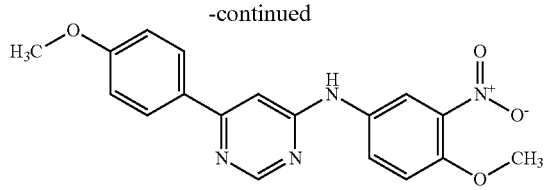

Title compound was prepared according to the method described in case of Example 61 using 4-methoxyphenyl-boronic acid as reactant Yield: 143 mg (38%). Ret. time: 3.08 min., (M+H)$^+$=353, (M+H)$^-$=351; $^1$HNMR (DMSO-d$_6$, 300 MHz), δ (ppm): 9.80 (s, 1H), 8.69 (s, 1H), 8.43 (s, 1H), 8.01 (d, 2H), 7.85 (d, 1H), 7.38 (d, 1H), 7.12 (d, 2H), 7.07 (s, 1H), 3.91 (s, 3H), 3.83 (s, 3H).

4-Methoxy-N$^1$-[6-(4-methoxy-phenyl)-pyrimidin-4-yl]-benzene-1,3-diamine (Example 66)

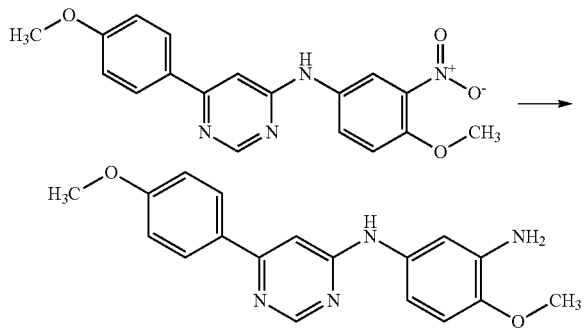

Title compound was prepared according to the method described in case of Example 59 using (4-Methoxy-3-nitro-phenyl)-[6-(4-methoxy-phenyl)-pyrimidin-4-yl]-amine (obtained in Example 65) as starting material. Yield: 129 mg (40%). Ret. time: 0.46-2.08-2.31 min., (M+H)$^+$=323, (M+H)$^-$=321; $^1$HNMR (DMSO-d$_6$, 300 MHz), δ (ppm): 9.17 (s, 1H), 8.55 (s, 1H), 7.95 (d, 2H), 7.06 (d, 1H), 7.04 (bs, 2H), 6.92 (s, 1H), 6.75 (bs, 2H), 4.79 (bs, 2H), 3.82 (s, 3H), 3.74 (s, 3H).

(4-Methoxy-3-nitro-phenyl)-[6-(3-methoxy-phenyl)-pyrimidin-4-yl]-amine (Example 67)

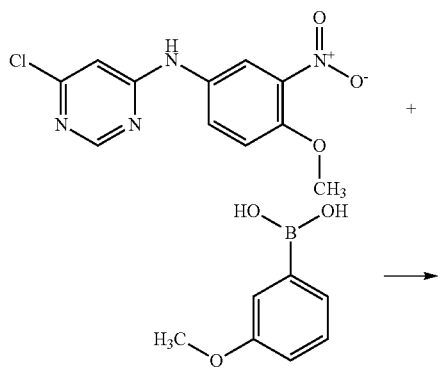

114
-continued

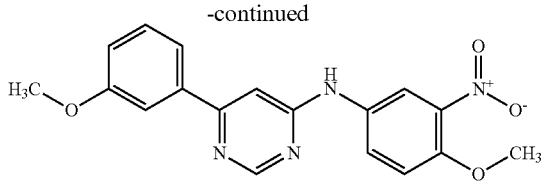

Title compound was prepared according to the method described in case of Example 61 using 3-methoxyphenyl-boronic acid as reactant Yield: 111 mg (30%). Ret. time: 3.36 min., (M+H)$^+$=352, (M+H)$^-$=350; $^1$HNMR (DMSO-d$_6$, 300 MHz), δ (ppm): 9.87 (s, 1H), 8.74 (s, 1H), 8.44 (s, 1H), 7.85 (d, 1H), 7.60 (bs, 2H), 7.45 (t, 1H), 7.39 (d, 1H), 7.20 (s, 1H), 7.10 (d, 1H), 3.92 (s, 3H), 3.85 (s, 3H).

4-Methoxy-N$^1$-[6-(3-methoxy-phenyl)-pyrimidin-4-yl]-benzene-1,3-diamine (Example 68)

Title compound was prepared according to the method described in case of Example 59 using (4-Methoxy-3-nitro-phenyl)-[6-(3-methoxy-phenyl)-pyrimidin-4-yl]-amine (obtained in Example 67) as starting material. Yield: 219 mg (68%). Ret. time: 0.45-2.39 min., (M+H)$^+$=323, (M+H)$^-$=321; $^1$HNMR (DMSO-d$_6$, 300 MHz), δ (ppm): 9.25 (s, 1H), 8.60 (s, 1H), 7.54 (m, 2H), 7.42 (t, 1H), 7.10 (m, 2H), 7.00 (s, 1H), 6.76 (bs, 2H), 4.79 (bs, 2H), 3.82 (s, 3H), 3.75 (s, 3H).

[6-(2-Benzyloxy-phenyl)-pyrimidin-4-yl]-(4-methoxy-3-nitro-phenyl)-amine (Example 69)

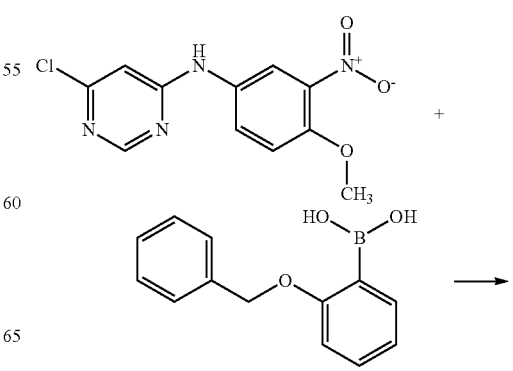

-continued

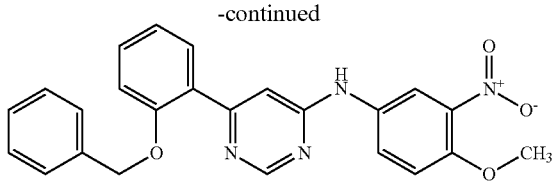

Title compound was prepared according to the method described in case of Example 61 using 2-benzyloxyphenyl-boronic acid as reactant Yield: 314 mg (73%). Ret. time: 3.51 min., (M+H)⁺=428, (M+H)⁻=426; ¹HNMR (DMSO-d₆, 300 MHz), δ (ppm): 9.78 (bs, 1H), 8.73 (s, 1H), 8.36 (s, 1H), 7.86 (t, 2H), 7.44 (bs, 4H), 7.35 (m, 4H), 7.21 (d, 1H), 7.08 (t, 1H), 5.28 (s, 2H), 3.91 (s, 3H).

2-[6-(3-Amino-4-methoxy-phenylamino)-pyrimidin-4-yl]-phenol (Example 70)

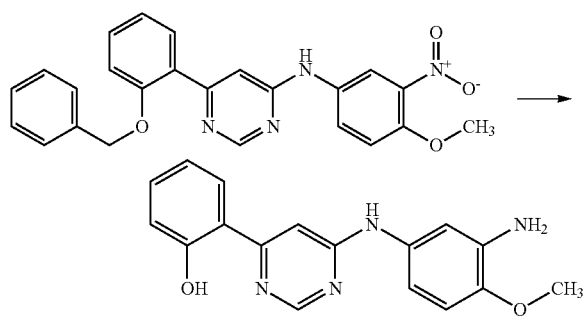

Title compound was prepared according to the method described in case of Example 59 using [6-(2-Benzyloxy-phenyl)-pyrimidin-4-yl]-(4-methoxy-3-nitro-phenyl)-amine (obtained in Example 69) as starting material. Yield: 128 mg (42%). Ret. time: 2.57 min., (M+H)⁺=309, (M+H)⁻=307; ¹HNMR (DMSO-d₆, 300 MHz), δ (ppm): 13.82 (s, 1H), 9.47 (s, 1H), 8.61 (s, 1H), 7.72 (d, 1H), 7.34 (t, 1H), 7.20 (s, 1H), 6.90 (m, 3H), 6.77 (bs, 2H), 4.83 (s, 2H), 3.78 (s, 3H).

N¹-[6-(2-Benzyloxy-phenyl)-pyrimidin-4-yl]-4-methoxy-benzene-1,3-diamine (Example 71)

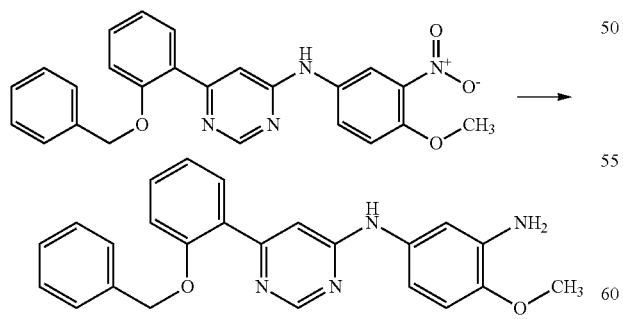

347 mg [6-(2-Benzyloxy-phenyl)-pyrimidin-4-yl]-(4-methoxy-3-nitro-phenyl)-amine (obtained in Example 69) (0.8 mmol) was dissolved in 30 ml MeOH and 731 mg SnCl₂×2H₂O (3.2 mmol) was added. The mixture was refluxed for 3 hours. Then it was poured onto 100 g ice and the pH was basified by addition of 5M NaOH solution. Mixture was extracted three times with 40-40 ml ethyl acetate. The combined organic layer was washed with brine, dried over MgSO₄ and evaporated under reduced pressure. Residue was recrystallized from a minimal amount of acetonitrile to get the pure product as an off white solid. Yield: 62 mg (19%). Ret. time: 2.97 min., (M+H)⁺=399, (M+H)⁻=397; ¹HNMR (DMSO-d₆, 300 MHz), δ (ppm): 9.14 (s, 1H), 8.58 (s, 1H), 7.81 (d, 1H), 7.37 (m, 7H), 7.19 (d, 1H), 7.05 (t, 1H), 6.82 (s, 1H), 6.69 (d, 1H), 6.64 (d, 1H), 5.21 (s, 2H), 4.77 (s, 2H), 3.73 (s, 3H).

[6-(2-Ethoxy-4-fluoro-phenyl)-pyrimidin-4-yl]-(4-methoxy-3-nitro-phenyl)-amine (Example 72)

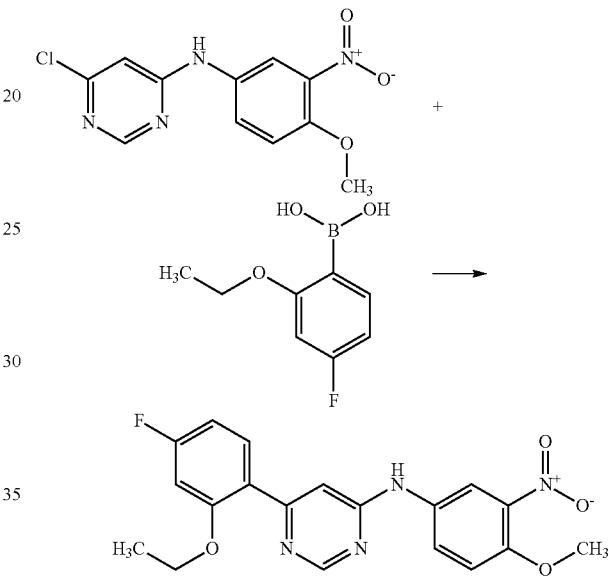

Title compound was prepared according to the method described in case of Example 61 using 2-ethoxy-4-fluoro-phenylboronic acid as reactant Yield: 187 mg (49%). Ret. time: 3.30 min., (M+H)⁺=385, (M+H)⁻=383; ¹HNMR (DMSO-d₆, 300 MHz), δ (ppm): 9.76 (s, 1H), 8.70 (s, 1H), 8.37 (s, 1H), 8.05 (t, 1H), 7.88 (d, 1H), 7.43 (s, 1H), 7.39 (d, 1H), 7.08 (d, 1H), 6.90 (t, 1H), 4.19 (q, 2H), 3.91 (s, 3H), 1.41 (t, 3H).

N¹-[6-(2-Ethoxy-4-fluoro-phenyl)-pyrimidin-4-yl]-4-methoxy-benzene-1,3-diamine (Example 73)

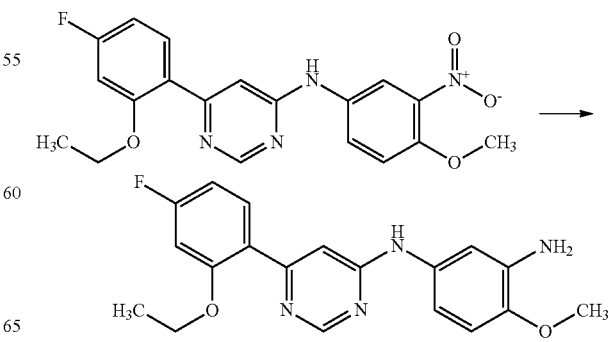

Title compound was prepared according to the method described in case of Example 59 using [6-(2-Ethoxy-4-fluoro-phenyl)-pyrimidin-4-yl]-(4-methoxy-3-nitro-phenyl)-amine (obtained in Example 72) as starting material. Yield: 177 mg (50%). Ret. time: 0.45-2.60 min., (M+H)$^+$= 355, (M+H)$^-$=353; $^1$HNMR (DMSO-d$_6$, 300 MHz), δ (ppm): 9.13 (s, 1H), 8.55 (s, 1H), 8.03 (t, 1H), 7.34 (s, 1H), 7.02 (d, 1H), 6.88-6.66 (m, 4H), 4.78 (s, 2H), 4.12 (q, 2H), 3.75 (s, 3H), 1.31 (t, 3H).

[6-(5-Fluoro-2-methoxy-phenyl)-pyrimidin-4-yl]-(4-methoxy-3-nitro-phenyl)-amine (Example 74)

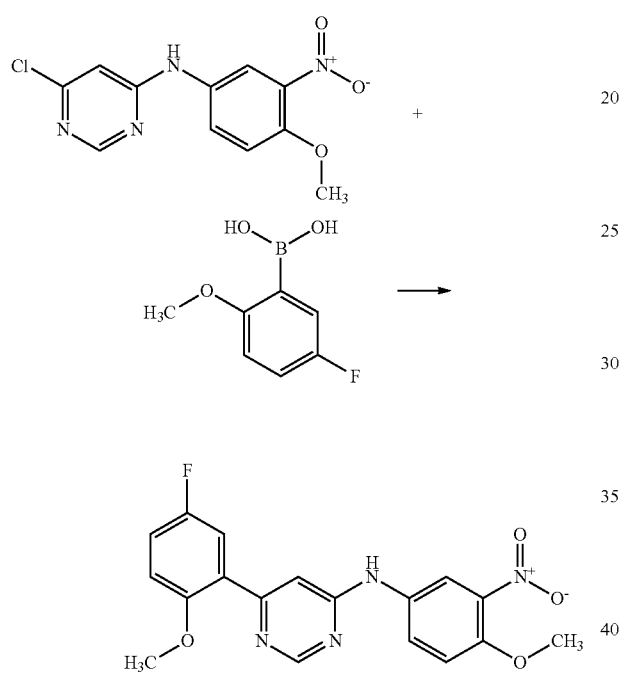

Title compound was prepared according to the method described in case of Example 61 using 5-fluoro-2-methoxy-phenylboronic acid as reactant Yield: 136 mg (37%). Ret. time: 3.25 min., (M+H)$^+$=371, (M+H)$^-$=369; $^1$HNMR (DMSO-d$_6$, 300 MHz), δ (ppm): 9.90 (s, 1H), 8.73 (s, 1H), 8.43 (s, 1H), 7.87 (d, 1H), 7.79 (d, 1H), 7.51 (s, 1H), 7.39 (dd, 1H), 7.35 (t, 1H), 7.23 (t, 1H), 3.91 (s, 6H).

N$^1$-[6-(5-Fluoro-2-methoxy-phenyl)-pyrimidin-4-yl]-4-methoxy-benzene-1,3-diamine (Example 75)

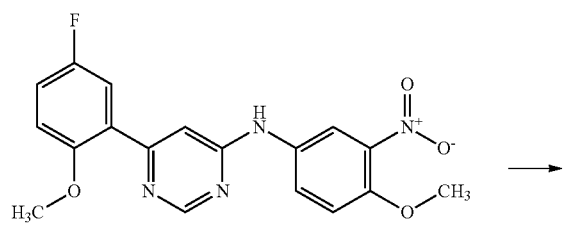

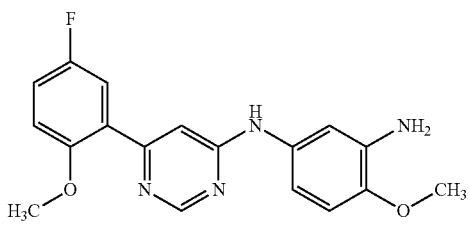

Title compound was prepared according to the method described in case of Example 59 using [6-(5-Fluoro-2-methoxy-phenyl)-pyrimidin-4-yl]-(4-methoxy-3-nitro-phenyl)-amine (obtained in Example 74) as starting material. Yield: 140 mg (41%). Ret. time: 0.45-2.36 min., (M+H)$^+$= 341, (M+H)$^-$=339; $^1$HNMR (DMSO-d$_6$, 300 MHz), δ (ppm): 9.26 (s, 1H), 8.58 (s, 1H), 7.74 (d, 1H), 7.42 (s, 1H), 7.28 (t, 1H), 7.18 (t, 1H), 6.92 (s, 1H), 6.75 (bs, 2H), 4.79 (s, 2H), 3.87 (s, 3H), 3.74 (s, 3H).

(4-Methoxy-3-nitro-phenyl)-[6-(2-phenoxy-phenyl)-pyrimidin-4-yl]-amine (Example 76)

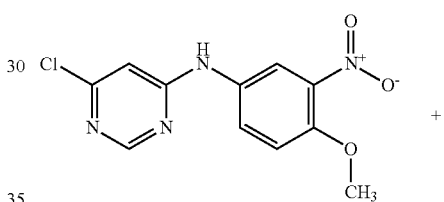

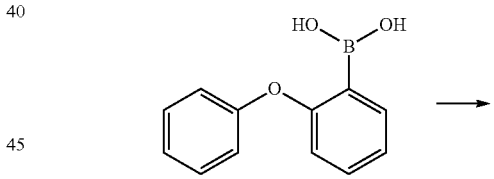

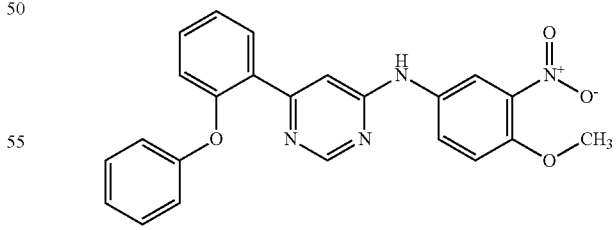

Title compound was prepared according to the method described in case of Example 61 using 2-phenoxyphenylboronic acid as reactant Yield: 188 mg (45%). Ret. time: 3.88 min., (M+H)$^+$=415, (M+H)$^-$=413; $^1$HNMR (DMSO-d$_6$, 300 MHz), δ (ppm): 9.82 (s, 1H), 8.72 (s, 1H), 8.35 (s, 1H), 8.06 (d, 1H), 7.82 (d, 1H), 7.38 (m, 6H), 7.17 (t, 1H), 7.00 (m, 3H), 3.90 (s, 3H).

4-Methoxy-N[1]-[6-(2-phenoxy-phenyl)-pyrimidin-4-yl]-benzene-1,3-diamine (Example 77)

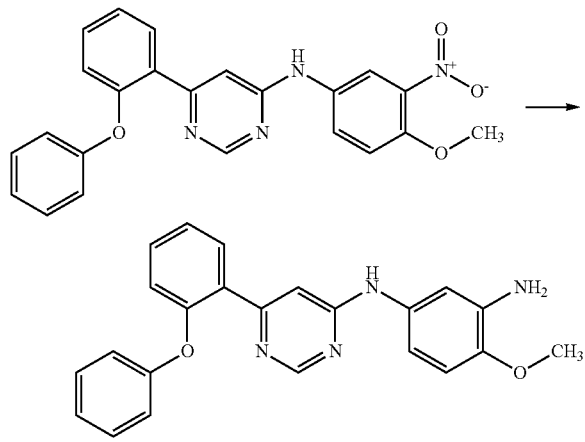

Title compound was prepared according to the method described in case of Example 59 using (4-Methoxy-3-nitro-phenyl)-[6-(2-phenoxy-phenyl)-pyrimidin-4-yl]-amine (obtained in Example 76) as starting material. Yield: 216 mg (56%). Ret. time: 2.99 min., (M+H)[+]=385, (M+H)[−]=383; $^1$HNMR (DMSO-d$_6$, 300 MHz), δ (ppm): 9.18 (s, 1H), 8.56 (s, 1H), 8.00 (d, 1H), 7.45 (t, 1H), 7.32 (m, 4H), 7.10 (t, 1H), 6.95 (m, 3H), 6.82 (s, 1H), 6.64 (bs, 2H), 4.74 (s, 2H), 3.73 (s, 3H).

[6-(2-Isopropoxy-phenyl)-pyrimidin-4-yl]-(4-methoxy-3-nitro-phenyl)-amine (Example 78)

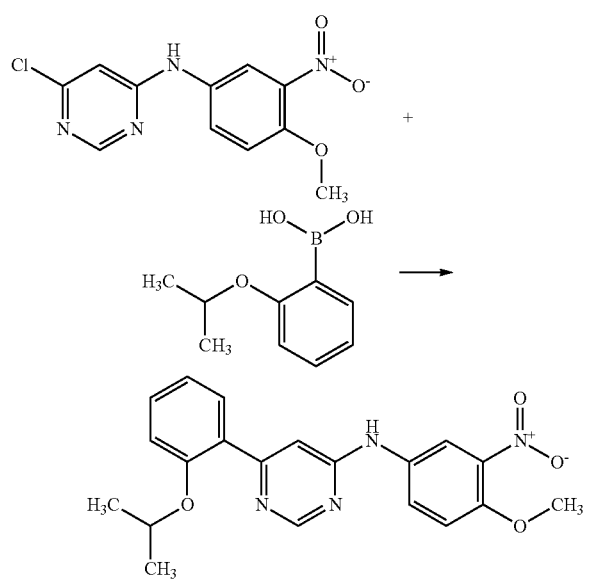

Title compound was prepared according to the method described in case of Example 61 using 2-isopropoxyphenyl-boronic acid as reactant Yield: 144 mg (38%). Ret. time: 3.21 min., (M+H)[+]=381, (M+H)[−]=379; $^1$HNMR (DMSO-d$_6$, 300 MHz), δ (ppm): 9.73 (s, 1H), 8.70 (s, 1H), 8.36 (s, 1H), 7.95 (d, 1H), 7.90 (d, 1H), 7.40 (m, 3H), 7.17 (d, 1H), 7.04 (t, 1H), 4.72 (m, 1H), 3.91 (s, 3H), 1.32 (d, 6H).

N[1]-[6-(2-Isopropoxy-phenyl)-pyrimidin-4-yl]-4-methoxy-benzene-1,3-diamine (Example 79)

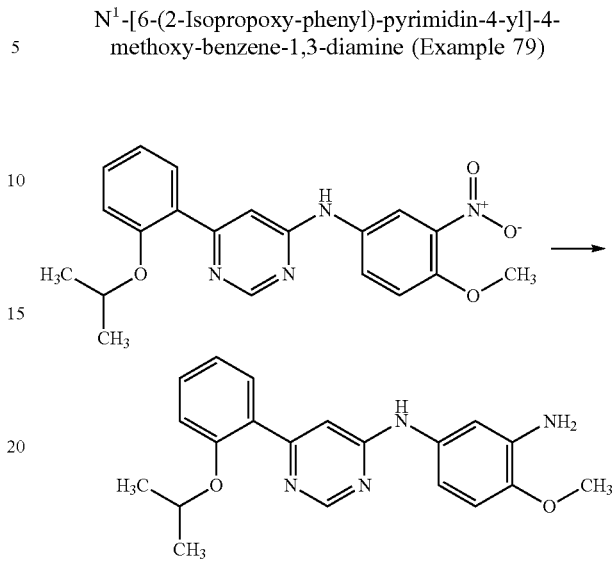

Title compound was prepared according to the method described in case of Example 59 using [6-(2-Isopropoxy-phenyl)-pyrimidin-4-yl]-(4-methoxy-3-nitro-phenyl)-amine (obtained in Example 78) as starting material. Yield: 87 mg (25%). Ret. time: 0.45-2.48-2.68 min., (M+H)[+]=351, (M+H)[−]=349; $^1$HNMR (DMSO-d$_6$, 300 MHz), δ (ppm): 9.08 (s, 1H), 8.56 (s, 1H), 7.93 (d, 1H), 7.38 (d, 1H), 7.35 (s, 1H), 7.12 (d, 1H), 7.01 (t, 1H), 6.81 (bs, 1H), 6.77 (d, 1H), 6.67 (d, 1H), 4.77 (s, 2H), 4.66 (m, 1H), 3.75 (s, 3H), 1.22 (d, 6H).

[6-(3-Fluoro-2-methoxy-phenyl)-pyrimidin-4-yl]-(4-methoxy-3-nitro-phenyl)-amine (Example 80)

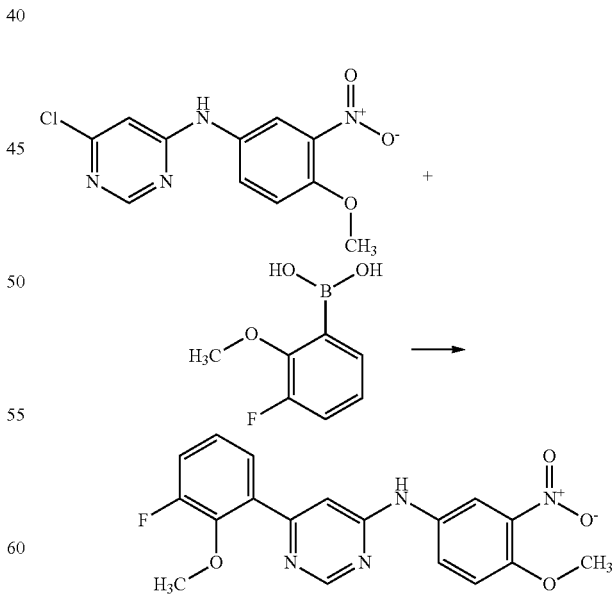

Title compound was prepared according to the method described in case of Example 61 using 3-fluoro-2-methoxy-phenylboronic acid as reactant Yield: 142 mg (38%). Ret. time: 3.31 min., (M+H)[+]=371, (M+H)[−]=369; $^1$HNMR (DMSO-d$_6$, 300 MHz), δ (ppm): 9.93 (s, 1H), 8.75 (s, 1H), 8.43 (d, 1H), 7.86 (dd, 1H), 7.73 (d, 1H), 7.39 (m, 3H), 7.24 (m, 1H), 3.91 (s, 3H), 3.87 (s, 3H).

N$^1$-[6-(3-Fluoro-2-methoxy-phenyl)-pyrimidin-4-yl]-4-methoxy-benzene-1,3-diamine (Example 81)

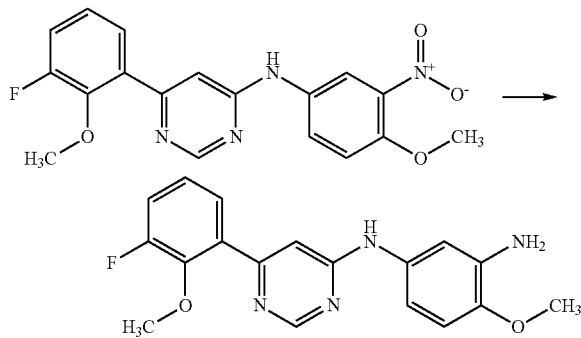

Title compound was prepared according to the method described in case of Example 59 using [6-(3-Fluoro-2-methoxy-phenyl)-pyrimidin-4-yl]-(4-methoxy-3-nitro-phenyl)-amine (obtained in Example 80) as starting material. Yield: 70 mg (21%). Ret. time: 0.45-2.46 min., (M+H)$^+$= 341, (M+H)$^-$=339; $^1$HNMR (DMSO-d$_6$, 300 MHz), δ (ppm): 9.29 (s, 1H), 8.60 (s, 1H), 7.68 (d, 1H), 7.37 (td, 1H), 7.20 (m, 2H), 6.90 (s, 1H), 6.78 (bs, 2H), 4.78 (s, 2H), 3.83 (s, 3H), 3.75 (s, 3H).

[6-(4,5-Difluoro-2-methoxy-phenyl)-pyrimidin-4-yl]-(4-methoxy-3-nitro-phenyl)-amine (Example 82)

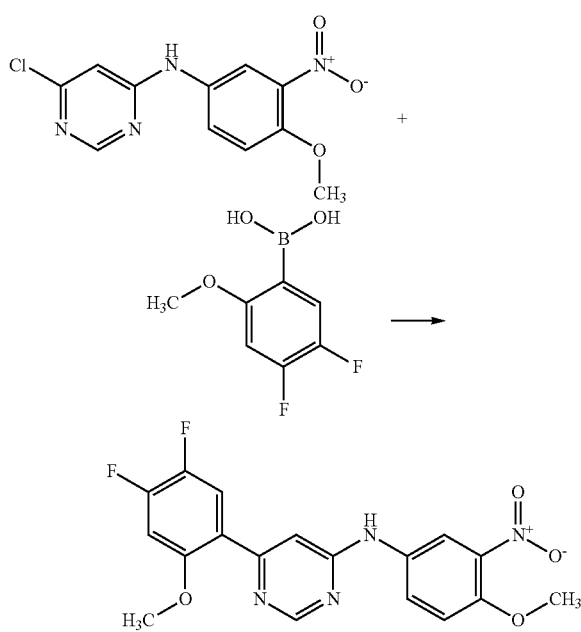

Title compound was prepared according to the method described in case of Example 61 using 4,5-difluoro-2-methoxyphenylboronic acid as reactant Yield: 144 mg (37%). Ret. time: 3.59 min., (M+H)$^+$=389, (M+H)$^-$=387;

$^1$HNMR (DMSO-d$_6$, 300 MHz), δ (ppm): 9.88 (s, 1H), 8.71 (s, 1H), 8.42 (d, 1H), 8.03 (dd, 1H), 7.85 (dd, 1H), 7.49 (d, 1H), 7.38 (m, 2H), 3.93 (s, 3H), 3.91 (s. 3H).

N$^1$-[6-(4,5-Difluoro-2-methoxy-phenyl)-pyrimidin-4-yl]-4-methoxy-benzene-1,3-diamine (Example 83)

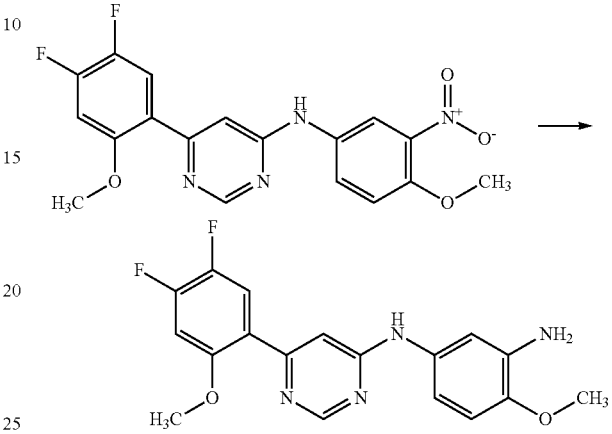

Title compound was prepared according to the method described in case of Example 59 using [6-(4,5-Difluoro-2-methoxy-phenyl)-pyrimidin-4-yl]-(4-methoxy-3-nitro-phenyl)-amine (obtained in Example 82) as starting material. Yield: 40 mg (11%). Ret. time: 0.45-2.60 min., (M+H)$^+$= 359, (M+H)$^-$=357; $^1$HNMR (DMSO-d$_6$, 300 MHz), δ (ppm): 9.26 (bs, 1H), 8.57 (s, 1H), 7.98 (t, 1H), 7.41 (s, 1H), 7.33 (dd, 1H), 6.92 (bs, 1H), 6.75 (bs, 2H), 4.78 (bs, 2H), 3.89 (s, 3H), 3.75 (s, 3H).

N-{5-[6-(4,5-Difluoro-2-methoxy-phenyl)-pyrimidin-4-ylamino]-2-methoxy-phenyl}-formamide (Example 84)

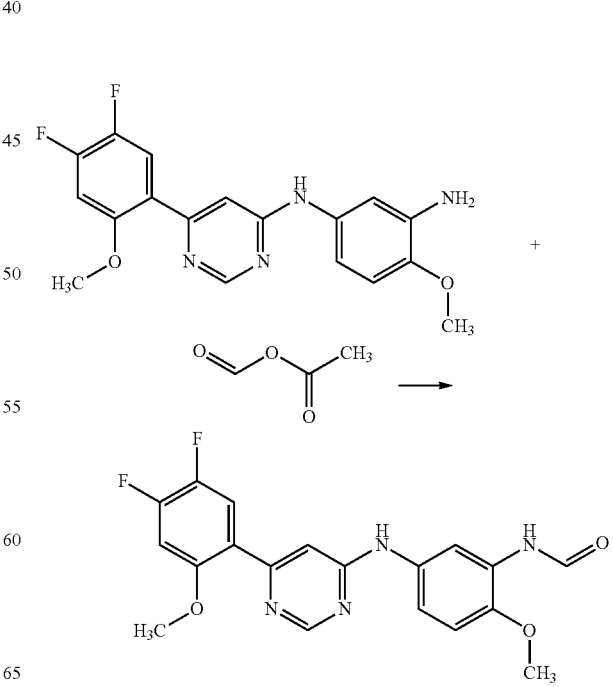

Title compound was prepared according to the method described in case of Example 55 using N¹-[6-(4,5-Difluoro-2-methoxy-phenyl)-pyrimidin-4-yl]-4-methoxy-benzene-1,3-diamine (obtained in Example 83) as starting material. Yield: 59 mg (22%). Ret. time: 2.69 min., (M+H)⁺=387, (M+H)⁻=385; ¹HNMR (DMSO-d$_6$, 300 MHz), δ (ppm): 9.66 (bs, 1H), 9.54 (s, 1H), 8.61 (s, 1H), 8.33 (s, 1H), 8.32 (s, 1H), 8.00 (t, 1H), 7.59 (d, 1H), 7.46 (s, 1H), 7.34 (dd, 1H), 7.04 (d, 1H), 3.90 (s, 3H), 7.02 (s, 3H).

[6-(4-Fluoro-2-isopropoxy-phenyl)-pyrimidin-4-yl]-(4-methoxy-3-nitro-phenyl)-amine (Example 85)

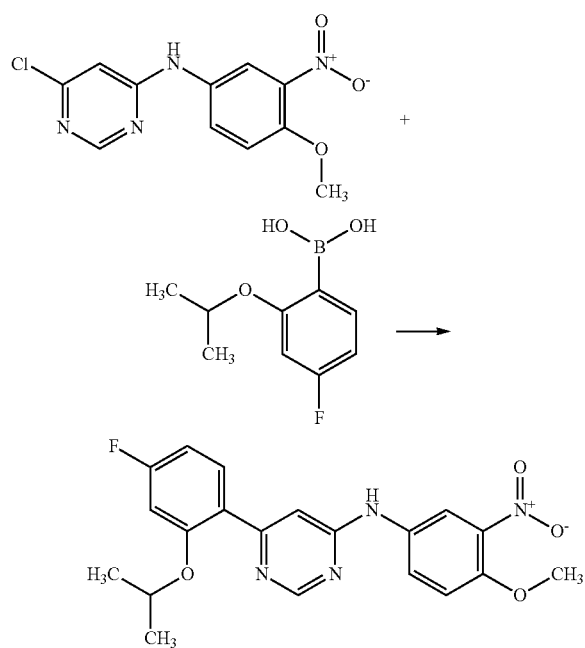

Title compound was prepared according to the method described in case of Example 61 using 4-fluoro-2-isopropoxyphenylboronic acid as reactant Yield: 292 mg (73%). Ret. time: 3.55 min., (M+H)⁺=399, (M+H)⁻=397; ¹HNMR (DMSO-d$_6$, 300 MHz), δ (ppm): 9.74 (bs, 1H), 8.69 (s, 1H), 8.35 (d, 1H), 8.03 (t, 1H), 7.89 (dd, 1H), 7.41 (s, 1H), 7.39 (d, 1H), 7.09 (dd, 1H), 6.87 (td, 1H), 4.77 (m, 1H), 3.91 (s, 3H), 1.34 (d, 6H).

N¹-[6-(4-Fluoro-2-isopropoxy-phenyl)-pyrimidin-4-yl]-4-methoxy-benzene-1,3-diamine (Example 86)

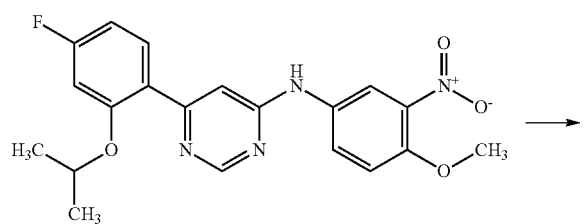

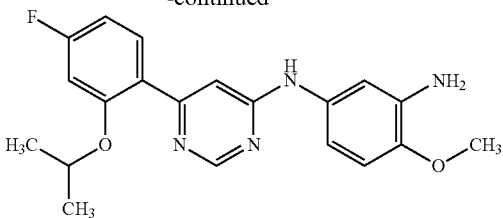

Title compound was prepared according to the method described in case of Example 59 using [6-(4-Fluoro-2-isopropoxy-phenyl)-pyrimidin-4-yl]-(4-methoxy-3-nitro-phenyl)-amine (obtained in Example 85) as starting material. Yield: 145 mg (40%). Ret. time: 2.80 min., (M+H)⁺=369, (M+H)⁻=367; ¹HNMR (DMSO-d$_6$, 300 MHz), δ (ppm): 9.10 (bs, 1H), 8.51 (s, 1H), 8.01 (t, 1H), 7.33 (s, 1H), 7.04 (dd, 1H), 6.82 (m, 3H), 6.66 (d, 1H), 4.78 (bs, 2H), 4.72 (m, 1H), 3.75 (s, 3H), 1.23 (d, 6H).

(3-Fluoro-4-methoxy-5-nitro-phenyl)-[6-(2-methoxy-phenyl)-pyrimidin-4-yl]-amine (Example 87)

Step 1

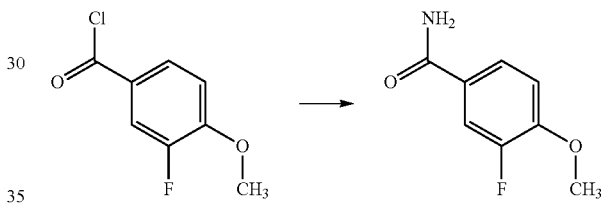

5.075 g 3-Fluoro-4-methoxy-benzoyl chloride (30 mmol) was dissolved in 30 ml dry dichloromethane and cooled to 0° C. This solution was added dropwise to a 150 ml 12% NH$_4$OH solution cooled in an ice bath. After stirring the mixture for an hour at room temperature the precipitated solid was collected by filtration and washed well with cold water. White solid was dried under vacuum over phosphorus pentoxide. Yield: 15.39 g (91%). Ret. time: 2.01 min., (M+H)⁺=170; ¹HNMR (DMSO-d$_6$, 300 MHz), δ (ppm): 7.89 (bs, 1H), 7.05 (m, 2H), 7.31 (bs, 1H), 7.22 (t, J=9.03 Hz, 1H), 3.89 (s, 3H).

Step 2

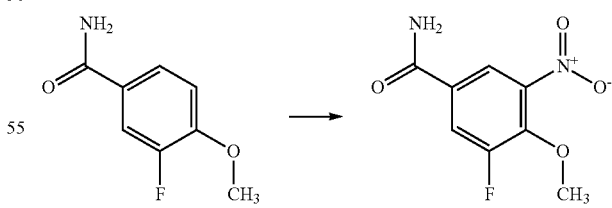

5.075 g 3-Fluoro-4-methoxy-benzamide (obtained in Step 1) (30 mmol) was added in portions to the previously prepared mixture of 10 ml 65% HNO$_3$ and 12 ml 96% H$_2$SO$_4$ at −5° C. The mixture was let to warm slowly to room temperature and was stirred further for an hour at RT. Then 300 g of ice was added and it was extracted four times with 50-50 ml ethyl acetate. The combined organic layer was washed with brine, dried over MgSO$_4$ and evaporated to dryness. The residue was recrystallized from a minimal amount of acetonitrile to get the pure product as a white solid. Yield: 5.08 g (79%). Ret. time: 2.50 min., (M+H)$^+$= 215, (M+H)$^-$=213; $^1$HNMR (DMSO-d$_6$, 300 MHz), δ (ppm): 8.25 (bs, 1H), 8.19 (bs, 1H), 8.11 (dd, J$^3$=12.30 Hz, J$^4$=1.71 Hz, 1H), 7.71 (bs, 1H), 4.06 (d, J=2.01 Hz, 3H).

Step 3

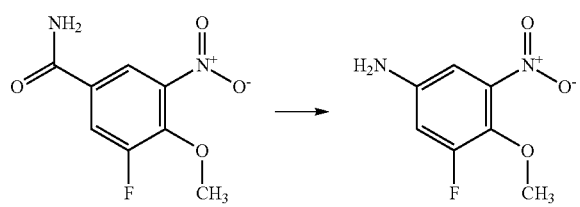

2.142 g 3-Fluoro-4-methoxy-5-nitro-benzamide (obtained in Step 2) (10 mmol) was added to the previously prepared solution of 30 ml 2M NaOH/aq and 0.615 ml bromine (12 mmol). The mixture was heated at 50° C. overnight. It was diluted with 30 ml water and it was extracted three times with 40-40 ml ethyl acetate. The combined organic layer was washed with brine, dried over MgSO$_4$ and evaporated to dryness. The residue was used without further purification. Yield: 216 mg (12%). Ret. time: 2.98 min., (M+H)$^+$=187; $^1$HNMR (DMSO-d$_6$, 300 MHz), δ (ppm): 6.83 (t, 1H), 6.73 (dd, J$^3$=13.20 Hz, J$^4$=2.70 Hz, 1H), 5.75 (s, 2H), 3.79 (s, 3H).

Step 4

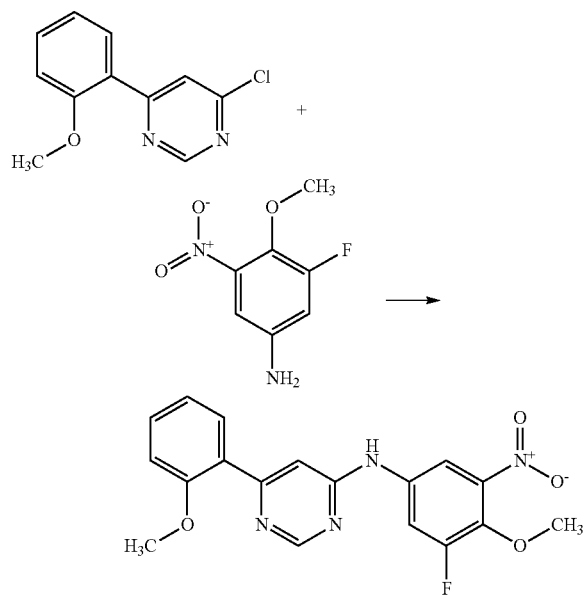

186 mg 3-Fluoro-4-methoxy-5-nitro-phenylamine (obtained in Step 3) (1 mmol) was added to a solution of 243 mg 4-chloro-6-(2-methoxy-phenyl)-pyrimidine (obtained in Example 32, Step 1) (1.1 mmol) in 25 ml of tert-butanol. 1 ml dry ethyl acetate saturated with HCl gas was added and the mixture was refluxed for 5 hours. Then it was poured onto 80 ml 5% NaHCO$_3$ solution and extracted three times with 40-40 ml ethyl acetate. The combined organic layer was washed with brine, dried over MgSO$_4$ and evaporated to dryness. The residue was recrystallized from a minimal amount of acetonitrile to get the pure product as a yellow solid. Yield: 178 mg (48%). Ret. time: 3.48 min., (M+H)$^+$= 371, (M+H)$^-$=369; $^1$HNMR (DMSO-d$_6$, 300 MHz), δ (ppm): 10.11 (bs, 1H), 8.80 (s, 1H), 8.13 (s, 1H), 8.09 (d, 1H), 8.00 (d, 1H), 7.48 (m, 2H), 7.20 (d, 1H), 7.09 (t, 1H), 3.94 (s, 3H), 3.92 (s, 3H).

5-Fluoro-4-methoxy-N$^1$-[6-(2-methoxy-phenyl)-pyrimidin-4-yl]-benzene-1,3-diamine (Example 88)

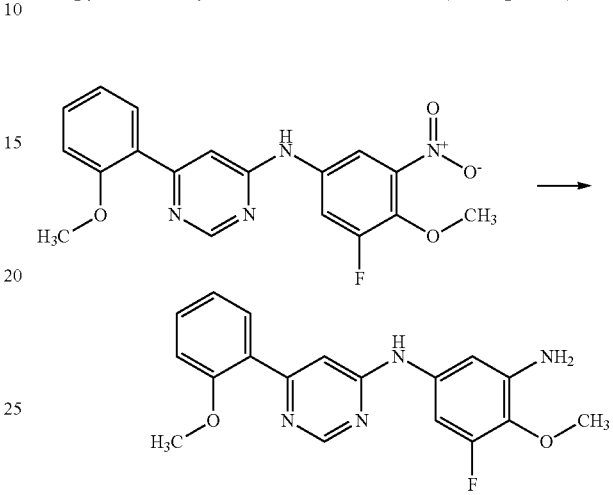

Title compound was prepared according to the method described in case of Example 59 using (3-Fluoro-4-methoxy-5-nitro-phenyl)-[6-(2-methoxy-phenyl)-pyrimidin-4-yl]-amine (obtained in Example 87) as starting material. Yield: 211 mg (62%). Ret. time: 2.57 min., (M+H)$^+$= 341, (M+H)$^-$=339; $^1$HNMR (DMSO-d$_6$, 300 MHz), δ (ppm): 9.39 (s, 1H), 8.65 (s, 1H), 7.93 (dd, 1H), 7.45 (dt, 1H), 7.40 (s, 1H), 7.17 (d, 1H), 7.07 (t, 1H), 6.91 (dd, 1H), 6.73 (s, 1H), 5.24 (bs, 2H), 3.89 (s, 3H), 3.70 (s, 1H).

N$^1$-[6-(2-Ethoxy-4-fluoro-phenyl)-pyrimidin-4-yl]-5-fluoro-4-methoxy-benzene-1,3-diamine (Example 89)

Step 1:

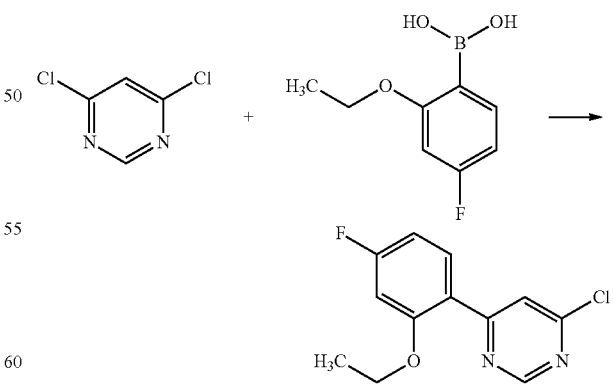

4-Chloro-6-(2-ethoxy-4-fluoro-phenyl)-pyrimidine was prepared according to the procedure described in case of Example 32, Step 1 using 2-ethoxy-4-fluorophenylboronic acid as reactant and the reaction was carried out in 10 mmol quantity. Yield: 1.67 g (66%). Ret. time: 4.49 min., (M+H)$^+$=

253; ¹HNMR (DMSO-d₆, 300 MHz), δ (ppm): 9.09 (s, 1H), 8.17 (s, 1H), 8.09 (t, J=7.23 Hz, 1H), 7.13 (dd, J³=11.43 Hz, J⁴=2.28 Hz, 1H), 6.96 (td, J³=8.55 Hz, J⁴=2.40 Hz, 1H), 4.21 (q, 2H), 1.40 (t, J=6.93 Hz, 3H).

Step 2

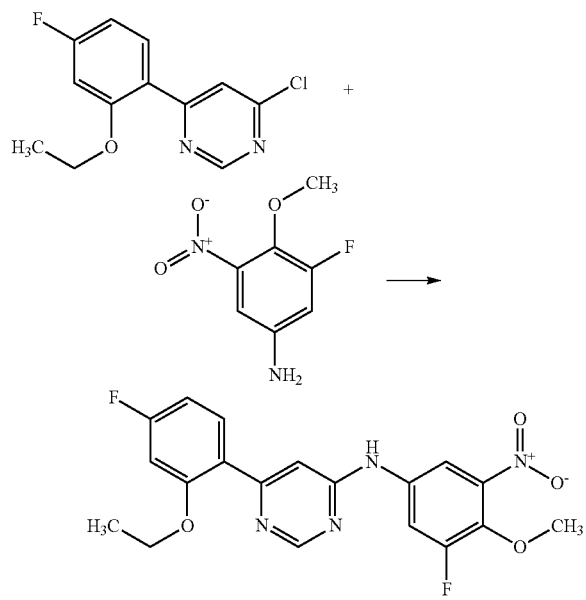

[6-(2-Ethoxy-4-fluoro-phenyl)-pyrimidin-4-yl]-(3-fluoro-4-methoxy-5-nitro-phenyl)-amine was prepared according to the method described in case of Example 87, Step 4 using 4-chloro-6-(2-ethoxy-4-fluoro-phenyl)-pyrimidine (obtained in Step 1) as starting material. Product was used directly in the next step without any analytical investigation. Yield: 322 mg (80%).

Step 3:

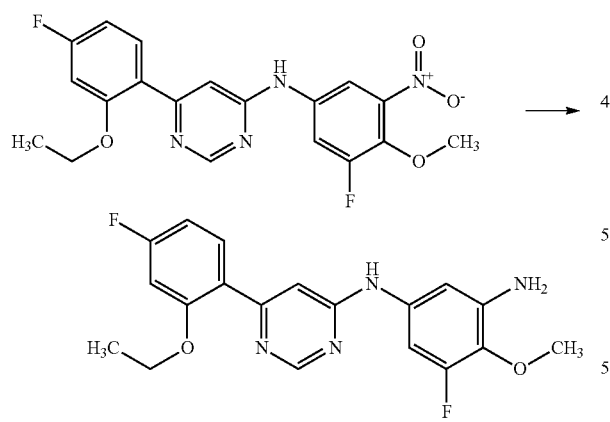

Title compound was prepared according to the method described in case of Example 59 using [6-(2-ethoxy-4-fluoro-phenyl)-pyrimidin-4-yl]-(3-fluoro-4-methoxy-5-nitro-phenyl)-amine (obtained in Step 2) as starting material. Yield: 181 mg (49%). Ret. time: 2.99 min., (M+H)⁺=373, (M+H)⁻=371; ¹HNMR (DMSO-d₆, 300 MHz), δ (ppm): 9.36 (bs, 1H), 8.63 (s, 1H), 8.03 (t, 1H), 7.42 (s, 1H), 7.05 (d, 1H), 6.86 (m, 2H), 6.66 (s, 1H), 5.27 (bs, 2H), 4.26 (q, 2H), 3.70 (s, 3H), 1.37 (t, 3H).

5-Fluoro-N¹-[6-(4-fluoro-2-methoxy-phenyl)-pyrimidin-4-yl]-4-methoxy-benzene-1,3-diamine (Example 90)

Step 1:

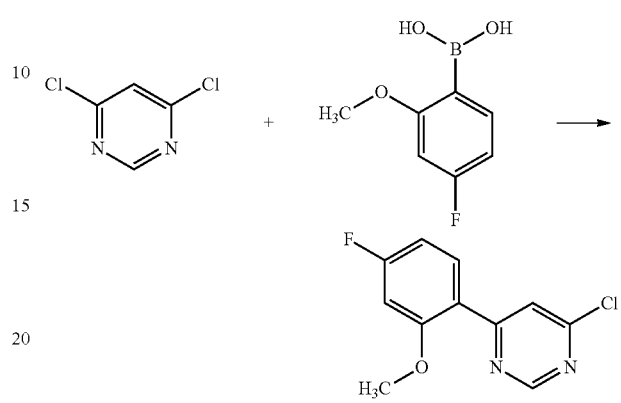

4-Chloro-6-(4-fluoro-2-methoxy-phenyl)-pyrimidine was prepared according to the procedure described in case of Example 32, Step 1 using 4-fluoro-2-methoxyphenylboronic acid as reactant and the reaction was carried out in 10 mmol quantity. Yield: 1.68 g (70%). Ret. time: 4.04 min., (M+H)⁺= 239; ¹HNMR (DMSO-d₆, 300 MHz), δ (ppm): 9.08 (s, 1H), 8.07 (m, 2H), 7.16 (d, J=11.25 Hz, 1H), 6.97 (t, J=8.58 Hz, 1H), 3.94 (s, 3H).

Step 2

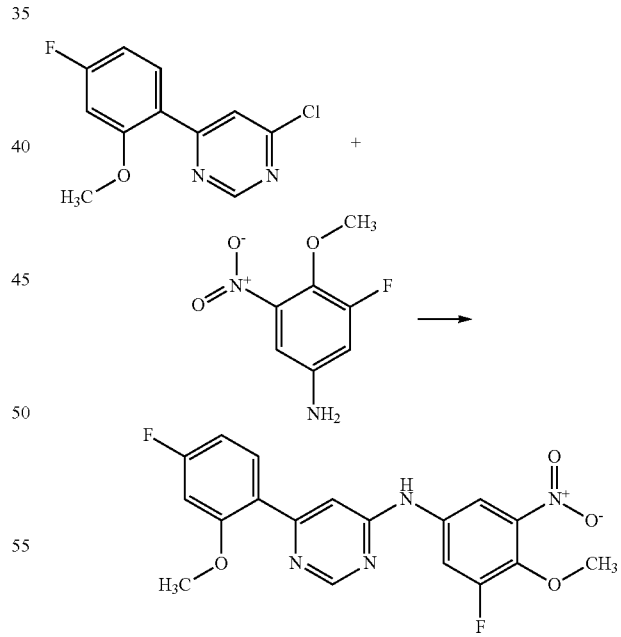

[6-(4-Fluoro-2-methoxy-phenyl)-pyrimidin-4-yl]-(3-fluoro-4-methoxy-5-nitro-phenyl)-amine was prepared according to the method described in case of Example 87, Step 4 using 4-chloro-6-(4-fluoro-2-methoxy-phenyl)-pyrimidine (obtained in Step 1) as starting material. Product was used directly in the next step without any analytical investigation. Yield: 302 mg (78%).

Step 3:

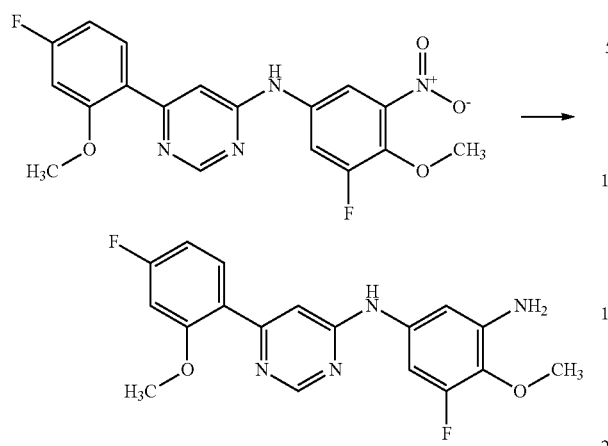

Title compound was prepared according to the method described in case of Example 59 using [6-(4-fluoro-2-methoxy-phenyl)-pyrimidin-4-yl]-(3-fluoro-4-methoxy-5-nitro-phenyl)-amine (obtained in Step 2) as starting material. Yield: 125 mg (35%). Ret. time: 2.78 min., $(M+H)^+=359$, $(M+H)^-=357$; $^1$HNMR (DMSO-$d_6$, 300 MHz), δ (ppm): 9.42 (bs, 1H), 8.64 (s, 1H), 8.02 (dd, 1H), 7.39 (d, 1H), 7.09 (dd, 1H), 6.90 (m, 2H), 6.71 (s, 1H), 5.26 (bs, 2H), 3.92 (s, 3H), 3.70 (s, 3H).

5-Fluoro-N$^1$-[6-(5-fluoro-2-methoxy-phenyl)-pyrimidin-4-yl]-4-methoxy-benzene-1,3-diamine (Example 91)

Step 1:

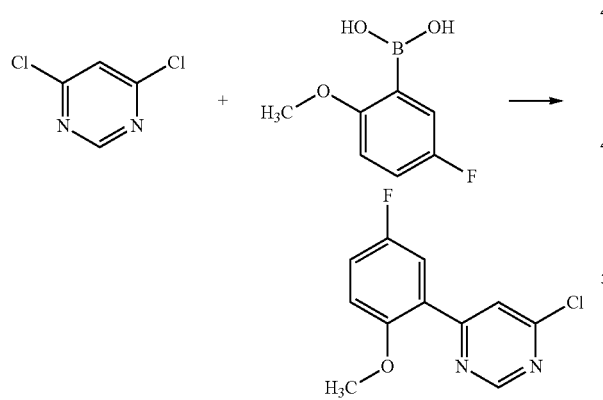

4-Chloro-6-(5-fluoro-2-methoxy-phenyl)-pyrimidine was prepared according to the procedure described in case of Example 32, Step 1 using 5-fluoro-2-methoxyphenylboronic acid as reactant and the reaction was carried out in 10 mmol quantity. Yield: 1.352 g (57%). Ret. time: 4.09 min., $(M+H)^+=239$; $^1$HNMR (DMSO-$d_6$, 300 MHz), δ (ppm): 9.12 (s, 1H), 8.17 (s, 1H), 7.78 (dd, $J^3=9.63$ Hz, $J^4=3.09$ Hz, 1H), 7.42 (dt, $J^3=8.46$ Hz, $J^4=3.21$ Hz, 1H), 7.26 (dd, $J^3=9.12$ Hz, $J^4=4.44$ Hz, 1H), 3.91 (s, 3H).

Step 2

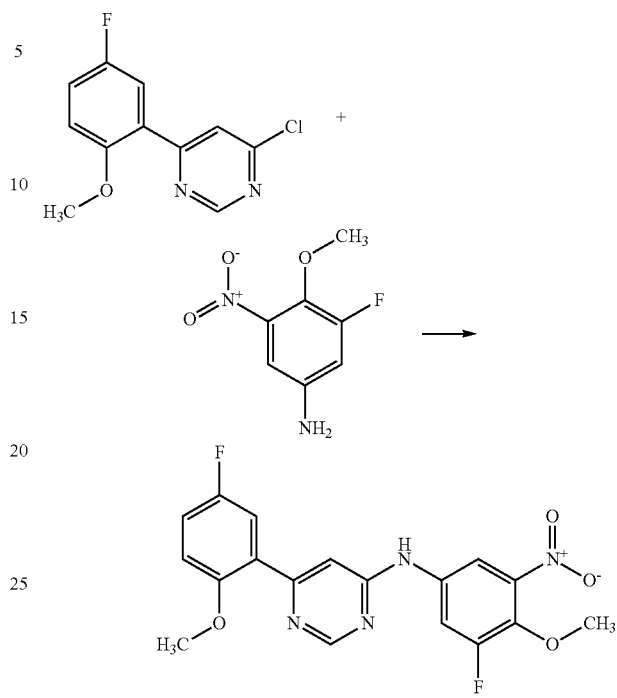

[6-(5-Fluoro-2-methoxy-phenyl)-pyrimidin-4-yl]-(3-fluoro-4-methoxy-5-nitro-phenyl)-amine was prepared according to the method described in case of Example 87, Step 4 using 4-chloro-6-(5-fluoro-2-methoxy-phenyl)-pyrimidine (obtained in Step 1) as starting material. Product was used directly in the next step without any analytical investigation. Yield: 339 mg (87%).

Step 3:

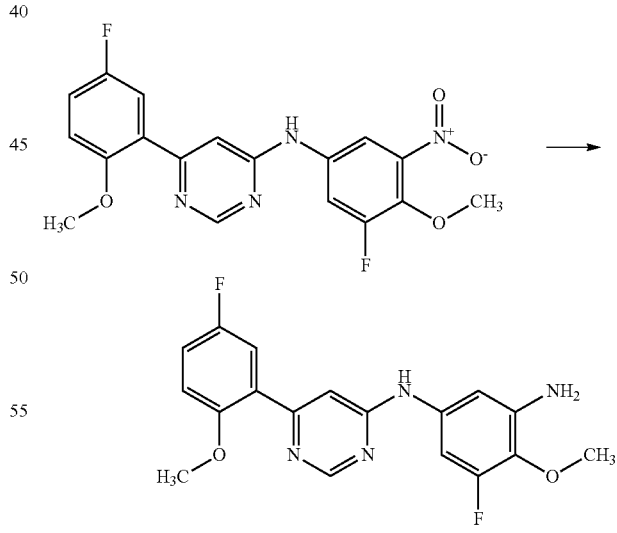

Title compound was prepared according to the method described in case of Example 59 using [6-(5-fluoro-2-methoxy-phenyl)-pyrimidin-4-yl]-(3-fluoro-4-methoxy-5-nitro-phenyl)-amine (obtained in Step 2) as starting material. Yield: 130 mg (36%). Ret. time: 2.87 min., $(M+H)^+=359$, $(M+H)^-=357$; $^1$HNMR (DMSO-$d_6$, 300 MHz), δ (ppm): 9.47 (s, 1H), 8.66 (s, 1H), 7.76 (dd, 1H), 7.49 (s, 1H), 7.32

(dt, 1H), 7.19 (dd, 1H), 6.91 (dd, 1H), 6.73 (s, 1H), 5.25 (bs, 2H), 3.90 (s, 3H), 3.71 (s, 3H).

4-Fluoro-6-methoxy-N³-[6-(2-methoxy-phenyl)-pyrimidin-4-yl]-benzene-1,3-diamine (Example 92)

Step 1

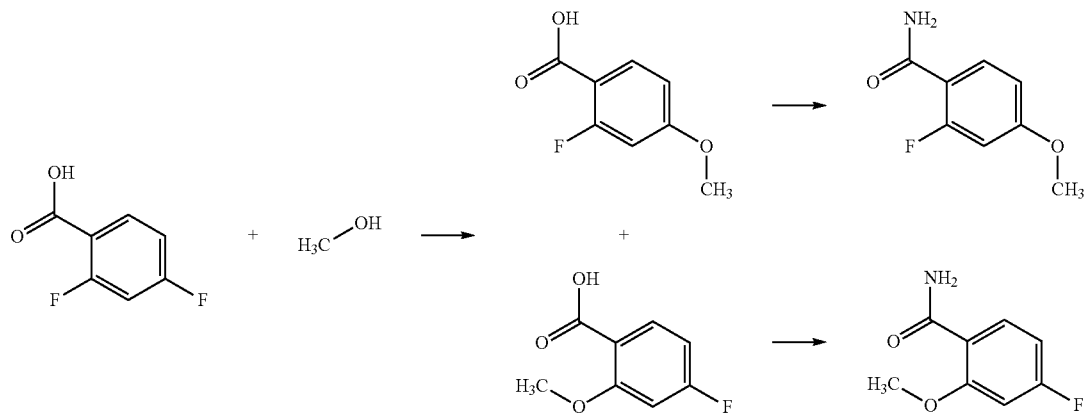

15.81 g 2,4-Diflourobenzoic acid (100 mmol) was dissolved in 200 ml DMSO and 10.80 g sodium methoxyide (200 mmol) was added. The mixture was heated at 80 C for 25 hours. Then it was poured onto 2000 g ice and pH was set to 1-2 by addition of saturated HCl solution. The precipitated solid was collected by filtration and dried under vacuum over phosphorus pentoxide for a day. The dry white solid was refluxed in 150 ml thionyl chloride in presence of 2-3 drops of dry DMF for 4 hours. Volatiles were removed by evaporation, toluene was added to the residue and it was evaporated off again. Finally the residue was taken up in 150 ml dry dichloromethane and was added dropwise to 300 ml cooled solution of 12% $NH_4OH$ in water. After the addition the mixture was stirred for an hour at room temperature, then it was extracted four times with 300-300 ml chloroform. The combined organic layer was washed with brine, dried over $MgSO_4$ and evaporated to dryness. The residue was purified by column chromatography on silica gel eluting with hexanes: ethyl acetate=1:1.

2-Fluoro-4-methoxy-benzamide was obtained as a white solid. Yield: 0.35 g (2%). Ret. time: 2.21 min., $(M+H)^+$=170; ¹HNMR (DMSO-$d_6$, 300 MHz), δ (ppm): 7.68 (t, J=8.67 Hz, 1H), 7.42 (bd, 2H), 6.86 (m, 2H), 3.81 (s, 3H).

4-Fluoro-2-methoxy-benzamide was obtained as a white solid. Yield: 9.66 g (57%). Ret. time: 2.36 min., $(M+H)^+$=170; ¹HNMR (DMSO-$d_6$, 300 MHz), δ (ppm): 7.86 (t, J=7.97 Hz, 1H), 7.54 (bd, 2H), 7.03 (dd, J³=11.40 Hz, J⁴=2.31 Hz, 1H), 6.85 (dt, J³=8.46 Hz, J⁴=2.37 Hz, 1H), 3.90 (s, 3H).

Step 2

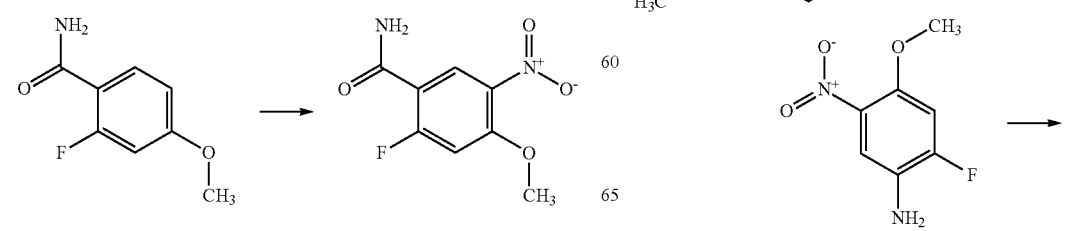

2-Fluoro-4-methoxy-5-nitro-benzamide was prepared according to the method described in case of Example 87, Step 2 using 2-fluoro-4-methoxy-benzamide (obtained in Step 1) as starting material and the reaction was carried out in 3.5 mmol quantity. Yield: 591 mg (79%). Ret. time: 2.14 min., $(M+H)^+$=215 (weak intensity); ¹HNMR (DMSO-$d_6$, 300 MHz), δ (ppm): 8.28 (d, J=7.29 Hz, 1H), 7.74 (bs, 2H), 7.39 (d, J=12.57 Hz, 1H), 3.99 (s, 3H).

Step 3

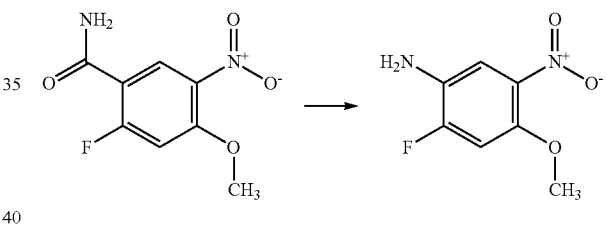

2-Fluoro-4-methoxy-5-nitro-phenylamine was prepared according to the method described in case of Example 87, Step 3 using 2-fluoro-4-methoxy-5-nitro-benzamide (obtained in Step 2) as starting material and the reaction was carried out in 2.5 mmol quantity. Product was used directly in the next step without any analytical investigation. Yield: 95 mg (20%).

Step 4

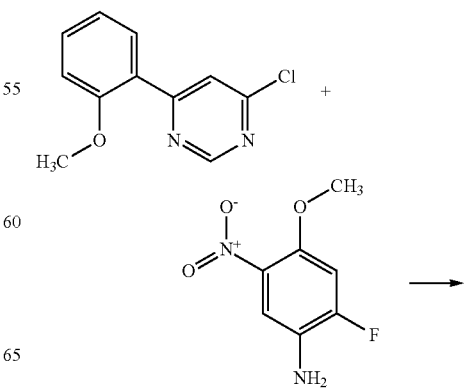

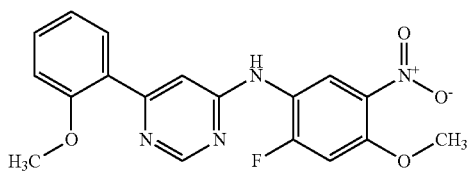

(2-Fluoro-4-methoxy-5-nitro-phenyl)-[6-(2-methoxy-phenyl)-pyrimidin-4-yl]-amine was prepared according to the method described in case of Example 87, Step 4 using 2-fluoro-4-methoxy-5-nitro-phenylamine (obtained in Step 3) as starting material and the reaction was carried out in 0.5 mmol quantity. Yield: 79 mg (44%). Ret. time: 2.90 min., (M+H)$^+$=371, (M+H)$^-$=369.

Step 5:

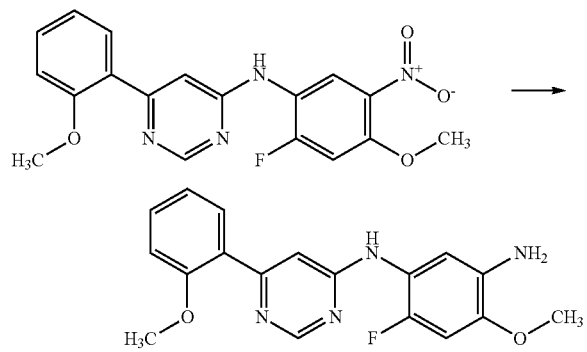

Title compound was prepared according to the method described in case of Example 59 using (2-fluoro-4-methoxy-5-nitro-phenyl)-[6-(2-methoxy-phenyl)-pyrimidin-4-yl]-amine (obtained in Step 4) as starting material and the reaction was carried out in 0.2 mmol quantity. Yield: 41 mg (61%). Ret. time: 2.27 min., (M+H)$^+$=341, (M+H)$^-$=339; $^1$HNMR (DMSO-d$_6$, 300 MHz), δ (ppm): 8.93 (s, 1H), 8.54 (s, 1H), 7.90 (d, 1H), 7.42 (td, 1H), 7.22 (s, 1H), 7.14 (d, 1H), 7.05 (t, 1H), 6.85 (m, 2H), 4.62 (bs, 2H), 3.84 (s, 3H), 3.78 (s, 3H).

Acetic Acid 2-methoxy-5-[6-(2-methoxy-phenyl)-pyrimidin-4-ylamino]-phenyl Ester (Example 93)

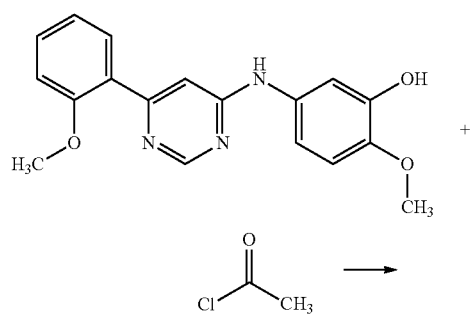

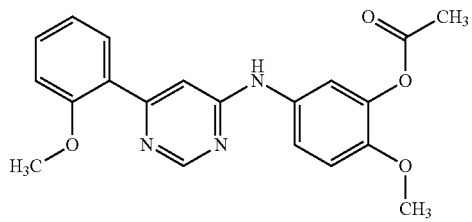

Title compound was prepared according to the method described in case of Example 26 using acetyl chloride as reagent. Yield: 112 mg (44%). Ret. time: 0.44-2.47-2.66 min., (M+H)$^+$=366, (M+H)$^-$=364; $^1$HNMR (DMSO-d$_6$, 300 MHz), δ (ppm): 9.54 (bs, 1H), 8.65 (s, 1H), 7.95 (d, 1H), 7.59 (s, 1H), 7.45 (t, 1H), 7.38 (s, 2H), 7.12 (m, 3H), 3.89 (s, 3H), 3.76 (s, 3H), 2.27 (s, 3H).

Dimethyl-carbamic Acid 2-methoxy-5-[6-(2-methoxy-phenyl)-pyrimidin-4-ylamino]-phenyl Ester (Example 94)

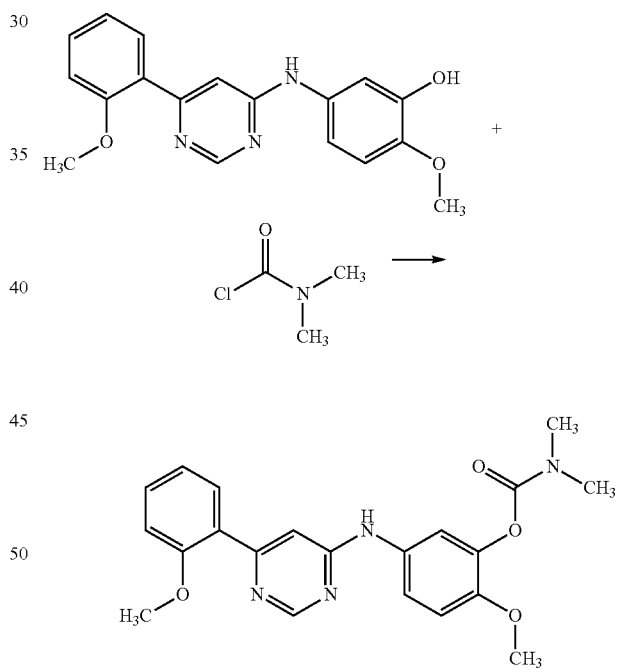

Title compound was prepared according to the method described in case of Example 26 using dimethylcarbamyl chloride as reagent. Yield: 185 mg (67%). Ret. time: 0.45-2.43-2.65 min., (M+H)$^+$=395, (M+H)$^-$=393; $^1$HNMR (DMSO-d$_6$, 300 MHz), δ (ppm): 9.51 (s, 1H), 8.65 (s, 1H), 7.95 (d, 1H), 7.57 (s, 1H), 7.45 (t, 1H), 7.38 (s, 1H), 7.37 (d, 1H), 7.18 (d, 1H), 7.07 (m, 2H), 3.89 (s, 3H), 3.75 (s, 3H), 3.05 (s, 3H), 2.91 (s, 3H).

Carbonic Acid 2-methoxy-5-[6-(2-methoxy-phenyl)-pyrimidin-4-ylamino]-phenyl Ester Methyl Ester (Example 95)

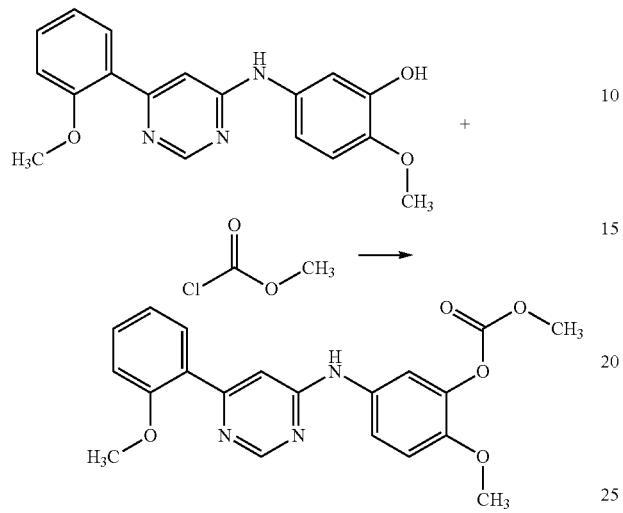

Title compound was prepared according to the method described in case of Example 26 using methyl chloroformate as reagent. Yield: 146 mg (55%). Ret. time: 2.75 min., (M+H)$^+$=382, (M+H)$^-$=380; $^1$HNMR (DMSO-d$_6$, 300 MHz), δ (ppm): 9.60 (bs, 1H), 8.66 (s, 1H), 7.95 (d, 1H), 7.70 (bs, 1H), 7.45 (m, 2H), 7.39 (s, 1H), 7.16 (t, 2H), 7.07 (t, 1H), 3.89 (s, 3H), 3.83 (s. 3H), 3.78 (s, 3H).

[6-(2-Methoxy-phenyl)-pyrimidin-4-yl]-(3-nitro-4-phenoxy-phenyl)-amine (Example 96)

Step 1

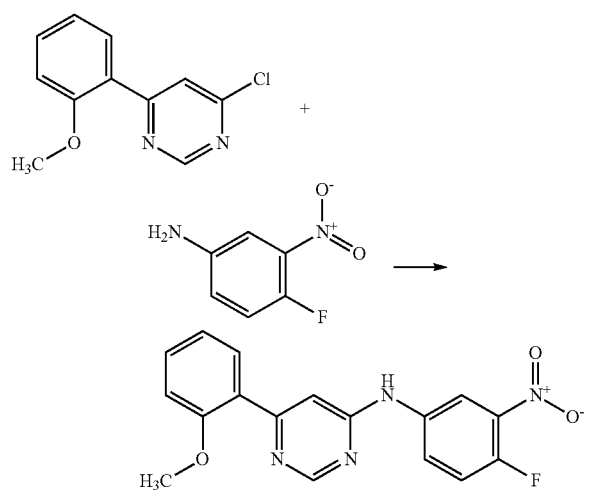

(4-Fluoro-3-nitro-phenyl)-[6-(2-methoxy-phenyl)-pyrimidin-4-yl]-amine was prepared according to the method described in case of Example 11, Step 1 using 4-fluoro-3-nitroaniline as reagent and the reaction was carried out in 15 mmol quantity. Yield: 4.80 g (94%). Ret. time: 3.13 min., (M+H)$^+$=341, (M+H)$^-$=339; $^1$HNMR (DMSO-d$_6$, 300 MHz), δ (ppm): 12.00 (bs, 1H); 8.90 (s, 1H); 8.79 (dd, 1H); 8.15-8.21 (m, 1H); 7.83 (d, 1H); 7.72 (s, 1H), 7.60-7.68 (m, 2H); 7.55 (t, 1H); 7.24 (d, 1H); 7.13 (t, 1H); 3.91 (s, 3H).

Step 2

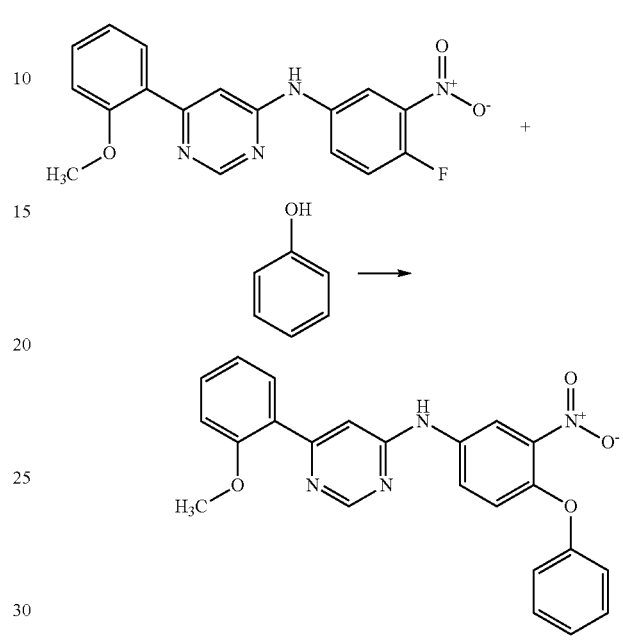

198 mg Phenol (2.1 mmol) was dissolved in 20 ml dry dimethylformamide and 88 mg NaH (60% dispersion in mineral oil) (2.2 mmol) was added at room temperature. After stirring the mixture for 15 minutes 681 mg (4-fluoro-3-nitro-phenyl)-[6-(2-methoxy-phenyl)-pyrimidin-4-yl]-amine (obtained in Step 1) (2 mmol) was added and the mixture was stirred at room temperature for 25 hours. Then it was poured onto 200 g ice and the precipitated solid was filtered off and washed well with water. The crude product was recrystallized from a minimal amount of acetonitrile to get a yellow solid. Yield: 629 mg (76%). Ret. time: 3.75 min., (M+H)$^+$=415, (M+H)$^-$=413; $^1$HNMR (DMSO-d$_6$, 300 MHz), δ (ppm): 10.07 (bs, 1H), 8.78 (s, 1H), 8.68 (s, 1H), 7.99 (d, 1H), 7.94 (d, 1H), 7.44 (m, 4H), 7.26-7.01 (m, 6H), 3.92 (s, 3H).

N$^1$-[6-(2-Methoxy-phenyl)-pyrimidin-4-yl]-4-phenoxy-benzene-1,3-diamine (Example 97)

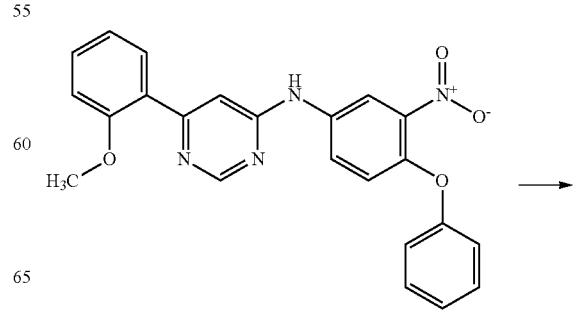

-continued

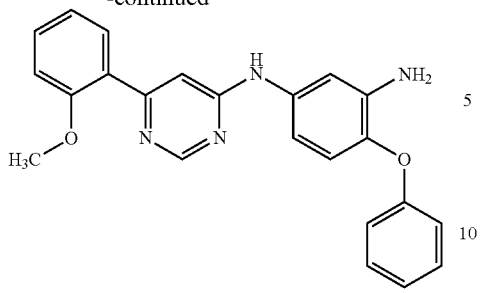

Title compound was prepared according to the method described in case of Example 59 using [6-(2-methoxy-phenyl)-pyrimidin-4-yl]-(3-nitro-4-phenoxy-phenyl)-amine (obtained in Example 96) as starting material. Yield: 93 mg (24%). Ret. time: 3.12 min., $(M+H)^+$=385, $(M+H)^-$=383; $^1$HNMR (DMSO-$d_6$, 300 MHz), δ (ppm): 9.38 (s, 1H), 8.64 (s, 1H), 7.94 (d, 1H), 7.46 (d, 1H), 7.42 (bs, 1H), 7.32 (t, 2H), 7.17 (m, 2H), 7.07 (t, 1H), 7.02 (t, 1H), 6.92-6.78 (m, 4H), 4.94 (bs, 2H), 3.89 (s, 3H).

{2-Methoxy-5-[6-(2-methoxy-phenyl)-pyrimidin-4-ylamino]-phenyl}-methyl-carbamic Acid Methyl Ester Hydrochloride (Example 98)

Step 1

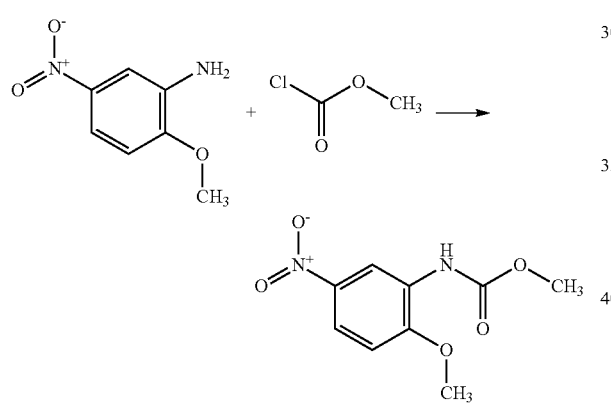

6.73 g 2-Methoxy-5-nitroaniline (40 mmol) was dissolved in 50 ml dry pyridine and cooled to 0° C. 4.16 g methyl chloroformate (44 mmol) was added dropwise and the mixture was stirred at room temperature for additional 2 hours. Then it was evaporated under reduced pressure, 200 ml 0.1 M HCl solution was added and was extracted three times with 50-50 ml ethyl acetate. The combined organic layer was washed with brine, dried over MgSO$_4$ and evaporated off. Crude product was recrystallized from a minimal amount of acetonitrile to get a light yellow solid. Yield: 5.73 g (63%). Ret. time: 3.24 min., $(M+H)^-$=225.

Step 2

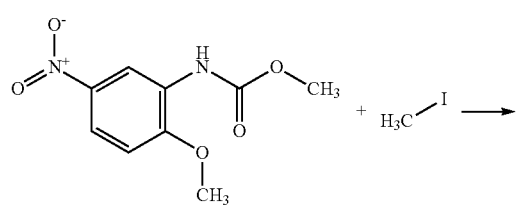

-continued

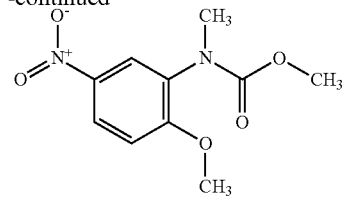

4.524 g (2-Methoxy-5-nitro-phenyl)-carbamic acid methyl ester (obtained in Step 1) (20 mmol) was dissolved in 30 ml dry dimethylformamide and 1.00 g NaH (60% dispersion in mineral oil) (25 mmol) was added at room temperature. After stirring the mixture for 15 minutes 3.123 g iodomethane (22 mmol) was added and the mixture was stirred at room temperature for 5 hours. Then it was poured onto 300 g ice and the precipitated white solid was filtered off and washed well with water. Product was dried under vacuum over phosphorus pentoxide for a day. Yield: 4.28 g (89%). Ret. time: 2.38 min., $(M+H)^+$=241 (weak intensity); $^1$HNMR (DMSO-$d_6$, 300 MHz), δ (ppm): 8.23 (dd, $J^3$=9.15 Hz, $J^4$=2.64 Hz, 1H), 8.16 (d, J=2.46 Hz, 1H), 7.33 (d, J=9.15 Hz, 1H), 3.95 (s, 3H), 3.56 (bs, 3H), 3.10 (s, 3H)

Step 3

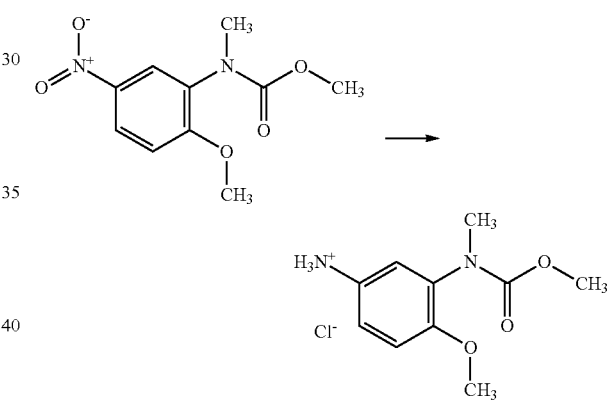

2.40 g (2-Methoxy-5-nitro-phenyl)-methyl-carbamic acid methyl ester (obtained in Step 2) (10 mmol) was dissolved in 80 ml methanol-dichloromethane=3-1 and 0.2 g Pd catalyst (10% Pd on activated carbon) was added carefully. The mixture was stirred vigorously in H$_2$ atmosphere under standard pressure at room temperature until TLC indicates the end of the reaction. Catalyst was filtered off and 2 ml of ethyl acetate saturated with HCl gas was added to the filtrate. It was then evaporated under reduced pressure to get the pure product as yellow solid. Compound was used in the next step without any further purification or analytical investigation. Yield: 1.94 g (79%).

Step 4

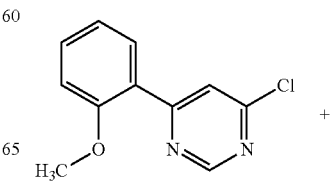

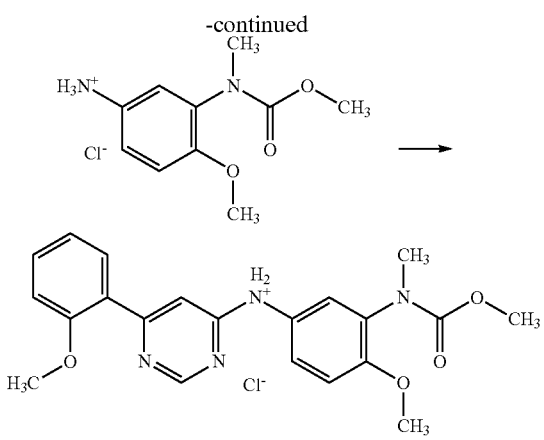

987 mg (5-Amino-2-methoxy-phenyl)-methyl-carbamic acid methyl ester hydrochloride (obtained in Step 3) (4 mmol) was added to a solution of 971 mg 4-chloro-6-(2-methoxy-phenyl)-pyrimidine (obtained in Example 32, Step 1) (4.4 mmol) in 60 ml of tert-butanol and the mixture was refluxed overnight. Then it was cooled to 30° C., the precipitated yellow solid was filtered off and washed with 2-propanol and diethyl ether. Yield: 926 mg (54%). Ret. time: 0.45-2.49-2.65 min., (M+H)$^+$=395, (M+H)$^-$=393; $^1$HNMR (DMSO-d$_6$, 300 MHz), δ (ppm): 11.46 (bs, 1H), 8.88 (s, 1H), 7.63 (m, 4H), 7.30 (m, 2H), 7.18 (m, 2H), 3.90 (s, 3H), 3.83 (s, 3H), 3.09 (s, 3H).

4-Methoxy-N$^1$-[6-(2-methoxy-phenyl)-pyrimidin-4-yl]-N$^3$-methyl-benzene-1,3-diamine (Example 99)

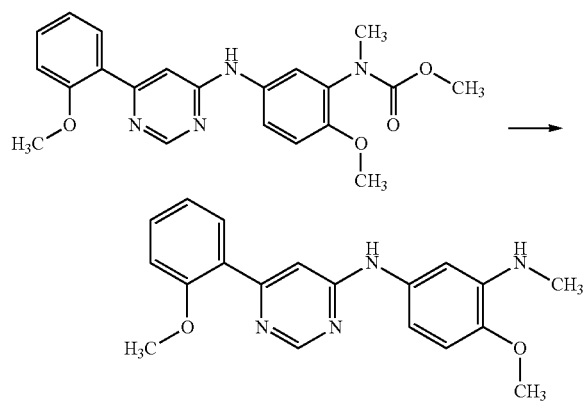

345 mg {2-Methoxy-5-[6-(2-methoxy-phenyl)-pyrimidin-4-ylamino]-phenyl}-methyl-carbamic acid methyl ester hydrochloride (obtained in Example 98) (0.8 mmol) was dissolved in 40 ml MeOH and 20 ml 4 M KOH/aq solution was added. The mixture was refluxed for 12 days. Then volatiles were distilled off under reduced pressure, water was added to the residue and it was extracted four times with 50-50 ml ethyl acetate. The combined organic layer was washed with brine, dried over MgSO$_4$ and evaporated to dryness. Residue was purified by column chromatography on silica gel eluting with chloroform applying 0%-2% methanol gradient. Finally it was recrystallized from a minimal amount of acetonitrile to get the pure product as an off white solid. Yield: 39 mg (15%). Ret. time: 0.45-2.27-2.54 min., (M+H)$^+$=337, (M+H)$^-$=335; $^1$HNMR (DMSO-d$_6$, 300 MHz), δ (ppm): 9.23 (s, 3H), 8.59 (s, 1H), 7.92 (d, 1H), 7.43 (t, 1H), 7.35 (s, 1H), 7.16 (d, 1H), 7.06 (t, 1H), 6.89 (d, 1H), 6.76 (d, 1H), 6.67 (s, 1H), 5.05 (m, 1H), 3.87 (s, 3H), 3.76 (s, 3H), 2.72 (d, 3H).

(4-Ethoxy-3-nitro-phenyl)-[6-(2-methoxy-phenyl)-pyrimidin-4-yl]-amine (Example 100)

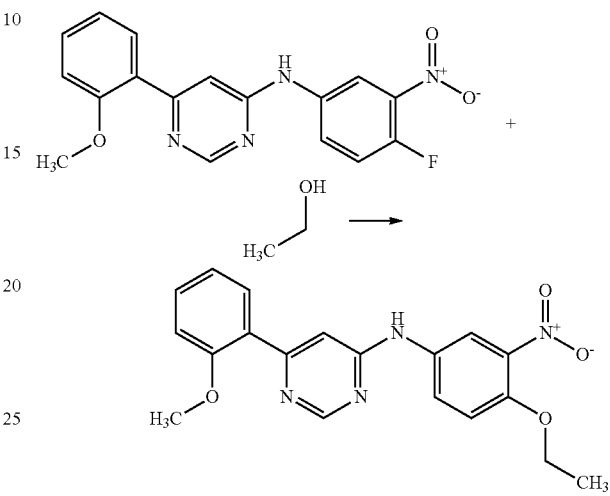

138 mg Sodium (6 mmol) was dissolved in 30 ml ethanol and 681 mg (4-fluoro-3-nitro-phenyl)-[6-(2-methoxy-phenyl)-pyrimidin-4-yl]-amine (obtained in Example 96, Step 1) (2 mmol) was added in one portion. The mixture was refluxed for 2 hours. The mixture was poured onto 150 g ice and it was extracted three times with 50-50 ml ethyl acetate. The combined organic layer was washed with brine, dried over MgSO$_4$ and evaporated to dryness. Residue was recrystallized from a minimal amount of acetonitrile to get pure product as an orange solid. Yield: 605 mg (83%). Ret. time: 3.09 min., (M+H)$^+$=367, (M+H)$^-$=365; $^1$HNMR (DMSO-d$_6$, 300 MHz), δ (ppm): 9.82 (s, 1H), 8.71 (s, 1H), 8.40 (s, 1H), 7.97 (d, 1H), 7.83 (t, 1H), 7.39 (m, 3H), 7.19 (d, 1H), 7.09 (d, 1H), 4.18 (q, 2H), 3.89 (s, 3H), 1.33 (t, 3H).

4-Ethoxy-N$^1$-[6-(2-methoxy-phenyl)-pyrimidin-4-yl]-benzene-1,3-diamine (Example 101)

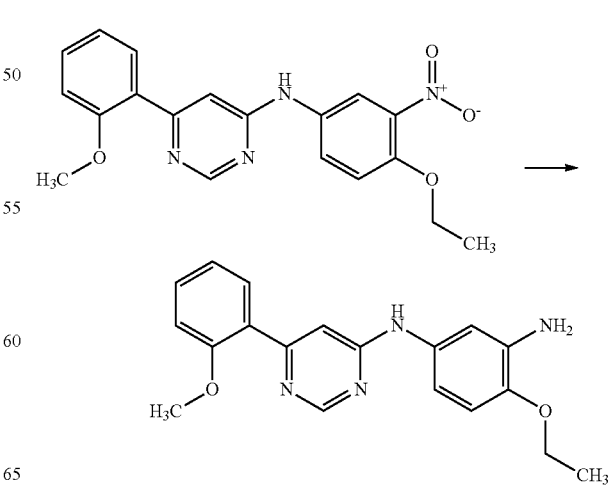

Title compound was prepared according to the method described in case of Example 59 using (4-Ethoxy-3-nitro-phenyl)-[6-(2-methoxy-phenyl)-pyrimidin-4-yl]-amine (obtained in Example 100) as starting material. Yield: 108 mg (32%). Ret. time: 0.45-2.38-2.55 min., (M+H)⁺=337, (M+H)⁻=335; ¹HNMR (DMSO-d₆, 300 MHz), δ (ppm): 9.16 (s, 1H), 8.57 (s, 1H), 7.91 (d, 1H), 7.43 (t, 1H), 7.33 (s, 1H), 7.15 (d, 1H), 7.05 (t, 1H), 6.93 (s, 1H), 6.74 (bs, 2H), 4.74 (bs, 2H), 3.98 (q, 2H), 3.86 (s, 3H), 1.33 (t, 3H).

[6-(4-Fluoro-2-methoxy-phenyl)-pyrimidin-4-yl]-(4-fluoro-3-nitro-phenyl)-amine (Example 102)

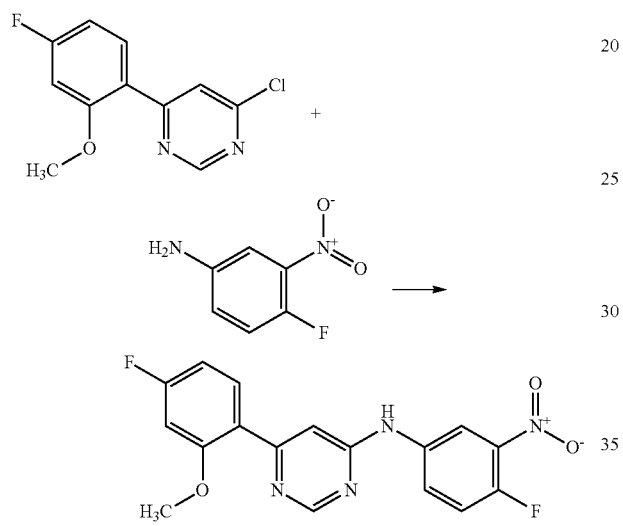

Title compound was prepared according to the method described in case of Example 96, Step 1 using 4-chloro-6-(4-fluoro-2-methoxy-phenyl)-pyrimidine (obtained in Example 90, Step 1) as starting material and the reaction was carried out in 4 mmol quantity. Yield: 960 mg (67%). Ret. time: 3.50 min., (M+H)⁺=359, (M+H)⁻=357; ¹HNMR (DMSO-d₆, 300 MHz), δ (ppm): 10.09 (s, 1H), 8.77 (s, 1H), 8.73 (dd, 1H), 8.02 (m, 2H), 7.57 (dd, 1H), 7.47 (s, 1H), 7.12 (dd, 1H), 6.93 (td, 1H), 3.94 (s, 3H).

(4-Ethoxy-3-nitro-phenyl)-[6-(4-fluoro-2-methoxy-phenyl)-pyrimidin-4-yl]-amine (Example 103)

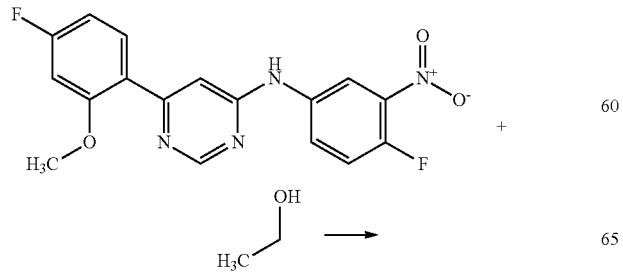

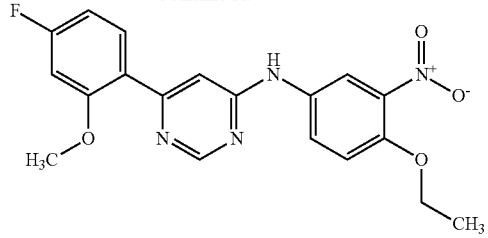

Title compound was prepared according to the method described in case of Example 100 using [6-(4-Fluoro-2-methoxy-phenyl)-pyrimidin-4-yl]-(4-fluoro-3-nitro-phenyl)-amine (obtained in Example 102) as starting material. Yield: 494 mg (64%). Ret. time: 3.35 min., (M+H)⁺=385, (M+H)⁻=383; ¹HNMR (DMSO-d₆, 300 MHz), δ (ppm): 9.90 (s, 1H), 8.70 (s, 1H), 8.41 (d, 1H), 8.05 (t, 1H), 7.84 (dd, 1H), 7.43 (s, 1H), 7.37 (d, 1H), 7.10 (dd, 1H), 6.92 (td, 1H), 4.19 (q, 2H), 3.93 (s, 3H), 1.34 (t, 3H).

4-Fluoro-N¹-[6-(4-fluoro-2-methoxy-phenyl)-pyrimidin-4-yl]-benzene-1,3-diamine (Example 104)

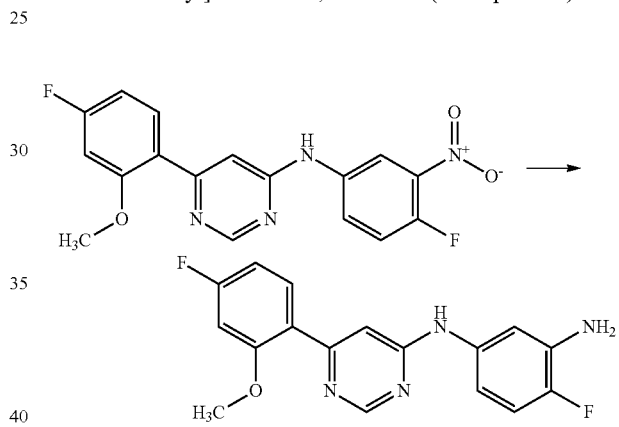

Title compound was prepared according to the method described in case of Example 59 using [6-(4-Fluoro-2-methoxy-phenyl)-pyrimidin-4-yl]-(4-fluoro-3-nitro-phenyl)-amine (obtained in Example 102) as starting material. Yield: 32 mg (10%). Ret. time: 2.62 min., (M+H)⁺=329, (M+H)⁻=327; ¹HNMR (DMSO-d₆, 300 MHz), δ (ppm): 9.34 (bs, 1H), 8.61 (s, 1H), 8.01 (t, 1H), 7.36 (s, 1H), 7.09 (td, 2H), 6.92 (m, 2H), 6.76 (m, 1H), 5.15 (s, 2H), 3.91 (s, 3H).

4-Ethoxy-N¹-[6-(4-fluoro-2-methoxy-phenyl)-pyrimidin-4-yl]-benzene-1,3-diamine (Example 105)

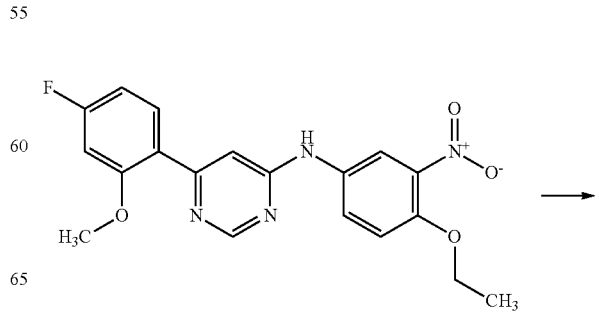

-continued

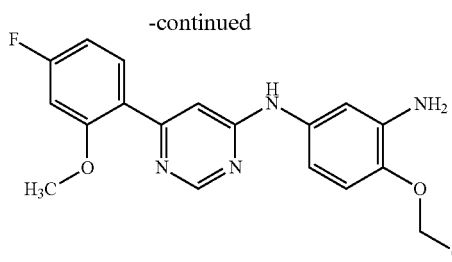

Title compound was prepared according to the method described in case of Example 59 using (4-Ethoxy-3-nitro-phenyl)-[6-(4-fluoro-2-methoxy-phenyl)-pyrimidin-4-yl]-amine (obtained in Example 103) as starting material. Yield: 329 mg (93%). Ret. time: 2.67 min., (M+H)$^+$=355, (M+H)$^-$= 353; $^1$HNMR (DMSO-d$_6$, 300 MHz), δ (ppm): 8.18 (bs, 1H), 8.56 (s, 1H), 7.99 (t, 1H), 7.32 (s, 1H), 7.06 (dd, 1H), 6.88 (m, 2H), 6.74 (m, 2H), 4.74 (bs, 2H), 3.97 (q, 2H), 3.89 (s, 3H), 1.33 (t, 3H).

2-Fluoro-N$^4$-[6-(2-methoxy-phenyl)-pyrimidin-4-yl]-N$^1$,N$^1$-dimethyl-benzene-1,4-diamine Hydrochloride (Example 106)

Step 1

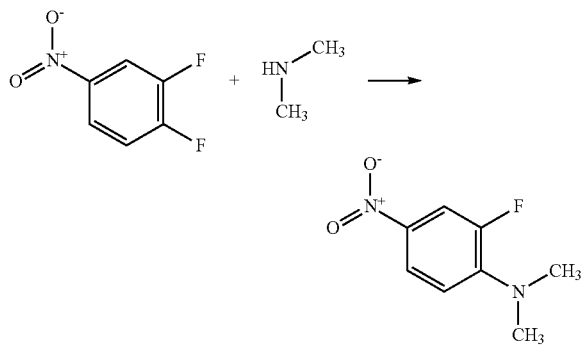

7.95 g 1,2-Difluoro-4-nitrobenzene (50 mmol) was dissolved in 100 ml EtOH and 25 ml of EtOH containing 5.6 M dimethylamine was added. The mixture was stirred at room temperature for 5 hours. Then it was poured onto 400 g ice and the precipitated yellow solid was collected by filtration. Filtrate was washed well with water and it was dried in vacuum desiccator over P$_2$O$_5$. Yield: 8.67 g (94%). Ret. time: 3.87 min., (M+H)$^+$=185 (weak intensity); $^1$HNMR (DMSO-d$_6$, 300 MHz), δ (ppm): 7.93 (m, 2H), 6.95 (t, J=9.06 Hz, 1H), 3.07 (s, 6H).

Step 2

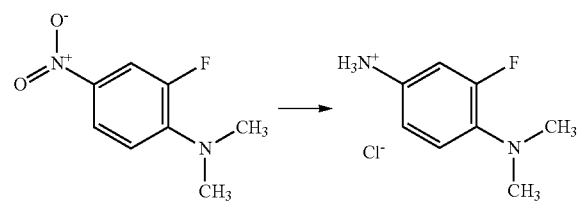

2-Fluoro-N$^1$,N$^1$-dimethyl-benzene-1,4-diamine hydrochloride was prepared according to the method described in case of Example 98, Step 3 using (2-fluoro-4-nitro-phenyl)-dimethyl-amine (obtained in Step 1) as starting material and the reaction was carried out in 5 mmol quantity. Yield: 635 mg (67%). Ret. time: 0.44 min., (M+H)$^+$=155.

Step 3

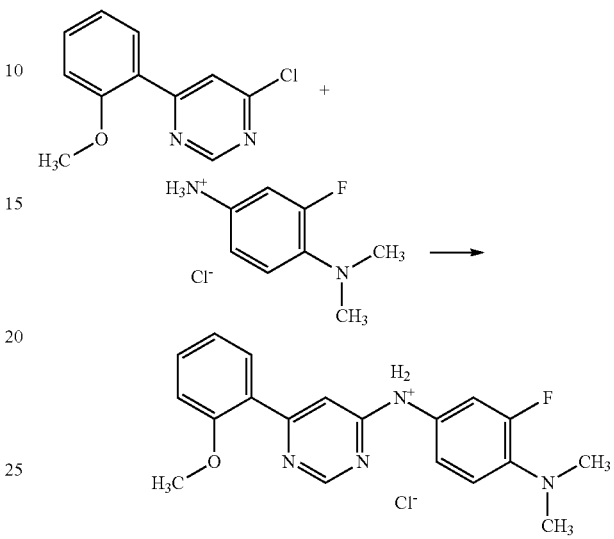

Title compound was prepared according to the method described in case of Example 98, Step 4 using 2-fluoro-N$^1$,N$^1$-dimethyl-benzene-1,4-diamine hydrochloride (obtained in Step 2) as starting material and the reaction was carried out in 0.7 mmol quantity. Yield: 118 mg (45%). Ret. time: 2.68 min., (M+H)$^+$=339, (M+H)$^-$=337; $^1$HNMR (DMSO-d$_6$, 300 MHz), δ (ppm): 11.95 (bs, 1H), 8.93 (s, 1H), 7.69 (bd, 1H), 7.63 (m, 2H), 7.44 (bs, 2H), 7.29 (d, 1H), 7.18 (m, 2H), 3.91 (s, 3H), 2.88 (s, 6H).

2-Chloro-5-[6-(2-methoxy-phenyl)-pyrimidin-4-ylamino]-phenol Hydrochloride (Example 107)

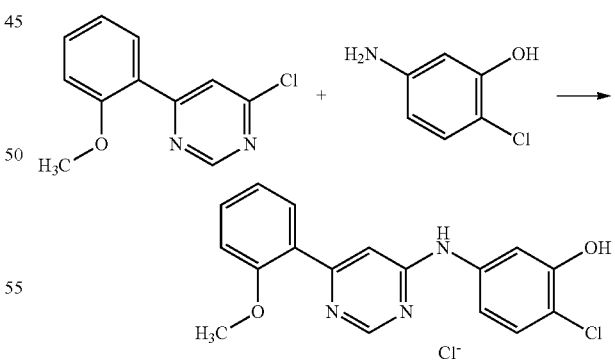

100 mg 5-Amino-2-chlorophenol (0.7 mmol) was added to a solution of 177 mg 4-chloro-6-(2-methoxy-phenyl)-pyrimidine (obtained in Example 32, Step 1) (0.8 mmol) in 40 ml of tert-butanol. 1 ml Dry ethyl acetate saturated with HCl gas was added and the mixture was refluxed for 5 hours. Then it was cooled to 40° C. and the precipitated solid was filtered off and washed with 2-propanol and diethyl ether. Yield: 180 mg (71%). Ret. time: 2.69 min., (M+H)$^+$=328, (M+H)⁻=326; ¹HNMR (DMSO-d₆, 300 MHz), δ (ppm): 11.38 (bs, 1H), 10.51 (bs, 1H), 8.90 (s, 1H), 7.68 (d, 1H), 7.62 (t, 1H), 7.40 (m, 3H), 7.22 (m, 3H), 3.91 (s, 3H).

2-Dimethylamino-5-[6-(2-methoxy-phenyl)-pyrimidin-4-ylamino]-phenol (Example 108)

Step 1

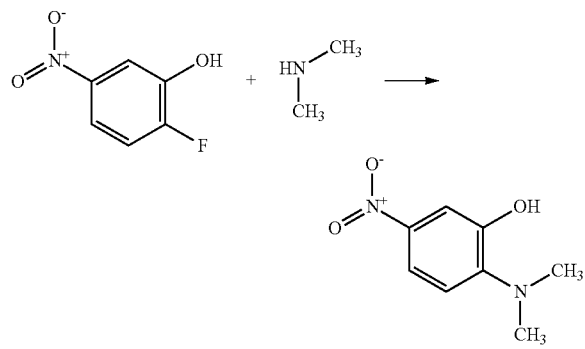

2-Dimethylamino-5-nitro-phenol was prepared according to the method described in case of Example 106, Step 1 using 2-fluoro-5-nitrophenol as starting material and the reaction was carried out in 5 mmol quantity. Product was used in the next step without any analytical investigation. Yield: 682 mg (75%). Ret. time: min., (M+H)⁺=, (M+H)⁻=; ¹HNMR (DMSO-d₆, 300 MHz), δ (ppm):

Step 2

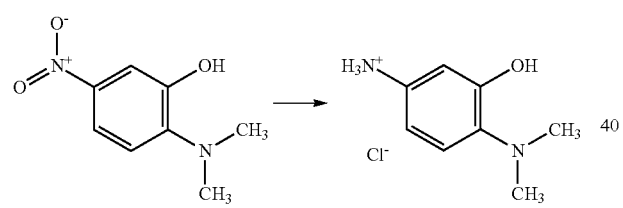

5-Amino-2-dimethylamino-phenol hydrochloride was prepared according to the method described in case of Example 98, Step 3 using 2-dimethylamino-5-nitro-phenol (obtained in Step 1) as starting material and the reaction was carried out in 5 mmol quantity. Yield: 897 mg (95%). Ret. time: 0.44 min., (M+H)⁺=153, (M+H)⁻=151.

Step 3

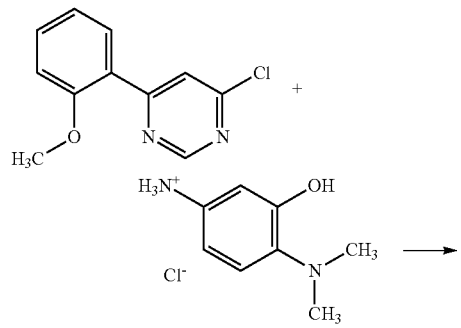

-continued

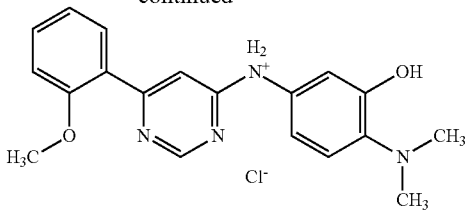

Title compound was prepared according to the method described in case of Example 98, Step 4 using 5-amino-2-dimethylamino-phenol hydrochloride (obtained in Step 2) as starting material and the reaction was carried out in 1 mmol quantity. Yield: 42 mg (11%). Ret. time: 0.44-1.82 min., (M+H)⁺=337, (M+H)⁻=335; ¹HNMR (DMSO-d₆, 300 MHz), δ (ppm): 11.57 (bs, 1H), 11.53 (bs, 1H), 8.90 (s, 1H), 7.73 (m, 2H), 7.64 (s, 1H), 7.59 (d, 1H), 7.53 (s, 1H), 7.37 (d, 1H), 7.28 (d, 1H), 7.17 (t, 1H), 3.91 (s, 3H), 3.14 (s, 6H).

2-Dimethylamino-5-[6-(2-methoxy-phenyl)-pyrimidin-4-ylamino]-benzamide (Example 109)

Step 1

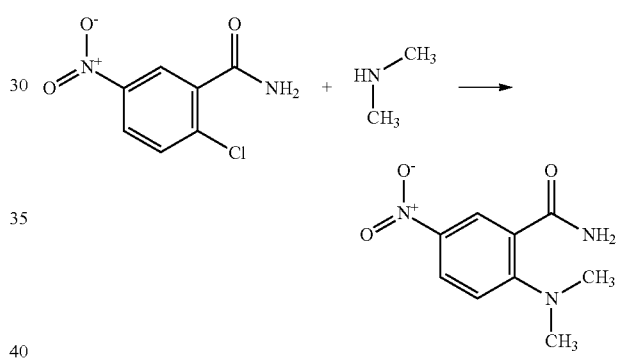

2-Dimethylamino-5-nitro-benzamide was prepared according to the method described in case of Example 106, Step 1 using 2-chloro-5-nitro-benzamide (obtained in Example 44, Step 1) as starting material and the reaction was carried out in 5 mmol quantity. Yield: 870 mg (83%). Ret. time: 0.45-2.19 min., (M+H)⁺=210; ¹HNMR (DMSO-d₆, 300 MHz), δ (ppm): 8.03 (m, 3H), 7.51 (s, 1H), 6.93 (d, J=9.48 Hz, 1H), 3.02 (s, 6H).

Step 2

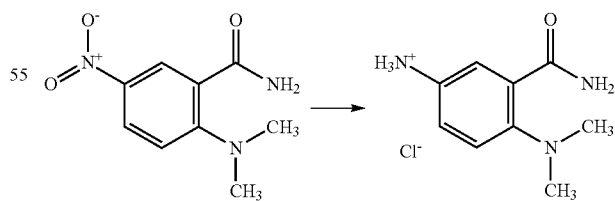

5-Amino-2-dimethylamino-benzamide hydrochloride was prepared according to the method described in case of Example 98, Step 3 using 2-dimethylamino-5-nitro-benzamide (obtained in Step 1) as starting material and the reaction was carried out in 3.8 mmol quantity. Yield: 704 mg (86%). Ret. time: 0.43 min., (M+H)⁺=180.

Step 3

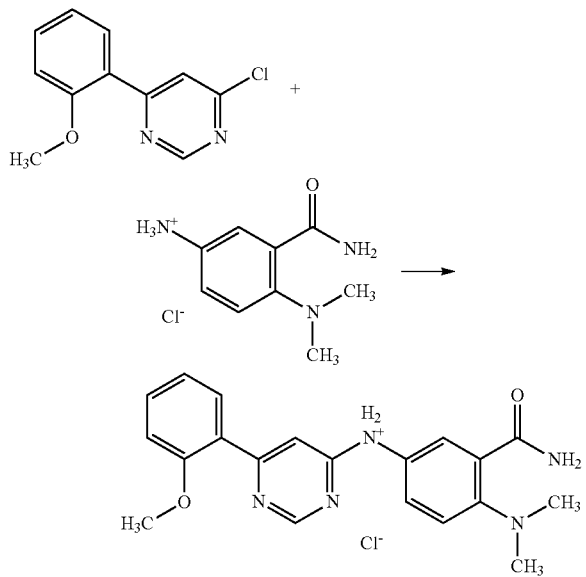

Title compound was prepared according to the method described in case of Example 98, Step 4 using 5-amino-2-dimethylamino-benzamide hydrochloride (obtained in Step 2) as starting material and the reaction was carried out in 1 mmol quantity. Yield: 137 mg (34%). Ret. time: 0.45-2.00 min., $(M+H)^+=364$, $(M+H)^-=362$; $^1$HNMR (DMSO-$d_6$, 300 MHz), δ (ppm): 12.00 (bs, 1H), 8.93 (bs, 1H), 8.78 (bs, 1H), 8.25 (m, 2H), 7.96 (m, 2H), 7.72 (d, 1H), 7.63 (t, 1H), 7.58 (s, 1H), 7.29 (d, 1H), 7.18 (t, 1H), 3.92 (s, 3H), 3.14 (s, 6H).

2-Ethoxy-5-[6-(2-methoxy-phenyl)-pyrimidin-4-ylamino]-phenol (Example 110)

Step 1

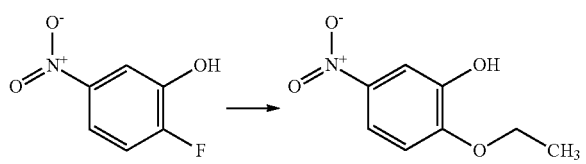

690 mg Sodium (30 mmol) was dissolved in 40 ml ethanol and 786 mg 2-fluoro-5-nitrophenol (5 mmol) was added in one portion. The mixture was refluxed for 3 days. The mixture was poured onto 150 g ice, pH was set to 1-2 by addition of 2 M HCl solution and it was extracted three times with 50-50 ml ethyl acetate. The combined organic layer was washed with brine, dried over MgSO$_4$ and evaporated to dryness. Residue was used in the next step without any further purification. Yield: 820 mg (90%). Ret. time: 3.11 min., $(M+H)^-=182$.

Step 2

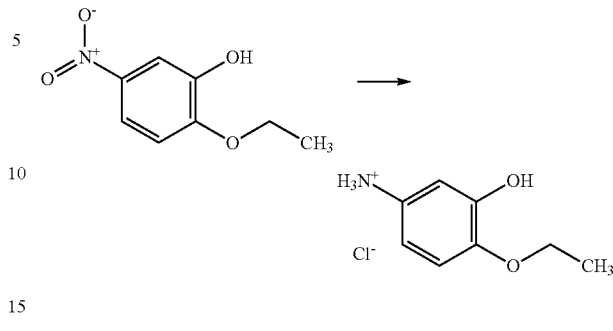

5-Amino-2-ethoxy-phenol hydrochloride was prepared according to the method described in case of Example 98, Step 3 using 2-ethoxy-5-nitro-phenol (obtained in Step 1) as starting material and the reaction was carried out in 5 mmol quantity. Product was used directly in the next step without any purification or analytical investigation. Yield: 804 mg (85%).

Step 3

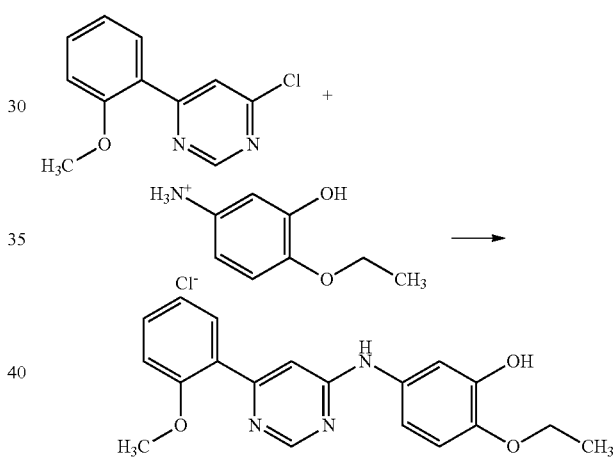

190 mg 5-Amino-2-ethoxy-phenol hydrochloride (obtained in Step 2) (1 mmol) was added to a solution of 265 mg 4-chloro-6-(2-methoxy-phenyl)-pyrimidine (obtained in Example 32, Step 1) (1.2 mmol) in 50 ml of tert-butanol. The mixture was refluxed for 5 hours. Then it was poured onto 100 ml 5% NaHCO$_3$ solution and extracted three times with 50-50 ml ethyl acetate. The combined organic layer was washed with brine, dried over MgSO$_4$ and evaporated to dryness. Residue was purified by column chromatography on silica gel eluting with chloroform applying 0%-2% methanol gradient. Finally it was recrystallized from a minimal amount of acetonitrile to get the pure product as an off white solid. Yield: 156 mg (46%). Ret. time: 0.45-2.36-2.58 min., $(M+H)^+=338$, $(M+H)^-=336$; $^1$HNMR (DMSO-$d_6$, 300 MHz), δ (ppm): 9.32 (s, 1H), 8.96 (bs, 1H), 8.61 (s, 1H), 7.93 (d, 1H), 7.44 (t, 1H), 7.35 (s, 1H), 7.21 (s, 1H), 7.16 (d, 1H), 7.07 (t, 1H), 6.98 (d, 1H), 6.87 (d, 1H), 3.98 (q, 2H), 3.88 (s, 3H), 1.31 (t, 3H).

2-Ethoxy-5-[6-(2-methoxy-phenyl)-pyrimidin-4-ylamino]-benzamide (Example 111)

Step 1

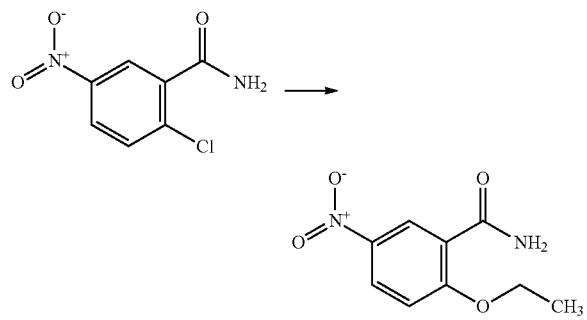

2-Ethoxy-5-nitro-benzamide was prepared according to the method described in case of Example 110, Step 1 using 2-chloro-5-nitro-benzamide (obtained in Example 44, Step 1) as starting material and the reaction was carried out in 5 mmol quantity, at room temperature in 2 hours. Yield: 975 mg (93%). Ret. time: 2.59 min., $(M+H)^+=211$ (weak intensity); $^1$HNMR (DMSO-$d_6$, 300 MHz), δ (ppm): 8.54 (s, 1H), 8.33 (d, J=9.15 Hz, 1H), 7.82 (bs, 1H), 7.68 (bs, 1H), 7.35 (d, J=9.15 Hz, 1H), 4.32 (q, 2H), 1.42 (t, J=6.84 Hz, 3H).

Step 2

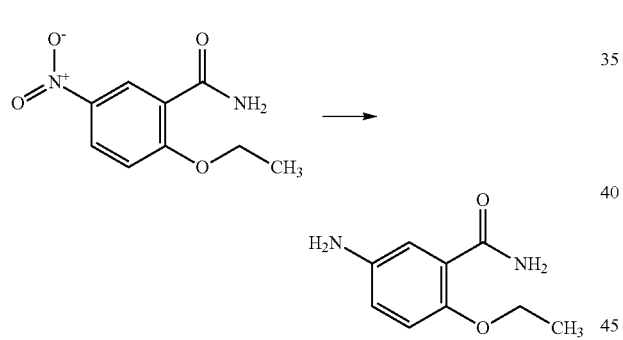

5-Amino-2-ethoxy-benzamide was prepared according to the method described in case of Example 59 using 2-ethoxy-5-nitro-benzamide (obtained in Step 1) as starting material and the reaction was carried out in 4 mmol quantity. Yield: 389 mg (54%). Ret. time: 0-44-0.77 min., $(M+H)^+=181$; $^1$HNMR (DMSO-$d_6$, 300 MHz), δ (ppm): 7.60 (bs, 1H), 7.36 (bs, 1H), 7.13 (d, J=2.19 Hz, 1H), 6.84 (d, J=8.64 Hz, 1H), 6.66 (dd, $J^3$=8.25 Hz, $J^4$=2.16 Hz, 1H), 4.79 (bs, 2H), 4.02 (q, 2H), 1.33 (t, J=5.94 Hz, 3H).

Step 3

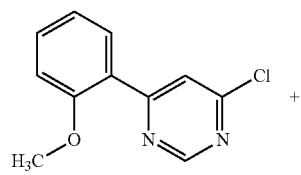

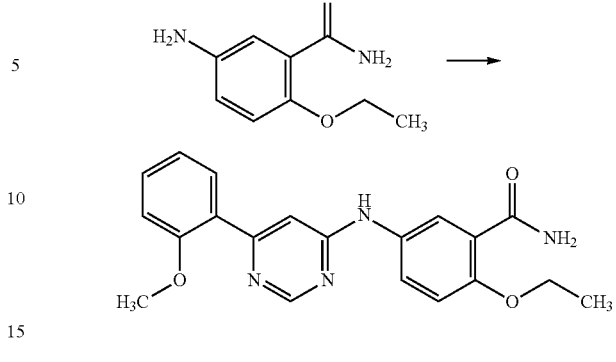

Title compound was prepared according to the method described in case of Example 11, Step 1 using 5-amino-2-ethoxy-benzamide (obtained in Step 2) as reagent and the reaction was carried out in 0.5 mmol quantity. Yield: 102 mg (56%). Ret. time: 0.45-2.18-2.45 min., $(M+H)^+=365$, $(M+H)^-=364$; $^1$HNMR (DMSO-$d_6$, 300 MHz), δ (ppm): 10.59 (bs, 1H), 8.78 (s, 1H), 8.08 (s, 1H), 7.79 (m, 2H), 7.57 (m, 3H), 7.33 (s, 1H), 7.16 (m, 3H), 4.19 (q, 2H), 3.89 (s, 3H), 1.40 (t, 3H).

2-Ethoxy-5-[6-(4-fluoro-2-methoxy-phenyl)-pyrimidin-4-ylamino]-benzamide (Example 112)

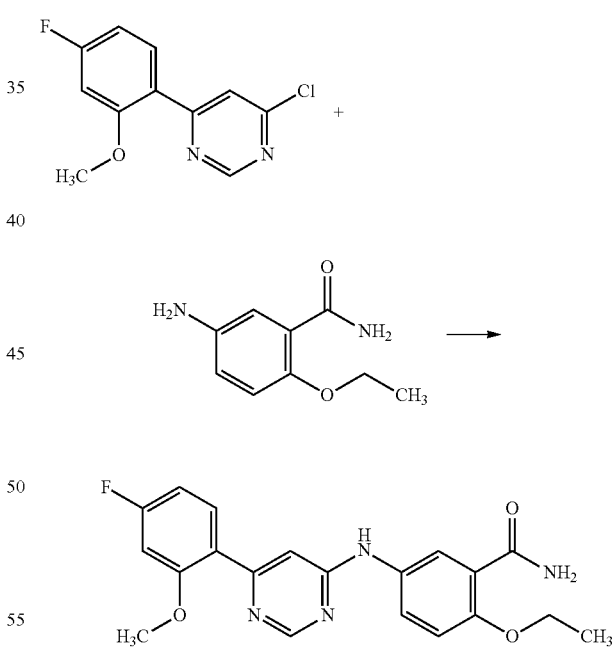

Title compound was prepared according to the method described in case of Example 111, Step 3 using 4-chloro-6-(4-fluoro-2-methoxy-phenyl)-pyrimidine (obtained in Example 90, Step 1) as starting material. Yield: 40 mg (21%). Ret. time: 0.46-2.37-2.56 min., $(M+H)^+=383$, $(M+H)^-=381$; $^1$HNMR (DMSO-$d_6$, 300 MHz), δ (ppm): 9.58 (bs, 1H), 8.63 (bs, 1H), 8.05 (bs, 2H), 7.84 (d, 1H), 7.64 (bs, 1H), 7.56 (bs, 1H), 7.37 (s, 1H), 7.12 (m, 2H), 6.90 (t, 1H), 4.16 (q, 2H), 3.91 (s, 3H), 1.39 (t, 3H).

2-Dimethylamino-5-[6-(4-fluoro-2-methoxy-phenyl)-pyrimidin-4-ylamino]-benzamide (Example 113)

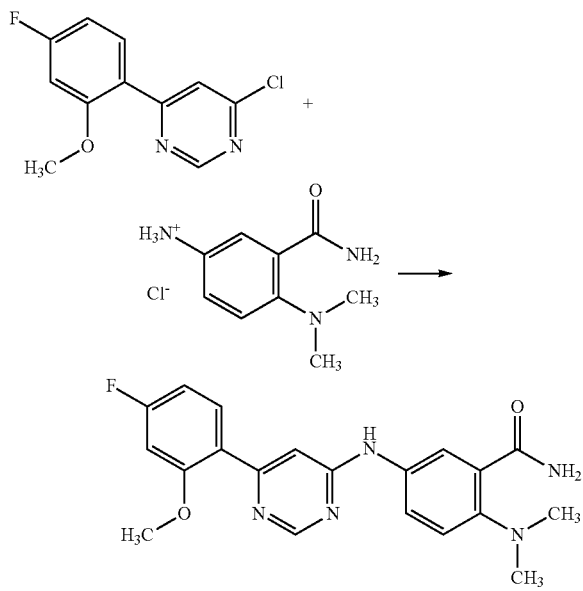

Title compound was prepared according to the method described in case of Example 110, Step 3 using 4-chloro-6-(4-fluoro-2-methoxy-phenyl)-pyrimidine (obtained in Example 90, Step 1) and 5-amino-2-dimethylamino-benzamide hydrochloride (obtained in Example 109, Step 2) as starting materials. The reaction was carried out in 0.6 mmol quantity. Yield: 50 mg (22%). Ret. time: 0.45-1.90-2.18 min., $(M+H)^+=382$, $(M+H)^-=380$; $^1$HNMR (DMSO-$d_6$, 300 MHz), δ (ppm): 9.62 (bs, 1H), 8.83 (bs, 1H), 8.64 (s, 1H), 8.04 (t, 1H), 7.99 (d, 1H), 7.82 (dd, 1H), 7.49 (bs, 1H), 7.40 (s, 1H), 7.25 (d, 1H), 7.09 (dd, 1H), 6.91 (td, 1H), 3.92 (s, 3H), 2.68 (s, 6H).

2-Ethoxy-5-[6-(4-fluoro-2-methoxy-phenyl)-pyrimidin-4-ylamino]-phenol (Example 114)

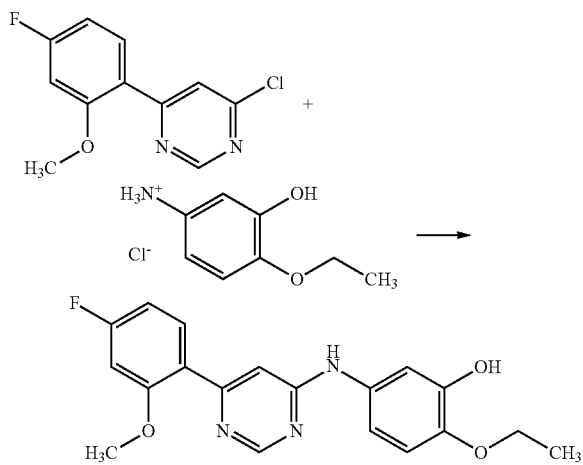

Title compound was prepared according to the method described in case of Example 110, Step 3 using 4-chloro-6-(4-fluoro-2-methoxy-phenyl)-pyrimidine (obtained in Example 90, Step 1) as starting material and the reaction was carried out in 0.6 mmol quantity. Yield: 80 mg (38%). Ret. time: 2.71 min., $(M+H)^+=356$, $(M+H)^-=354$; $^1$HNMR (DMSO-$d_6$, 300 MHz), δ (ppm): 9.32 (s, 1H), 8.95 (bs, 1H), 8.60 (s, 1H), 8.01 (t, 1H), 7.34 (s, 1H), 7.20 (bs, 1H), 7.08 (dd, 1H), 6.96 (td, 1H), 6.89 (m, 2H), 3.98 (q, 2H), 3.90 (s, 3H), 1.31 (t, 3H).

(3-Bromo-4-methoxy-phenyl)-[6-(2-methoxy-phenyl)-pyrimidin-4-yl]-amine (Example 115)

Step 1

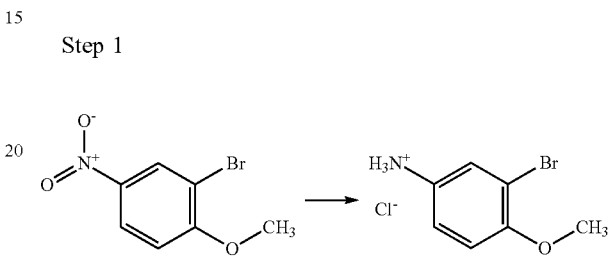

3.48 g 2-bromo-4-nitroanisole (15 mmol) was dissolved in 100 ml MeOH and 13.54 g SnCl$_2$×2H$_2$O (60 mmol) was added. The mixture was refluxed for 4 hours. Then it was poured onto 300 g ice and the pH was basified by addition of 5M NaOH solution. Mixture was extracted three four times with 50-50 ml ethyl acetate. The combined organic layer was washed with brine, dried over MgSO$_4$, 10 ml dry ethyl acetate saturated with HCl gas was added and evaporated under reduced pressure. Residue was used without any further purification and analytical investigation. Yield: 3.31 g (93%).

Step 2

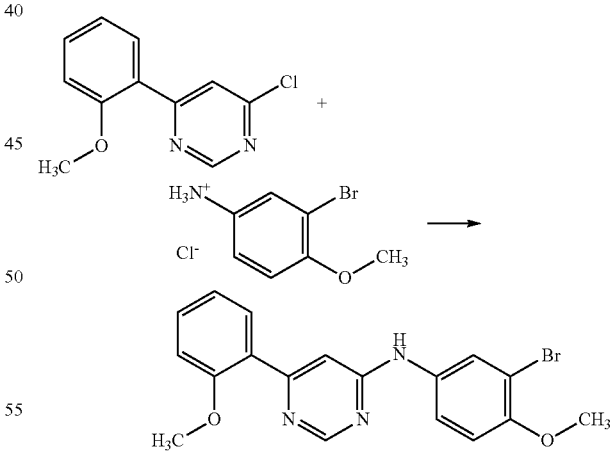

Title compound was prepared according to the method described in case of Example 110, Step 3 using 3-bromo-4-methoxy-phenylamine hydrochloride (obtained in Step 1) as starting material and the reaction was carried out in 15 mmol quantity. Yield: 1.86 g (32%). Ret. time: 2.98 min., $(M+H)^+=386$, $(M+H)^-=384$; $^1$HNMR (DMSO-$d_6$, 300 MHz), δ (ppm): 8.56 (s, 1H), 8.57 (s, 1H), 8.07 (s, 1H), 7.95 (d, 1H), 7.55 (d, 1H), 7.45 (t, 1H), 7.38 (s, 1H), 7.18 (d, 1H), 7.09 (m, 2H), 3.90 (s, 3H), 3.83 (s, 3H).

[6-(2-Methoxy-phenyl)-pyrimidin-4-yl]-[4-methoxy-3-(1,2,3,6-tetrahydro-pyridin-4-yl)-phenyl]-amine (Example 116)

Step 1

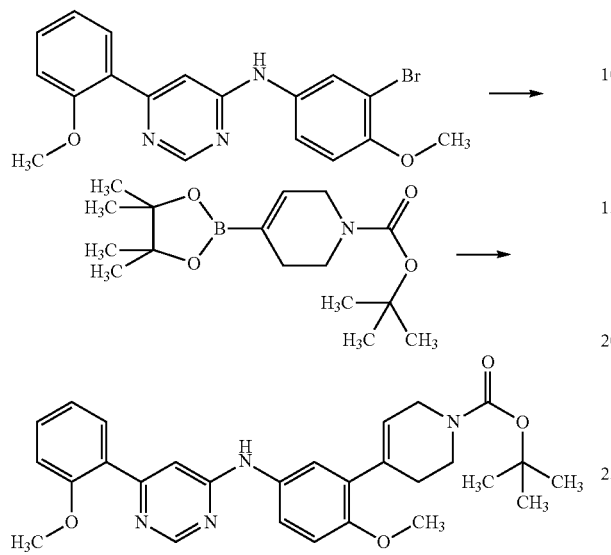

695 mg (3-Bromo-4-methoxy-phenyl)-[6-(2-methoxy-phenyl)-pyrimidin-4-yl]-amine (obtained in Example 115) (1.8 mmol) was dissolved in 40 ml 1,2-dimethoxyethane and the flask was filled with argon properly. 116 mg Tetrakis(thriphenylphosphine) palladium[0] (0.10 mmol) was added and the mixture was stirred at room temperature for 30 minutes. Then 649 mg 4-(4,4,5,5-tetramethyl-[1,3,2]dioxa-borolan-2-yl)-3,6-dihydro-2H-pyridine-1-carboxylic acid tert-butyl ester (2.1 mmol), 848 mg Na$_2$CO$_3$ (8 mmol) and 8 ml water were added under argon atmosphere. The mixture was refluxed for 25 hours. Then it was evaporated under reduced pressure, 150 ml water was added and it was extracted three times with 40-40 ml ethyl acetate. The combined organic layer was washed with brine, decolorized with activated carbon, dried over MgSO$_4$ and evaporated under reduced pressure. Residue was purified by column chromatography on silica gel eluting with chloroform applying 0%-4% methanol gradient. It became an amorphous light yellow solid upon standing. Yield: 524 mg (60%). Ret. time: 3.62 min., (M+H)$^+$=489, (M+H)$^-$=487.

Step 2

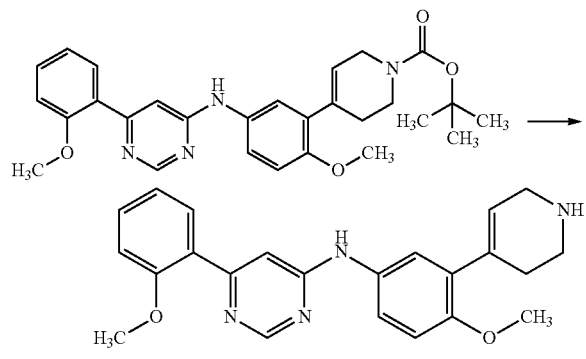

488 mg 4-{5-[6-(2-Ethoxy-phenyl)-pyrimidin-4-ylamino]-2-methoxy-phenyl}-3,6-dihydro-2H-pyridine-1-carboxylic acid tert-butyl ester (obtained in Step 1) (1 mmol) was dissolved in 40 ml dry dichloromethane and 1 ml of trifuoroacetic acid was added. The mixture was stirred at room temperature for 5 days. Then it was evaporated under reduced pressure and the residue was purified by column chromatography emuting with chloroform:MeOH:triethyl-amine=100:10:0.5. Finally the product was crystallized from a minimal amount of acetonitrile. Yield: 242 mg (62%). Ret. time: 0.44-2.09 min., (M+H)$^+$=389, (M+H)$^-$=387; $^1$HNMR (DMSO-d$_6$, 300 MHz), δ (ppm): 9.38 (bs, 1H), 8.62 (s, 1H), 7.93 (d, 1H), 7.52 (d, 1H), 7.44 (t, 1H), 7.36 (bs, 2H), 7.17 (d, 1H), 7.07 (t, 1H), 6.97 (d, 1H), 5.79 (bs, 1H), 3.88 (s, 3H), 3.74 (s, 3H), 3.33 (bs, 3H), 2.87 (t, 2H), 2.31 (bs, 2H).

N-{5-[6-(4-Fluoro-2-methoxy-phenyl)-pyrimidin-4-ylamino]-2-methoxy-phenyl}-acetamide (Example 117)

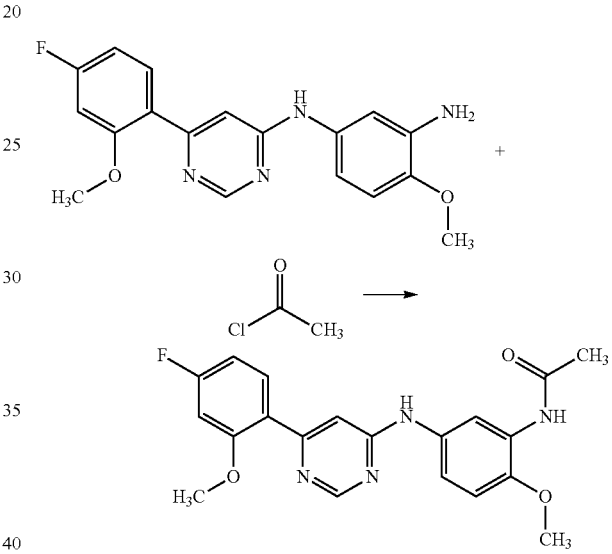

Title compound was prepared according to the method described in case of Example 50 using [6-(4-Fluoro-2-methoxy-phenyl)-pyrimidin-4-yl]-(4-methoxy-3-nitro-phenyl)-amine (obtained in Example 64) as starting material. Yield: 146 mg (38%). Ret. time: 0.46-2.24-2.49 min., (M+H)$^+$=383, (M+H)$^-$=381; $^1$HNMR (DMSO-d$_6$, 300 MHz), δ (ppm): 9.45 (s, 1H), 9.11 (bs, 1H), 8.59 (s, 1H), 8.15 (bs, 1H), 8.01 (t, 1H), 7.52 (d, 1H), 7.36 (s, 1H), 7.06 (d, 1H), 7.03 (d, 1H), 6.90 (t, 1H), 3.90 (s, 3H), 3.82 (s, 3H), 2.10 (s, 3H).

{5-[6-(4-Fluoro-2-methoxy-phenyl)-pyrimidin-4-ylamino]-2-methoxy-phenyl}-carbamic Acid Methyl Ester (Example 118)

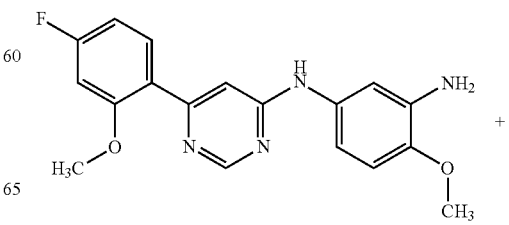

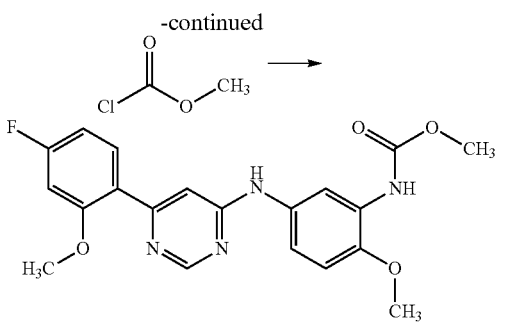

Title compound was prepared according to the method described in case of Example 51 using [6-(4-Fluoro-2-methoxy-phenyl)-pyrimidin-4-yl]-(4-methoxy-3-nitro-phenyl)-amine (obtained in Example 64) as starting material. Yield: 196 mg (49%). Ret. time: 2.80 min., (M+H)$^+$=399, (M+H)$^-$=397; $^1$HNMR (DMSO-d$_6$, 300 MHz), δ (ppm): 9.46 (s, 1H), 8.60 (s, 1H), 8.42 (bs, 1H), 8.02 (t, 1H), 7.91 (bs, 1H), 7.46 (d, 1H), 7.36 (s, 1H), 7.80 (d, 1H), 7.00 (d, 1H), 6.90 (t, 1H), 3.90 (s, 3H), 3.79 (s, 3H), 3.66 (s, 3H).

{5-[6-(4-Fluoro-2-methoxy-phenyl)-pyrimidin-4-ylamino]-2-methoxy-phenyl}-urea (Example 119)

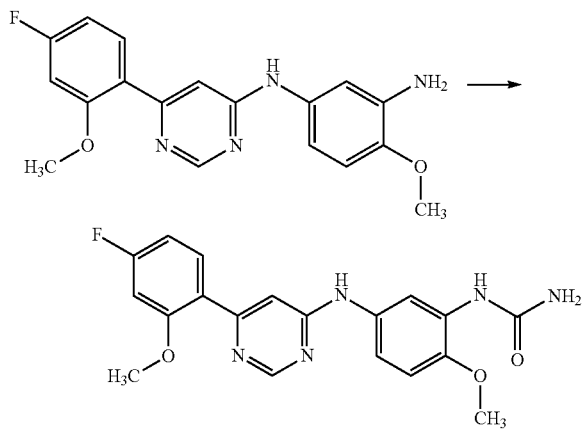

Title compound was prepared according to the method described in case of Example 56 using [6-(4-Fluoro-2-methoxy-phenyl)-pyrimidin-4-yl]-(4-methoxy-3-nitro-phenyl)-amine (obtained in Example 64) as starting material. Yield: 243 mg (63%). Ret. time: 0.44-2.07-2.39 min., (M+H)$^+$=384, (M+H)$^-$=382; $^1$HNMR (DMSO-d$_6$, 300 MHz), δ (ppm): 9.38 (s, 1H), 8.58 (s, 1H), 8.19 (d, 1H), 8.00 (t, 1H), 7.96 (s, 1H), 7.41 (d, 1H), 7.36 (s, 1H), 7.06 (dd, 1H), 6.90 (m, 2H), 6.22 (bs, 2H), 3.89 (s, 3H), 3.83 (s, 3H).

(4-Benzyloxy-3-methoxy-phenyl)-[6-(2-methoxy-phenyl)-pyrimidin-4-yl]-amine (Example 120)

Step 1

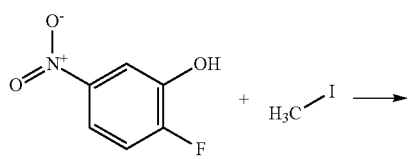

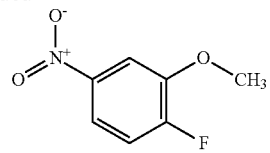

1.57 g 2-Fluoro-5-nitrophenol (10 mmol) was dissolved in 50 ml dry acetonitrile. 2.07 g potassium carbonate (15 mmol) and 1.70 g iodomethane (12 mmol) were added. The mixture was refluxed for 2 hours. Then it was poured onto 100 g ice and the mixture was extracted three times with 40-40 ml ethyl acetate. The combined organic layer was washed with brine, dried over MgSO$_4$ and evaporated under reduced pressure. Residue was crystallized upon cooling and was used without any further purification or analytical investigation. Yield: 1.62 g (95%).

Step 2

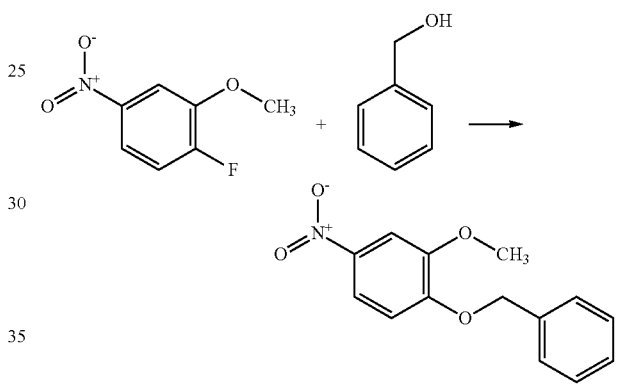

1.08 g Benzyl alcohol (10 mmol) was dissolved in 15 ml dry dimethylformamide and 480 mg NaH (60% dispersion in mineral oil) (12 mmol) was added at room temperature. After stirring the mixture for 15 minutes 1.54 g 1-fluoro-2-methoxy-4-nitro-benzene (obtained in Step 1) (9 mmol) was added and the mixture was stirred at room temperature for an hour. Then it was poured onto 100 g ice and the mixture was extracted three times with 40-40 ml ethyl acetate. The combined organic layer was washed with brine, dried over MgSO$_4$ and evaporated under reduced pressure. Residue was crystallized from a minimal amount of MeOH to get a yellow solid. Yield: 1.70 g (73%). Ret. time: 4.31 min., very low ion intensity in ESI-MS; $^1$HNMR (DMSO-d$_6$, 300 MHz), δ (ppm): 7.89 (dd, J$^3$=8.94 Hz, J$^4$=2.61 Hz, 1H), 7.76 (d, J=2.58 Hz, 1H), 7.48-7.31 (m, 5H), 7.27 (d, J=9.00 Hz, 1H), 5.25 (s, 2H), 3.89 (s, 3H).

Step 3

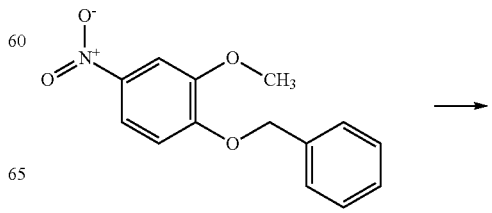

-continued

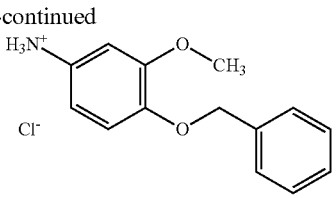

1.65 g 1-Benzyloxy-2-methoxy-4-nitro-benzene (obtained in Step 2) (6.36 mmol) was dissolved in 80 ml tert-butanol and 5.744 g SnCl$_2$×2H$_2$O (25.46 mmol) was added. The mixture was refluxed for 4 hours. Then it was poured onto 300 g ice and the pH was basified by addition of 5M NaOH solution. Mixture was extracted three four times with 50-50 ml ethyl acetate. The combined organic layer was washed with brine, dried over MgSO$_4$, 3 ml dry ethyl acetate saturated with HCl gas was added and evaporated under reduced pressure. Residue was used without any further purification or analytical investigation. Yield: 1.30 g (77%).

Step 4

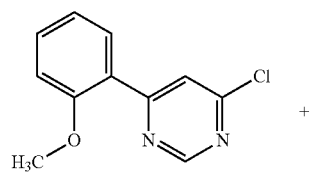

+

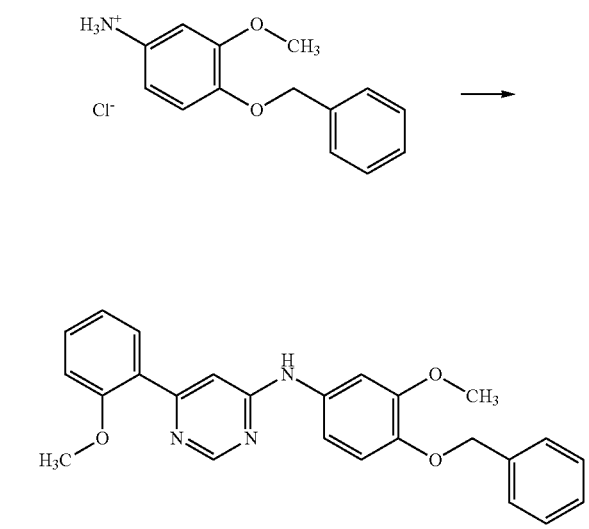

Title compound was prepared according to the method described in case of Example 110, Step 3 using 4-benzyloxy-3-methoxy-phenylamine hydrochloride (obtained in Step 3) as starting material and the reaction was carried out in 2 mmol quantity. Yield: 390 mg (47%). Ret. time: 3.33 min., (M+H)$^+$=414, (M+H)$^-$=412; $^1$HNMR (DMSO-d$_6$, 300 MHz), δ (ppm): 9.44 (bs, 1H), 8.63 (s, 1H), 7.94 (dd, 1H), 7.38 (m, 8H), 7.21 (t, 2H), 7.09 (t, 1H), 7.01 (d, 1H), 5.06 (s, 2H), 3.88 (s, 3H), 3.79 (s, 3H).

2-Methoxy-4-[6-(2-methoxy-phenyl)-pyrimidin-4-ylamino]-phenol (Example 121)

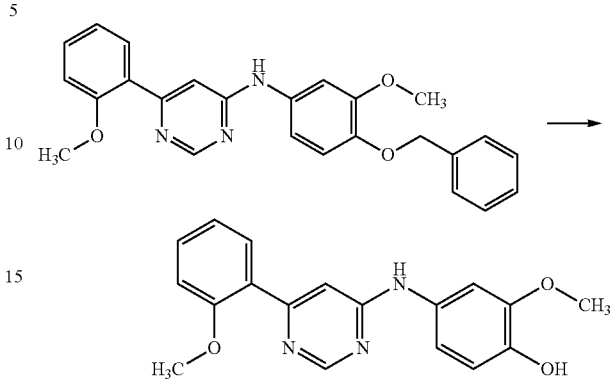

Title compound was prepared according to the method described in case of Example 59 using (4-benzyloxy-3-methoxy-phenyl)-[6-(2-methoxy-phenyl)-pyrimidin-4-yl]-amine (obtained in Example 120) as starting material and the reaction was carried out in 0.5 mmol quantity. Yield: 143 mg (87%). Ret. time: 0.44-1.96-2.34 min., (M+H)$^+$=324, (M+H)$^-$=322; $^1$HNMR (DMSO-d$_6$, 300 MHz), δ (ppm): 9.30 (bs, 1H), 8.71 (bs, 1H), 8.59 (s, 1H), 7.92 (dd, 1H), 7.43 (dt, 1H), 7.32 (s, 1H), 7.23 (d, 1H), 7.16 (d, 1H), 7.06 (m, 2H), 6.76 (d. 1H), 3.97 (s, 3H), 3.77 (s, 3H).

5-[6-(5-Fluoro-2-methoxy-phenyl)-pyrimidin-4-ylamino]-2-methoxy-phenol (Example 122)

Step 1

5-(6-Chloro-pyrimidin-4-ylamino)-2-methoxy-phenol was prepared according to the method described in case of Example 61, Step 1 using 5-amino-2-methoxyphenol as starting material. Yield: 3.29 g (87%). Ret. time: 2.66 min., (M+H)$^+$=252, (M+H)$^-$=250; $^1$HNMR (DMSO-d$_6$, 300 MHz), δ (ppm): 9.57 (s, 1H), 9.10 (s, 1H), 8.39 (s, 1H), 7.05 (s, 1H), 6.90 (m, 2H), 6.67 (s, 1H), 3.74 (s, 3H).

Step 2

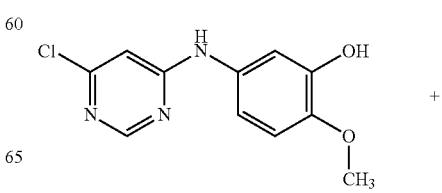

+

-continued

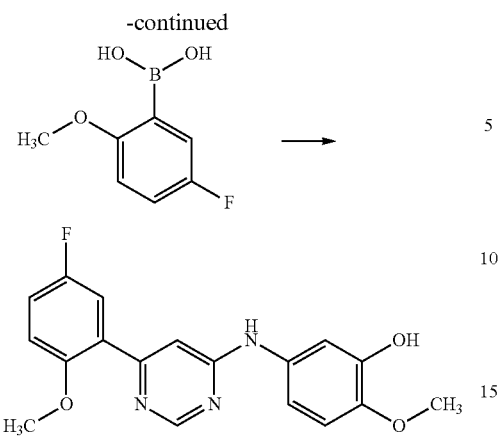

Title compound was prepared according to the method described in case of Example 74 using 5-(6-Chloro-pyrimidin-4-ylamino)-2-methoxy-phenol (obtained in Example 122, Step 1) as starting material. Yield: 44 mg (13%). Ret. time: 0.44-2.27-2.51 min., (M+H)$^+$=342, (M+H)$^-$=340; $^1$HNMR (DMSO-d$_6$, 300 MHz), δ (ppm): 9.38 (s, 1H), 9.02 (s, 1H), 8.62 (s, 1H), 7.76 (dd, 1H), 7.44 (s, 1H), 7.29 (dt, 1H), 7.19 (m, 2H), 7.00 (dd, 1H), 6.89 (d, 1H), 3.88 (s, 3H), 3.75 (s, 3H).

5-[6-(4-Fluoro-2-methoxy-phenyl)-pyrimidin-4-ylamino]-2-methoxy-phenol (Example 123)

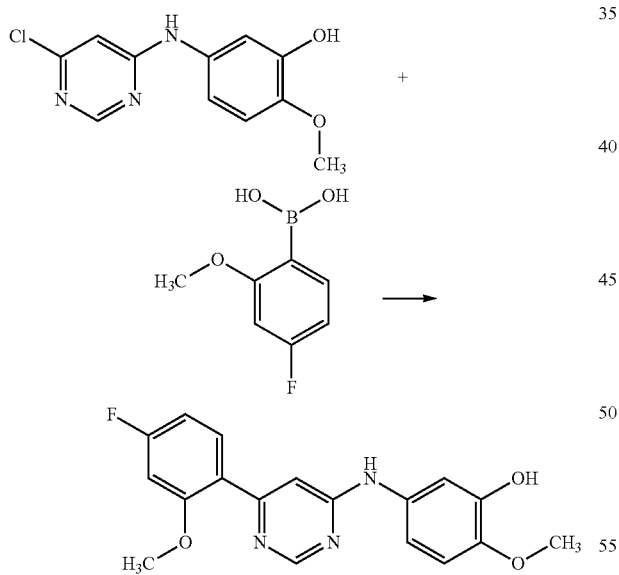

Title compound was prepared according to the method described in case of Example 63 using 5-(6-Chloro-pyrimidin-4-ylamino)-2-methoxy-phenol (obtained in Example 122, Step 1) as starting material. Yield: 42 mg (12%). Ret. time: 0.45-2.20-2.48 min., (M+H)$^+$=342, (M+H)$^-$=340; $^1$HNMR (DMSO-d$_6$, 300 MHz), δ (ppm): 9.32 (s, 1H), 9.01 (s, 1H), 8.59 (s, 1H), 8.01 (t, 1H), 7.34 (s, 1H), 7.18 (s, 1H), 7.07 (dd, 1H), 6.99 (dd, 1H), 6.91 (m, 2H), 3.91 (s, 3H), 3.74 (s, 3H).

5-[6-(2-Ethoxy-phenyl)-pyrimidin-4-ylamino]-2-methoxy-phenol (Example 124)

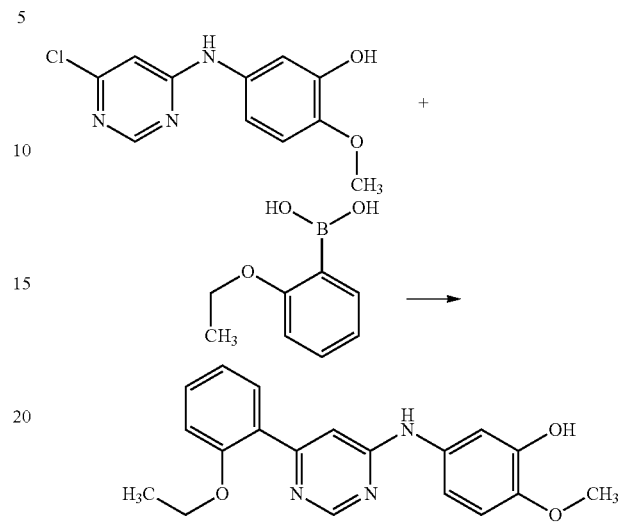

Title compound was prepared according to the method described in case of Example 61, Step 2 using 5-(6-Chloro-pyrimidin-4-ylamino)-2-methoxy-phenol (obtained in Example 122, Step 1) as starting material. Yield: 47 mg (14%). Ret. time: 0.43-2.40-2.58 min., (M+H)$^+$=338, (M+H)$^-$=336; $^1$HNMR (DMSO-d$_6$, 300 MHz), δ (ppm): 9.24 (s, 1H), 9.02 (s, 1H), 8.60 (s, 1H), 7.95 (d, 1H), 7.41 (d, 1H), 7.38 (s, 1H), 7.07 (m, 3H), 6.90 (m, 2H), 4.12 (q, 2H), 3.75 (s, 3H), 1.33 (t, 3H).

Carbonic Acid 5-[6-(4-fluoro-2-methoxy-phenyl)-pyrimidin-4-ylamino]-2-methoxy-phenyl Ester Methyl Ester (Example 125)

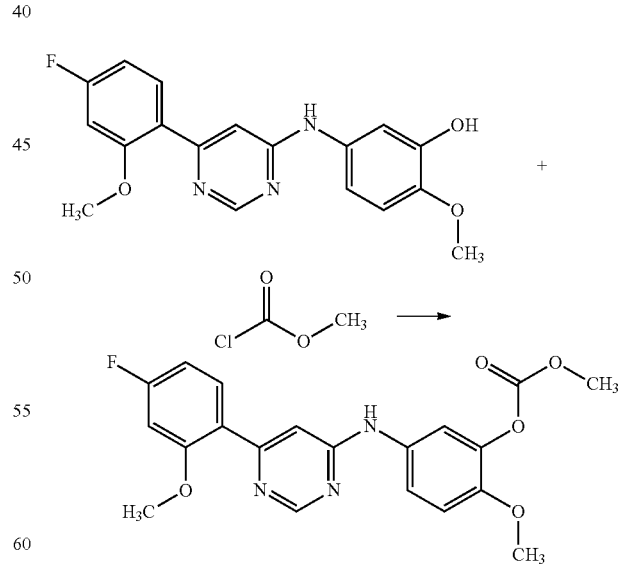

Title compound was prepared according to the method described in case of Example 95 using 5-[6-(4-Fluoro-2-methoxy-phenyl)-pyrimidin-4-ylamino]-2-methoxy-phenol (obtained in Example 123) as starting material. Yield: 54 mg (19%). Ret. time: 2.89 min., (M+H)$^+$=400, (M+H)$^-$=398;

¹HNMR (DMSO-d₆, 300 MHz), δ (ppm): 11.62 (b, 1H), 8.86 (s, 1H), 7.76 (t, 1H), 7.67 (s, 1H), 7.52 (d, 1H), 7.31 (s, 1H), 7.21 (m, 2H), 7.02 (td, 1H), 3.91 (s, 3H), 3.84 (s, 3H), 3.82 (s, 3H).

Acetic Acid 5-[6-(4-fluoro-2-methoxy-phenyl)-pyrimidin-4-ylamino]-2-methoxy-phenyl Ester (Example 126)

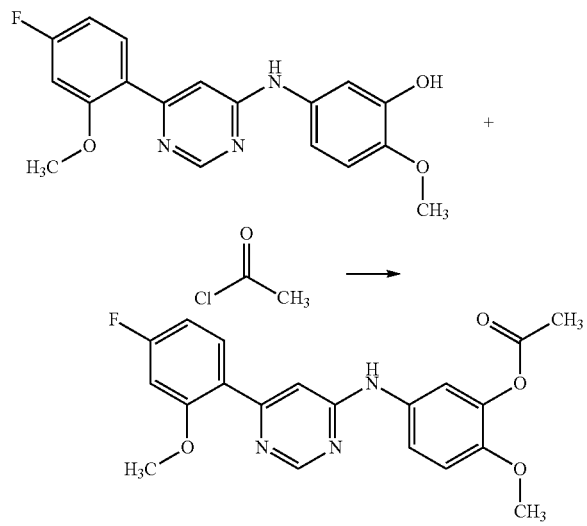

Title compound was prepared according to the method described in case of Example 93 using 5-[6-(4-Fluoro-2-methoxy-phenyl)-pyrimidin-4-ylamino]-2-methoxy-phenol (obtained in Example 123) as starting material. Yield: 42 mg (16%). Ret. time: 2.83 min., (M+H)⁺=384, (M+H)⁻=382; ¹HNMR (DMSO-d₆, 300 MHz), δ (ppm): 9.56 (s, 1H), 8.64 (s, 1H), 8.03 (t, 1H), 7.59 (s, 1H), 7.39 (dd, 1H), 7.36 (s, 1H), 7.10 (m, 2H), 6.91 (t, 1H), 3.91 (s, 3H), 3.75 (s, 3H), 2.27 (s, 3H).

5-[6-(5-Fluoro-2-methoxy-phenyl)-pyrimidin-4-ylamino]-2-methoxy-benzamide (Example 127)

Step 1

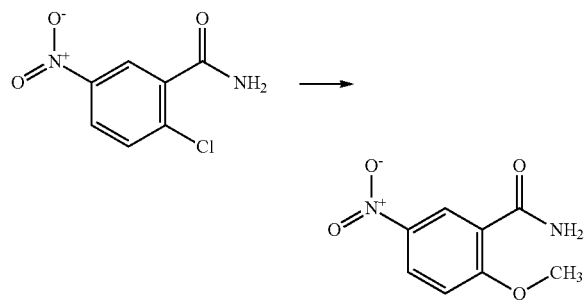

8.28 g Sodium (360 mmol) was dissolved in 200 ml methanol and 12.04 g 2-chloro-5-nitro-benzamide (obtained in Example 44, Step 1) (60 mmol) was added in one portion. The mixture was refluxed for 2 hours. The mixture was poured onto 150 g ice, pH was set to 6-8 by addition of 10 M HCl solution and it was extracted four times with 150-150 ml ethyl acetate. The combined organic layer was washed with brine, dried over MgSO₄ and evaporated to dryness. Residue was crystallized from a minimal amount of acetonitrile to get pore product as orange crystals. Yield: 8.83 g (75%). Ret. time: 2.25 min., (M+H)⁺=167; ¹HNMR (DMSO-d₆, 300 MHz), δ (ppm): 8.55 (d, J=2.97 Hz, 1H), 8.35 (dd, J³=9.15 Hz, J⁴=3.00 Hz, 1H), 7.79 (bs, 2H), 7.36 (d, J=9.21 Hz, 1H), 4.02 (s, 3H).

Step 2

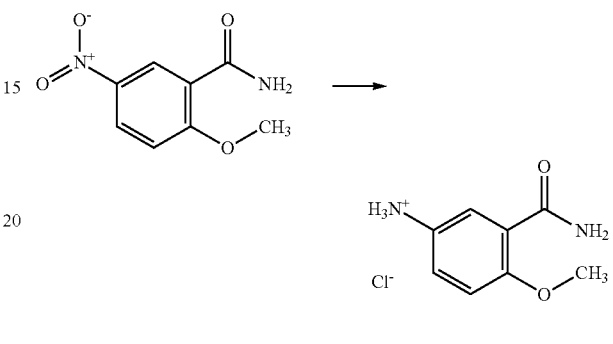

5-Amino-2-methoxy-benzamide hydrochloride was prepared according to the method described in case of Example 59 using 2-methoxy-5-nitro-benzamide (obtained in Step 1) as starting material and the reaction was carried out in 50 mmol quantity. Hydrochloric acid salt was prepared by addition of saturated solution of HCl gas in dry ethyl acetate to the solution of the pure product. Solvents were evaporated off at the end. Yield: 8.02 g (79%). Ret. time: 0.44 min., (M+H)⁺=167.

Step 3

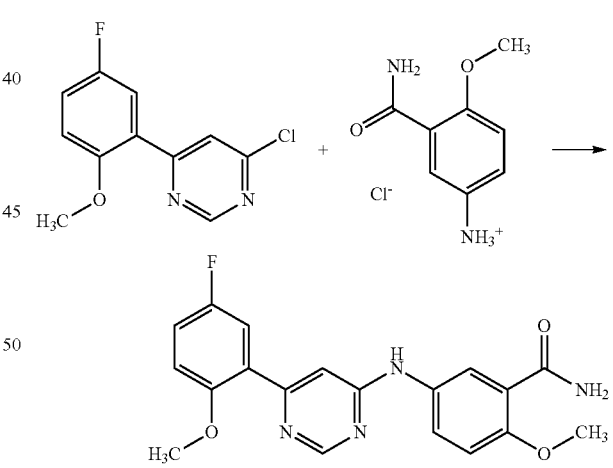

Title compound was prepared according to the method described in case of Example 110, Step 3 using 4-chloro-6-(5-fluoro-2-methoxy-phenyl)-pyrimidine (obtained in Example 91, Step 1) and 5-amino-2-methoxy-benzamide hydrochloride (obtained in Step 2) as starting materials. The reaction was carried out in 0.5 mmol quantity. Yield: 88 mg (48%). Ret. time: 0.44-2.26-2.39 min., (M+H)⁺=369, (M+H)⁻=367; ¹HNMR (DMSO-d₆, 300 MHz), δ (ppm): 9.63 (s, 1H), 8.65 (s, 1H), 8.04 (d, 1H), 7.86 (d, 1H), 7.78 (dd, 1H), 7.67 (bs, 1H), 7.53 (bs, 1H), 7.47 (s, 1H), 7.30 (BT, 1H), 7.18 (m, 2H), 3.89 (s, 3H).

5-[6-(4-Fluoro-2-methoxy-phenyl)-pyrimidin-4-ylamino]-2-methoxy-benzamide (Example 128)

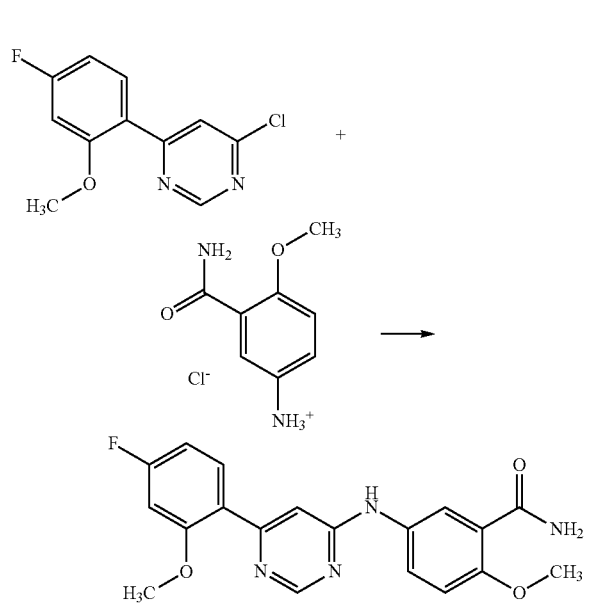

Title compound was prepared according to the method described in case of Example 110, Step 3 using 4-chloro-6-(4-fluoro-2-methoxy-phenyl)-pyrimidine (obtained in Example 90, Step 1) and 5-amino-2-methoxy-benzamide hydrochloride (obtained in Example 127, Step 2) as starting materials. The reaction was carried out in 0.5 mmol quantity. Yield: 73 mg (40%). Ret. time: 0.45-2.11-2.38 min., (M+H)$^+$=369, (M+H)$^-$=367; $^1$HNMR (DMSO-d$_6$, 300 MHz), δ (ppm): 9.56 (s, 1H), 8.63 (s, 1H), 8.03 (bs, 2H), 7.85 (d, 1H), 7.67 (bs, 1H), 7.53 (bs, 1H), 7.37 (s, 1H), 7.15 (d, 1H), 7.08 (d, 1H), 6.90 (BT, 1H), 3.92 (s, 3H), 3.89 (s, 3H).

5-[6-(2-Ethoxy-phenyl)-pyrimidin-4-ylamino]-2-methoxy-benzamide (Example 129)

Step 1:

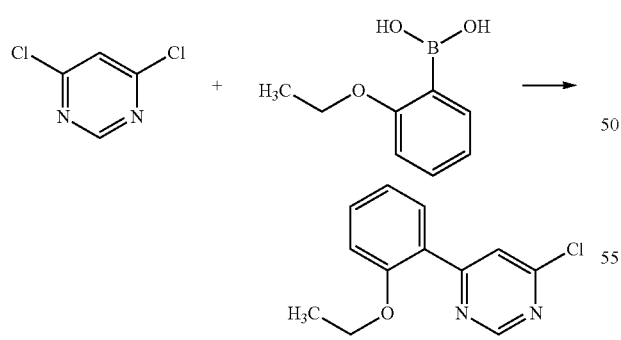

4-Chloro-6-(2-ethoxy-phenyl)-pyrimidine was prepared according to the procedure described in case of Example 32, Step 1 using 2-ethoxy-phenylboronic acid as reactant and the reaction was carried out in 10 mmol quantity. Yield: 1.74 g (74%). Ret. time: 4.31 min., (M+H)$^+$=235; $^1$HNMR (DMSO-d$_6$, 300 MHz), δ (ppm): 9.10 (s, 1H), 8.20 (s, 1H), 8.01 (dd, J$^3$=7.74 Hz, J$^4$=1.59 Hz, 1H), 7.53 (m, 1H), 7.21 (d, J=8.37 Hz, 1H), 7.12 (t, J=7.62 Hz, 1H), 4.19 (q, 2H), 1.39 (t, 3H).

Step 2

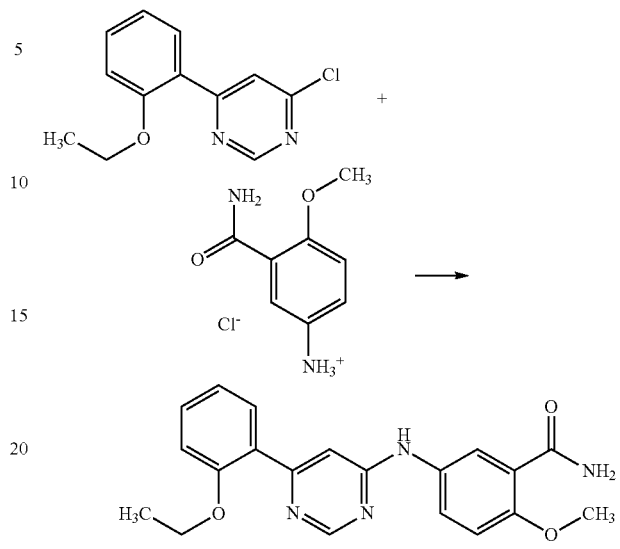

Title compound was prepared according to the method described in case of Example 110, Step 3 using 4-chloro-6-(2-ethoxy-phenyl)-pyrimidine (obtained in Step 1) and 5-amino-2-methoxy-benzamide hydrochloride (obtained in Example 127, Step 2) as starting materials. The reaction was carried out in 0.5 mmol quantity. Yield: 88 mg (48%). Ret. time: 2.33 min., (M+H)$^+$=365, (M+H)$^-$=363; $^1$HNMR (DMSO-d$_6$, 300 MHz), δ (ppm): 9.50 (s, 1H), 8.64 (s, 1H), 7.99 (d, 1H), 7.96 (dd, 1H), 7.88 (dd, 1H), 7.67 (bs, 1H), 7.53 (bs, 1H), 7.41 (m, 2H), 7.39 (m, 2H), 7.05 (t, 1H), 4.14 (q, 2H), 3.90 (s, 3H), 1.36 (t, 3H).

5-[6-(2-Ethoxy-4-fluoro-phenyl)-pyrimidin-4-ylamino]-2-methoxy-benzamide (Example 130)

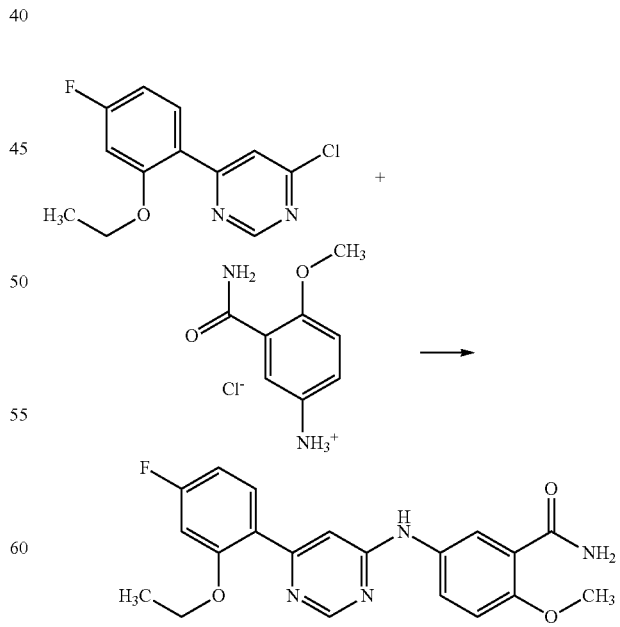

Title compound was prepared according to the method described in case of Example 110, Step 3 using 4-chloro-6-(2-ethoxy-4-fluoro-phenyl)-pyrimidine (obtained in Example 89, Step 1) and 5-amino-2-methoxy-benzamide hydrochloride (obtained in Example 127, Step 2) as starting materials. The reaction was carried out in 0.5 mmol quantity. Yield: 49 mg (26%). Ret. time: 0.43-2.43-2.55 min., (M+H)$^+$= 383, (M+H)$^-$=381; $^1$HNMR (DMSO-d$_6$, 300 MHz), δ (ppm): 9.52 (bs, 1H), 8.62 (s, 1H), 8.05 (t, 1H), 7.99 (d, 1H), 7.88 (d, 1H), 7.67 (bs, 1H), 7.54 (bs, 1H), 7.38 (s, 1H), 7.15 (d, 1H), 7.05 (d, 1H), 6.89 (t, 1H), 4.16 (q, 2H), 3.89 (s, 3H), 1.37 (t, 3H).

5-[6-(2-Ethoxy-5-fluoro-phenyl)-pyrimidin-4-ylamino]-2-methoxy-benzamide (Example 131)

Step 1:

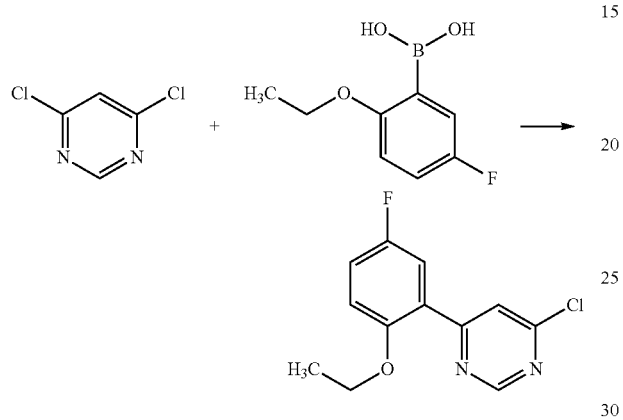

4-Chloro-6-(2-ethoxy-5-fluoro-phenyl)-pyrimidine was prepared according to the procedure described in case of Example 32, Step 1 using 2-ethoxy-5-fluorophenylboronic acid as reactant and the reaction was carried out in 10 mmol quantity. Yield: 1.75 g (69%). Ret. time: 4.53 min., (M+H)$^+$= 253; $^1$HNMR (DMSO-d$_6$, 300 MHz), δ (ppm): 9.12 (s, 1H), 8.24 (s, 1H), 7.79 (dd, J$^3$=9.72 Hz, J$^4$=3.12 Hz, 1H), 7.39 (m, 1H), 7.24 (q, 1H), 4.18 (q, 2H), 1.38 (t, 3H).

Step 2

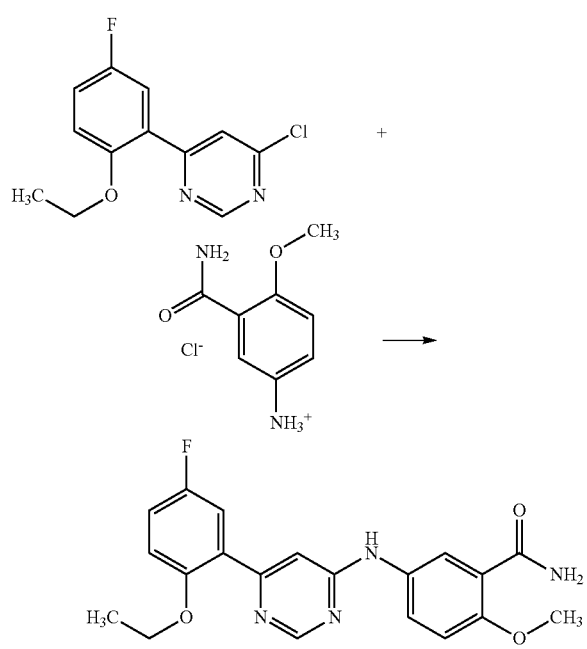

Title compound was prepared according to the method described in case of Example 110, Step 3 using 4-chloro-6-(2-ethoxy-5-fluoro-phenyl)-pyrimidine (obtained in Step 1) and 5-amino-2-methoxy-benzamide hydrochloride (obtained in Example 127, Step 2) as starting materials. The reaction was carried out in 0.5 mmol quantity. Yield: 58 mg (30%). Ret. time: 2.60 min., (M+H)$^+$=383, (M+H)$^-$=381; $^1$HNMR (DMSO-d$_6$, 300 MHz), δ (ppm): 9.59 (bs, 1H), 8.65 (s, 1H), 8.00 (d, 1H), 7.87 (d, 1H), 7.78 (dd, 1H), 7.68 (bs, 1H), 7.56 (bs, 1H), 7.48 (s, 1H), 7.27 (m, 1H), 7.17 (m, 2H), 4.13 (q, 2H), 3.89 (s, 3H), 1.35 (t, 3H.).

2-Chloro-4-[6-(2-methoxy-phenyl)-pyrimidin-4-ylamino]-benzamide (Example 132)

Step 1:

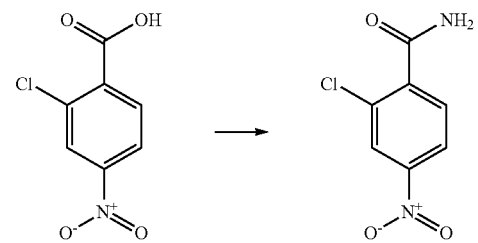 [SMILES: O=C(O)c1ccc([N+](=O)[O-])cc1Cl ; NC(=O)c1ccc([N+](=O)[O-])cc1Cl]

2-Chloro-4-nitro-benzamide was prepared according to the method described in case of Example 44, Step 1 using 2-chloro-4-nitro-benzoic acid as starting material and the reaction was carried out in 50 mmol quantity. Yield: 9.20 g (92%). Ret. time: 2.16 min., (M+H)$^-$=199 (weak intensity); $^1$HNMR (DMSO-d$_6$, 300 MHz), δ (ppm): 8.32 (s, 1H), 8.23 (d, J=8.37 Hz, 1H), 8.11 (bs, 1H), 7.86 (bs, 1H), 7.71 (d, J=7.62 Hz, 1H).

Step 2:

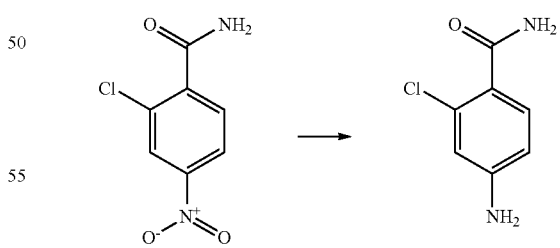

4-Amino-2-chloro-benzamide was prepared according to the method described in case of Example 44, Step 2 using 2-chloro-4-nitro-benzamide (obtained in Step 1) as starting material and the reaction was carried out in 5 mmol quantity. Yield: 545 mg (64%). Ret. time: 0.46-0.75 min., (M+H)$^+$= 171; $^1$HNMR (DMSO-d$_6$, 300 MHz), δ (ppm): 7.38 (bs, 1H), 7.23 (d, J=8.34 Hz, 1H), 6.57 (d, J=1.68 Hz, 1H), 6.47 (dd, J$^3$=8.34 Hz, J$^4$=1.71 Hz, 1H), 5.66 (bs, 2H).

Step 3:

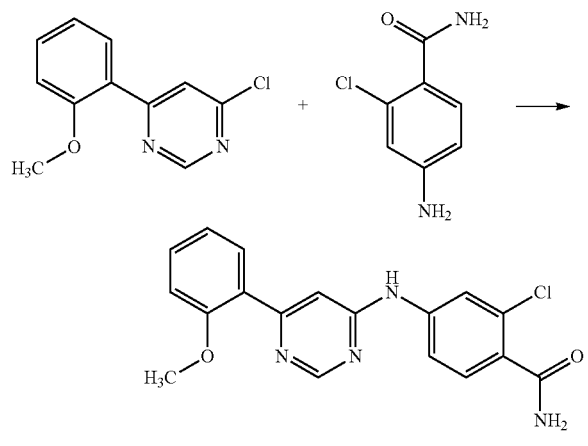

Title compound was prepared according to the method described in case of Example 11, Step 1 using 4-amino-2-chloro-benzamide (obtained in Step 2) as reagent and the reaction was carried out in 0.5 mmol quantity. Yield: 142 mg (80%). Ret. time: 0.44-2.01-2.23 min., (M+H)$^+$=355, (M+H)$^-$=353; $^1$HNMR (DMSO-d$_6$, 300 MHz), δ (ppm): 9.93 (s, 1H), 8.78 (s, 1H), 8.06 (s, 1H), 7.98 (dd, 1H), 7.74 (bs, 1H), 7.61 (dd, 1H), 7.47 (m, 4H), 7.20 (d, 1H), 7.09 (t, 1H), 3.92 (s, 3H).

2-Methoxy-4-[6-(2-methoxy-phenyl)-pyrimidin-4-ylamino]-benzoic Acid Methyl Ester (Example 133)

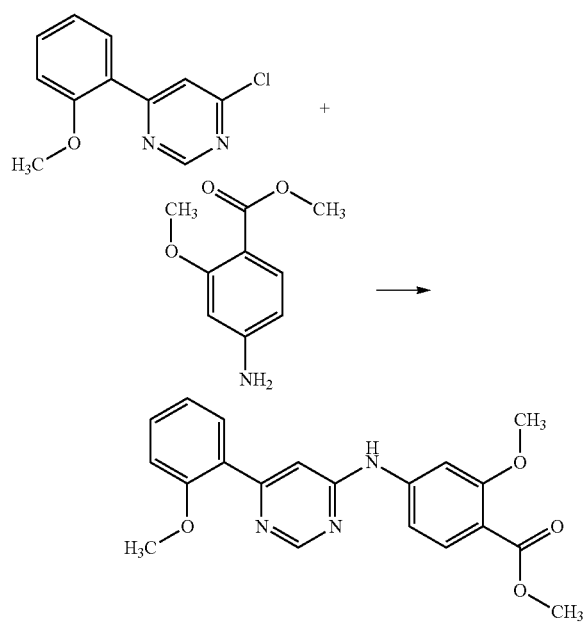

Title compound was prepared according to the method described in case of Example 11, Step 1 using methyl 4-amino-2-methoxybenzoate as reagent and the reaction was carried out in 7 mmol quantity. Yield: 2.31 g (90%). Ret. time: 2.76 min., (M+H)$^+$=366, (M+H)$^-$=364; $^1$HNMR (DMSO-d$_6$, 300 MHz), δ (ppm): 9.98 (s, 1H), 8.79 (s, 1H), 7.98 (dd, 1H), 7.73 (d, 1H), 7.63 (d, 1H), 7.55 (s, 1H), 7.49 (dd, 1H), 7.45 (t, 1H), 7.20 (d, 1H), 7.09 (t, 1H), 3.92 (s, 3H), 3.84 (s, 3H), 3.75 (s, 3H).

2-Methoxy-4-[6-(2-methoxy-phenyl)-pyrimidin-4-ylamino]-N-methylbenzamide (Example 134)

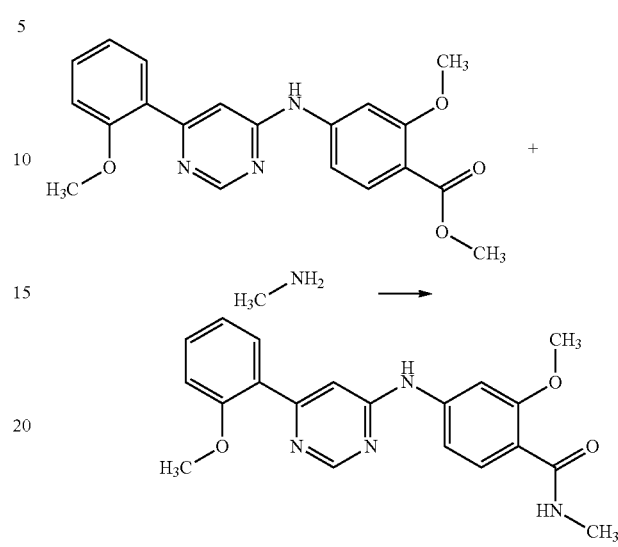

Title compound was prepared according to the method described in case of Example 25 using 2-methoxy-4-[6-(2-methoxy-phenyl)-pyrimidin-4-ylamino]-benzoic acid methyl ester (obtained in Example 133) as starting material and the reaction was carried out in 1 mmol quantity. Yield: 200 mg (55%). Ret. time: 0.45-2.15-2.35 min., (M+H)$^+$= 365, (M+H)$^-$=363; $^1$HNMR (DMSO-d$_6$, 300 MHz), δ (ppm): 9.88 (s, 1H), 8.77 (s, 1H), 7.99 (m, 2H), 7.84 (d, 1H), 7.64 (s, 1H), 7.53 (s, 1H), 7.46 (m, 2H), 7.20 (d, 1H), 7.09 (t, 1H), 3.92 (s, 6H), 2.81 (d, 3H).

N-(2-Hydroxy-ethyl)-2-methoxy-4-[6-(2-methoxy-phenyl)-pyrimidin-4-ylamino]-benzamide (Example 135)

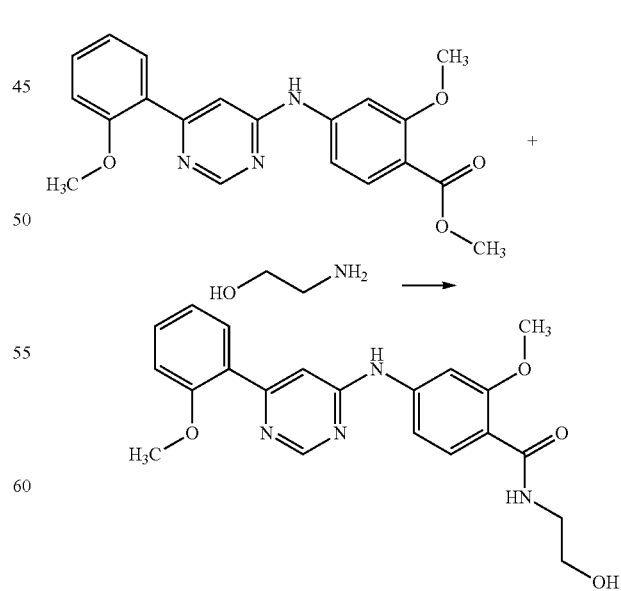

Title compound was prepared according to the method described in case of Example 48 using 2-methoxy-4-[6-(2- methoxy-phenyl)-pyrimidin-4-ylamino]-benzoic acid methyl ester (obtained in Example 133) as starting material and the reaction was carried out in 0.6 mmol quantity. Yield: 157 mg (66%). Ret. time: 0.46-1.94-2.28 min., (M+H)$^+$= 395, (M+H)$^-$=393; $^1$HNMR (DMSO-d$_6$, 300 MHz), δ (ppm): 9.92 (s, 1H), 8.78 (s, 1H), 8.15 (t, 1H), 7.98 (dd, 1H), 7.88 (d, 1H), 7.67 (d, 1H), 7.54 (s, 1H), 7.44 (m, 2H), 7.20 (d, 1H), 7.09 (t, 1H), 4.78 (t, 1H), 3.94 (s, 3H), 3.92 (s, 3H), 3.52 (q, 2H), 3.37 (q, 2H).

2-Methoxy-4-[6-(2-methoxy-phenyl)-pyrimidin-4-ylamino]-benzamide (Example 136)

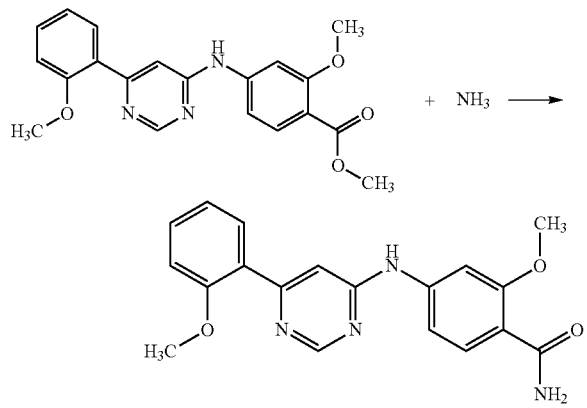

365 mg 2-methoxy-4-[6-(2-methoxy-phenyl)-pyrimidin-4-ylamino]-benzoic acid methyl ester (obtained in Example 133) (1 mmol) was dissolved in 4 ml of methanol saturated with NH$_3$ gas and was heated in a sealed tube at 150° C. for an hour applying microwave irradiation. Then it was evaporated under reduced pressure and the residue was recrystallized from a minimal amount of acetonitrile to get the pure product as a white solid. Yield: 186 mg (53%). Ret. time: 0.45-2.33 min., (M+H)$^+$=351, (M+H)$^-$=349; $^1$HNMR (DMSO-d$_6$, 300 MHz), δ (ppm): 9.91 (s, 1H), 8.78 (s, 1H), 7.98 (d, 1H), 7.87 (d, 1H), 7.64 (s, 1H), 7.49 (m, 4H), 7.37 (bs, 1H), 7.20 (d, 1H), 7.09 (t, 1H), 3.93 (s, 3H), 3.92 (s, 3H).

3-Fluoro-2-methoxy-5-[6-(2-methoxy-phenyl)-pyrimidin-4-ylamino]-benzamide (Example 137)

Step 1

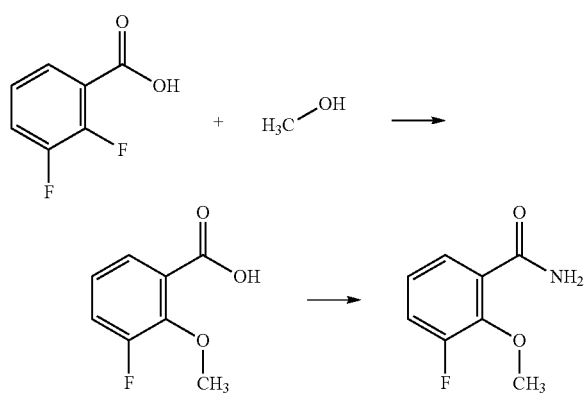

3-Fluoro-2-methoxy-5-nitro-benzamide was prepared according to the method described in case of Example 92, Step 1 using 3-fluoro-2-methoxy-benzoic acid as starting material. Yield: 10.70 g (63%). Ret. time: 2.35 min., (M+H)$^+$= 170 (weak intensity); $^1$HNMR (DMSO-d$_6$, 300 MHz), δ (ppm): 7.63 (bd, 2H), 7.38 (m, 2H), 7.16 (m, 1H), 3.90 (s, 3H).

Step 2

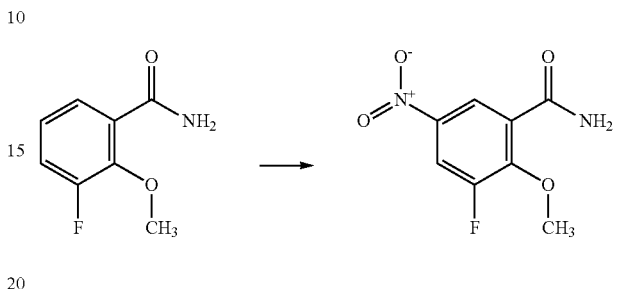

3-Fluoro-2-methoxy-5-nitro-benzamide was prepared according to the method described in case of Example 87, Step 2 using 3-fluoro-2-methoxy-benzamide (obtained in Step 1) as starting material. Yield: 5.07 g (79%). Ret. time: 2.56 min., (M+H)$^+$=215 (weak intensity); $^1$HNMR (DMSO-d$_6$, 300 MHz), δ (ppm): 8.33 (dd, J$^3$=11.55 Hz, J$^4$=2.64 Hz, 1H), 8.25 s, 1H), 7.89 (bs, 1H), 4.09 (d, J=3.12 Hz, 3H).

Step 3

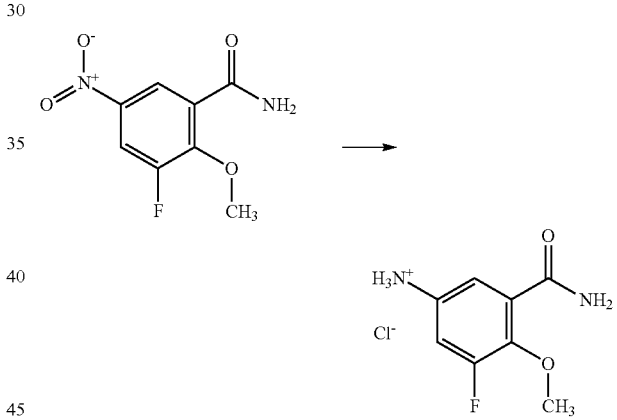

5-Amino-3-fluoro-2-methoxy-benzamide hydrochloride was prepared according to the method described in case of Example 59 using 3-fluoro-2-methoxy-5-nitro-benzamide (obtained in Step 2) as starting material and the reaction was carried out in 50 mmol quantity. Hydrochloric acid salt was prepared by addition of saturated solution of HCl gas in dry ethyl acetate to the solution of the pure product. Solvents were evaporated off at the end. Yield: 8.00 g (73%). Ret. time: 0.47-1.37 min., (M+H)$^+$=185.

Step 4

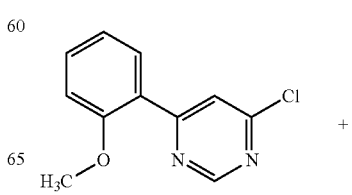

-continued

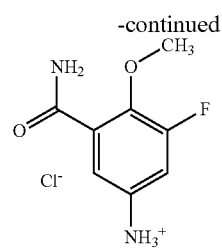

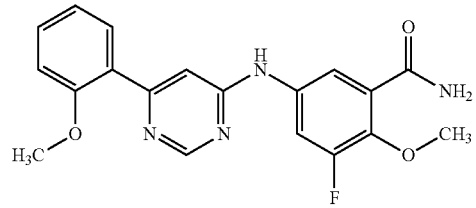

Title compound was prepared according to the method described in case of Example 110, Step 3 using 5-amino-3-fluoro-2-methoxy-benzamide hydrochloride (obtained in Step 3) as starting material. Yield: 244 mg (66%). Ret. time: 2.53 min., (M+H)$^+$=369, (M+H)$^-$=367; $^1$HNMR (DMSO-d$_6$, 300 MHz), δ (ppm): 8.95 (s, 1H), 8.74 (s, 1H), 8.06 (dd, 1H), 7.97 (dd, 1H), 7.72 (bs, 1H), 7.64 (bs, 2H), 7.46 (m, 2H), 7.19 (d, 1H), 7.08 (t, 1H), 3.91 (s, 3H), 3.87 (s, 3H).

3-Fluoro-5-[6-(4-fluoro-2-methoxy-phenyl)-pyrimidin-4-ylamino]-2-methoxy-benzamide (Example 138)

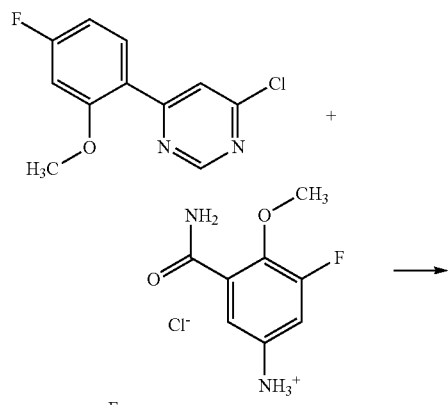

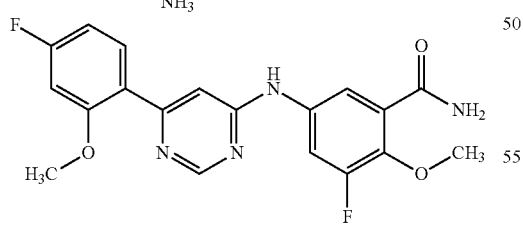

Title compound was prepared according to the method described in case of Example 110, Step 3 using 4-chloro-6-(4-fluoro-2-methoxy-phenyl)-pyrimidine (obtained in Example 90, Step 1) and 5-amino-3-fluoro-2-methoxy-benzamide hydrochloride (obtained in Example 137, Step 3) as starting materials. Yield: 298 mg (77%). Ret. time: 2.70 min., (M+H)$^+$=387, (M+H)$^-$=385; $^1$HNMR (DMSO-d$_6$, 300 MHz), δ (ppm): 9.85 (s, 1H), 8.72 (s, 1H), 8.07 (d, 1H), 8.03 (dd, 1H), 7.72 (bs, 1H), 7.63 (s, 2H), 7.45 (s, 1H), 7.11 (dd, 1H), 6.92 (td, 1H), 3.93 (s, 3H), 3.87 (s, 1H).

5-[6-(2-Ethoxy-4-fluoro-phenyl)-pyrimidin-4-ylamino]-3-fluoro-2-methoxy-benzamide (Example 139)

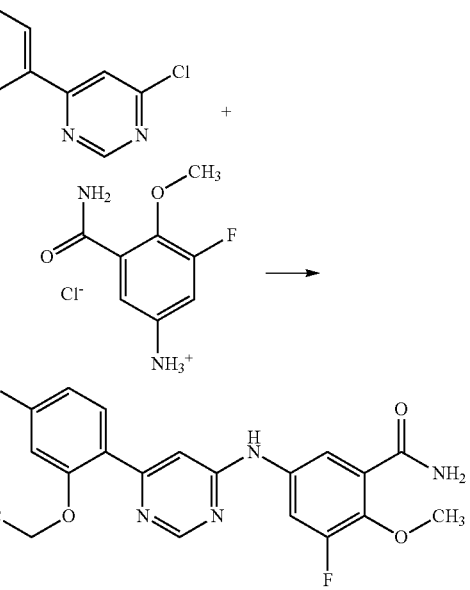

Title compound was prepared according to the method described in case of Example 110, Step 3 using 4-chloro-6-(2-ethoxy-4-fluoro-phenyl)-pyrimidine (obtained in Example 89, Step 1) and 5-amino-3-fluoro-2-methoxy-benzamide hydrochloride (obtained in Example 137, Step 3) as starting materials. Yield: 88 mg (22%). Ret. time: 2.92 min., (M+H)$^+$=401, (M+H)$^-$=399; $^1$HNMR (DMSO-d$_6$, 300 MHz), δ (ppm): 9.81 (s, 1H), 8.72 (s, 1H), 8.06 (d, 1H), 8.05 (s, 1H), 7.72 (bs, 1H), 7.61 (bs, 2H), 7.45 (s, 1H), 7.07 (d, 1H), 6.90 (t, 1H), 4.19 (q, 2H), 3.87 (s, 3H), 1.42 (t, 3H).

3-Fluoro-5-[6-(5-fluoro-2-methoxy-phenyl)-pyrimidin-4-ylamino]-2-methoxy-benzamide (Example 140)

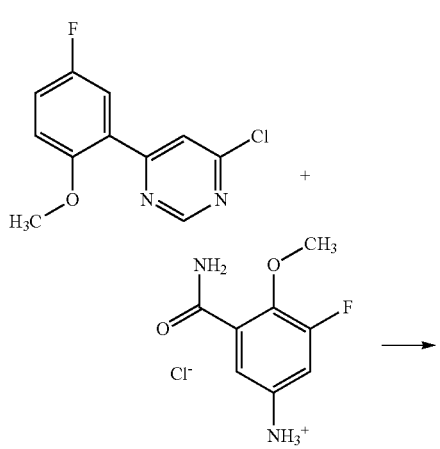

173

-continued

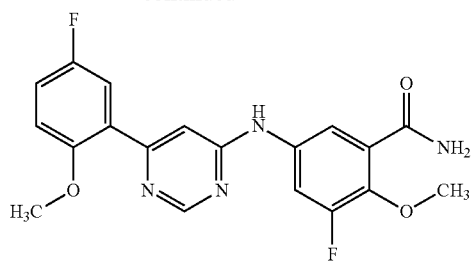

Title compound was prepared according to the method described in case of Example 110, Step 3 using 4-chloro-6-(5-fluoro-2-methoxy-phenyl)-pyrimidine (obtained in Example 91, Step 1) and 5-amino-3-fluoro-2-methoxy-benzamide hydrochloride (obtained in Example 137, Step 3) as starting materials. Yield: 260 mg (67%). Ret. time: 2.87 min., (M+H)$^+$=387, (M+H)$^-$=385; $^1$HNMR (DMSO-d$_6$, 300 MHz), δ (ppm): 9.91 (bs, 1H), 8.75 (s, 1H), 8.04 (dd, 1H), 7.79 (dd, 1H), 7.72 (bs, 1H), 7.64 (bs, 2H), 7.54 (s, 1H), 7.32 (m, 1H), 7.22 (m, 1H), 3.91 (s, 3H), 3.87 (s, 3H).

5-[6-(2-Ethoxy-phenyl)-pyrimidin-4-ylamino]-3-fluoro-2-methoxy-benzamide (Example 141)

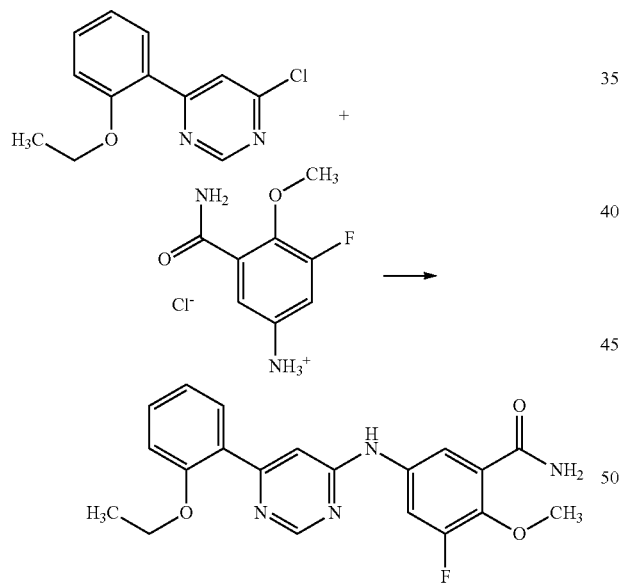

Title compound was prepared according to the method described in case of Example 110, Step 3 using 4-chloro-6-(2-ethoxy-phenyl)-pyrimidine (obtained in Example 129, Step 1) and 5-amino-3-fluoro-2-methoxy-benzamide hydrochloride (obtained in Example 137, Step 3) as starting materials. Yield: 280 mg (73%). Ret. time: 2.70 min., (M+H)$^+$=383, (M+H)$^-$=381; $^1$HNMR (DMSO-d$_6$, 300 MHz), δ (ppm): 9.79 (bs, 1H), 8.74 (s, 1H), 8.08 (dd, 1H), 7.97 (d, 1H), 7.72 (bs, 1H), 7.62 (bs, 2H), 7.48 (s, 1H), 7.43 (t, 1H), 7.16 (d, 1H), 7.06 (t, 1H), 4.17 (q, 2H), 3.88 (s, 3H), 1.41 (t, 3H).

174

5-[6-(2-Ethoxy-5-fluoro-phenyl)-pyrimidin-4-ylamino]-3-fluoro-2-methoxy-benzamide (Example 142)

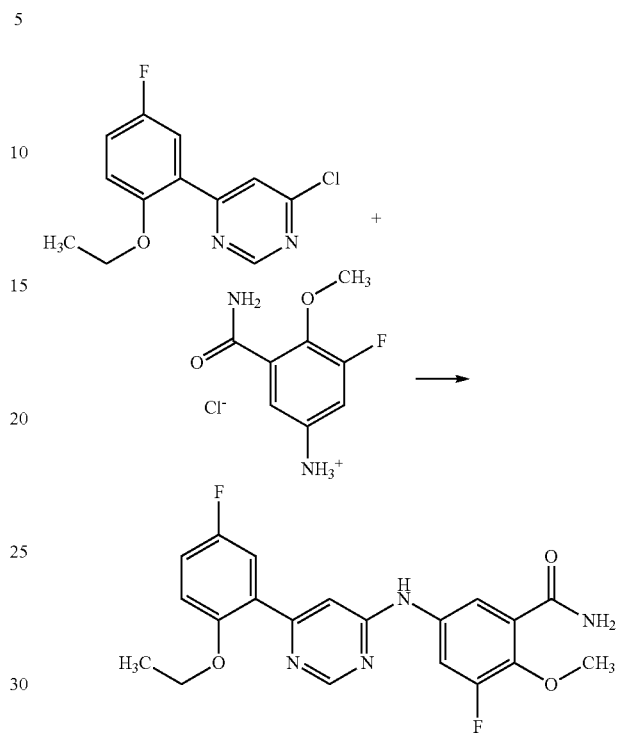

Title compound was prepared according to the method described in case of Example 110, Step 3 using 4-chloro-6-(2-ethoxy-5-fluoro-phenyl)-pyrimidine (obtained in Example 131, Step 1) and 5-amino-3-fluoro-2-methoxy-benzamide hydrochloride (obtained in Example 137, Step 3) as starting materials. Yield: 266 mg (66%). Ret. time: 3.13 min., (M+H)$^+$=401, (M+H)$^-$=399; $^1$HNMR (DMSO-d$_6$, 300 MHz), δ (ppm): 9.88 (bs, 1H), 8.74 (s, 1H), 8.08 (dd, 1H), 7.78 (dd, 1H), 7.73 (bs, 1H), 7.64 (bs, 1H), 7.62 (bs, 1H), 7.55 (s, 1H), 7.29 (m, 1H), 7.19 (m, 1H), 4.16 (q, 2H), 3.88 (s, 3H), 1.40 (t, 3H).

4-Fluoro-2-methoxy-5-[6-(2-methoxy-phenyl)-pyrimidin-4-ylamino]-benzamide (Example 143)

Step 1

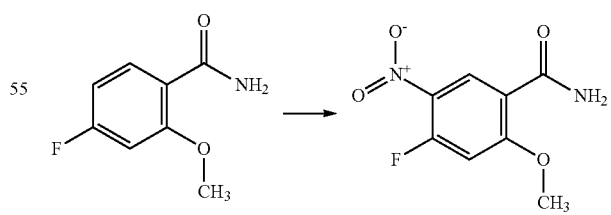

4-Fluoro-2-methoxy-5-nitro-benzamide was prepared according to the method described in case of Example 87, Step 2 using 4-fluoro-2-methoxy-benzamide (obtained in Example 92, Step 1) as starting material and the reaction was carried out in 45 mmol quantity. Yield: 8.12 g (84%). Ret. time: 2.37 min., (M+H)$^+$=215 (weak intensity); $^1$HNMR (DMSO-d$_6$, 300 MHz), δ (ppm): 8.53 (d, J=9.12 Hz, 1H), 7.78 (bd, 2H), 7.40 (d, J=13.65 Hz, 1H), 4.02 (s, 3H).

Step 2

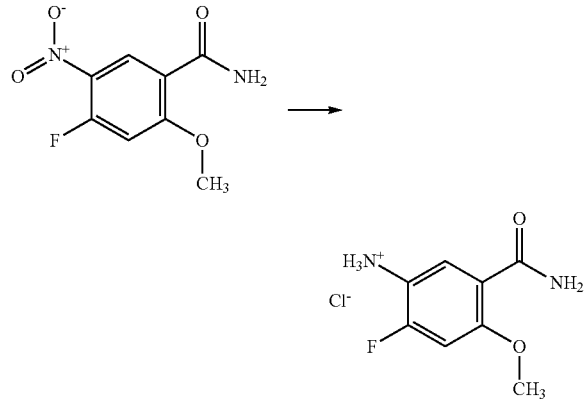

5-Amino-4-fluoro-2-methoxy-benzamide hydrochloride was prepared according to the method described in case of Example 59 using 4-fluoro-2-methoxy-5-nitro-benzamide (obtained in Step 1) as starting material and the reaction was carried out in 40 mmol quantity. Hydrochloric acid salt was prepared by addition of saturated solution of HCl gas in dry ethyl acetate to the solution of the pure product. Solvents were evaporated off at the end. Yield: 5.02 g (68%). Ret. time: 0.46-0.71 min., (M+H)$^+$=185.

Step 3

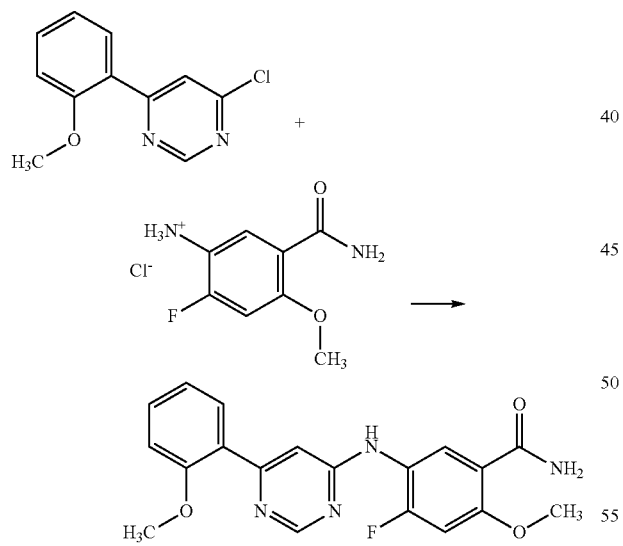

Title compound was prepared according to the method described in case of Example 110, Step 3 using 5-amino-4-fluoro-2-methoxy-benzamide hydrochloride (obtained in Step 2) as starting material. Yield: 189 mg (51%). Ret. time: 0.45-2.13-2.35 min., (M+H)$^+$=369, (M+H)$^-$=367; $^1$HNMR (DMSO-d$_6$, 300 MHz), δ (ppm): 9.22 (s, 1H), 8.58 (s, 1H), 8.15 (d, 1H), 7.93 (d, 1H), 7.62 (bs, 1H), 7.58 (bs, 1H), 7.44 (t, 1H), 7.35 (s, 1H), 7.17 (m, 2H), 7.06 (t, 1H), 3.92 (s, 3H), 3.87 (s, 3H).

4-Fluoro-5-[6-(5-fluoro-2-methoxy-phenyl)-pyrimidin-4-ylamino]-2-methoxy-benzamide (Example 144)

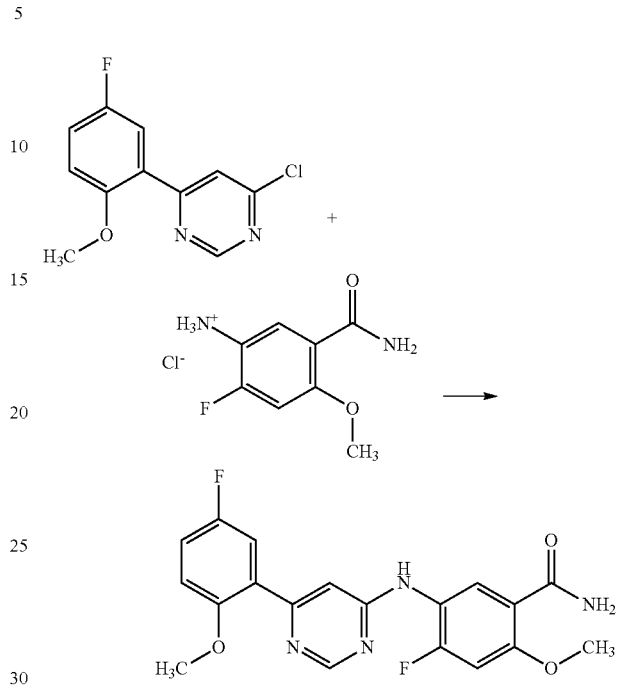

Title compound was prepared according to the method described in case of Example 110, Step 3 using 4-chloro-6-(5-fluoro-2-methoxy-phenyl)-pyrimidine (obtained in Example 91, Step 1) and 5-amino-4-fluoro-2-methoxy-benzamide hydrochloride (obtained in Example 143, Step 2) as starting materials. Yield: 124 mg (32%). Ret. time: 2.51 min., (M+H)$^+$=387, (M+H)$^-$=385; $^1$HNMR (DMSO-d$_6$, 300 MHz), δ (ppm): 9.31 (s, 1H), 8.59 (s, 1H), 8.15 (d, 1H), 7.75 (dd, 1H), 7.62 (bs, 1H), 7.58 (bs, 1H), 7.44 (s, 1H), 7.30 (m, 1H), 7.18 (m, 2H), 3.92 (s, 3H), 3.87 (s, 3H).

5-[6-(2-Ethoxy-phenyl)-pyrimidin-4-ylamino]-4-fluoro-2-methoxy-benzamide (Example 145)

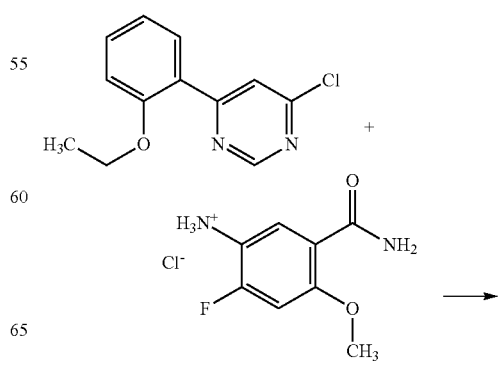

177

-continued

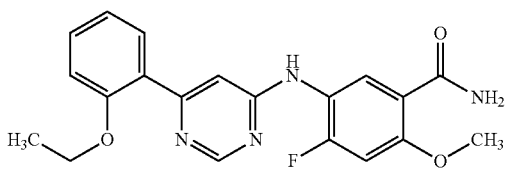

Title compound was prepared according to the method described in case of Example 110, Step 3 using 4-chloro-6-(2-ethoxy-phenyl)-pyrimidine (obtained in Example 129, Step 1) and 5-amino-4-fluoro-2-methoxy-benzamide hydrochloride (obtained in Example 143, Step 2) as starting materials. Yield: 150 mg (39%). Ret. time: 0.45-2.33-2.51 min., (M+H)$^+$=383, (M+H)$^-$=381; $^1$HNMR (DMSO-d$_6$, 300 MHz), δ (ppm): 9.19 (s, 1H), 8.58 (s, 1H), 8.05 (d, 1H), 8.00 (d, 1H), 7.62 (bs, 1H), 7.59 (bs, 1H), 7.41 (t, 1H), 7.33 (s, 1H), 7.20 (d, 1H), 7.12 (d, 1H), 7.04 (t, 1H), 4.10 (q, 2H), 3.93 (s, 3H), 1.28 (t, 3H).

4-Fluoro-5-[6-(4-fluoro-2-methoxy-phenyl)-pyrimidin-4-ylamino]-2-methoxy-benzamide (Example 146)

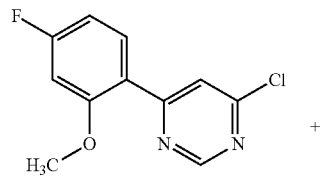

+

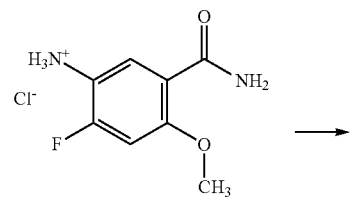

→

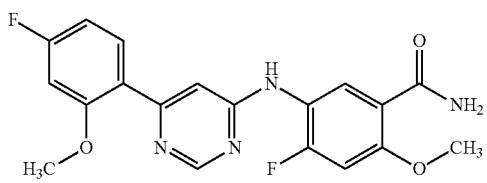

Title compound was prepared according to the method described in case of Example 110, Step 3 using 4-chloro-6-(4-fluoro-2-methoxy-phenyl)-pyrimidine (obtained in Example 90, Step 1) and 5-amino-4-fluoro-2-methoxy-benzamide hydrochloride (obtained in Example 143, Step 2) as starting materials. Yield: 281 mg (73%). Ret. time: 0.45-2.38 min., (M+H)$^+$=387, (M+H)$^-$=385; $^1$HNMR (DMSO-d$_6$, 300 MHz), δ (ppm): 9.23 (s, 1H), 8.57 (s, 1H), 8.15 (d, 1H), 8.01 (t, 1H), 7.62 (bs, 1H), 7.58 (bs, 1H), 7.34 (s, 1H), 7.18 (d, 1H), 7.07 (d, 1H), 6.90 (td, 1H), 3.92 (s, 3H), 3.89 (s, 3H).

178

5-[6-(2-Ethoxy-4-fluoro-phenyl)-pyrimidin-4-ylamino]-4-fluoro-2-methoxy-benzamide (Example 147)

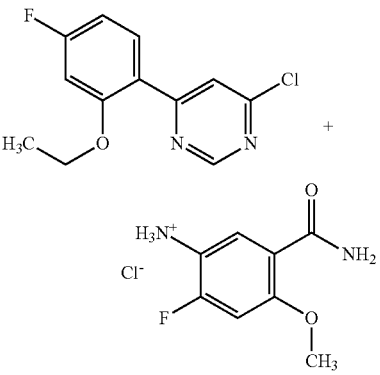

+

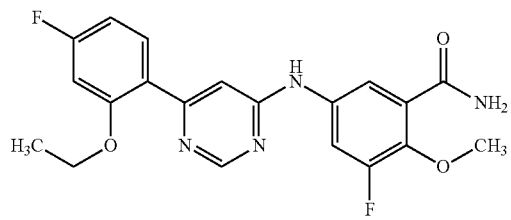

→

Title compound was prepared according to the method described in case of Example 110, Step 3 using 4-chloro-6-(2-ethoxy-4-fluoro-phenyl)-pyrimidine (obtained in Example 89, Step 1) and 5-amino-4-fluoro-2-methoxy-benzamide hydrochloride (obtained in Example 143, Step 2) as starting materials. Yield: 153 mg (38%). Ret. time: 2.65 min., (M+H)$^+$=401, (M+H)$^-$=399; $^1$HNMR (DMSO-d$_6$, 300 MHz), δ (ppm): 9.21 (s, 1H), 8.57 (s, 1H), 8.05 (m, 2H), 7.62 (bs, 1H), 7.59 (bs, 1H), 7.30 (s, 1H), 7.12 (d, 1H), 7.02 (dd, 1H), 6.88 (t, 1H), 4.12 (q, 2H), 3.93 (s, 3H), 1.28 (t, 3H).

5-[6-(2-Ethoxy-5-fluoro-phenyl)-pyrimidin-4-ylamino]-4-fluoro-2-methoxy-benzamide (Example 148)

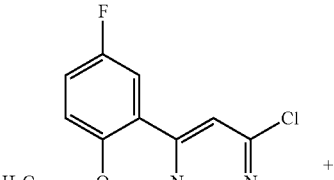

+

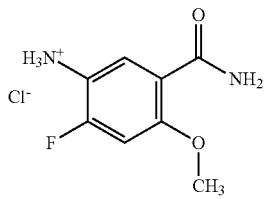

→

-continued

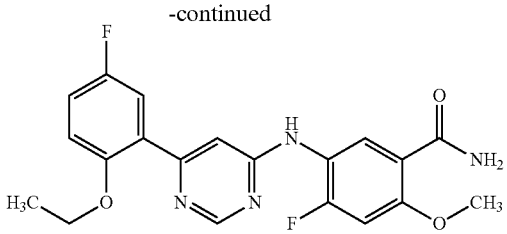

Title compound was prepared according to the method described in case of Example 110, Step 3 using 4-chloro-6-(2-ethoxy-5-fluoro-phenyl)-pyrimidine (obtained in Example 131, Step 1) and 5-amino-4-fluoro-2-methoxy-benzamide hydrochloride (obtained in Example 143, Step 2) as starting materials. Yield: 257 mg (64%). Ret. time: 2.75 min., $(M+H)^+ = 401$, $(M+H)^- = 399$; $^1$HNMR (DMSO-$d_6$, 300 MHz), δ (ppm): 9.28 (s, 1H), 8.59 (s, 1H), 8.14 (d, 1H), 7.79 (dd, 1H), 7.62 (bs, 1H), 7.59 (bs, 1H), 7.40 (s, 1H), 7.22 (m, 3H), 4.09 (q, 2H), 3.93 (s, 3H), 1.27 (t, 3H).

What is claimed is:
1. A compound having formula (I):

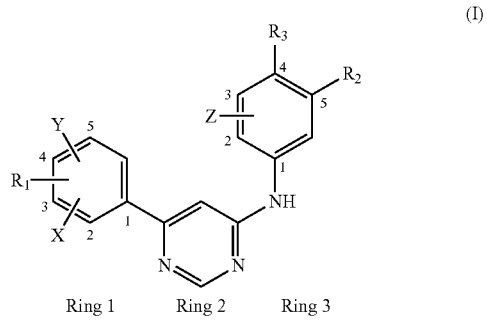

where
X, Y and Z are H, F, or Cl;
R$_1$ is OR, where R is hydrogen or a group selected from straight or branched C$_1$-C$_6$ alkyl, C$_2$-C$_6$ alkenyl, C$_2$-C$_6$ alkynyl, C$_3$-C$_6$ cycloalkyl, heterocyclyl, CF$_3$, CCl$_3$, and aryl in positions 2, 3 or 4;
R$_2$ is OH, alkoxy, aryloxy, CH$_2$OR (where R is H, linear or branched aryl, cycloalkyl or alkyl), CH$_2$NR'R" (where R' and R" are independently H, linear or branched aryl, cycloalkyl or alkyl), CHO, OCOW (where W is linear or branched aryl or alkyl or C-(halogen)$_3$), CONR'R" (where R' and R" independently are H, alkyl, cycloalkyl or aryl), COOR (where R is H, alkyl, cycloalkyl or aryl), CH$_2$NHSO$_2$R (where R is H, alkyl, cycloalkyl or aryl), Cl, Br, F, substituted or unsubstituted CH$_2$—N-benzimidazole, CONHNR'R" (where R' and R" independently are H, alkyl, cycloalkyl or aryl), NRCOOR' (where R and R' are independently H, alkyl, cycloalkyl or aryl), NH$_2$, NR'R" (where R' and R" independently are alkyl, cycloalkyl or aryl), NHCOR (where R is H, alkyl, cycloalkyl or aryl), nitro, OCH$_2$CH$_2$-heterocyclyl, OCOR (where R is H, alkyl, cycloalkyl or aryl), OCONR'R" (where R' and R" are independently H, alkyl, cycloalkyl or aryl), OCOOR (where R is H, alkyl, cycloalkyl or aryl), NHCOOCH$_2$C-halo$_3$, NRCONR'R" (where R, R' and R" are H, alkyl, cycloalkyl or aryl), NHSO$_2$R (where R is H, alkyl, cycloalkyl or aryl), NHSO$_2$NR'R" (where R' and R" independently are H, alkyl, cycloalkyl or aryl),

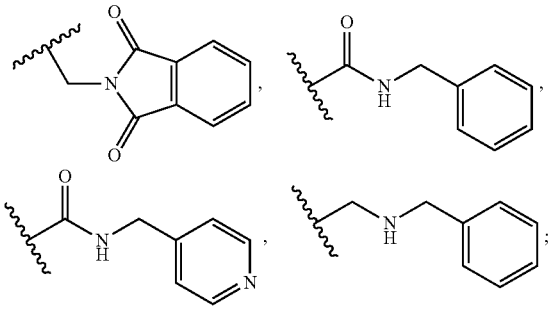

and R$_3$ is OH, alkoxy, aryloxy, NR'R" (where R' and R" are H), NHCOR (where R is H, alkyl, cycloalkyl or aryl), and CONR'R" (where R' and R" independently are H, alkyl, cycloalkyl or aryl.

2. A compound according to claim 1, wherein R$_1$ is OR, where R is H, methyl, isopropyl or ethyl.
3. A compound according to claim 1, wherein R$_1$ is 2'-OR, where R is H, methyl, isopropyl or ethyl.
4. A compound according to claim 1, wherein Z is H or F.
5. A compound according to claim 1, wherein R$_2$ is selected from the group consisting of OH, linear or branched alkoxy, CH$_2$OR (where R is alkyl), NH$_2$, CH$_2$NH$_2$, OCOC(CH$_3$)$_3$, CONH$_2$, Cl, Br, unsubstituted CH$_2$—N-benzimidazole, NHSO$_2$R (where R is alkyl or aryl) and NHSO$_2$NR'R" (where R' and R" independently are H, alkyl, or aryl), OCH$_2$CH$_2$-heterocyclyl, OCOR (where R is H, alkyl, cycloalkyl or aryl), OCONR'R" (where R' and R" are independently H, alkyl, cycloalkyl or aryl).
6. A compound according to claim 1, wherein R$_3$ is OH, linear or branched alkoxy, NR'R" (where R' and R" independently are H), CONR'R" (where R' and R" independently are H, alkyl, cycloalkyl or aryl).
7. A compound according to claim 1, wherein R$_2$ is selected from the group consisting of OH, linear or branched alkoxy, CONH$_2$, OCOC(CH$_3$)$_3$, Cl, unsubstituted CH$_2$N-benzimidazole and R$_3$ is alkoxy.
8. A compound according to claim 1, wherein X, Y and Z are H or F, R$_2$ is linear or branched alkoxy, CONH$_2$, OCOC(CH$_3$)$_3$, Cl, unsubstituted CH$_2$—N-benzimidazole and R$_3$ is alkoxy.
9. A compound according to claim 1, wherein X, Y and Z are H or F, R$_1$ is methoxy or ethoxy, R$_2$ is linear or branched alkoxy, CONH$_2$, Cl, Br, unsubstituted CH$_2$—N-benzimidazole and R$_3$ is alkoxy.
10. A compound according to claim 1, wherein X and Y are 4'-F, 5'-F or H and Z is 2'-F or H, R$_1$ is 2'-OR, where R is H, methyl, ethyl, or isopropyl, R$_2$ is linear or branched alkoxy, CONH$_2$, Cl, Br, unsubstituted CH$_2$—N-benzimidazole and R$_3$ is OR' (where R' is alkyl).
11. A pharmaceutical composition comprising a pharmaceutically acceptable excipient, diluent or carrier and a therapeutically effective amount of a A compound according to any one of claims 1 to 10.
12. A compound according to any one of claims 1-10, selected from the list
5-[6-(4-Fluoro-2-methoxy-phenyl)-pyrimidin-4-ylamino]-2-methoxy-phenol;
N-(3-(benzyloxy)-4-methoxyphenyl)-6-(2-methoxyphenyl)pyrimidin-4-amine;

N-(3-fluoro-4-methoxyphenyl)-6-(2-methoxyphenyl)pyrimidin-4-amine;
2-methoxy-5-(6-(2-methoxyphenyl)pyrimidin-4-ylamino)phenol;
4-methoxy-$N^1$-(6-(2-methoxyphenyl)pyrimidin-4-yl)benzene-1,3-diamine;
2-methoxy-5-(6-(2-methoxyphenyl)pyrimidin-4-ylamino)benzamide;
{2-Methoxy-5-[6-(2-methoxy-phenyl)-pyrimidin-4-ylamino]-phenyl}-carbamic acid methyl ester;
(2-methoxy-5-(6-(2-methoxyphenyl)pyrimidin-4-ylamino)phenyl)(methylsulfamoyl)amine;
N-benzyl-2-methoxy-5-(6-(2-methoxyphenyl)pyrimidin-4-ylamino)benzamide;
(2-methoxy-5-(6-(2-methoxyphenyl)pyrimidin-4-ylamino)phenyl)methanol;
2-methoxy-5-(6-(2-methoxyphenyl)pyrimidin-4-ylamino)-N-methylbenzamide;
N-(4-methoxy-3-nitrophenyl)-6-(2-methoxyphenyl)pyrimidin-4-amine;
$N^1$-[6-(2-Isopropoxy-phenyl)-pyrimidin-4-yl]-4-methoxy-benzene-1,3-diamine;
N-(3-((dimethylamino)methyl)-4-methoxyphenyl)-6-(2-methoxyphenyl)pyrimidin-4-amine;
N-(4-methoxy-3-((phenylamino)methyl)phenyl)-6-(2-methoxyphenyl)pyrimidin-4-amine;
2-(2-methoxy-5-(6-(2-methoxyphenyl)pyrimidin-4-ylamino)benzyl)isoindoline-1,3-dione;
4-Fluoro-5-[6-(4-fluoro-2-methoxy-phenyl)-pyrimidin-4-ylamino]-2-methoxy-benzamide;
5-[6-(4-Fluoro-2-methoxy-phenyl)-pyrimidin-4-ylamino]-2-methoxy-benzamide;
4-Fluoro-2-methoxy-5-[6-(2-methoxy-phenyl)-pyrimidin-4-ylamino]-benzamide;
5-[6-(2-Ethoxy-phenyl)-pyrimidin-4-ylamino]-4-fluoro-2-methoxy-benzamide;
5-[6-(2-Ethoxy-4-fluoro-phenyl)-pyrimidin-4-ylamino]-4-fluoro-2-methoxy-benzamide;
4-(6-(2-methoxyphenyl)pyrimidin-4-ylamino)-2-nitrophenol;
N-(3-((benzylamino)methyl)-4-methoxyphenyl)-6-(2-methoxyphenyl)pyrimidin-4-amine;
N-(3-(aminomethyl)-4-methoxyphenyl)-8-(2-methoxyphenyl)pyrimidin-4-amine;
3-Fluoro-5-[6-(4-fluoro-2-methoxy-phenyl)-pyrimidin-4-ylamino]-2-methoxy-benzamide;
3-Fluoro-5-[6-(5-fluoro-2-methoxy-phenyl)-pyrimidin-4-ylamino]-2-methoxy-benzamide.

13. Ethyl 2-chloro-5-(6-(2-methoxyphenyl)pyrimidin-4-ylamino)benzoate.

14. 2-Fluoro-$N^4$-[6-(2-methoxy-phenyl)-pyrimidin-4-yl]-$N^1,N^1$-dimethyl-benzene-1,4-diamine.

15. 2-Dimethylamino-5-[6-(2-methoxy-phenyl)-pyrimidin-4-ylamino]-phenol.

16. 2-Dimethylamino-5-[6-(2-methoxy-phenyl)-pyrimidin-4-ylamino]-benzamide.

17. Ethyl 5-(6-(2-methoxyphenyl)pyrimidin-4-ylamino)-2-morpholinobenzoate.

18. 2-(2-chloro-5-(6-(2-methoxyphenyl)pyrimidin-4-ylamino)benzyl)isoindoline-1,3-dione.

19. 2-chloro-5-(6-(2-methoxyphenyl)pyrimidin-4-ylamino)benzamide.

20. N-(3-((1H-benzo[d]imidazol-1-yl)methyl)-4-(4-methylpiperazin-1-yl)phenyl)-6-(2-methoxyphenyl)pyrimidin-4-amine.

\* \* \* \* \*